United States Patent
Si et al.

(10) Patent No.: US 10,800,741 B2
(45) Date of Patent: Oct. 13, 2020

(54) QUINOLINE COMPOUND, PREPARATION METHOD AND MEDICAL USE THEREFOR

(71) Applicant: ANCUREALL PHARMACEUTICAL (SHANGHAI) CO., LTD., Shanghai (CN)

(72) Inventors: Jutong Si, Shanghai (CN); Meifeng Jiang, Shanghai (CN); Jiayan Li, Shanghai (CN); Han Zeng, Shanghai (CN); Huabin Yang, Shanghai (CN)

(73) Assignee: Ancureall Pharmaceutical (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 16/480,292

(22) PCT Filed: Feb. 6, 2018

(86) PCT No.: PCT/CN2018/075392
§ 371 (c)(1),
(2) Date: Jul. 23, 2019

(87) PCT Pub. No.: WO2018/145621
PCT Pub. Date: Aug. 16, 2018

(65) Prior Publication Data
US 2019/0375714 A1    Dec. 12, 2019

(30) Foreign Application Priority Data
Feb. 7, 2017 (CN) .......................... 2017 1 0067692

(51) Int. Cl.
*C07D 215/16* (2006.01)
*A61P 35/00* (2006.01)
*C07D 401/12* (2006.01)
*A61K 31/47* (2006.01)

(52) U.S. Cl.
CPC ............ *C07D 215/16* (2013.01); *A61P 35/00* (2018.01); *C07D 401/12* (2013.01)

(58) Field of Classification Search
None
See application file for complete search history.

(56) References Cited

U.S. PATENT DOCUMENTS

2019/0169163 A1* 6/2019 Yin ...................... C07D 215/46

FOREIGN PATENT DOCUMENTS

| CN | 1308310 C | 4/2007 |
|---|---|---|
| WO | 2016/161952 A1 | 10/2016 |
| WO | 2018/028591 A1 | 2/2018 |

OTHER PUBLICATIONS

Silverman, Prodrugs and Drug Delivery Systems, The Organic Chemistry of Drug Designs and Drug Action, pp. 352-399 (Year: 1992).*
Dienstmann, R. et al., "Genomic aberrations in the FGFR pathway: opportunities for targeted therapies in solid tumors", Annals of Oncology, 25:552-563 (2014).
Thussbas, Christoph et al., "FGFR4 ARG388 Allele is Associated with Resistance to Adjuvant Therapy in Primary Breast Cancer", Journals of Clinical Oncology, 24(23):3747-3755 (Aug. 10, 2006).
Ulaganathan, Vijay K. et al., "Germline variant FGFR4 p.G388R exposes a membrane-proximal STAT3 binding site", Nature, 528:570-587 (Dec. 2015).
Manchado, Eusebio et al., "A combinatorial strategy for treating KRAS-mutant lung cancer", Nature, 534:647-666 (Jun. 30, 2016).
Bertotti, Andrea et al., "The genomic landscape of response to EGFR blockade in colorectal cancer", Nature, 526:263-280 (Oct. 8, 2015).
Helsten, Teresa et al., "The FGFR Landscape in Cancer: Analysis of 4,853 Tumors by Next-Generation Sequencing", Clin Cancer Res, 22:259-267 (2016).
Millis, Sherri Z. et al., "Landscape of Phosphatidylinositol-3-Kinase Pathway Alterations Across 19784 Diverse Solid Tumors", JAMA Oncology, 2(12):1565-1573 (Dec. 2016).
Vanhaesebroeck, Bart et al., "The emerging mechanisms of isoform-specific PI3K signalling", Nat Rev Mol Cell Biol., 11(5):329-341 (2010).
Klüter, Sabine et al., "Displacement Assay for the Detection of Stabilizers of Inactive Kinase Conformations", J. Med. Chem., 53:357-367 (Nov. 23, 2009).

* cited by examiner

*Primary Examiner* — Zinna Northington Davis
(74) *Attorney, Agent, or Firm* — Rodney J. Fuller; Booth Udall Fuller, PLC

(57) ABSTRACT

The present invention relates to a quinoline compound, as well as a preparation method and medical use therefor. Specifically, the present invention relates to a novel quinolone compound represented by the general formula (I) and a method for preparing the same, as well as a use therefor as an inhibitor for a plurality of protein kinases, and a use in the prevention and/or treatment of cancer in particular; the definition of each group in the general formula (I) is the same as the definition in the description.

18 Claims, No Drawings

QUINOLINE COMPOUND, PREPARATION METHOD AND MEDICAL USE THEREFOR

CROSS REFERENCE TO RELATED APPLICATIONS

This application is the U.S. National Stage of International Application No. PCT/CN2018/075392, filed on Feb. 6, 2018, which claims the benefit of and priority to Chinese Patent Application No. 201710067692.5, filed on Feb. 7, 2017, the contents of each of which are expressly incorporated herein by reference in their entireties.

FIELD OF THE INVENTION

The present invention which belongs to the field of medicine relates to a new type of quinoline compound, its preparation method and a pharmaceutical composition comprising the same, and use of it as multi-protein kinase inhibitor, and in the prevention and/or treatment of cancer.

BACKGROUND OF THE INVENTION

Cancer, including leukemia, is one of the major diseases leading to clinical death of human beings. Millions of patients worldwide die of cancer every year. Malignant tumors such as lung cancer, gastric cancer, breast cancer, pancreatic cancer, liver cancer, intestinal cancer, ovarian cancer, cervical cancer, esophageal cancer, nasopharyngeal cancer, leukemia and malignant lymphoma have a high mortality rate. Although the clinical early detection or correct diagnosis and treatment effect for cancer patients have been improved by genetic screening, molecular diagnosis and precision medicine, there are still no effective methods or drugs up to now that can eradicate or cure most cancers, especially advanced, refractory, recurrent and drug-resistant malignant tumors. High quality anticancer drugs with good specificity, high activity, low toxicity and none acquired resistance are urgently needed for clinical treatment.

The occurrence, development, metastasis, deterioration, recurrence and drug resistance of cancer are related to many factors. The abnormality of normal intracellular molecular signal transduction pathway is one of the most important factors that lead to cell transformation and cancerization, especially the multifunctional signal transduction pathway of protein kinase mediated by transmembrane receptor. Protein kinases are essential enzymes for important physiological functions such as cell growth, development, differentiation, metabolism, aging and apoptosis. Many abnormal protein kinases can directly lead to different types of diseases in clinical practice, such as cancer, inflammation, diseases of immune system and nervous system, and cardiovascular and cerebrovascular diseases. Tyrosine (Tyr) protein kinase and serine/threonine (Ser/Thr) protein kinase are two kinases that have been extensively studied and applied. After decades of unremitting efforts, many tyrosine kinases (e.g. EGFR, HER2/3/4, VEGFR, PDGFR, Met, IGF-1R, FGFR, CSF-1R, Trk receptor, Ephrin receptor, TAM receptor, Tie 2, FLT-3, RET, ALK, BCR-ABL, JAKs, SRC, FAK, BTK, SYK and BLK, etc.) and serine/threonine protein kinases (e.g., PI3K, ATM/ATR, Akt, mTOR, aurora kinase, Ras, Raf, MAPKs, GSK3, AMPK, PIM and CDK-sEtc.) are identified as target protein molecules for different clinical diseases. Some protein kinase inhibitors have been successfully applied in clinical practice and have shown good therapeutic effects.

Fibroblast growth factor receptor (FGFR) is a kind of transmembrane receptor protein, which is a tyrosine kinase. The kinase family is mainly composed of FGFR1, FGFR2, FGFR3 and FGFR4. Fibroblast growth factor (as a ligand) binds to the corresponding FGFRs (as a receptor), activates the important FGFRs/RAS/MAPK and FGFRs/PI3K/AKT signaling pathways, and controls and regulates many physiological functions of cells. Basic research and clinical genome big data showed that abnormal FGFR1-4 gene (such as point mutation, amplification, expression and rearrangement, and the like) can directly lead to cellular transformation and cancerization. These abnormal genes are closely related to cancer cell proliferation, survival and metastasis, invasion, tumor neovascularization, recurrence, and drug resistance. In clinical cancer patients, abnormal FGFR signal transduction pathway is mainly manifested in the following aspects: (i) gene amplification or overexpression; (ii) FGFR mutation produces ligand-independent activation or reduces ligand-binding dependent activation; (iii) translocation forms FGFR-fusion protein and generates ligand-independent activation; (iv) a selective cut between FGFR, which changes and increases the selectivity for stimulating the tumor cells growth receptor FGF; (v) up-regulating FGF expression in cancer or stromal cells, enhancing FGF release from the extracellular matrix, and resulting in paracrine/autocrine activation pathway. The degree of FGFR1-4 gene abnormality (such as overexpression, amplification, point mutation, insertion and rearrangement, and the like) is related to the type of cancer, and there are certain differences (Dienstmann R et al., Ann Oncol. 2014, 25:552-63). Helsten T et al. has found that 7.1% of cancers had FGFR aberrations (FGFR1 accounted for 3.5%, FGFR2 for about 1.5%, FGFR3 for 2.0% and 0.5% for FGFR4) by new generation sequencing technology to analyze 4583 different tumor samples, among which 66% were gene amplification, 26% were mutations, and 8% were rearrangements. Moreover, there are significant difference for FGFR1-4 aberrations rate in different types of cancer, for example urothelial carcinoma (32%), breast cancer (18%), endometrial cancer (≥13%), squamous lung cancer (≤13%), ovarian cancer (≤9%), bile duct carcinoma (≤7%), glioma (7.6%), adenocarcinoma of gastroesophageal junction (6.7%), non-small cell lung cancer (5.2%), pancreatic cancer (4.7%), renal cell carcinoma (4.6%), head and neck squamous cell carcinoma (4.6%), colorectal cancer (4.4%), sarcoma (4.0%), neuroendocrine (3.7%), melanoma (1.5%), lymphosarcoma (1.3%).

In different types of tumors, FGFR1-4 gene mutations often occur in the extracellular/transmembrane domain and intracellular kinase domain of FGFR protein molecules. For example, P252T (lung cancer) and P252S (melanoma) are mutations in the extracellular/transmembrane domain of FGFR1. Mutations of FGFR2 D101Y, S252W, P253R, A314D, A315T, S373C and Y376C can be detected in endometrial cancer. In bladder cancer, mutations of FGFR3 R248C, S249C, G370C, S371C, Y373C, G380R and A391E can be detected. Mutations in FGFR4 Y367C and G338R can be detected in breast cancer. These transmembrane domain mutations enable FGFRs to form dimer and form ligand-independent constitutive activators (Thussbas C U et al., J Clin Oncol. (2006) 10; 24 (23): 3747-55. Laganathan V K et al., Nature. (2015) 528:570-4). Mutations in the kinase domain of FGFRs kinases (e.g., N549K or K659E in FGFR1, N550K or K660E/M/N in FGFR2, N540S/K or K650M/N/Q/T in FGFR3, and N535D/K or V550E/L in FGFR4) often directly enhance the kinase activity and lead to ligand independent constitutive activators and drug resistance. In addition to the above FGFRs gene amplification/ overexpression or gene mutation, fusion proteins (e.g. BCR-FGFR1, CNTRL-FGFR1, CUX1-FGFR1, FGFR1OP-FGFR1, FGFR10P2-FGFR1, LRRFIP1-FGFR1, MYO18A-FGFR1, RANBP2-FGFR1, TPR-FGFR1, TRIM24-FGFR1, ZMYM2-FGFR1, and ETV6-FGFR3 non-receptor FGFR kinase fusion, and FGFR1-TACC1, FGFR2-AFF3, FGFR2-BICC1, FGFR2-CASP7, FGFR2-CCAR2, FGFR2-CCDC6, FGFR2-CIT, FGFR2-OFD1, FGFR2-PPHLN1, FGFR3-BAIAP2L1, FGFR3-JAKMIP1, and FGFR3-TACC3 C-terminal changed transmembrane FGFR fusion) formed by gene translocation also occurred in different cancer patients, especially in myeloproliferative tumors.

During the clinical treatment of tumors, more and more data have been found that the activation of FGFR signaling pathway is closely related to the development of drug resistance of many anticancer drugs. For example, the clinical application of MEK inhibitor Trametinib is activated by the compensatory response of FGFR1-mediated signaling pathway, resulting in signal bounce and adaptive drug tolerance. When combined with FGFR1 inhibitor, the anti-tumor activity of Trametinib can be enhanced (Manchado E et al., Nature, 2016. 534 (7609): 647-51). Bertotti A et al. reported that the primary and secondary resistance of the monoclonal antibodies of epidermal growth factor receptor (EGFR) (cetuximab and panitumumab) which were used for the targeted treatment of colorectal cancer is also related to FGFR1 gene amplification in addition to the KRAS, ERBB2, EGFR, PDGFRA and MAP2K1 gene mutations (Bertotti A et al. Nature. 2015; 526:526-263). These data suggest that FGFRs are closely associated with cancer, and inhibition of FGFRs may be an important option for the treatment of multiple types of tumors including drug resistance (Helsten T et al., Clin Cancer res. 2016, 22:259-67). In spite of a number of different FGFR inhibitors (broad spectrum or selective, such as BGJ398, AZD4547, Ponatinib, jnj-42756493 and Lenvatinib, and the like) at different stages of clinical trials, new high-quality FGFR small molecule inhibitors, which especially can effectively target FGFR signaling pathways or related signaling are urgently needed.

Type III receptor Tyrosine Kinase is a family consisting of FMS-like Tyrosine Kinase 3 (FLT3), colony stimulating factor 1 receptor CSF1R, platelet derived growth factor receptor PDGFRα/β, and stem cell factor receptor KIT, and the amino acids of their protein kinase domain have a high degree of similarity. Under normal physiological environment of growth and development, the expression of these genes is mainly in the early development of brain, liver, placenta, reproductive gland and hematopoietic cells, which has important physiological functions. When these genes have aberration, they can directly cause cell tumorigenic transformation, which is also associated with the occurrence, development, invasion, metastasis, deterioration, recurrence and drug resistance of cancer cells. For example, about 30% of patients with acute myeloid leukemia (AML) have mutations in the FLT3 internal tandem repeats (ITD, 19-28%) and tyrosine kinase domain (TKD, 5-10%) mutation. FLT3 mutation rate is 2% in patients with moderate or high-risk myelodysplastic syndrome (MDS). In APL patients, the mutation rate of FLT3 is less than 5%. The incidence is less than 1% in ALL, and it is mainly seen in ALL cases with biphenotype. FLT3 mutations (such as FLT3-ITD or FLT3-ITD/TKD double mutations) can lead to the phosphorylation of FLT3 protein itself, leading to the independent continuous activation of FLT3 ligand and the abnormality of its downstream signal transduction, thus promoting proliferation and inhibiting apoptosis. Similarly, persistent high levels of PDGFs and PDGFR α/β expression and genetic mutations are detected in malignant tumor cells such as glioma, kaposi's sarcoma, prostate cancer, and pancreatic cancer.

The phosphoinositol-3-kinase (PI3K) signaling pathway regulates many basic biological processes such as cell cycle, cell proliferation, survival, and migration. Class I of PI3K is a heterodimer composed of a catalytic subunit (p110) and a regulatory subunit (p85), which plays an important role in cell signal transduction together with activated receptor tyrosine kinase (RTK), G protein-coupled receptor or activated RAS. In many types of tumors, the phosphoinositide 3-kinase (PI3K)/AKT/mTOR signaling pathway is abnormally activated. In particular, PI3K catalyzed subunit (PIK3 CA) presenting high frequency of mutations (e.g. H1047R and E545K allele mutations) is one of the most common high frequency mutations in clinical oncology patients (Millis S Z et al., JAMA Oncol. 2016). So 65-1573; Vanhaesebroeck B et al., Nat Rev Mol Cell Biol. 2010; 11 (5): 329-41). Many studies have found that targeted inhibition of PI3KCA can effectively inhibit tumor cell culture in vitro and tumor growth in animals, which is a high quality and ideal target protein molecule. Certain PI3Ks, mTOR or AKT and dual PI3K/mTOR inhibitors have been used in the clinical treatment of cancer, such as Everolimus and PI3KCD inhibitor Idelalisib. During the research and development of a new generation of multi-protein kinase inhibitors, the inventor accidentally discovered that the compound of the present invention could not only effectively inhibit the proliferation of tumor cells with abnormal expression of FGFRs, FLT3-ITD, BCR-ABL, KIT and PDGFR α/β oncogenes in vitro, but also inhibit the growth of cancer cells with PI3KCA gene amplification/high expression or mutation, especially the growth of tumor cells with multiple oncogenes, including drug-resistant cells.

SUMMARY OF THE INVENTION

The object of the present invention is to provide a small molecule compound inhibitor of polyprotein kinase with high specificity, activity and low toxicity.

Firstly, the present invention provides a compound of general formula (I), or a pharmaceutically acceptable salt, solvate, metabolite or prodrug thereof:

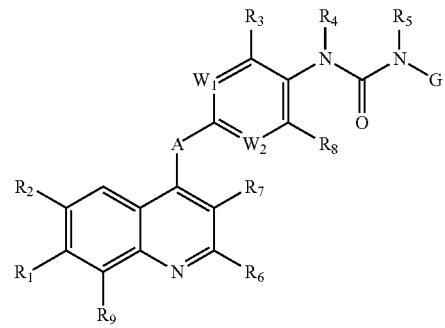

wherein:
A is selected from the group consisting of $NR_4$, S and O;
$W_1$ and $W_2$ are each independently selected from the group consisting of N and $CR_3$;
$R_1$ is selected from the group consisting of H and $OR_{10}$;
$R_{10}$ is selected from the group consisting of hydrogen, alkyl, alkenyl, alkynyl, cycloalkyl, —R''$OR^x$, —R''N($R^y$)($R^z$), —R''S(O)$_n$N($R^y$)($R^z$) and —R''S(O)$_n R^x$; wherein the alkyl, alkenyl, alkynyl and cycloalkyl are each independently and optionally further substituted with one or more groups selected from the group consisting of halogen, cyano, hydroxyl, amino and alkyl;

$R_2$ is selected from the group consisting of Q groups and the following structures:

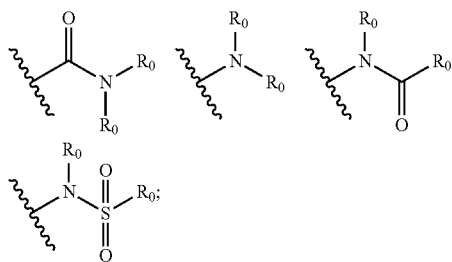

$R_0$ is identical or different and each independently selected from the group consisting of hydrogen, alkyl, cycloalkyl, alkenyl and alkynyl, wherein the alkyl is optionally substituted with one or more alkoxy groups;

$R_3$ and $R_8$ are each independently selected from the group consisting of halogens, —N $(R^y)(R^z)$ and Q groups;

$R_4$ is selected from the group consisting of hydrogen, alkyl, alkoxy and cycloalkyl;

$R_6$ is selected from the group consisting of hydrogen, halogen, alkyl, haloalkyl, alkoxy, —$OR^uOR^x$, —$OR^uN(R^y)(R^z)$ and —$N(R^y)(R^z)$;

$R_7$ is selected from the group consisting of hydrogen, halogen, alkyl and cyano;

$R_9$ is selected from the group consisting of hydrogen, halogen, alkyl and haloalkyl;

$R_5$ is selected from the group consisting of hydrogen, alkyl, alkoxy and cycloalkyl; and G is selected from the group consisting of heteroaryl and heterocyclyl that are not thiazolyl or imidazolyl; wherein the heteroaryl and heterocyclyl are each independently and optionally substituted with one or more groups selected from the group consisting of halogen, alkyl, alkenyl, alkynyl, alkoxy, hydroxyl, amino, acyl, cycloalkyl, heterocyclyl, aryl, heteroaryl and

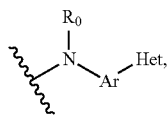

wherein the alkyl, alkenyl, alkynyl, alkoxy, acyl, cycloalkyl, heterocyclyl, aryl and heteroaryl are each independently and optionally substituted with one or more groups selected from the group consisting of halogen, alkyl haloalkyl, alkenyl, alkynyl, aryl, hydroxyl, alkoxy, haloalkoxy, —$N(R^y)$ $(R^z)$, cycloalkyl, heterocyclyl, ester and cyano groups; or $R_5$ and G are taken together with the nitrogen atom to which they are attached to form a heterocyclyl or heteroaryl group, wherein the heterocyclyl and heteroaryl are each independently and optionally substituted with one or more groups selected from the group consisting of halogen, alkyl, alkenyl, alkynyl, alkoxy, hydroxyl, amino, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more groups selected from the group consisting of halogen, alkyl, haloalkyl, alkenyl, alkynyl, aryl, hydroxyl, alkoxy, haloalkoxy, cycloalkyl, ester, and cyano;

Ar is an aryl group optionally substituted with one or more $R_0$;

Het is a heterocyclyl group optionally substituted with one or more $R_0$;

$R^u$ is selected from the group consisting of a bond, alkylene, alkenylene and alkynylene;

$R^x$ is selected from the group consisting of hydrogen, alkyl, cycloalkyl, hydroxyalkyl, haloalkyl, alkenyl and alkynyl; or $R^uOR^x$ together form an oxygen-containing 3-7 membered heterocyclic ring, which is optionally substituted with one or more groups selected from the group consisting of halogen, haloalkyl, alkyl, aryl, alkenyl, and alkynyl;

$R^y$ and $R^z$ are each independently selected from the group consisting of hydrogen, alkyl, alkoxy, aryl, alkenyl, alkynyl, cycloalkyl, haloalkoxy and haloalkyl; or $R^y$ and $R^z$ are taken together with the nitrogen atom to which they are attached to form heterocyclyl or heteroaryl, wherein the heterocyclyl and heteroaryl are each independently and optionally substituted with one or more groups selected from the group consisting of halogen, haloalkyl, alkyl, aryl, acyl, alkenyl and alkynyl, wherein the alkyl is optionally substituted with one or more groups selected from the group consisting of alkoxy and cycloalkyl group;

Q is selected from the group consisting of hydrogen, hydroxyl, alkyl, alkoxy, cycloalkyl, alkenyl, alkynyl, cyano, nitro, aryl, heterocyclyl and heteroaryl; wherein the alkyl, alkoxy, cycloalkyl, alkenyl, alkynyl, aryl, heterocyclyl and heteroaryl are each independently and optionally substituted with one or more groups selected from the group consisting of hydroxyl, halogen and alkyl;

n is 0, 1, or 2.

In a preferred embodiment of the present invention, the compound of general formula (I) or a pharmaceutically acceptable salt, solvate, metabolite or prodrug thereof according to the present invention, wherein $W_1$ and $W_2$ are selected from the group consisting of N and $CR_3$ respectively, and $R_3$ is selected from the group consisting of hydrogen, alkyl and halogen.

In another preferred embodiment of the present invention, the compound of general formula (I) or a pharmaceutically acceptable salt, solvate, metabolite or prodrug thereof according to the present invention,
wherein: A is selected from the group consisting of NH and O.

In another preferred embodiment of the present invention, the compound of general formula (I) or a pharmaceutically acceptable salt, solvate, metabolite or prodrug thereof according to the present invention, wherein $R_2$ is selected from the group consisting of the Q group or the following structure:

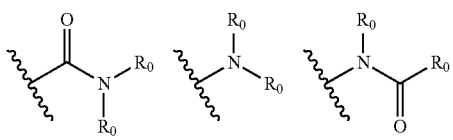

Q is selected from the group consisting of hydrogen, cyano, nitro, $C_1$-$C_6$ alkyl, $C_1$-$C_6$ haloalkyl, $C_1$-$C_6$ alkoxy, $C_1$-$C_6$ haloalkoxy, $C_3$-$C_7$ cycloalkyl, $C_5$-$C_7$ aryl, 5 to 7 membered heterocyclyl and 5 to 7 membered heteroaryl;

$R_2$ is preferably selected from the group consisting of hydrogen, cyano, nitro, $C_1$-$C_6$ alkyl and the following structures:

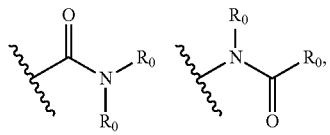

$R_0$ is as defined in general formula (I) above.

In another preferred embodiment of the present invention, the compound of general formula (I) or a pharmaceutically acceptable salt, solvate, metabolite or prodrug thereof according to the present invention, wherein $R_3$ and $R_8$ are independently selected from the group consisting of hydrogen, halogen, alkyl, alkoxy, haloalkoxy, and —N($R^y$)($R^z$); preferably, $R_3$ and $R_8$ are each independently selected from the group consisting of hydrogen, halogen, $C_1$-$C_6$ alkyl, $C_1$-$C_6$ alkoxy, $C_1$-$C_6$ haloalkoxy and —N($R^y$)($R^z$), $R^y$ and $R^z$ are as defined in general formula (I) above.

In another preferred embodiment of the present invention, the compound of general formula (I) or a pharmaceutically acceptable salt, solvate, metabolite or prodrug thereof according to the present invention, wherein $R_4$ is selected from the group consisting of hydrogen, alkyl and alkoxy;

preferably, $R_4$ is selected from the group consisting of hydrogen and alkyl.

In another preferred embodiment of the present invention, the compound of general formula (I) or a pharmaceutically acceptable salt, solvate, metabolite or prodrug thereof according to the present invention, wherein $R_6$ is selected from the group consisting of hydrogen, halogen, alkyl and alkoxy;

preferably, $R_6$ is selected from the group consisting of hydrogen and halogen.

In another preferred embodiment of the present invention, the compound of general formula (I) or a pharmaceutically acceptable salt, solvate, metabolite or prodrug thereof according to the present invention, wherein $R_7$ is selected from the group consisting of hydrogen and cyano;

preferably, $R_7$ is selected from the group consisting of hydrogen.

In another preferred embodiment of the present invention, the compound of general formula (I) or a pharmaceutically acceptable salt, solvate, metabolite or prodrug thereof according to the present invention, wherein $R_1$ is $OR_{10}$, $R_{10}$ is selected from the group consisting of hydrogen, $C_1$-$C_6$ alkyl, —$R''OR^x$ and —$R''N(R^y)(R^z)$, $R''$ is $C_1$-$C_6$ alkylene, $R^x$ is selected from the group consisting of hydrogen, $C_1$-$C_6$ alkyl, $C_1$-$C_6$ hydroxyalkyl and $C_1$-$C_6$ haloalkyl, $R^y$ and $R^z$ are taken together with the nitrogen atom to which they are attached to form 5 to 7 membered heterocyclyl or heteroaryl group, preferably morpholinyl, piperidinyl, piperazinyl, azacycloheptanyl, pyridinyl or pyrimidinyl; wherein the 5 to 7 membered heterocyclyl and heteroaryl are each optionally substituted with one or more groups selected from the group consisting of halogen, acyl, $C_1$-$C_6$ alkyl, $C_1$-$C_6$ haloalkyl and $C_6$-$C_{10}$ aryl, wherein the $C_1$-$C_6$ alkyl is optionally substituted with one or more groups selected from the group consisting of $C_1$-$C_6$ alkoxyl and $C_3$-$C_7$ cycloalkyl.

In another preferred embodiment of the present invention, the compound of general formula (I) or a pharmaceutically acceptable salt, solvate, metabolite or prodrug thereof according to the present invention, wherein:

$R_5$ is selected from the group consisting of hydrogen and alkyl; and G is selected from the group consisting of 5 to 7 membered heteroaryl and 5 to 7 membered heterocyclyl group that are not thiazolyl and imidazolyl, preferably

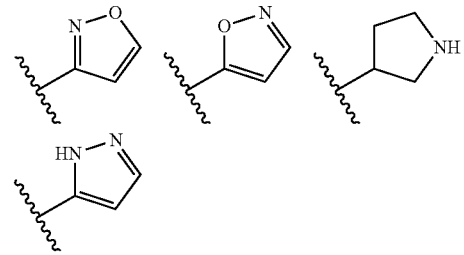

the 5 to 7 membered heteroaryl group and 5 to 7 membered heterocyclyl group are each independently and optionally substituted with one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxyl, amino, acyl, $C_3$-$C_7$ cycloalkyl, 5 to 7 membered heterocyclyl, $C_5$-$C_7$ aryl and 5 to 7 membered heteroaryl groups, wherein the acyl, $C_1$-$C_6$ alkyl, $C_1$-$C_6$ alkoxy, $C_3$-$C_7$ cycloalkyl, 5 to 7 membered heterocyclyl, $C_5$-$C_7$ aryl and 5 to 7 membered heteroaryl are each independently and optionally substituted with one or more groups selected from the group consisting of halogen, $C_2$-$C_6$ alkenyl, hydroxyl, $C_1$-$C_6$ alkyl, $C_1$-$C_6$ alkoxy, $C_1$-$C_6$ haloalkyl, —N($R^y$)($R^z$), $C_1$-$C_6$ haloalkoxy, 5 to 7 membered heterocyclyl, esters and cyano; or, $R_5$ and G are taken together with the nitrogen atom to which they are attached to form 5 to 7 membered heterocyclyl or 5 to 7 membered heteroaryl groups, preferably pyrrolyl, pyrazolyl, or imidazolyl, wherein the 5 to 7 membered heterocyclyl or 5 to 7 membered heteroaryl are each independently or optionally substituted with one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxyl, amino, $C_3$-$C_7$ cycloalkyl, 5 to 7 membered heterocyclyl, $C_5$-$C_7$ aryl and 5 to 7 membered heteroaryl;

$R^y$ and $R^z$ are each independently selected from the group consisting of hydrogen, $C_1$-$C_6$ alkyl, and $C_1$-$C_6$ haloalkyl group; or $R^y$ and $R^z$ are taken together with the nitrogen atom to which they are attached to form 5 to 7 membered heterocyclyl or 5 to 7 membered heteroaryl groups, wherein the 5 to 7 membered heterocyclyl or 5 to 7 membered heteroaryl are each independently and optionally substituted with one or more groups selected from the group consisting of halogen, $C_1$-$C_6$ haloalkyl and $C_1$-$C_6$ alkyl.

In another preferred embodiment of the present invention, the compound of general formula (I) or a pharmaceutically acceptable salt, solvate, metabolite or prodrug thereof according to the present invention, wherein:

$R_5$ is selected from the group consisting of hydrogen and alkyl; and G is selected from the group consisting of the following pyrazolyl and isoxazolyl:

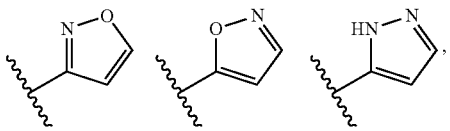 [SMILES: *c1ccon1 ; *c1ccno1 ; *c1ccn[nH]1]

wherein the pyrazolyl and isoxazolyl are each independently and optionally substituted with one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxyl, amino, acyl, $C_3$-$C_7$ cycloalkyl, 5 to 7 membered heterocyclyl, $C_5$-$C_7$ aryl and 5 to 7 membered heteroaryl; wherein the acyl, $C_1$-$C_6$ alkyl, $C_1$-$C_6$ alkoxy, $C_3$-$C_7$ cycloalkyl, 5 to 7 membered heterocyclyl, $C_5$-$C_7$ aryl and 5 to 7 membered heteroaryl are each independently and optionally substituted with one or more groups selected from the group consisting of halogen, $C_2$-$C_6$ alkenyl, hydroxyl, $C_1$-$C_6$ alkyl, $C_1$-$C_6$ alkoxy, $C_1$-$C_6$ haloalkyl, —N($R^y$)($R^z$), $C_1$-$C_6$ haloalkoxy, 5-7 membered heterocyclyl, ester and cyano; or $R_5$ and G are taken together with the nitrogen atom to which they are attached to form 5 to 7 membered heterocyclyl or 5 to 7 membered heteroaryl, preferably pyrrolyl, pyrazolyl or imidazolyl, wherein the 5 to 7 membered heterocyclyl or 5 to 7 membered heteroaryl are each independently and optionally substituted with one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxyl, amino, $C_3$-$C_7$ cycloalkyl, 5 to 7 membered heterocyclyl, $C_5$-$C_7$ aryl and 5 to 7 membered heteroaryl;

$R^y$ and $R^z$ are each independently selected from the group consisting of hydrogen, $C_1$-$C_6$ alkyl and $C_1$-$C_6$ haloalkyl; or $R^y$ and $R^z$ are taken together with the nitrogen atom to which they are attached to form 5 to 7 membered heterocyclyl or 5 to 7 membered heteroaryl; wherein the 5 to 7 membered heterocyclyl or 5 to 7 membered heteroaryl are each independently or optionally substituted with one or more groups selected from the group consisting of halogen, $C_1$-$C_6$ haloalkyl and $C_1$-$C_6$ alkyl.

Typical compounds of general formula (I) of the present invention include but are not limited to:

4-{4-[3-(5-tert-butyl-isoxazol-3-yl)-ureido]-phenoxy}-7-methoxyquinolin-6-carboxamide;
4-{4-[3-(5-tert-butyl-isoxazol-3-yl)-ureido]-3-chloro-phenoxy}-7-methoxyquinolin-6-carboxamide;
4-{3-bromo-4-[3-(5-tert-butyl-isoxazol-3-yl)-ureido]-phenoxy}-7-methoxyquinolin-6-carboxamide;
4-{4-[3-(5-tert-butyl-2H-pyrazol-3-yl)-ureido]-3-trifluoromethyl-phenoxy}-7-methoxyquinolin-6-carboxamide;
4-{4-[3-(5-tert-butyl-isoxazol-3-yl)-ureido]-3-methoxy-phenoxy}-7-methoxyquinolin-6-carboxamide;
4-{4-[3-(5-tert-butyl-isoxazol-3-yl)-ureido]-3-methyl-phenoxy}-7-methoxyquinolin-6-carboxamide;
4-{2-bromo-4-[3-(5-tert-butyl-isoxazol-3-yl)-ureido]-phenoxy}-7-methoxyquinolin-6-carboxamide;
4-{4-[3-(5-tert-butyl-isoxazol-3-yl)-ureido]-2-chloro-phenoxy}-7-methoxyquinolin-6-carboxamide;
4-{4-[3-(5-tert-butyl-isoxazol-3-yl)-ureido]-2-fluoro-phenoxy}-7-methoxyquinolin-6-carboxamide;
4-[4-[3-(5-tert-butyl-isoxazol-3-yl)-ureido]-3-(4-methyl-piperazin-1-yl)-phenoxy]-7-methoxyquinolin-6-carboxamide;
4-{4-[3-(5-tert-butyl-isoxazol-3-yl)-1-methyl-ureido]-phenoxy}-7-methoxyquinolin-6-carboxamide;
4-{4-[3-(5-tert-butyl-isoxazol-3-yl)-3-methyl-ureido]-3-chloro-phenoxy}-7-methoxyquinolin-6-carboxamide;
4-{4-[3-(3-tert-butyl-isoxazol-5-yl)-ureido]-3-chloro-phenoxy}-7-methoxyquinolin-6-carboxamide;
4-{4-[3-(5-tert-butyl-isoxazol-3-yl)-ureido]-3-chloro-phenoxy}-7-methoxyquinolin-6-carboxylic acid methylamide;
4-{4-[3-(3-tert-butyl-isoxazol-5-yl)-ureido]-3-chloro-phenoxy}-7-methoxyquinolin-6-carboxylic acid methylamide;
4-{4-[3-(5-tert-butyl-isoxazol-3-yl)-ureido]-3-chloro-phenoxy}-7-methoxyquinolin-6-carboxylic acid diethylamide;
4-{4-[3-(5-tert-butyl-isoxazol-3-yl)-ureido]-3-chloro-phenoxy}-7-methoxyquinolin-6-carboxylic acid (2-methoxyethyl)amide;
1-(5-tert-butyl-isoxazol-3-yl)-3-[2-chloro-4-(7-methoxy-6-nitro-quinolin-4-yloxy)-phenyl]-urea;
1-(5-tert-butyl-isoxazol-3-yl)-3-[2-chloro-4-(6-cyano-7-methoxy-quinolin-4-yloxy)-phenyl]-urea;
N-(4-{4-[3-(5-tert-butyl-isoxazol-3-yl)-ureido]-3-chloro-phenoxy}-7-methoxyquinolin-6-yl)-acetamide;
N-(4-{4-[3-(5-tert-butyl-isoxazol-3-yl)-ureido]-3-chloro-phenoxy}-7-methoxyquinolin-6-yl)-propionamide;
N-(4-{4-[3-(5-tert-butyl-isoxazol-3-yl)-ureido]-3-chloro-phenoxy}-7-methoxyquinolin-6-yl)-acrylamide;
Cyclopentane carboxylic acid (4-{4-[3-(5-tert-butyl-isoxazol-3-yl)-ureido]-3-chloro-phenoxy}-7-methoxyquinolino-6-yl)-amide;
4-{5-[3-(5-tert-butyl-isoxazol-3-yl)-ureido]-pyridin-2-yloxy}-7-methoxyquinolin-6-carb oxamide;
4-{4-[3-(5-tert-butyl-2H-pyrazol-3-yl)-ureido]-3-chloro-phenoxy}-7-methoxyquinolin-6-carboxamide;
4-{4-[3-(5-tert-butyl-2-methyl-2H-pyrazol-3-yl)-ureido]-3-chloro-phenoxy}-7-methoxy quinolin-6-carboxamide;
4-{4-[3-(5-tert-butyl-2-ethyl-2H-pyrazol-3-yl)-ureido]-3-chloro-phenoxy}-7-methoxyquinolin-6-carboxamide;
4-{4-[3-(2-acryloyl-5-tert-butyl-2H-pyrazol-3-yl)-ureido]-3-chloro-phenoxy}-7-methoxyquinolin-6-carboxamide;
4-{4-[3-(5-tert-butyl-2-propanoyl-2H-pyrazol-3-yl)-ureido]-3-chloro-phenoxy}-7-methoxyquinolin-6-carboxamide;
4-{4-[3-(5-tert-butyl-2-cyclopentyl-2H-pyrazol-3-yl)-ureido]-3-chloro-phenoxy}-7-methoxyquinolin-6-carboxamide;
4-(4-{3-[5-tert-butyl-2-(2-morpholin-4-yl-ethyl)-2H-pyrazol-3-yl]-ureido}-3-chloro-phenoxy)-7-methoxyquinolin-6-carboxamide;
4-(4-{3-[5-tert-butyl-2-(2-hydroxy-ethyl)-2H-pyrazol-3-yl]-ureido}-3-chloro-phenoxy)-7-methoxyquinolin-6-carboxamide;
4-{4-[3-(5-tert-butyl-2H-pyrazol-3-yl)-ureido]-3-trifluoromethyl-phenoxy}-7-methoxyquinolin-6-carboxamide;
4-{4-[3-(5-tert-butyl-2H-pyrazol-3-yl)-ureido]-3-methyl-phenoxy}-7-methoxyquinolin-6-carboxamide;
4-{4-[3-(5-tert-butyl-2H-pyrazol-3-yl)-ureido]-2-methyl-phenoxy}-7-methoxyquinolin-6-carboxamide;
4-{4-[3-(5-tert-butyl-2H-pyrazol-3-yl)-ureido]-2-chloro-phenoxy}-7-methoxyquinolin-6-carboxamide;
4-{4-[3-(5-tert-butyl-2H-pyrazol-3-yl)-ureido]-2,3-dichloro-phenoxy}-7-methoxyquinol in-6-carboxamide;
4-{4-[3-(5-tert-butyl-2-methyl-2H-pyrazol-3-yl)-ureido]-2,3-dichloro-phenoxy}-7-methoxyquinolin-6-carboxamide;
4-{4-[3-(5-tert-butyl-2-methyl-2H-pyrazol-3-yl)-ureido]-3-chloro-phenoxy}-2-chloro-7-methoxyquinolin-6-carboxamide;
4-{3-chloro-4-[3-(5-isopropyl-2H-pyrazol-3-yl)-ureido]-phenoxy}-7-methoxyquinolin-6-carboxamide;

4-{3-chloro-4-[3-(5-cyclopropyl-2H-pyrazol-3-yl)-ureido]-phenoxy}-7-methoxyquinolin-6-carboxamide;

4-{4-[3-(5-tert-butyl-2H-pyrazol-3-yl)-ureido]-3-chloro-phenoxy}-7-(2-methoxy-ethoxy)-quinolin-6-carboxamide;

4-{4-[3-(5-tert-butyl-2H-pyrazol-3-yl)-ureido]-3-chloro-phenoxy}-7-isopropoxy-quinolin-6-carboxamide;

4-{4-[3-(5-tert-butyl-2-methyl-2H-pyrazol-3-yl)-ureido]-3-chloro-phenoxy}-7-(2-methoxy-ethoxy)-quinolin-6-carboxamide;

4-{4-[3-(5-tert-butyl-2H-pyrazol-3-yl)-ureido]-3-chloro-phenoxy}-7-methoxyquinolin-6-carboxylic acid carboxamide;

4-{4-[3-(5-tert-butyl-2-methyl-2H-pyrazol-3-yl)-ureido]-3-chloro-phenoxy}-7-methoxy quinolin-6-carboxylic acid carboxamide;

4-{4-[3-(5-tert-butyl-2H-pyrazol-3-yl)-ureido]-3-chloro-phenoxy}-7-methoxy quinolin-6-carboxylic acid carboxamide;

4-{4-[3-(5-tert-butyl-2-cyclopentyl-2H-pyrazol-3-yl)-ureido]-3-chloro-phenoxy}-7-methoxyquinolin-6-carboxylic acid carboxamide;

4-{4-[3-(5-tert-butyl-2H-pyrazol-3-yl)-ureido]-3-methyl-phenoxy}-7-methoxyquinolin-6-carboxylate acid carboxamide;

4-{4-[3-(5-tert-butyl-2-methyl-2H-pyrazol-3-yl)-ureido]-3-methyl-phenoxy}-7-methoxyquinolin-6-carboxylic acid carboxamide;

4-{4-[3-(5-tert-butyl-2H-pyrazol-3-yl)-ureido]-3-trifluoromethyl-phenoxy}-7-methoxyquinolin-6-carboxylic acid carboxamide;

4-{4-[3-(5-tert-butyl-2H-pyrazol-3-yl)-ureido]-2-methyl-phenoxy}-7-methoxyquinolin-6-carboxylate acid carboxamide;

4-{4-[3-(5-tert-butyl-2-methyl-2H-pyrazol-3-yl)-ureido]-2-methyl-phenoxy}-7-methoxy quinolin-6-carboxylic acid carboxamide;

4-{4-[3-(5-tert-butyl-2H-pyrazol-3-yl)-ureido]-2-chloro-phenoxy}-7-methoxyquinolin-6-carboxylic acid carboxamide;

4-{4-[3-(5-tert-butyl-2-methyl-2H-pyrazol-3-yl)-ureido]-2-chloro-phenoxy}-7-methoxy quinolin-6-carboxylic acid carboxamide;

4-{4-[3-(5-tert-butyl-2H-pyrazol-3-yl)-ureido]-2,3-dichloro-phenoxy}-7-methoxyquinolin-6-carboxylic acid carboxamide;

4-{4-[3-(5-tert-butyl-2-methyl-2H-pyrazol-3-yl)-ureido]-2,3-dichloro-phenoxy}-7-methoxy quinolin-6-carboxylic acid carboxamide;

4-{4-[3-(5-tert-butyl-2H-pyrazol-3-yl)-ureido]-3-chloro-phenoxy}-7-(2-methoxy-ethoxy)-quinolin-6-carboxylic acid carboxamide;

4-{4-[3-(5-tert-butyl-2-methyl-2H-pyrazol-3-yl)-ureido]-3-chloro-phenoxy}-7-(2-methoxy-ethoxy)-quinolin-6-carboxylic acid carboxamide;

4-{4-[3-(5-tert-butyl-2-methyl-2H-pyrazol-3-yl)-ureido]-2,3-dichloro-phenoxy}-7-(2-methoxy-ethoxy)-quinolin-6-carboxylic acid carboxamide;

4-{4-[3-(5-tert-butyl-2H-pyrazol-3-yl)-ureido]-3-chloro-phenoxy}-7-methoxyquinolin-6-carboxylic acid diethylamide;

4-{4-[3-(5-tert-butyl-2H-pyrazol-3-yl)-ureido]-3-chloro-phenoxy}-7-methoxyquinolin-6-carboxylic acid (2-methoxy-ethyl)-amide;

N-(4-{4-[3-(5-tert-butyl-2H-pyrazol-3-yl)-ureido]-3-chloro-phenoxy}-7-methoxyquinolin-6-yl)-acetamide;

N-(4-{4-[3-(5-tert-butyl-2H-pyrazol-3-yl)-ureido]-3-chloro-phenoxy}-7-methoxyquinolin-6-yl)-propionamide;

Cyclopentane carboxylic acid (4-{4-[3-(5-tert-butyl-2H-pyrazol-3-yl)-ureido]-3-chloro-phenoxy}-7-methoxyquinolin-6-yl)-amide;

N-[4-{4-[3-(5-tert-butyl-2H-pyrazol-3-yl)-ureido]-3-chloro-phenoxy}-7-(2-methoxy-ethoxy)-quinolin-6-yl]-acetamide;

1-(5-tert-butyl-2H-pyrazol-3-yl)-3-[2-chloro-4-(6-cyano-7-methoxy-quinolin-4-yloxy)-phenyl]-urea;

N-(4-{4-[3-(5-tert-butyl-2H-pyrazol-3-yl)-ureido]-3-chloro-phenoxy}-3-cyano-7-ethoxy quinolin-6-yl)acetamide;

4-{3-chloro-4-[3-(1-propionyl-pyrrolidin-3-yl)-ureido]-phenoxy}-7-methoxyquinolin-6-carboxamide;

4-{4-[3-(1-acryloylpyrrolidin-3-yl)-ureido]-3-chloro-phenoxy}-7-methoxyquinolin-6-carboxamide;

4-[2,3-Dichloro-4-(3-{6-[4-(4-ethyl-piperazin-1-yl)-phenylamino]-pyrimidin-4-yl}-ureido)-phenoxy]-6-methoxy-quinolin-6-carboxamide;

4-{4-[(5-amino-3-tert-butyl-pyrazol-1-carbonyl)-amino]-3-chloro-phenoxy}-7-methoxy quinolin-6-carboxylic acid methylamide;

4-{4-[(5-amino-3-tert-butyl-pyrazol-1-carbonyl)-amino]-3-methoxy-phenoxy}-7-methoxyquinolin-6-carboxamide;

4-{3-chloro-4-[(4,7-dihydro-5H-thieno[2,3-c]pyridin-6-carbonylamino]-phenoxy}-7-methoxyquinolin-6-carboxamide;

4-{2,3-dichloro-4-[(4-methyl-piperazin-1-carbonyl)-amino]-phenoxy}-7-(2-methoxy-ethoxy)-quinolin-carboxylic acid methylamide;

4-{2,3-dichloro-4-[(pyrrolidin-1-carbonyl)-amino]-phenoxy}-7-(2-methoxy-ethoxy)-quinolin-6-carboxylic acid methylamide;

4-{4-[3-(5-tert-butyl-isoxazol-3-yl)-ureido]-3-chlorophenylamino}-7-methoxyquinolin-6-carboxamide;

4-{4-[3-(5-tert-butyl-isoxazol-3-yl)-ureido]-phenylamino}-7-methoxyquinolin-6-carboxamide;

4-{4-[3-(5-tert-butyl-2H-pyrazol-3-yl)-ureido]-3-chloro-phenylamino}-7-methoxyquinolin-6-carboxamide;

4-{4-[3-(5-tert-butyl-2H-pyrazol-3-yl)-ureido]-3-chloro-phenoxy}-7-hydroxy-quinolin-6-carboxamide;

4-{4-[3-(5-tert-butyl-2H-pyrazol-3-yl)-ureido]-3-chloro-phenoxy}-7-(2-morpholin-4-yl-ethoxy) pyridine-6-carboxamide;

4-{4-[3-(5-tert-butyl-2H-pyrazol-3-yl)-ureido]-3-chloro-phenoxy}-7-[3-(4-methyl-piperazin-1-yl)-propoxy]-quinolin-6-carboxamide;

4-{4-[3-(5-tert-butyl-2H-pyrazol-3-yl)-ureido]-3-chloro-phenoxy}-7-(2-dimethylamino-ethoxy)-quinolin-6-carboxamide;

4-{4-[3-(5-tert-butyl-2H-pyrazol-3-yl)-ureido]-3-chloro-phenoxy}-7-(2-piperidin-1-yl-ethoxy)-quinolin-pyridin-6-carboxamide;

4-{4-[3-(5-tert-butyl-2H-pyrazol-3-yl)-ureido]-3-chloro-phenoxy}-7-{3-[4-(2-methoxy-ethyl) piperazin-1-yl]-propoxy}-quinolin-6-carboxamide;

4-{4-[3-(5-tert-butyl-2H-pyrazol-3-yl)-ureido]-3-chloro-phenoxy}-7-[3-(4-phenyl-piperazin-1-yl)-propoxy]-quinolin-6-carboxamide;

7-[3-(4-tert-butyl-piperazin-1-yl)-propoxy]-4-{4-[3-(5-tert-butyl-2H-pyrazol-3-yl)-ureido]-3-chlorophenoxy}-quinolin-6-carboxamide;

4-{4-[3-(5-tert-butyl-2H-pyrazol-3-yl)-ureido]-3-chloro-phenoxy}-7-[3-(4-methyl-[1,4]-1-yl)-propoxy]-quinolin-6-carboxamide;

4-{4-[3-(5-tert-butyl-2H-pyrazol-3-yl)-ureido]-3-chloro-phenoxy}-7-[3-(4-isobutyl-piperazin-1-yl)-propoxy]-quinolin-6-carboxamide;

4-{4-[3-(5-tert-butyl-2H-pyrazol-3-yl)-ureido]-3-chloro-phenoxy}-7-[3-(4-cyclohexylmethyl)-piperazin-1-yl)-propoxy]-quinolin-6-carboxamide;

7-[3-(4-acetyl-piperazin-1-yl)-propoxy]-4-{4-[3-(5-tert-butyl-2H-pyrazol-3-yl)-ureido]-3-chloro-phenoxy}-quinolin-6-carboxamide;

4-{4-[3-(5-tert-butyl-2H-pyrazol-3-yl)-ureido]-2,3-dichloro-phenoxy}-7-hydroxy-quinolin-6-carboxamide;

4-{4-[3-(5-tert-butyl-2H-pyrazol-3-yl)-ureido]-2,3-dichloro-phenoxy}-7-(2-dimethylamino)-ethoxy)carboxamide;

4-{4-[3-(5-tert-butyl-2H-pyrazol-3-yl)-ureido]-2,3-dichloro-phenoxy}-7-(2-morpholin-4-yl-ethoxy)-quinolin-6-carboxamide;

4-{4-[3-(5-tert-butyl-2H-pyrazol-3-yl)-ureido]-2,3-dichloro-phenoxy}-7-[3-(4-methyl-pyridin-3-yl)-propoxy]-quinolin-6-carboxamide;

4-{4-[3-(5-tert-butyl-2H-pyrazol-3-yl)-ureido]-2,3-dichloro-phenoxy}-7-(2-piperidin-1-yl-ethoxy)-quinolin-6-carboxamide;

4-{4-[3-(5-tert-butyl-2H-pyrazol-3-yl)-ureido]-2-chloro-phenylamino}-7-methoxy-quinolin-6-carboxamide;

4-{4-[3-(5-tert-butyl-2H-pyrazol-3-yl)-ureido]-2-methyl-phenylamino}-7-methoxy-quinolin-6-carboxamide;

4-{4-[3-(5-tert-butyl-isoxazol-3-yl)-ureido]-2-methyl-phenylamino}-7-methoxy-quinolin-6-carboxamide;

4-{4-[3-(5-tert-butyl-isoxazol-3-yl)-ureido]-2-chloro-phenylamino}-7-methoxy-quinolin-6-carboxamide;

N-(4-{4-[3-(5-tert-butyl-2H-pyrazol-3-yl)-ureido]-2-chloro-phenoxy}-7-methoxy-quinolin-6-yl)-acetamide;

N-(4-{4-[3-(5-tert-butyl-2H-pyrazol-3-yl)-ureido]-2-fluoro-phenoxy}-7-methoxy-quinolin-6-yl)-acetamide;

N-(4-{4-[3-(5-tert-butyl-2H-pyrazol-3-yl)-ureido]-2-methyl-phenoxy}-7-methoxy-quinolin-6-yl)-acetamide;

N-(4-{5-[3-(5-tert-butyl-2H-pyrazol-3-yl)-ureido]-pyridin-2-yloxy}-7-methoxy-quinolin-6-yl)-acetamide;

N-(4-{4-[3-(5-tert-butyl-2H-pyrazol-3-yl)-ureido]-2-chloro-phenoxy}-7-methoxy-quinolin-6-yl)-acrylamide;

4-{4-[3-(5-tert-butyl-2H-pyrazol-3-yl)-ureido]-2-ethyl-phenoxy}-7-methoxy-quinolin-6-carboxamide;

4-{4-[3-(5-tert-butyl-2H-pyrazol-3-yl)-ureido]-2-isopropyl-phenoxy}-7-methoxy-quinolin-6-carboxamide;

4-{5-[3-(5-tert-butyl-2H-pyrazol-3-yl)-ureido]-pyridin-2-yloxy}-7-methoxy-quinolin-6-carboxamide;

4-{4-[3-(5-tert-butyl-2H-pyrazol-3-yl)-ureido]-2,3-dimethyl-4-phenoxy}-7-methoxy-quinolin-6-carboxamide;

4-{4-[3-(5-tert-butyl-2-methyl-2H-pyrazol-3-yl)-ureido]-2,3-dimethyl-phenoxy}-7-methoxy-quinolin-6-carboxamide;

4-{4-[3-(5-tert-butyl-2-methyl-2H-pyrazol-3-yl)-ureido]-3-chloro-2-methyl-phenoxy}-7-methoxy-carboxamide;

4-{4-[3-(5-tert-butyl-2-methyl-2H-pyrazol-3-yl)-ureido]-3-chloro-2-methyl-phenoxy}-7-methoxy-quinolin-6-carboxamide;

1-(5-tert-butyl-isoxazol-3-yl)-3-[2-chloro-4-(8-fluoro-quinolin-4-yloxy)-phenyl]-urea;

1-(5-tert-butyl-isoxazol-3-yl)-3-[2-chloro-4-(8-trifluoromethyl-quinolin-4-yloxy)-phenyl]-urea;

1-(5-tert-butyl-isoxazol-3-yl)-3-[2-chloro-4-(2-trifluoromethyl-quinolin-4-yloxy)-phenyl]-urea;

N-[4-{4-[3-(5-tert-butyl-2H-pyrazol-3-yl)-ureido]-phenoxy}-7-(2-methoxy-ethoxy)-quinolin-6-yl]-acetamide;

N-{4-{4-[3-(5-tert-butyl-2-methyl-2H-pyrazol-3-yl)-ureido]-phenoxy}-7-(2-methoxy-ethoxy)-quinolin-6-yl]-acetamide;

N-[4-{4-[3-(5-tert-butyl-2-cyclopropylmethyl-2H-pyrazol-3-yl)-ureido]-phenoxy}-7-(2-methoxy-ethoxy)-quinolin-6-yl]-acetamide;

N-[4-(4-{3-[5-tert-butyl-2-(2-dimethylamino-ethyl)-2H-pyrazol-3-yl]-ureido}-phenoxy)-7-(2-methoxyethoxy)-quinolin-6-yl]-acetamide;

N-[4-{4-[3-(5-tert-butyl-2-piperidin-4-yl-2H-pyrazol-3-yl)-ureido]-phenoxy}-7-(2-methoxy-ethoxy)-quinolin-6-yl]-acetamide;

N-[4-(4-{3-[5-tert-butyl-2-(1-methyl-piperidin-4-yl)-2H-pyrazol-3-yl]-ureido}-phenoxy (7-(2-methoxy-ethoxy)-quinolin-6-yl]-acetamide;

N-[4-(4-{3-[5-tert-butyl-2-(2-morpholin-4-yl-ethyl)-2H-pyrazol-3-yl]-ureido}-phenoxy (7-(2-methoxy-ethoxy)-quinolin-6-yl]-acetamide;

N-[4-(4-{3-[5-tert-butyl-2-(2-morpholin-4-yl-ethyl)-2H-pyrazol-3-yl]-ureido}-3-chloro-phenoxy)-7-(2-methoxy-ethoxy)-quinolin-6-yl]-acetamide;

N-[4-{4-[3-(5-tert-butyl-2-methyl-2H-pyrazol-3-yl)-ureido]-3-chloro-phenoxy}-7-(2-methoxy-ethoxy)-quinolin-6-yl]-acetamide;

N-[4-{4-[3-(5-tert-butyl-2-cyclopropylmethyl-2H-pyrazol-3-yl)-ureido]-3-chloro-phenoxy}-7-(2-methoxy-ethoxy)-quinolin-6-yl]-acetamide;

N-[4-(4-{3-[5-tert-butyl-2-(1-methyl-piperidin-4-yl)-2H-pyrazol-3-yl]-ureido}-3-chloro-phenoxy)-7-(2-methoxy-ethoxy)-quinolin-6-yl]-acetamide;

N-[4-(4-{3-[5-tert-butyl-2-(2-dimethylamino-ethyl)-2H-pyrazol-3-yl]-ureido}-3-chloro-phenoxy)-7-(2-methoxy-ethoxy)-quinolin-6-yl]-acetamide;

N-[4-{4-[3-(5-tert-butyl-2H-pyrazol-3-yl)-ureido]-3-fluoro-phenoxy}-7-(2-methoxy-ethoxy)-quinolin-6-yl]-acetamide;

N-[4-{4-[3-(5-tert-butyl-2H-pyrazol-3-yl)-ureido]-3-chloro-phenoxy}-7-(3-methoxy-propoxy)-quinolin-6-yl]-acetamide;

N-{4-{4-[3-(5-tert-butyl-2H-pyrazol-3-yl)-ureido]-3-chloro-phenoxy}-7-[3-(4-methyl-piperazin-1-yl)-propoxy]-quinolin-6-yl}-acetamide;

N-[4-{4-[3-(5-tert-butyl-2H-pyrazol-3-yl)-ureido]-3-chloro-phenoxy}-7-(2-hydroxy-ethoxy)-quinolin-6-yl]-acetamide;

N-[4-{4-[3-(5-tert-butyl-2H-pyrazol-3-yl)-ureido]-3-chloro-phenoxy}-7-(2-morpholin-4-yl-ethoxy)-quinolin-6-yl]-acetamide;

N-[4-{4-[3-(5-tert-butyl-2H-pyrazol-3-yl)-ureido]-3-methyl-phenoxy}-7-(2-methoxy-ethoxy)-quinolin-6-yl]-acetamide;

N-[4-{4-[3-(5-tert-butyl-2-cyclopropylmethyl-2H-pyrazol-3-yl)-ureido]-2-fluoro-phenoxy}-7-(2-methoxy-ethoxy)-quinolin-6-yl]-acetamide;

N-[4-{4-[3-(5-tert-butyl-2-methyl-2H-pyrazol-3-yl)-ureido]-2-chloro-phenoxy}-7-(2-methoxy-ethoxy)-quinolin-6-yl]-acetamide;

N-[4-(4-{3-[5-tert-butyl-2-(2-morpholin-4-yl-ethyl)-2H-pyrazol-3-yl]-ureido}-2-fluoro-phenoxy)-7-(2-methoxy-ethoxy)-quinolin-6-yl]-acetamide;

N-[4-(4-{3-[5-tert-butyl-2-(2-morpholin-4-yl-ethyl)-2H-pyrazol-3-yl]-ureido}-2-chloro-phenoxy)-7-(2-methoxy-ethoxy)-quinolin-6-yl]-acetamide;

4-{4-[3-(5-tert-butyl-2H-pyrazol-3-yl)-ureido]-3-chloro-phenoxy}-7-(3-morpholin-4-yl-propoxy)-quinoline 6-carboxamide;

4-{4-[3-(5-tert-butyl-2-cyclopentyl-2H-pyrazol-3-yl)-ureido]-3-chloro-phenoxy}-7-[3-(4-methyl-piperazinyl-piperidin-1-yl)-propoxy]-quinolin-6-carboxamide;

4-{4-[3-(5-tert-butyl-2-cyclopentyl-2H-pyrazol-3-yl)-ureido]-3-chloro-phenoxy}-7-(3-morpholin-4-yl-propoxy)-quinolin-6-carboxamide;
or a pharmaceutically acceptable salt, solvate, metabolite or prodrug thereof.

Another aspect of the present invention is to provide a deuterated compound of general formula (I) or a pharmaceutically acceptable salt, solvate, metabolite or prodrug thereof according to the present invention, wherein one or more H atoms in the compound of general formula (I) is independently replaced by D atom for increasing in vivo metabolic stability, wherein the compound includes but is not limited to:

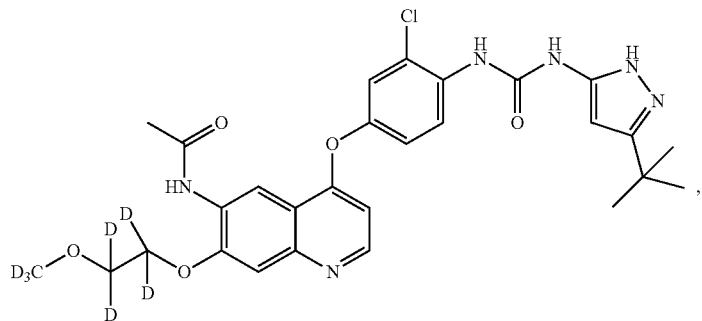

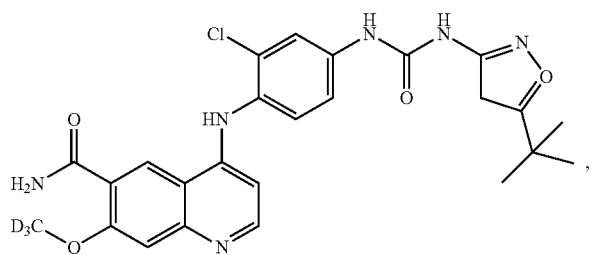

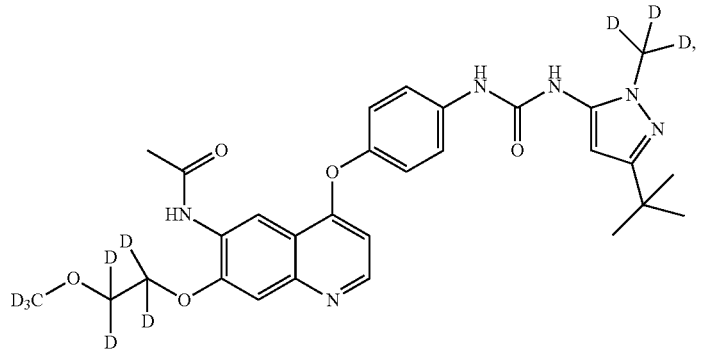

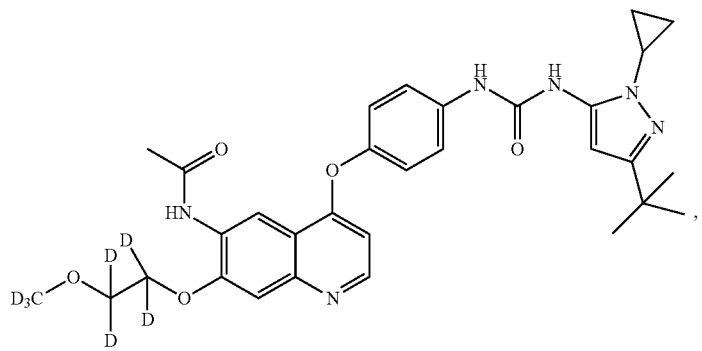

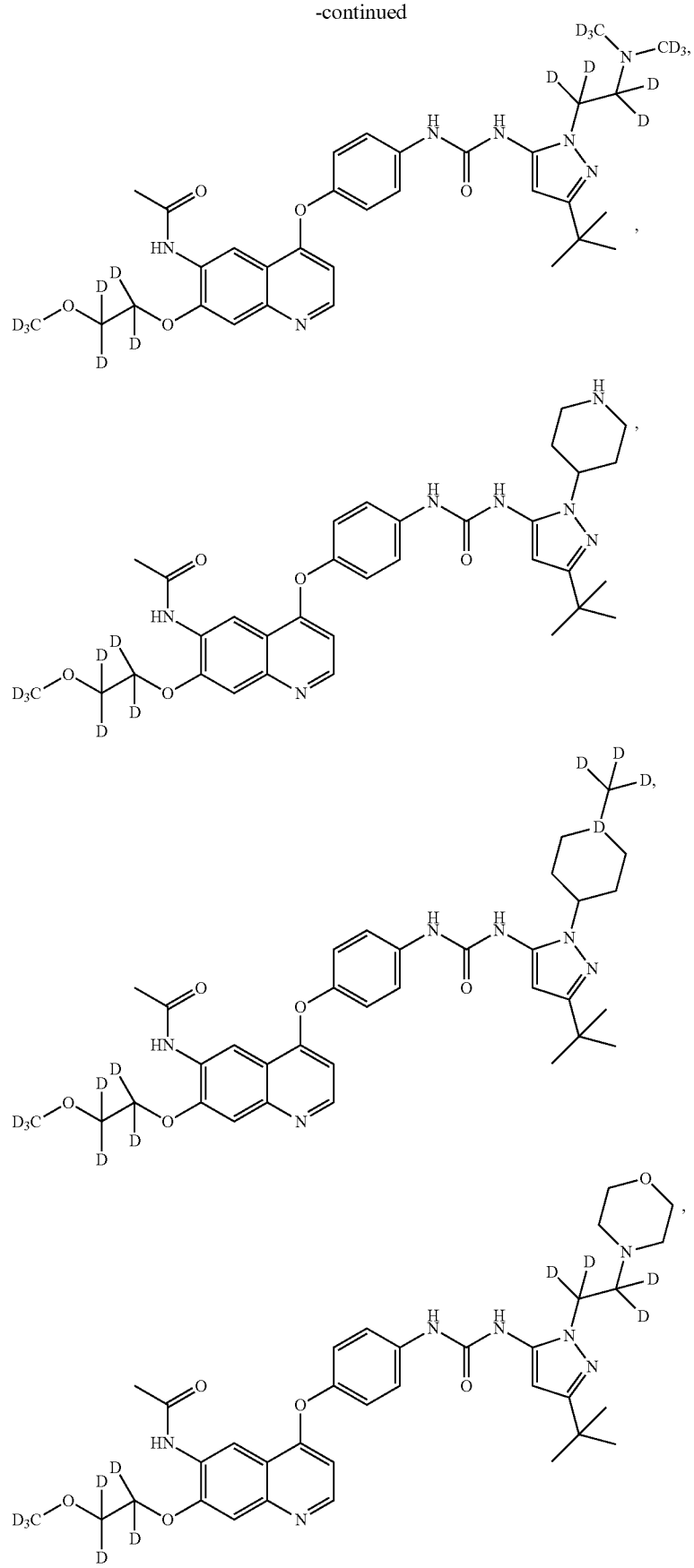

-continued
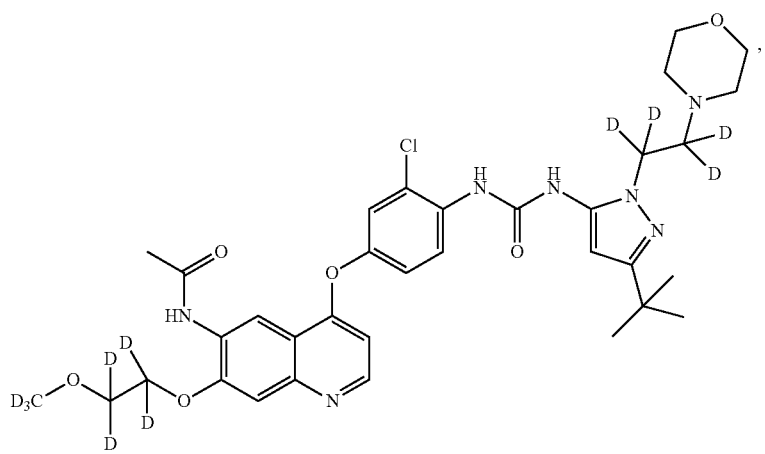
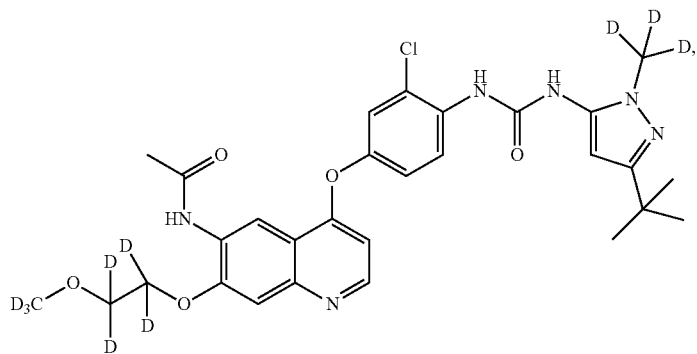
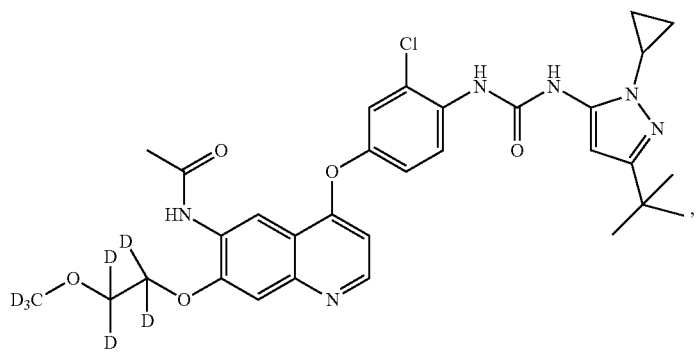
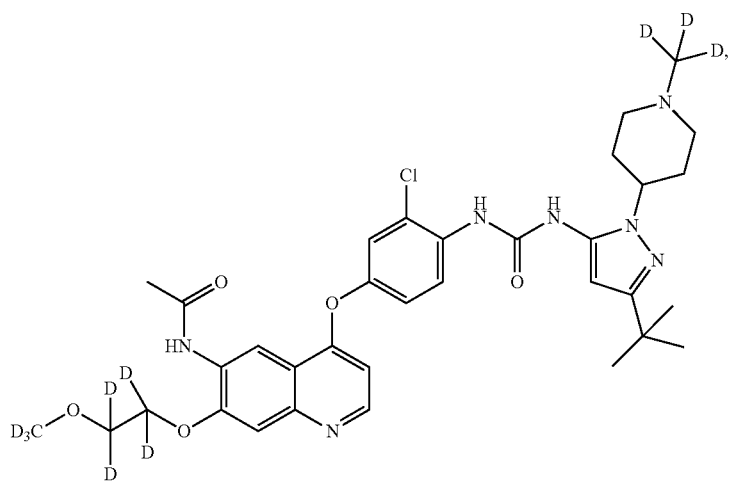

-continued
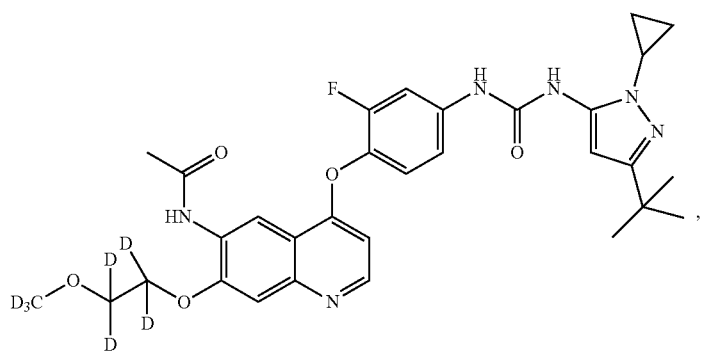
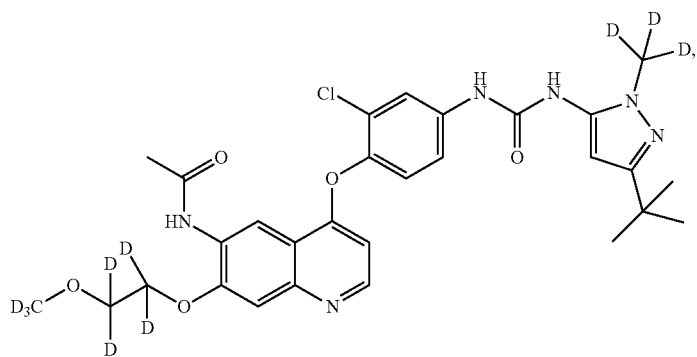
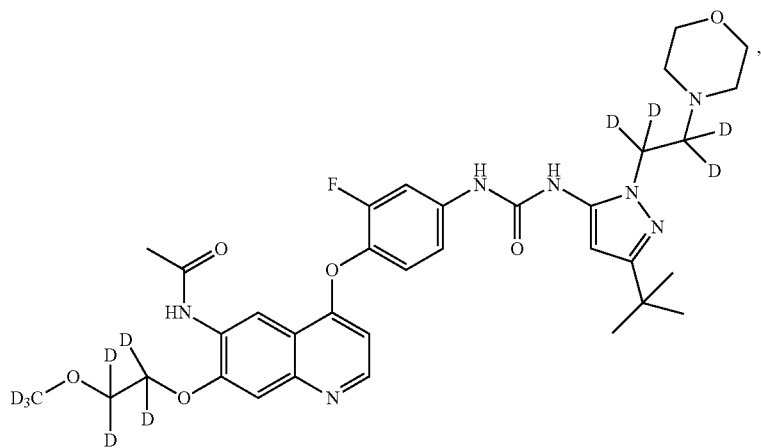
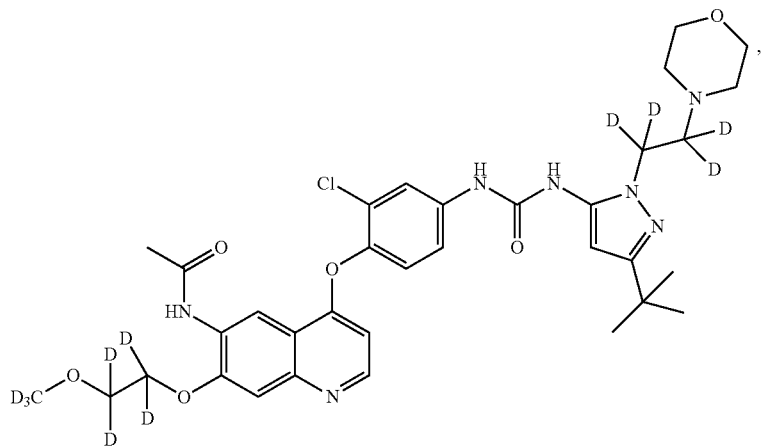

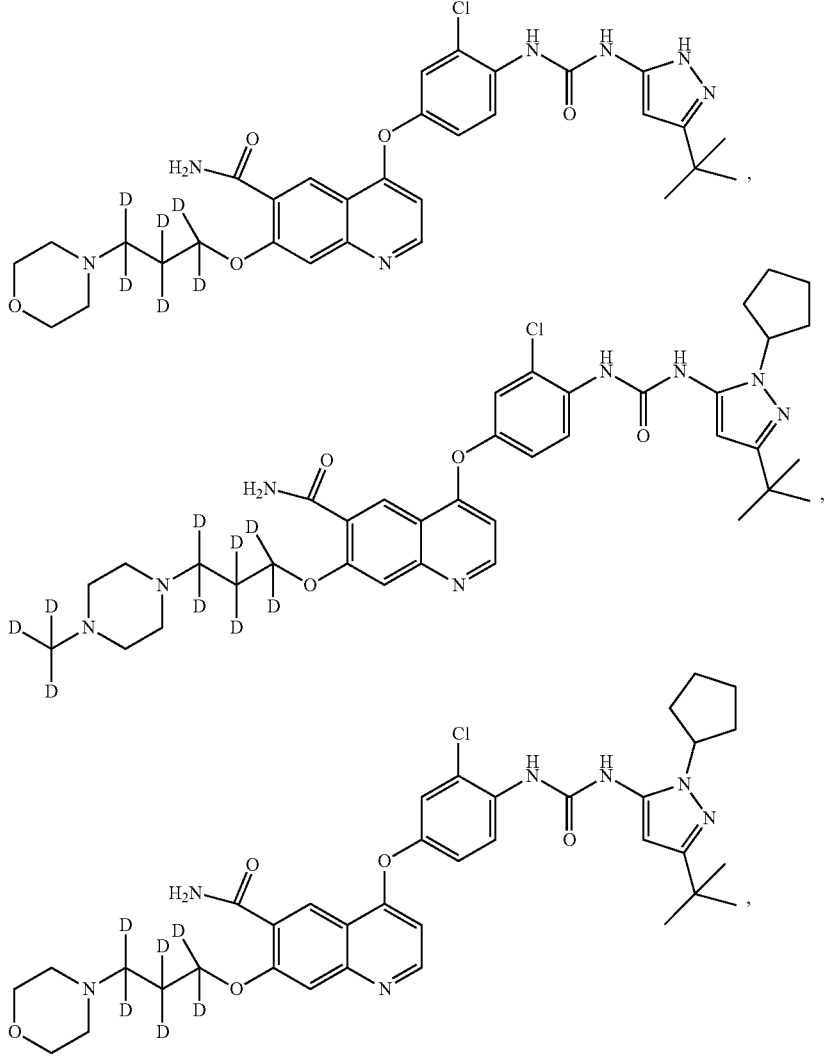
Another aspect of the present invention is to provide a method for preparing the compound of general formula (I) or a pharmaceutically acceptable salt, solvate, metabolite or prodrug thereof, comprising the following steps:
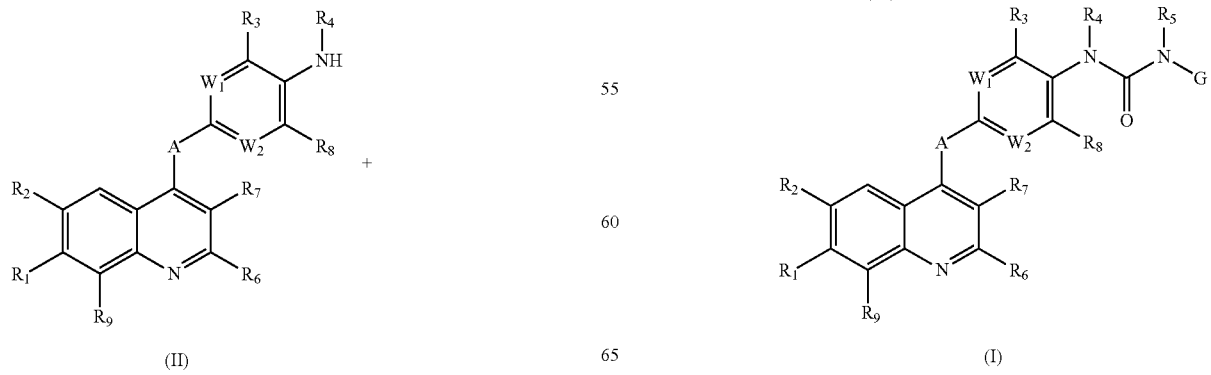

the compound of formula (II) is reacted with a compound of formula (III) in the present of a base in a suitable solvent to give the compound of general formula (I);
the solvent is preferably selected from the group consisting of THF, acetonitrile, dichloromethane and toluene,
the base is preferably selected from the group consisting of triethylamine, N,N-diisopropylethylamine, DMAP, and pyridine;
$R_1$, $R_2$, $R_3$, $R_4$, $R_5$, $R_6$, $R_7$, $R_8$, $R_9$, A, $W_1$, $W_2$ and G are as defined in general formula (I) above, preferably $R_5$ is hydrogen.

Another aspect of the present invention is to provide a method for preparing the compound of general formula (I) or a pharmaceutically acceptable salt, solvate, metabolite or prodrug thereof, comprising the following steps:

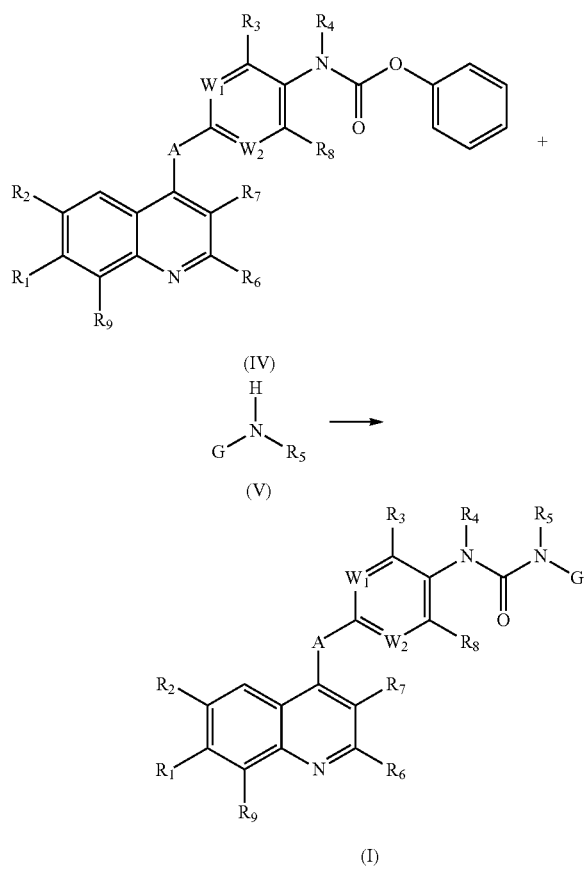

the compound of formula (IV) is reacted with the compound of formula (V) in the N,N-diisopropylethylamine, DMAP, and pyridine;
$R_1$, $R_2$, $R_3$, $R_4$, $R_5$, $R_6$, $R_7$, $R_8$, $R_9$, A, $W_1$, $W_2$ and G are as defined in general formula (I) above, preferably $R_4$ is hydrogen.

The present invention further relates to a pharmaceutical composition comprising a therapeutically effective amount of the compound of general formula (I) or a pharmaceutically acceptable salt, solvate, metabolite or prodrug thereof according to the present invention, or the deuterated compound of general formula (I) or a pharmaceutically acceptable salt, solvate, metabolite or prodrug thereof according to the present invention, as well as one or more pharmaceutically acceptable carriers.

The present invention further relates to use of the compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same, in the preparation of protein kinase inhibitor; preferably, the protein kinase is selected from the group consisting of ABL1, AXL, EGFR, FGFR1-4, FLT3, KIT, MERTK, PDGFRα/β, RET, ROS1, NTRK1-3, SRC protein kinase family and PIK3CA.

The present invention further relates to use of the compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same, in the preparation of medicaments for the prevention and/or treatment of cancer, especially in mammals including humans.

Such cancers include, but are not limited to lung cancer, gastric cancer, liver cancer, bile duct cancer, breast cancer, nasopharyngeal cancer, pancreatic cancer, ovarian cancer, cervical cancer, endometrial cancer, colorectal cancer, glioma, melanoma, prostate cancer, kidney cancer, esophageal cancer, mesothelioma, head and neck cancer, bladder cancer, salivary gland cancer, anaplastic large cell lymphoma, leukemia, lymphoma, non-hodgkin's lymphoma or multiple myeloma and the like.

The present invention further relates to a compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same, for use as a drug.

The present invention further relates to a compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same, for use as a protein kinase inhibitor; preferably, the protein kinase is selected from the group consisting of ABL1, AXL, EGFR, FGFR1-4, FLT3, KIT, MERTK, PDGFRα/β, RET, ROS1, NTRK1-3, SRC protein kinase family and PIK3CA.

The present invention further relates to a compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same, for use as a drug for the prevention and/or treatment of cancer, especially in mammals including humans. Such cancers include, but are not limited to lung cancer, gastric cancer, liver cancer, bile duct cancer, breast cancer, nasopharyngeal cancer, pancreatic cancer, ovarian cancer, cervical cancer, endometrial cancer, colorectal cancer, glioma, melanoma, prostate cancer, kidney cancer, esophageal cancer, mesothelioma, head and neck cancer, bladder cancer, salivary gland cancer, anaplastic large cell lymphoma, leukemia, lymphoma, non-hodgkin's lymphoma or multiple myeloma and the like.

The invention further relates to a method for inhibiting protein kinase, which includes administering to a patient in need of it an inhibitory effective amount of the compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same. The protein kinase is preferably selected from the group consisting of ABL1, AXL, EGFR, FGFR1-4, FLT3, KIT, MERTK, PDGFRα/β, RET, ROS1, NTRK1-3, SRC protein kinase family and PIK3CA.

The present invention further relates to a method for the prevention and/or treatment of cancer, especially in mammals including humans, which includes administering to a patient in need of it a therapeutically effective amount of the compound of general formula (I) or a pharmaceutically acceptable salt, solvate, metabolite or prodrug thereof, or the deuterated compound of general formula (I) or a pharmaceutically acceptable salt, solvate, metabolite or prodrug thereof according to the present invention, or a pharmaceutical composition comprising the same. Such cancers include, but are not limited to lung cancer, gastric cancer, liver cancer, bile duct cancer, breast cancer, nasopharyngeal cancer, pancreatic cancer, ovarian cancer, cervical cancer, endometrial cancer, colorectal cancer, glioma, melanoma, prostate cancer, kidney cancer, esophageal cancer, mesothelioma, head and neck cancer, bladder cancer, salivary gland cancer, anaplastic large cell lymphoma, leukemia, lymphoma, non-hodgkin's lymphoma or multiple myeloma and the like.

DETAILED DESCRIPTION OF THE INVENTION

Unless otherwise specified, all technical and scientific terms used herein have the same meaning as commonly understood by the person skilled in the art. All the patents, applications, published applications, and other publications are incorporated herein by reference in their entirety. If there are multiple definitions for the terms used herein, unless otherwise indicated, the terms in this section shall prevail. If the number of any given substituent is not specified, one or more substituents may be present. For example, "haloalkyl" may contain one or more of the same or different halogens. In the description herein, if the chemical structure is inconsistent with the chemical name, the chemical structure shall prevail. As used herein, abbreviations for any protecting groups, amino acids, and other compounds are indicated by their commonly accepted abbreviations or indicated according to the IUPAC-IUB Commission on Biochemical Nomenclature (refer to Biochem. 1972, 77:942-944), unless otherwise specified.

Unless there is a contrary statement, the following terms used in the specification and claims have the following meanings.

The term "alkyl" refers to a saturated straight or branched aliphatic hydrocarbon group including 1-20 carbon atoms. Preferably, an alkyl group is an alkyl having 1 to 18 carbon atoms, more preferably 1 to 10 carbon atoms, even more preferably 1 to 6 carbon atoms, most preferably 1-4 carbon atoms. Representative examples include, but are not limited to, methyl, ethyl, n-propyl, isopropyl, n-butyl, isobutyl, sec-butyl, tert-butyl, n-pentyl, iso-pentyl, neopentyl, hexyl, isohexyl, n-heptyl, isoheptyl, n-octyl, isooctyl, n-decyl, n-decyl and the like. In the present description, "alkyl" further includes a cyclicalkyl group having 3 to 10 carbon atoms, preferably 3 to 8 carbon atoms, more preferably 4 to 6 carbon atoms, such as cyclopropyl, cyclobutyl, cyclopentyl, cyclohexyl, cycloheptyl, cyclooctyl, cyclononyl, cyclodecyl, decahydronaphthalenyl, norbornane and adamantyl. Alkyl may be substituted or unsubstituted. When substituted, the substituents may be substituted at any available point, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxy, and carboxylic acid ester groups.

The term "alkenyl" refers to a straight or branched hydrocarbon group consisting of carbon and hydrogen atoms which comprises at least one double bond and connected to the remaining part of the molecule by a single bond or double bond. It preferably has 2 to 10 carbon atoms, more preferably 2 to 6 carbon atoms, even more preferably 2 to 4 carbon atoms. Non-limited examples include vinyl, propenyl, butenyl, pentenyl, pentadienyl, hexenyl. The alkenyl group may be substituted or unsubstituted, and when substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, amino, haloalkyl, hydroxyalkyl, carboxyl, and carboxylic acid ester groups.

The term "alkynyl" refers to a straight or branched hydrocarbon chain group consisting of carbon and hydrogen atoms which comprises at least one triple bond, and connected to the remaining part of the molecule by a single bond or triple bond. It preferably has 2 to 10 carbon atoms, more preferably 2 to 6 carbon atoms, even more preferably 2 to 4 carbon atoms. Non-limited examples include ethynyl, propynyl, butynyl, pentynyl, hexynyl. An alkynyl group may be substituted or unsubstituted, and when substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, amino, haloalkyl, hydroxyalkyl, carboxyl, and carboxylic acid ester groups.

The term "cycloalkyl" refers to saturated or partially unsaturated monocyclic or polycyclic ring hydrocarbon group containing 3 to 20 carbon atoms, preferably 3 to 12 carbon atoms, more preferably 3 to 10 carbon atoms, most preferably 3 to 7 carbon atoms. Non-limited examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclohexenyl. Polycyclic cycloalkyl groups include spiro, fused, and bridged cycloalkyl groups. Cycloalkyl can be optionally substituted or unsubstituted. When substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxy, and carboxylic acid ester groups.

The term "heterocyclyl" refers to a saturated or partially unsaturated monocyclic or polycyclic ring hydrocarbon group containing 3 to 20 ring atoms, wherein one or more ring atoms is selected from the group consisting of nitrogen, oxygen, or $S(O)m$ (m is an integer between 0 to 2), but excludes —O—O—, —O—S— or —S—S— moiety, and the remaining ring atoms are carbons. Preferably, 3 to 12 ring atoms are included, of which 1 to 4 atoms are heteroatoms, more preferably the heterocyclyl ring contains 3 to 10 ring atoms, even more preferably the heterocyclyl ring contains 5 to 7 ring atoms. Non-limited examples of monocyclic heterocyclyl include pyrrolidinyl, piperidinyl, piperazinyl, morpholinyl, thiomorpholinyl, homopiperazinyl, pyranyl, tetrahydrofuranyl and the like. Polycyclic heterocyclyl include spiro, fused and bridged heterocyclyl. The heterocyclic group may be optionally substituted or unsubstituted. When substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxy, and carboxylic acid ester groups. The heterocyclyl may be fused to an aryl, heteroaryl, or cycloalkyl ring, wherein the ring attached to the parent structure is a heterocyclyl ring. The non-limited examples include:

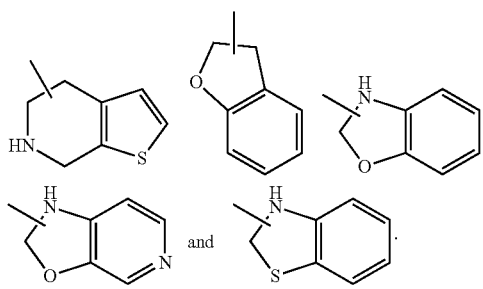

The term "aryl" refers to an all-carbon monocyclic or fused polycyclic (i.e., rings that share adjacent pairs of carbon atoms) groups having a conjugated π-electron system, preferably 5 to 10 members, more preferably 5 to 7 members, even more preferably phenyl and naphthyl, most preferably phenyl. The aryl group may be completely aromatic, such as phenyl, naphthyl, anthryl, or phenanthryl. The aryl group may also be a combination of an aromatic ring and a non-aromatic ring, for example, indene, fluorene and acenaphthene and the like. The aryl ring may be fused to a heteroaryl, heterocyclyl, or cycloalkyl ring, wherein the ring attached to the parent structure is an aryl ring. The non-limited examples include:

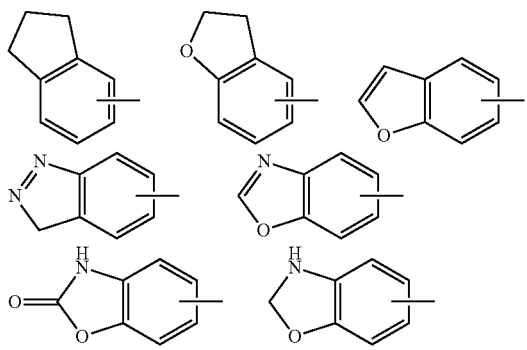

-continued

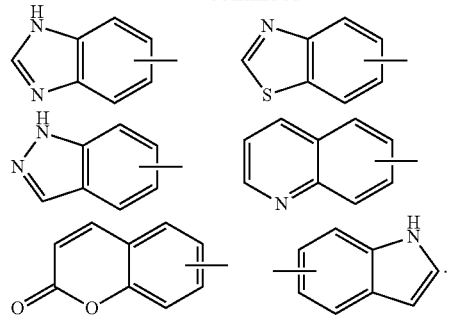

The aryl group may be substituted or unsubstituted. When substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, and carboxylic acid ester groups.

The term "heteroaryl" refers to a heteroaryl system containing 1 to 4 heteroatoms and 5 to 14 ring atoms, wherein the heteroatom is selected from the group consisting of oxygen, sulfur and nitrogen. Heteroaryl is preferably 5 to 10 membered, more preferably 5 to 7 membered, and even more preferably 5 or 6 membered, such as thiadiazolyl, pyrazolyl, oxazolyl, oxadiazolyl, imidazolyl, triazolyl, thiazolyl, furyl, thienyl, pyridyl, pyrrolyl, N-alkylpyrrolyl, pyrimidyl, pyrazinyl, imidazolyl, tetrazolyl, and the like. The heteroaryl ring may be fused to an aryl, heterocyclyl, or cycloalkyl ring, where the ring attached to the parent structure is a heteroaryl ring. The non-limited examples include:

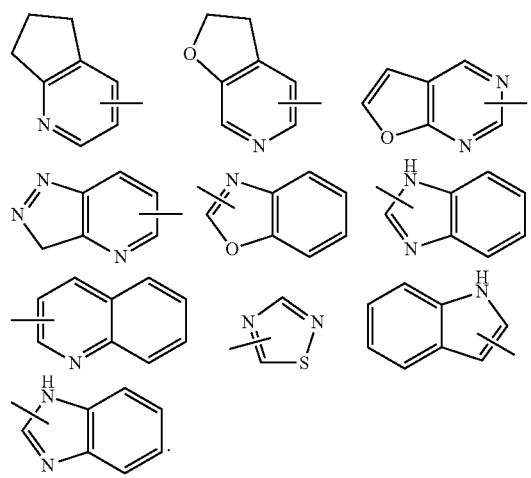

Heteroaryl may be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocycloalkylthio, amino, haloalkyl, hydroxyalkyl, carboxyl, and carboxylic acid ester groups.

The term "alkoxyl" refers to —O-(alkyl) and —O-(unsubstituted cycloalkyl), wherein the alkyl and cycloalkyl are as defined above. Non-limited examples include methoxyl, ethoxyl, propoxyl, butoxyl, cyclopropyloxyl, cyclobutyloxyl, cyclopentyloxyl, cyclohexyloxyl and on the like. Alkoxyl may be optionally substituted or unsubstituted.

When substituted, the substituent is preferably one or more groups independently selected from the group consisting of alkyl, alkenyl, alkynyl, alkoxyl, alkylthiol, alkylamino, halogen, thiol, hydroxyl, nitro, cyano, cycloalkyl, heterocyclyl, aryl, heteroaryl, cycloalkoxyl, heterocycloalkoxyl, cycloalkylthio heterocycloalkylthio, amino, haloalkyl, hydroxyalkyl, carboxyl, and carboxylic acid ester groups.

The term "haloalkyl" refers to an alkyl group in which one or more hydrogen atoms is replaced by a halogen, wherein the alkyl is as defined above. Non-limited examples include chloromethyl, trifluoromethyl, 1-chloro-2-fluoroethyl, 2,2-difluoroethyl, 2-fluoropropyl, 2-fluoropropan-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethyl-ethyl.

The term "halogen" includes fluorine, chlorine, bromine, and iodine.

The term "cyano" refers to —CN group.
The term "hydroxy" refers to —OH group.
The term "amino" refers to —$NH_2$ group.
The term "nitro" refers to —$NO_2$ group.
The term "hydroxyalkyl" refers to an alkyl substituted with hydroxyl, wherein the alkyl is as defined above.

The term "hydroxyalkoxyl" refers to an alkoxy substituted with hydroxy, wherein the alkoxy is defined as above.

The term "acyl" refers to —C(O)R, wherein R refers to an alkyl, cycloalkyl, alkenyl, alkynyl, wherein the alkyl, cycloalkyl, alkenyl, and alkynyl are defined as above.

Non-limited examples include acetyl, propionyl, butyryl, pentanoyl, hexanoyl, vinylacyl, and acryloyl.

The term "amido" refers to —NHC(O)OR, where R refers to an alkyl, alkenyl, alkynyl, wherein the alkyl, alkenyl, and alkynyl are defined as above. Non-limited examples include carboxamido, acetamido, propionamido, butyrylamino, pentanoylamino, hexanoylamino, vinylacylamino, and acryloylamino.

The term "ester group" refers to —C(O)OR, where R refers to an alkyl group or a cycloalkyl group, wherein the alkyl and cycloalkyl are defined as above. Non-limited examples include ethyl ester group, propyl ester group, butyl ester group, pentyl ester group, cyclopropyl ester group, cyclobutyl ester group, cyclopentyl ester group, and cyclohexyl ester group.

"Optionally substituted" in the present description means unsubstituted or substituted by one or more (e.g. 2, 3, 4) substituents, wherein the substituent is selected from the group consisting of halogen, alkyl, alkenyl, alkynyl, haloalkyl, alkoxy, aryl, haloaryl, aryloxy, arylalkyl, arylalkoxy, heterocycloalkyloxy, haloarylalkyloxy, alkylamino, alkylacyl, cyano, heterocyclyl and the like. These substituents can be further substituted. For example, the alkyl as a substituent is also optionally substituted by one or more groups selected from the group consisting of halogen, hydroxyl, alkoxy, alkylamino, pyrrolidinyl, phenyl, pyridyl, and halophenyl. The heterocyclyl group as a substituent is also optionally substituted by one or more groups selected from the group consisting of halogen, alkyl, and alkoxy group.

The term "pharmaceutical composition" refers to a mixture comprising one or more of the compounds described herein, or a physiologically/pharmaceutically acceptable salt or prodrug thereof, and other chemical components, as well as other components such as physiology/pharmaceutically acceptable carrier and excipients. The purpose of the pharmaceutical composition is to promote the administration to the organism, which facilitates the absorption of the active ingredient and thereby exerts biological activity.

Synthetic Method of the Present Compounds

In order to achieve the purpose of the present invention, the present invention mainly applies the following synthetic solutions.

Formula (I)

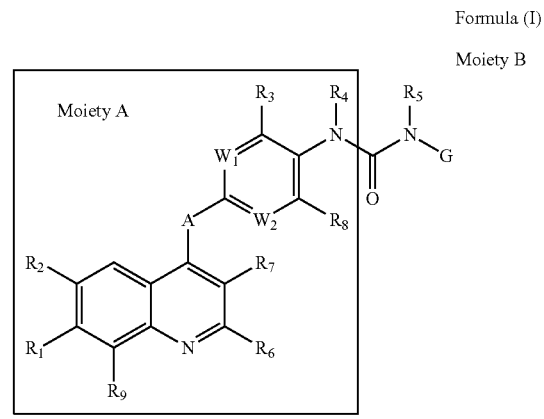

The first synthetic solution of the present compound is done by dividing the structure of the present compound of general formula (I) into moiety A and moiety B as above, wherein moiety A is an amine intermediate compound of formula (II), and moiety B is an active ester intermediate compound of formula (III).

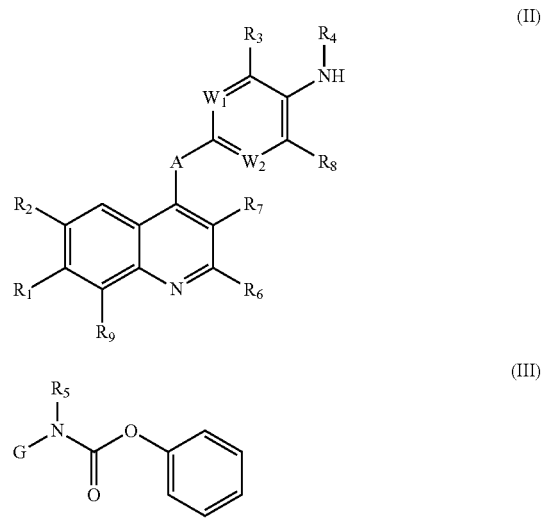

1. The synthetic method of the amine intermediate compound of formula (II) is as follows:

Scheme 1

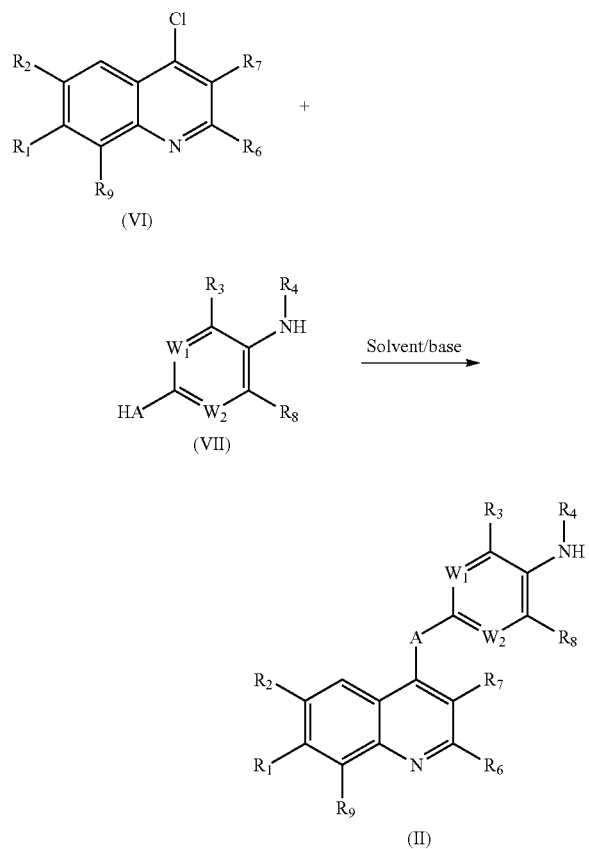

The quinoline intermediate compound of formula (VI) is reacted with the intermediate compound of (VII) under appropriate temperature and pH (base) in a suitable solvent to give the intermediate compound of formula (II); wherein the base may be, for example, sodium hydroxide, potassium carbonate, cesium carbonate and the like; the solvent may be, for example, DMSO, DMF, isopropyl alcohol, acetonitrile and the like.

The quinoline intermediate of formula (VI) is mainly synthesized by the following two methods:

Method 1:

Scheme 2

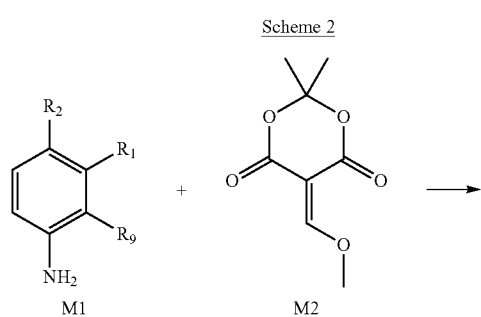

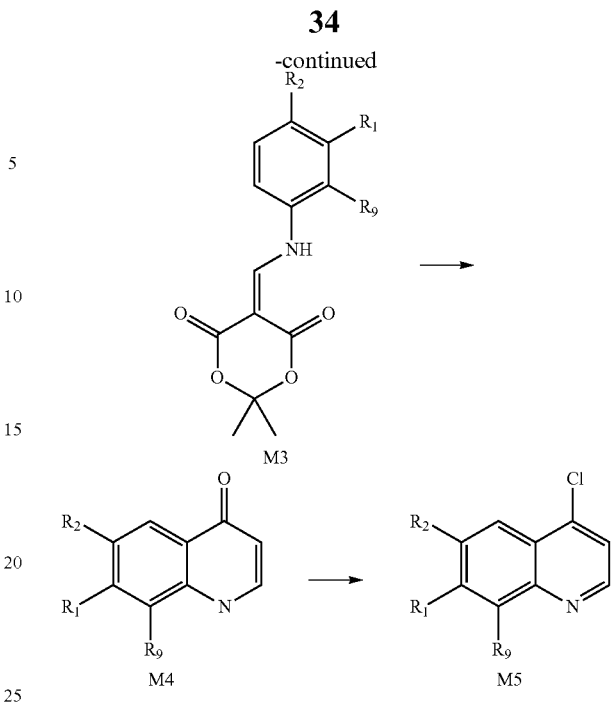

Intermediates M1 and M2 are reacted in a suitable solvent under appropriate temperature to give intermediate M3; wherein the solvent may be, for example ethanol, methanol, and the like. Then, intermediate product M3 is subjected to a cyclization reaction under high temperature in a suitable solvent to give intermediate M4; wherein the solvent may be, for example, diphenyl ether-biphenyl eutectic, diphenyl ether, and the like. Finally, intermediate M4 is subjected to chlorination with a suitable chlorinating agent under appropriate temperature to give intermediate M5; wherein the chlorinating agent may be, for example, thionyl chloride, phosphorus oxychloride and the like.

Method 2:

Scheme 3

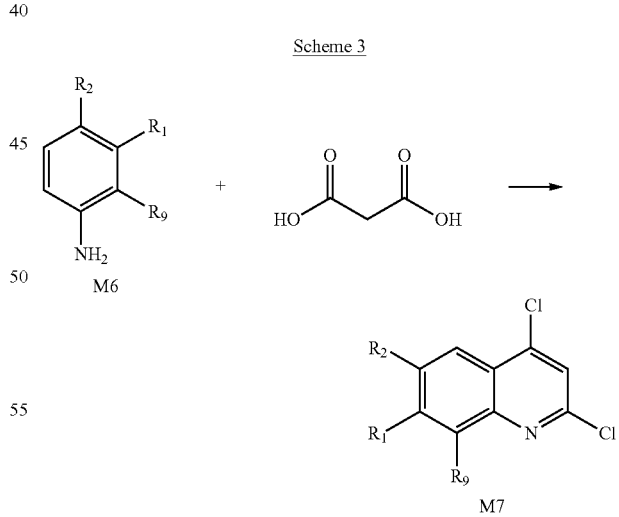

The intermediate M6 and malonic acid are subjected to cyclization reaction in phosphorus oxychloride under appropriate temperature placed to give the intermediate M7.

2. The synthesis of the active ester intermediate compound of formula (III)

1) The synthesis of pyrazole intermediates is shown as follows,

Scheme 4

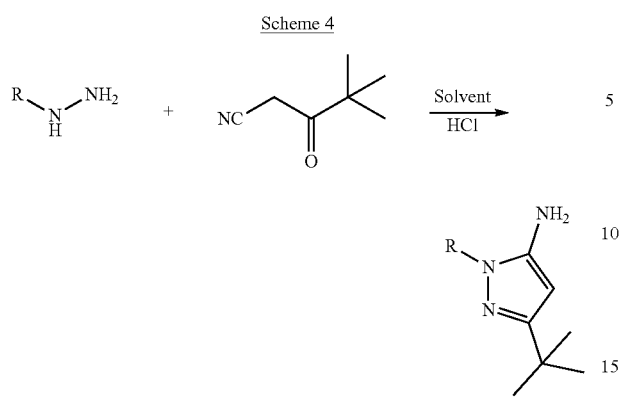

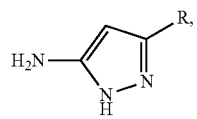

then the amine intermediates of moiety A are prepared into active esters, that is, the second method for synthesizing the compound of the present invention. The structure of the compound of general formula (I) is divided into moiety A and moiety B, wherein moiety A is an active ester intermediate compound of formula (IV), and moiety B is an amine intermediate compound of formula (V), which is shown as scheme 6 below, The pyrazole intermediate is obtained by reaction in the presence of acid catalysis in a suitable solvent under appropriate temperature and pH; wherein the solvent may be, for example, ethanol, and the acid may be, for example, hydrochloric acid.

R is selected from the group consisting of alkyl, aryl and heteroaryl groups, and the alkyl, aryl and heteroaryl groups, if any, are each independently and optionally substituted with one or more groups selected from the group consisting of halogen, hydroxyl and alkyl groups.

2) Other isooxazole intermediates are commercially available.

3) The synthetic method of active ester

If the intermediate of moiety B has only one urea-forming site, it can be prepared into active ester according to the scheme 5 shown below,

Scheme 5

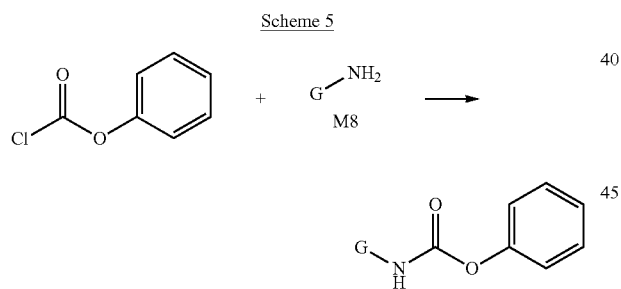

Phenyl chloroformate is reacted with the corresponding amine (intermediate M8) in the presence of a base catalysis in a suitable solvent at appropriate temperature and pH conditions, to obtain the corresponding active ester; wherein the solvent may be, for example, ethyl acetate, dichloromethane, tetrahydrofuran, acetone, acetonitrile, water, and the like, and the base may be, for example, pyridine, sodium bicarbonate, potassium carbonate, triethylamine, sodium hydroxide and the like. Since the difference among the groups linked to the amino groups results in different reactivity, so the bases selected are slightly different during the reaction. The person skilled in the art can make routine selections according to the conventional technical knowledge in the art.

If there are two urea-forming sites (—NH— and —NH$_2$—) in the intermediate of moiety B, for example

Scheme 6

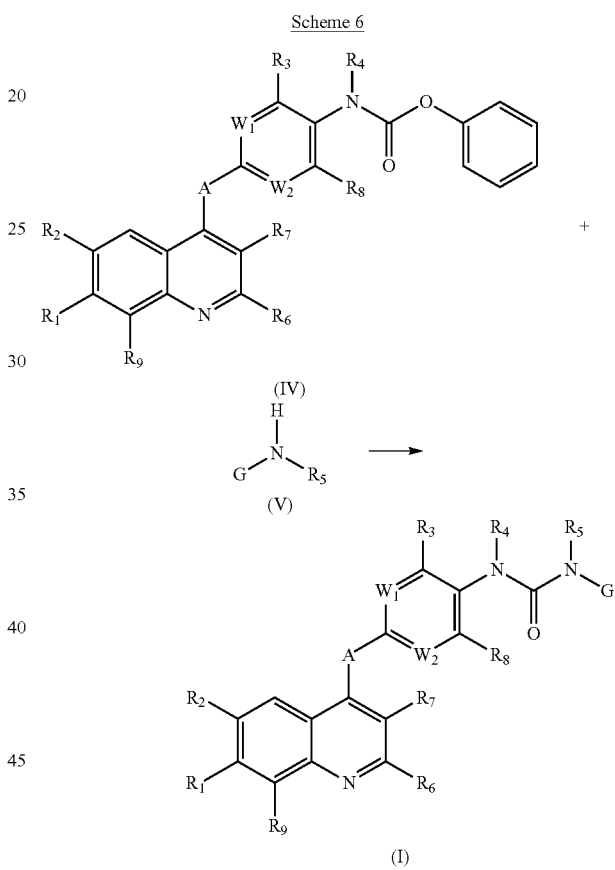

Among them, the preparation method of the active ester intermediate compound of formula (IV) of moiety A is similar to that with moiety B as active ester above. That is, the amine intermediate compound of formula (II) of moiety A is reaction with phenyl chloroformate in the presence of a base catalysis in a suitable solvent under appropriate temperature and pH conditions, to obtain an active ester intermediate of moiety A.

Finally, as previously described, an intermediate compound of formula (II) and an intermediate compound of formula (III), or an intermediate compound of formula (IV) and an intermediate compound of formula (V), are subjected to a reaction in the presence of a base in a suitable solvent to obtain the compound of general formula (I); wherein the solvent is preferably THF, acetonitrile, methylene chloride, or toluene; and the base is preferably triethylamine, N,N-diisopropylethylamine, DMAP, or pyridine.

Wherein, $R_1$, $R_2$, $R_3$, $R_4$, $R_5$, $R_6$, $R_7$, $R_8$, $R_9$, A, $W_1$, $W_2$ and G are as defined in general formula (I).

Synthetic Method of the Urea Compound of the Present Invention.

The synthetic method of the urea compound of the present invention mainly employs an active ester method, but is not limited to this method. The amine intermediate of moiety A and the active ester of moiety B or the active ester of moiety A and the amine intermediate of moiety B, are subjected to a reaction in the presence of a base such as triethylamine or DMAP, in a suitable solvent such as THF and acetonitrile, under appropriate temperature and pH conditions; thereby an active ester is eliminated one molecule of phenol to obtain the corresponding isocyanate intermediates, which are then reacted with the corresponding amines in the presence of a base to obtain the final urea compound.

The prodrug of the compound of general formula (I) of the present invention should follow the prodrug design principle, and can release the original active compound of formula (I) by enzymatic hydrolysis, hydrolysis, acid hydrolysis or metabolic degradation under normal physiological conditions in body. A prodrug includes, but is not limited to, esterification of hydroxyl groups on the compound (such as the formation of phosphates and carbonates), the protection of amino groups and carboxyl groups. Prodrug design references (1) Karaman R, Prodrugs design based on inter- and intramolecular chemical processes. Chem Biol Drug Des. 82 (6): 643-68, 2013; (2) Rautio J et al. Prodrugs: design and clinical applications. Nat Rev Drug Discov. 7(3):255-70 2008; (3) Jampilek J. Prodrugs: pharmaceutical design and current perspectives. Curr Pharm Des. 17(32):3480-1, 2011; (4) Bundgaard H. Design of Progrugs. Elsevier, 1985.

The pharmaceutically acceptable salt of the compound of general formula (I) of the present invention may be an acid addition salt or a base addition salt. The acid may be an inorganic acid, including but not limited to hydrochloric acid, sulfuric acid, phosphoric acid, or hydrobromic acid; or may be an organic acid, including but not limited to citric acid, maleic acid, oxalic acid, formic acid, acetic acid, propionic acid, valeric acid, glycolic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid, p-toluenesulfonic acid. The base may be an inorganic base, including but not limited to sodium hydroxide, potassium hydroxide, magnesium hydroxide, or calcium hydroxide; or may be an organic base, including but not limited to ammonium hydroxide, triethylamine, N,N-dibenzyl ethylenediamine, chloroprocaine, choline, ammonia, diethanolamine and other hydroxy alkyl amines, ethylene diamine, N-methyl glucosamine, procaine, N-benzyl phenylethylamine, arginine, or lysine; or may be an alkali metal salt, including but not limited to lithium, potassium or sodium salts; or may be an alkaline earth metal salt, including but not limited to barium, calcium or magnesium salts; or may be a transition metal salt, including but not limited to zinc salt; or may be other metal salts, including but not limited to sodium hydrogen phosphate or disodium hydrogen phosphate.

In another aspect of the present invention, a compound of general formula (I) or a pharmaceutically acceptable salt or prodrug thereof is prepared into a clinically acceptable pharmaceutical composition. According to clinical indications, administration route and way, such pharmaceutical preparations include, but are not limited to, oral preparations such as tablets, gels, soft/hard capsules, emulsions, dispersible powders, granules, and water/oil emulsions; injections including intravenous injections, intramuscular injections, intraperitoneal injections, rectal administration suppositories, and intracranial injections, which may be aqueous solutions or oil solutions; topical preparations including creams, ointments, gels, water/oil solutions, and inclusion preparations; inhalation dosage forms including fine powders, liquid aerosols, and various dosage forms suitable for implantation in vivo.

The pharmaceutical composition of the present invention may be added with a pharmaceutically acceptable carrier, diluent or excipient as needed. These carriers, diluents, or excipients should comply with the rules of the pharmaceutical preparation process and be compatible with the active ingredients. Carriers for solid oral preparations include, but are not limited to, mannitol, lactose, starch, magnesium stearate, cellulose, glucose, sucrose, cyclodextrin, and vitamin E-PEG 1000 which is a molecular carrier for facilitating intestinal absorption. Oral preparations may be added with suitable colorants, sweeteners, flavoring agents and preservatives.

The compound of general formula (I) or the pharmaceutically acceptable salt or prodrug thereof is administered to warm-blooded animals with a unit dose of 0.01-100 mg/kg. However, as is well known to those skilled in the art, the dose of the drug to be administered depends on a number of factors, including but not limited to the activity of the specific compound used, the age, weight, health, behavior, and diet of the patient, the time and mode of administration, the rate of excretion, the combination of other drugs and the like. Thus, the optimal treatment regimen such as the mode of treatment, the daily administration dose of the compound represented by general formula (I), or the type of pharmaceutically acceptable salt can be validated according to a conventional treatment regimen.

The compound of general formula (I) or the pharmaceutically acceptable salt or prodrug thereof can be used as a monotherapy or a combination therapy with one or more of the following therapies: radiation therapy, chemotherapy, immunotherapy, tumor vaccine, oncolytic virus therapy, RNAi, cancer adjuvant therapy, bone marrow transplantation and stem cell transplantation, including but not limited to the following anti-tumor drugs and treatment methods:

1) Alkylating agents, such as cisplatin, cisplatin, oxaliplatin, chlorambucil, cyclophosphamide, nitrogen mustard, melphalan, temozolomide, busulfan, and nitrosoureas.

2) Anti-tumor antibiotics, such as doxorubicin, bleomycin, doxorubicin, daunorubicin, epirubicin, idarubicin, mitomycin C, actinomycin, or mithramycin; anti-mitotic drugs such as vincristine, vinblastine, vindesine, vinorelbine, paclitaxel, taxotere, and Polo kinase inhibitors.

3) Antimetabolites and antifolates, such as fluoropyrimidine, methotrexate, cytarabine, azacitidine, decitabine, raltitrexed, hydroxyurea, IDH1/IDH2 mutant inhibitor.

4) Topoisomerase inhibitors such as epipodophyllotoxin, camptothecin, irinotecan.

5) Cell growth inhibitors, such as anti-estrogen/anti-androgen drugs, such as tamoxifen, fulvestrant, toremifene, raloxifene, droloxifene, idoxifene, bicalutamide, flutamide, nilutamide, and cyproterone acetate;

LHRH antagonists or LHRH agonists, such as goserelin, leuprolide, and buserelin; progestogens such as megestrol acetate;

Aromatase inhibitors, such as anastrozole, letrozole, vorozole, exemestane, and 5a-reductase inhibitors such as finasteride.

6) Anti-invasive agents, such as c-Src kinase family inhibitors, metalloproteinase inhibitors, inhibitors of urokinase plasminogen activator receptor function, and heparinase-like antibodies.
7) Growth function inhibitors, e.g. growth factor antibodies and growth factor receptor antibodies such as anti-HER2 antibody Trastuzumab, anti-EGFR antibody Panitumumab, anti-EGFR antibody Cetuximab; such inhibitors also include other tyrosine kinase inhibitors and serine/threonine kinase inhibitors, such as Ras/Raf signal conduction inhibitor, cell signaling inhibitors of MEK and/or AKT kinase, c-kit inhibitor, abl kinase inhibitor, PI3 kinase inhibitor, JAKs and STAT3 inhibitor, FLT3 kinase inhibitor, CSF-1R kinase inhibitor, IGF receptor kinase inhibitor, aurora kinase inhibitor, NTRKA/B/C kinase inhibitor, cyclin-dependent kinase inhibitors, e.g. CDK2 and or CDK4, CDK6 inhibitor and transcription kinase CDK7/9/12/13 inhibitor.
8) Antiangiogenic agents, e.g. Bevacizumab, a drug that inhibits vascular endothelial growth factor, and VEGF receptor tyrosine kinase inhibitor.
9) Epigenetic inhibitors such as histone deacetylase (HDAC) inhibitors, DNA methyltransferase (DNMT) inhibitors, histone acetyltransferase inhibitors, histone demethylase inhibitors, histone methyltransferase inhibitors, and the like.
10) Poly ADP-ribose polymerase inhibitors (PARPi) such as Olaparib, Rucaparib and Niraparib.
11) Tumor immunotherapy, including any in vitro and in vivo methods to increase the immunogenicity of a patient for tumor cells. For example, transfections of cytokines IL-2, IL-4, or GM-CSF; methods of reducing the ineffectiveness of T cells such as anti-PD-1/PD-L mAbs; methods of using transfected immune cells such as dendritic cells transfected with cytokines; methods of using the tumor cell lines transfected with cytokines; methods of reducing the functions of immunosuppressive cells such as regulatory T cells, myeloid-derived suppressor cells, or dendritic cells expressing indoleamine 2,3-deoxygenase; agonist that increases immune cell activity; as well as methods of cancer vaccines consisting of tumor-associated antigen proteins or peptides.
12) Chimeric antigen receptor T-cell immunotherapy (CART).
13) Oncogene therapy such as CRISPR-Cas 9, RNAi and gene transduction.

EXAMPLES

The present invention will be illustrated in detail with reference to the following examples. However, it should be understood that the present invention is not limited to these examples.

The structure of the compound is determined by nuclear magnetic resonance (NMR) or/and mass spectrometry (MS). The NMR shift ($\delta$) is given by the unit of $10^{-6}$ (ppm). The NMR is determined by a (Bruker AVANCE-400) NMR spectrometer. The solvents used are deuterated dimethyl sulfoxide (DMSO-$d_6$), deuterated chloroform (CDCl$_3$), deuterated methanol (CD$_3$OD), and the internal standard is tetramethylsilane (TMS).

MS is determined using a liquid chromatography mass spectrometer (Thermo, Ultimate 3000/MSQ).

HPLC is performed by a high-pressure liquid chromatograph (Agilent 1260 Infinity, Gemini C18 250×4.6 mm, 5u column).

The silica gel plate HSGF245 used for thin layer chromatography (TLC) has a specification of 0.15 mm to 0.2 mm. The specifications for the separation and purification of the product by thin-layer chromatography are 0.9 mm to 1.0 mm (Yantai Yellow Sea).

Column chromatography generally applies 200-300 mesh silica gel as the carrier (Yantai Yellow Sea silica gel).

The known raw materials of the present invention may be synthesized using or in accordance with methods known in the prior art, or purchased from Shanghai Darui Fine Chemicals Co., Ltd., Shanghai Titan Technology Co., Ltd., Shanghai Runjie Chemical Reagent Co., Ltd., TCI, or Aldrich Chemical Company. If the experimental conditions are not specified in the examples, usually the conventional conditions or conditions recommended by the raw material or product manufacturers are adopted. Reagents that are not specified the sources are conventional reagents purchased from the market.

Unless otherwise specified in the examples, the reactions can all be carried out under an argon or nitrogen atmosphere. The argon or nitrogen atmosphere means that the reaction flask is connected to an argon or nitrogen gas balloon of approximately 1 L in volume.

Unless otherwise specified in the examples, the solution refers to an aqueous solution.

Unless otherwise specified in the examples, the reaction temperature is room temperature, approximately 20° C. to 30° C.

The progress of the reaction in the examples may be monitored by thin layer chromatography (TLC). The developing agent used for the reaction, the system of the eluent used for the purification of the column chromatography, and the developing system of the thin layer chromatography includes: A: dichloromethane/methanol system, B: n-hexane/ethyl acetate system, C: petroleum ether and ethyl acetate system. The volume ratio of the solvent is adjusted depending on the polarity of the compound, and may be adjusted by adding a small amount of an alkaline or acidic reagent such as triethylamine or acetic acid.

Example 1

Preparation of 4-{4-[3-(5-tert-butyl-isoxazol-3-yl)-ureido]-phenoxy}-7-methoxyquinolin-6-carboxamide

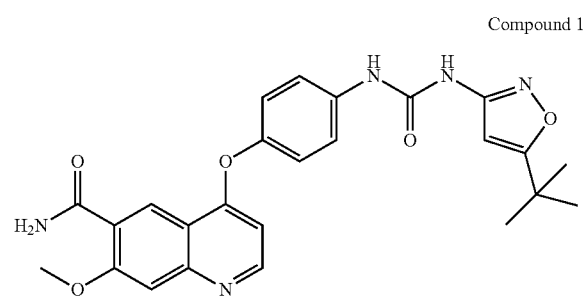 [SMILES: COc1cc2nccc(Oc3ccc(NC(=O)Nc4cc(C(C)(C)C)on4)cc3)c2cc1C(N)=O]

Compound 1

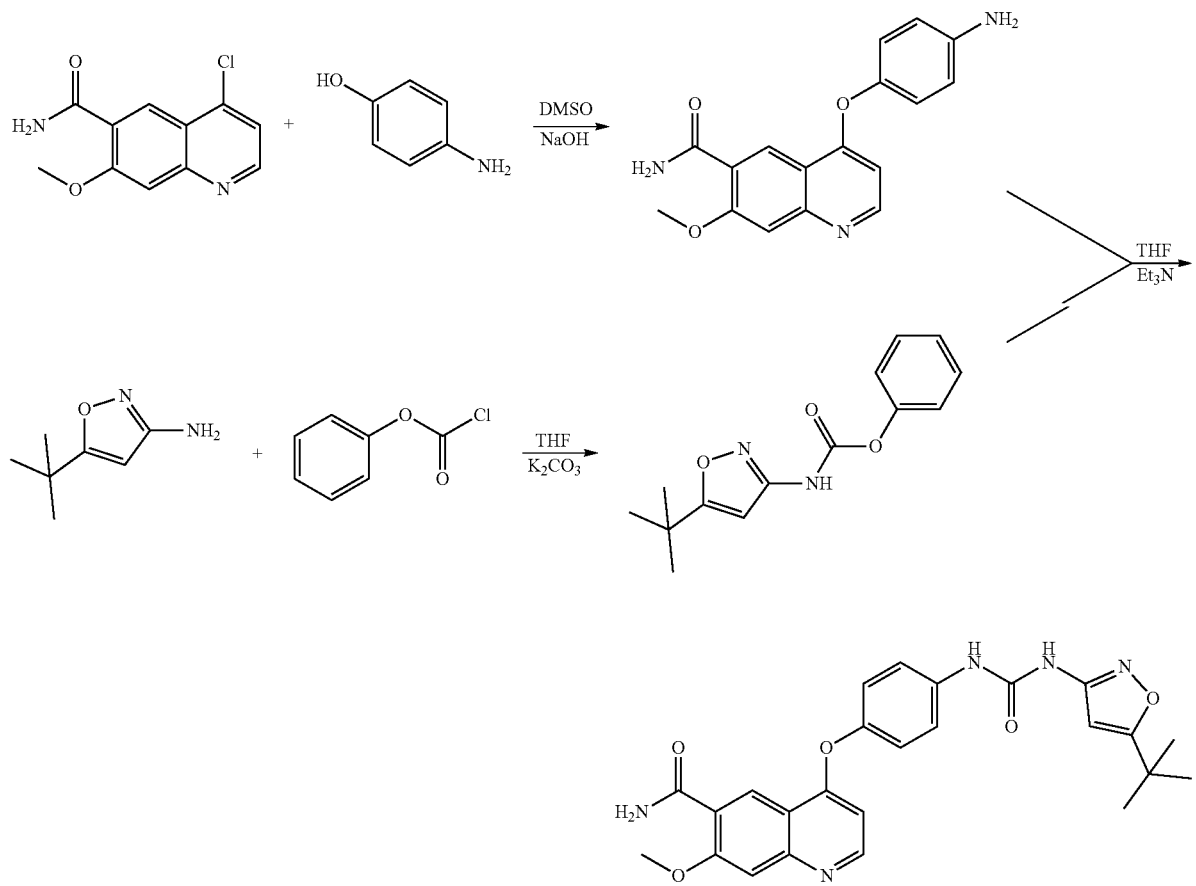

Step 1: Preparation of 4-(4-aminophenoxy)-7-methoxy-quinolin-6-carboxamide

At room temperature, 4-aminophenol (purchased from TCI) (461 mg, 4.22 mmol) was dissolved in 10 ml of DMSO, and sodium hydroxide (340 mg, 8.44 mmol) was added. The mixture was stirred at room temperature for 30 min, then 4-chloro-7-methoxy-quinolin-6-carboxamide (500 mg, 2.11 mmol) (purchased from Shanghai Titan) was added. The mixture was heated to 100° C. and reacted for 1 hour. The reaction solution was cooled to room temperature, slowly poured into water, and extracted with ethyl acetate (80 ml×3). The organic phase was washed twice with saturated NaCl solution, dried over anhydrous sodium sulfate, filtered and the filtrate was concentrated under reduced pressure. The residues were purified via column chromatography (eluent: dichloromethane/methanol) to give 270 mg yellow solid.

Step 2: Preparation of Phenyl (5-tert-butyl-isoxazol-3-yl)-carbamate (active ester)

5-tert-Butyl-isoxazol-3-ylamine (TCI) (39 g, 0.28 mol) was dissolved in 600 ml of THF and potassium carbonate (115 g, 0.8 mol) was added at room temperature. The mixture was cooled in an ice bath to 0-5° C. and phenyl chloroformate (Shanghai Dari) (65 g, 0.4 mol) was slowly added dropwise. After addition, the ice bath was removed and the temperature was slowly raised to room temperature. After the reaction was completed by TLC monitoring, the reaction solution was poured into water and extracted with ethyl acetate (600 ml×2). The organic phase was washed with saturated NaCl solution (500 mL×2), dried over anhydrous sodium sulfate, filtered, and the filtrate was concentrated under a reduced pressure to give 70.5 g crude product, which was directly used for the next step without purification.

Step 3: Preparation of 4-{4-[3-(5-tert-butyl-isoxazol-3-yl)-ureido]-phenoxy}-7-methoxyquinolin-6-carboxamide The 4-(4-aminophenoxy)-7-methoxy-quinolin-6-carboxamide (270 mg, 0.873 mmol) obtained in Step 1, phenyl (5-tert-butyl-isoxazol-3-yl)-carbamate (454 mg, 1.746 mmol) obtained in Step 2 and triethylamine (353 mg, 3.492 mmol) were dissolved in 10 ml of THF and the reaction mixture was refluxed overnight. The next day, the reaction solution was concentrated under a reduced pressure, and the residues were purified via column chromatography (eluent: dichloromethane/methanol) to give 220 mg of 4-{4-[3-(5-tert-butyl-isoxazol-3-yl)-ureido]-phenoxy}-7-methoxy quinolin-6-carboxamide, as a white solid.

1HNMR (DMSO-d6, 400 MHz) δ: 9.55 (s, 1H), 8.97 (s, 1H), 8.69 (s, 1H), 8.66-8.67 (d, 1H), 7.86 (br, 1H), 7.74 (br, 1H), 7.60-7.62 (d, 2H), 7.52 (s, 1H), 7.25-7.27 (d, 2H), 6.52 (s, 1H), 6.48-6.49 (d, 1H), 4.04 (s, 3H), 1.31 (s, 9H).

LC-MS: ESI 476.1 (M+H)+.

Example 2

Preparation of 4-{4-[3-(5-tert-butyl-isoxazol-3-yl)-ureido]-3-chloro-phenoxy}-7-methoxyquinolin-6-carboxamide (Compound 2)

Compound 2

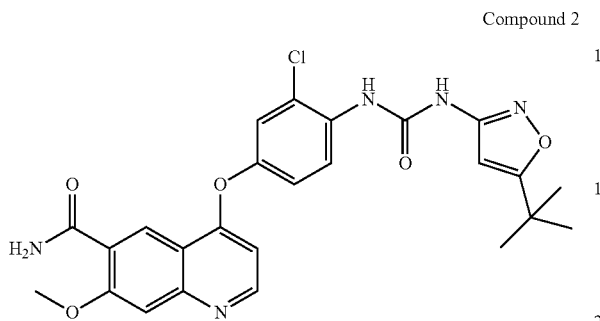

The preparation method was the same as Example 1, except that 4-amino-3-chlorophenol hydrochloride (TCI) was used instead of 4-aminophenol in Step 1 to give 4-{4-[3-(5-tert-butyl-isoxazol-3-yl)-ureido]-3-chloro-phenoxy}-7-methoxyquinolin-6-carboxamide.

$^1$HNMR (DMSO-$d_6$, 400M Hz) δ: 10.24 (s, 1H), 8.79 (s, 1H), 8.69 (s, 1H), 8.69-8.70 (d, 1H), 8.67 (s, 1H), 8.27-8.29 (d, 1H), 7.86 (br, 1H), 7.74 (br, 1H), 7.59-7.60 (d, 1H), 7.53 (s, 1H), 7.30-7.33 (dd, 1H), 6.57-6.59 (d, 1H), 6.48 (s, 1H), 4.07 (s, 3H), 1.31 (s, 9H).

LC-MS: ESI 510.1 (M+H)$^+$.

Example 3

Preparation of 4-{3-bromo-4-[3-(5-tert-butyl-isoxazol-3-yl)-ureido]-phenoxy}-7-methoxyquinolin-6-carboxamide (Compound 3)

Compound 3

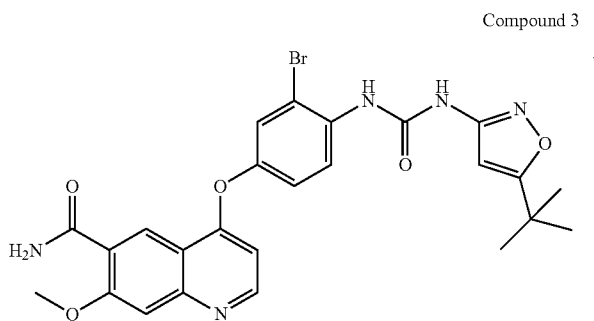

The preparation method was the same as Example 1, except that 4-amino-3-bromophenol (TCI) was used instead of 4-aminophenol in Step 1 to give 4-{3-bromo-4-[3-(5-tert-butyl-isoxazol-3-yl)-ureido]-phenoxy}-7-methoxyquinolin-6-carboxamide.

$^1$HNMR (DMSO-d6, 400 MHz) δ: 10.31 (s, 1H), 8.64-8.70 (m, 3H), 8.18-8.20 (d, 1H), 7.87 (br, 1H), 7.75 (br, 1H), 7.71-7.72 (d, 1H), 7.54 (s, 1H), 7.34-7.37 (dd, 1H), 6.57-6.59 (d, 1H), 6.47 (s, 1H), 4.04 (s, 3H), 1.31 (s, 9H).

LC-MS: ESI 555.0 (M+H)$^+$.

Example 4

Preparation of 4-{4-[3-(5-tert-butyl-2H-pyrazol-3-yl)-ureido]-3-trifluoromethyl-phenoxy}-7-methoxy-quinolin-6-carboxamide (Compound 4)

Compound 4

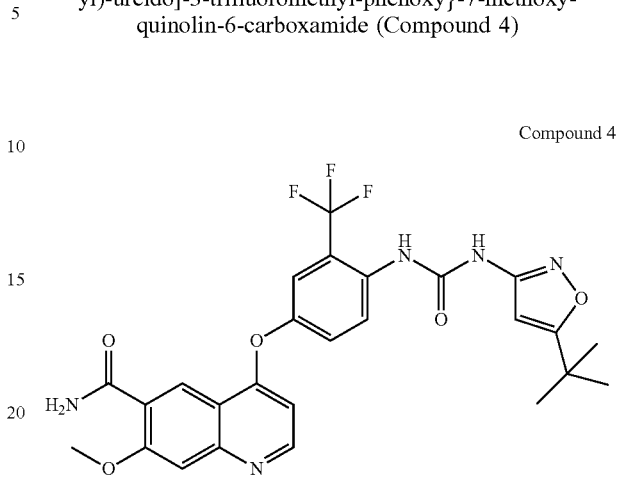

The preparation method was the same as Example 1, except that 4-amino-3-trifluoromethylphenol (TCI) was used instead of 4-aminophenol in Step 1 to give 4-{4-[3-(5-tert-butyl-2H-pyrazol-3-yl)-ureido]-3-trifluoromethyl-phenoxy}-7-methoxyquinolin-6-carboxamide. 1HNMR (DMSO-d6, 400 MHz) δ: 10.22 (s, 1H), 8.70-8.72 (d, 1H), 8.69 (s, 1H), 8.56 (s, 1H), 8.04-8.06 (d, 1H), 7.87 (br, 1H), 7.76 (br, 1H), 7.71-7.72 (d, 1H), 7.63-7.66 (dd, 1H), 7.55 (s, 1H), 6.59-6.60 (d, 1H), 6.46 (s, 1H), 4.05 (s, 3H), 1.30 (s, 9H).

LC-MS: ESI 544.1 (M+H)$^+$.

Example 5

Preparation of 4-{4-[3-(5-tert-butyl-isoxazol-3-yl)-ureido]-3-methoxy-phenoxy}-7-methoxyquinolin-6-carboxamide (Compound 5)

Compound 5

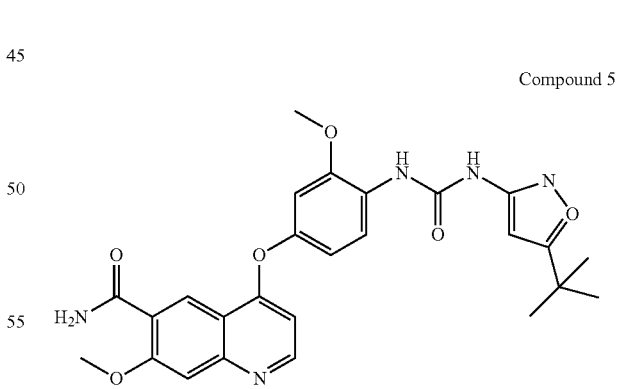

The preparation method was the same as Example 1, except that 4-amino-3-methoxyphenol (TCI) was used instead of 4-aminophenol in Step 1 to give 4-{4-[3-(5-tert-butyl-isoxazol-3-yl)-ureido]-3-methoxy-phenoxy}-7-methoxyquinolin-6-carboxamide.

1HNMR (DMSO-d6, 400 MHz) δ: 10.07 (s, 1H), 8.74 (s, 1H), 8.72 (s, 1H), 8.66-8.68 (d, 1H), 8.21-8.23 (d, 1H), 7.87 (br, 1H), 7.75 (br, 1H), 7.52 (s, 1H), 7.08-7.09 (d, 1H), 6.85-6.88 (dd, 1H), 6.54-6.56 (d, 1H), 6.48 (s, 1H), 4.04 (s, 3H), 3.89 (s, 3H), 1.30 (s, 9H).
LC-MS: ESI 506.1.1 (M+H)+.

Example 6

Preparation of 4-{4-[3-(5-tert-butyl-isoxazol-3-yl)-ureido]-3-methyl-phenoxy}-7-methoxyquinolin-6-carboxamide (Compound 6)

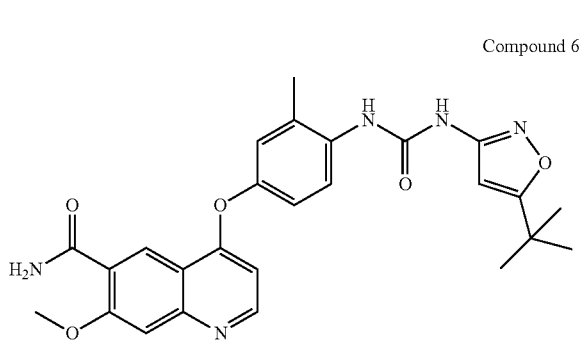 [SMILES: COc1cc2nccc(Oc3ccc(NC(=O)Nc4cc(C(C)(C)C)on4)c(C)c3)c2cc1C(N)=O]

Compound 6

The preparation method was the same as Example 1, except that 4-amino-3-methylphenol (TCI) was used instead of 4-aminophenol in Step 1 to give 4-{4-[3-(5-tert-butyl-isoxazol-3-yl)-ureido]-3-methyl-phenoxy}-7-methoxyquinolin-6-carboxamide.

1HNMR (DMSO-d6, 400 MHz) δ: 9.91 (s, 1H), 8.69 (s, 1H), 8.66-8.67 (d, 1H), 8.36 (s, 1H), 7.98-8.00 (d, 1H), 7.87 (br, 1H), 7.75 (br, 1H), 7.52 (s, 1H), 7.20-7.21 (d, 1H), 7.11-7.14 (dd, 1H), 6.49-6.51 (d, 1H), 6.47 (s, 1H), 4.04 (s, 3H), 2.29 (s, 3H), 1.30 (s, 9H).
LC-MS: ESI 490.2 (M+H)+.

Example 7

Preparation of 4-{2-Bromo-4-[3-(5-tert-butyl-isoxazol-3-yl)-ureido]-phenoxy}-7-methoxyquinolin-6-carboxamide (Compound 7)

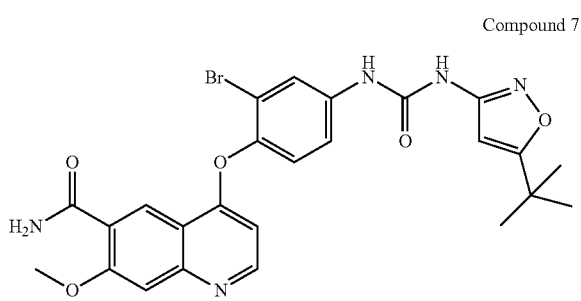 [SMILES: COc1cc2nccc(Oc3ccc(NC(=O)Nc4cc(C(C)(C)C)on4)cc3Br)c2cc1C(N)=O]

Compound 7

The preparation method was the same as Example 1, except that 4-amino-2-bromophenol (TCI) was used instead of 4-aminophenol in Step 1 to give 4-{2-bromo-4-[3-(5-tert-butyl-isoxazol-3-yl)-ureido]-phenoxy}-7-methoxyquinolin-6-carboxamide.

1HNMR (DMSO-d6, 400 MHz) δ: 9.69 (s, 1H), 9.14 (s, 1H), 8.72 (s, 1H), 8.66-8.68 (d, 1H), 8.09-8.10 (d, 1H), 7.88 (br, 1H), 7.77 (br, 1H), 7.54 (s, 1H), 7.44-7.49 (dd, 1H), 7.42-7.44 (d, 1H), 6.54 (s, 1H), 6.38-6.39 (d, 1H), 4.04 (s, 3H), 1.31 (s, 9H).
LC-MS: ESI 555.0 (M+H)+.

Example 8

Preparation of 4-{4-[3-(5-tert-butyl-isoxazol-3-yl)-ureido]-2-chloro-phenoxy}-7-methoxyquinolin-6-carboxamide (Compound 8)

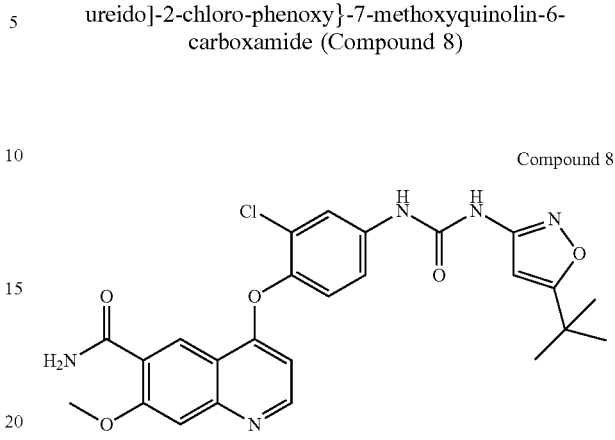

Compound 8

The preparation method was the same as Example 1, except that 4-amino-2-chlorophenol (TCI) was used instead of 4-aminophenol in Step 1 to give 4-{4-[3-(5-tert-butyl-isoxazol-3-yl)-ureido]-2-chloro-phenoxy}-7-methoxyquinolin-6-carboxamide.

1HNMR (DMSO-d6, 400 MHz) δ: 9.70 (s, 1H), 9.16 (s, 1H), 8.71 (s, 1H), 8.67-8.68 (d, 1H), 7.96 (s, 1H), 7.89 (br, 1H), 7.71 (br, 1H), 7.54 (s, 1H), 7.46 (m, 2H), 6.53 (s, 1H), 6.40-6.41 (d, 1H), 4.04 (s, 3H), 1.30 (s, 9H).
LC-MS: ESI 510.1 (M+H)+.

Example 9

Preparation of 4-{4-[3-(5-tert-butyl-isoxazol-3-yl)-ureido]-2-fluoro-phenoxy}-7-methoxyquinolin-6-carboxamide (Compound 9)

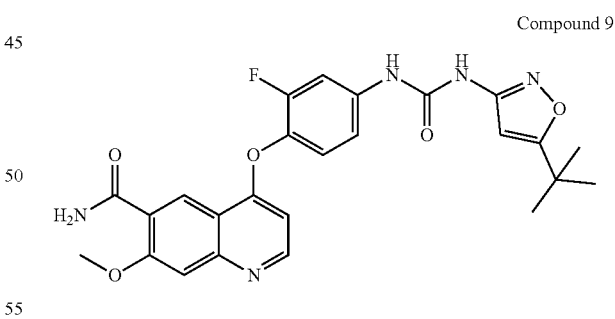

Compound 9

The preparation method was the same as Example 1, except that 4-amino-2-fluorophenol (TCI) was used instead of 4-aminophenol in Step 1 to give 4-{4-[3-(5-tert-butyl-isoxazol-3-yl)-ureido]-2-fluoro-phenoxy}-7-methoxyquinolin-6-carboxamide.

1HNMR (DMSO-d6, 400 MHz) δ: 9.67 (s, 1H), 9.17 (s, 1H), 8.70 (s, 1H), 8.68-8.69 (d, 1H), 7.88 (br, 1H), 7.75-7.79 (m, 2H), 7.54 (s, 1H), 7.43-7.47 (t, 1H), 7.28-7.31 (m, 1H), 6.51-6.53 (m, 2H), 6.48 (s, 1H), 4.04 (s, 3H), 1.30 (s, 9H).
LC-MS: ESI 494.1 (M+H)+.

Example 10

Preparation of 4-[4-[3-(5-tert-butyl-isoxazol-3-yl)-ureido]-3-(4-methyl-piperazin-1-yl)-phenoxy]-7-methoxyquinolin-6-carboxamide (Compound 10)

Compound 10

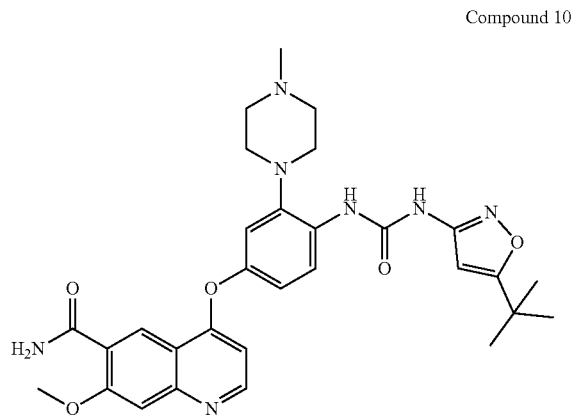 [SMILES: COc1cc2nccc(Oc3ccc(NC(=O)Nc4cc(C(C)(C)C)on4)c(N4CCN(C)CC4)c3)c2cc1C(N)=O]

The preparation method was the same as Example 1, except that 4-amino-3-(4-methylpiperazin-1-yl)-phenol (TCI) was used instead of 4-aminophenol in Step 1 to give 4-[4-[3-(5-tert-butyl-isoxazol-3-yl)-ureido]-3-(4-methyl-piperazin-1-yl)-phenoxy]-7-methoxyquinolin-6-carboxamide.

$^1$HNMR (DMSO-d6, 400 MHz) δ: 10.43 (s, 1H), 8.85 (br, 1H), 871 (s, 1H), 8.65-8.66 (d, 1H), 8.19-8.22 (d, 1H), 7.87 (br, 1H), 7.76 (br, 1H), 7.52 (s, 1H), 7.16-7.17 (d, 1H), 7.01-7.04 (dd, 1H), 6.51-6.52 (d, 1H), 6.40 (s, 1H), 4.04 (s, 3H), 4.05 (s, 3H), 2.93 (m, 4H), 2.58 (m, 4H), 2.26 (s, 3H), 1.31 (s, 9H).

LC-MS: ESI 574.1 (M+H)$^+$.

Example 11

Preparation of 4-{4-[3-(5-tert-butyl-isoxazol-3-yl)-1-methyl-ureido]-phenoxy}-7-methoxyquinolin-6-carboxamide (Compound 11)

Compound 11

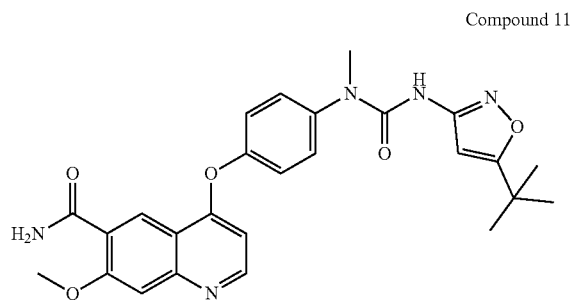 [SMILES: COc1cc2nccc(Oc3ccc(N(C)C(=O)Nc4cc(C(C)(C)C)on4)cc3)c2cc1C(N)=O]

The preparation method was the same as Example 1, except that 4-methylamino-phenol (TCI) was used instead of 4-aminophenol in Step 1 to give 4-{4-[3-(5-tert-butyl-isoxazol-3-yl)-1-methyl-ureido]-phenoxy}-7-methoxyquinolin-6-carboxamide.

$^1$HNMR (DMSO-d6, 400 MHz) δ: 9.35 (s, 1H), 8.71-8.72 (d, 1H), 8.69 (s, 1H), 7.88 (br, 1H), 7.76 (br, 1H), 7.53 (s, 1H), 7.45-7.47 (d, 2H), 7.32-7.34 (d, 2H), 6.66-6.67 (d, 1H), 6.51 (s, 1H), 4.04 (s, 3H), 3.30 (s, 3H), 1.31 (s, 9H).

LC-MS: ESI 490.3 (M+H)$^+$.

Example 12

Preparation of 4-{4-[3-(5-tert-butyl-isoxazol-3-yl)-3-methyl-ureido]-3-chloro-phenoxy}-7-methoxyquinolin-6-carboxamide (Compound 12)

Compound 12

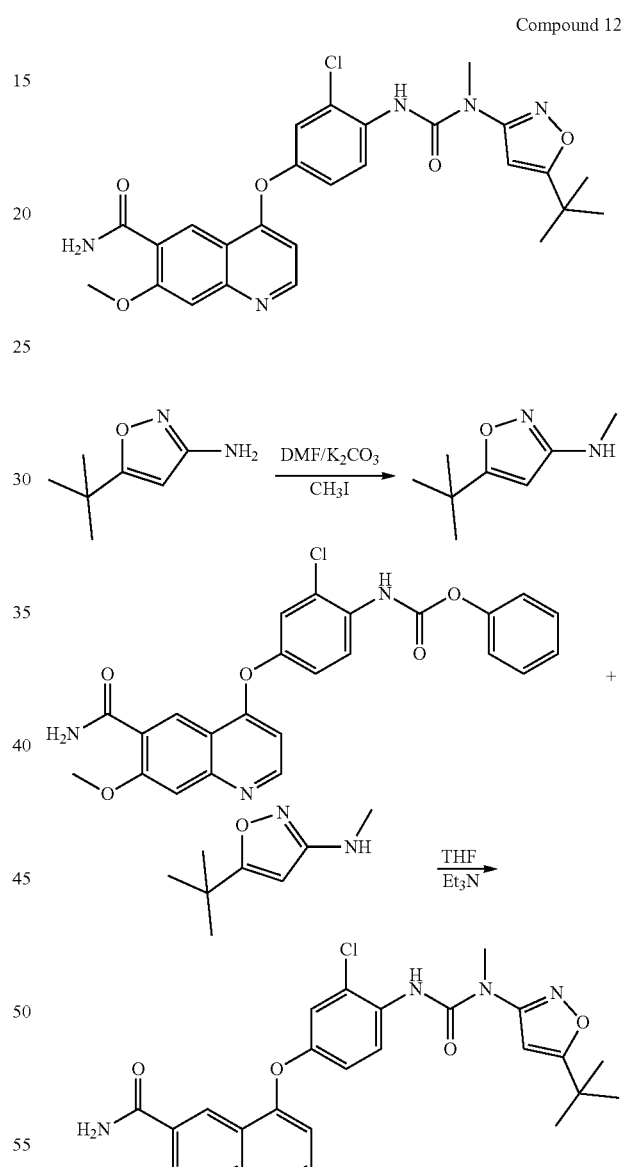

Step 1: Preparation of (5-tert-butyl-isoxazol-3-yl)-methyl-amine

At room temperature, 3-amino-5-tert-butyl isoxazole (purchased from TCI) (350 mg, 2.50 mmol) was dissolved in 10 ml of DMF, and potassium carbonate (1.04 g, 7.50 mmol) and iodomethane (426 mg, 3.0 mmol) were added successively at room temperature. The mixture was stirred at room temperature under nitrogen atmosphere for 15 h. The reaction solution was slowly poured into water, and extracted with ethyl acetate (30 ml×3). The organic phase was washed twice with saturated NaCl solution, dried over anhydrous sodium sulfate, filtered and the filtrate was concentrated under reduced pressure. The residues were purified via column chromatography (eluent: dichloromethane/methanol) to give 40 mg oil.

Step 2: Preparation of 4-{4-[3-(5-tert-butyl-isoxazol-3-yl)-3-methyl-ureido]-3-chloro-phenoxy}-7-methoxyquinolin-6-carboxamide The (5-tert-butyl-isoxazol-3-yl)-methyl-amine (28 mg, 0.181 mmol) obtained in Step 1, phenyl [4-(6-carbamoyl-7-methoxy-quinolin-4-yloxy)-2-chloro-phenyl]-carbamate (prepared in Step 2 of Example 25) (84 mg, 0.181 mmol) and triethylamine (73 mg, 0.725 mmol) were dissolved in 10 ml of THF and the reaction mixture was refluxed overnight. The next day, the reaction solution was concentrated under a reduced pressure, and the residues were purified via column chromatography (eluent: dichloromethane/methanol) to give 30 mg of 4-{4-[3-(5-tert-butyl-isoxazol-3-yl)-3-methyl-ureido]-3-chloro-phenoxy}-7-methoxyquinolin-6-carboxamide, as a solid.

$^1$HNMR (DMSO-d6, 400 MHz) δ: 10.21 (s, 1H), 8.70-8.71 (d, 1H), 8.67 (s, 1H), 7.88 (br, 1H), 7.76 (br, 1H), 7.62 (d, 1H), 7.54 (s, 1H), 7.33-7.36 (dd, 1H), 6.58-6.59 (d, 1H), 6.58 (s, 1H), 4.04 (s, 3H), 3.39 (s, 3H), 1.31 (s, 9H).

LC-MS: ESI 524.2 (M+H)+.

Example 13

Preparation of 4-{4-[3-(3-tert-butyl-isoxazol-5-yl)-ureido]-3-chloro-phenoxy}-7-methoxyquinolin-6-carboxamide (Compound 13)

Compound 13

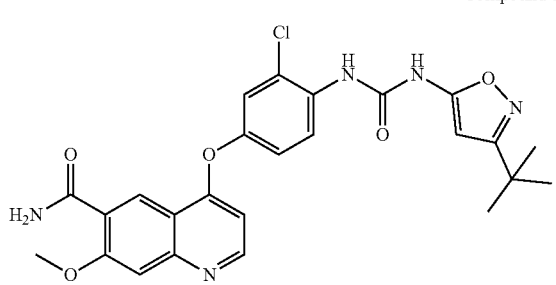

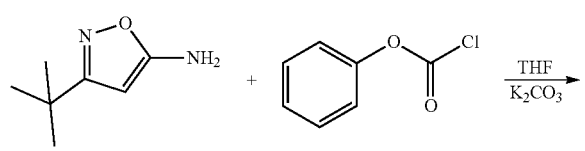

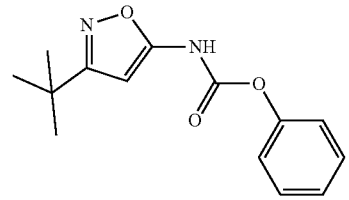

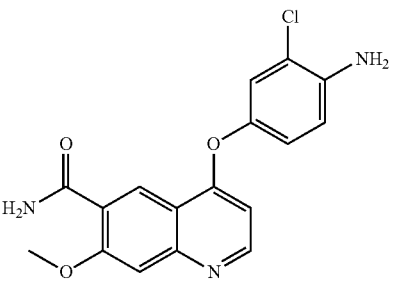

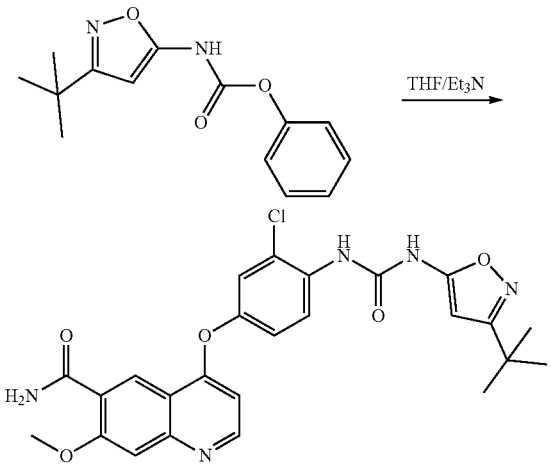

Step 1: Preparation of phenyl (3-tert-butyl-isoxazol-5-yl)-carbamate

The preparation method was the same as step 2 of example 1, except that 3-tert-butyl-isoxazol-5-ylamine (TCI) was used instead of 5-tert-butyl-isoxazol-3-ylamine in Step 2 of example 1.

Step 2: Preparation of 4-{4-[3-(3-tert-butyl-isoxazol-5-yl)-ureido]-3-chloro-phenoxy}-7-methoxy-quinolin-6-carboxamide The preparation method was the same as step 3 of example 1, except that phenyl (3-tert-butyl-isoxazol-5-yl)-carbamate was used instead of phenyl (5-tert-butyl-isoxazol-3-yl)-carbamate in Step 3 of example 1.

$^1$HNMR (DMSO-d6, 400 MHz) δ: 10.78 (s, 1H), 8.69-8.70 (d, 1H), 8.67 (s, 1H), 8.24-8.26 (d, 1H), 7.87 (br, 1H), 7.75 (br, 1H), 7.60-7.61 (d, 1H), 7.54 (s, 1H), 7.31-7.34 (dd, 1H), 6.58-6.59 (d, 1H), 6.09 (s, 1H), 4.04 (s, 3H), 1.27 (s, 9H).

LC-MS: ESI 510.1 (M+H)$^+$.

Example 14

Preparation of 4-{4-[3-(5-tert-butyl-isoxazol-3-yl)-ureido]-3-chloro-phenoxy}-7-methoxyquinolin-6-carboxamide (Compound 14)

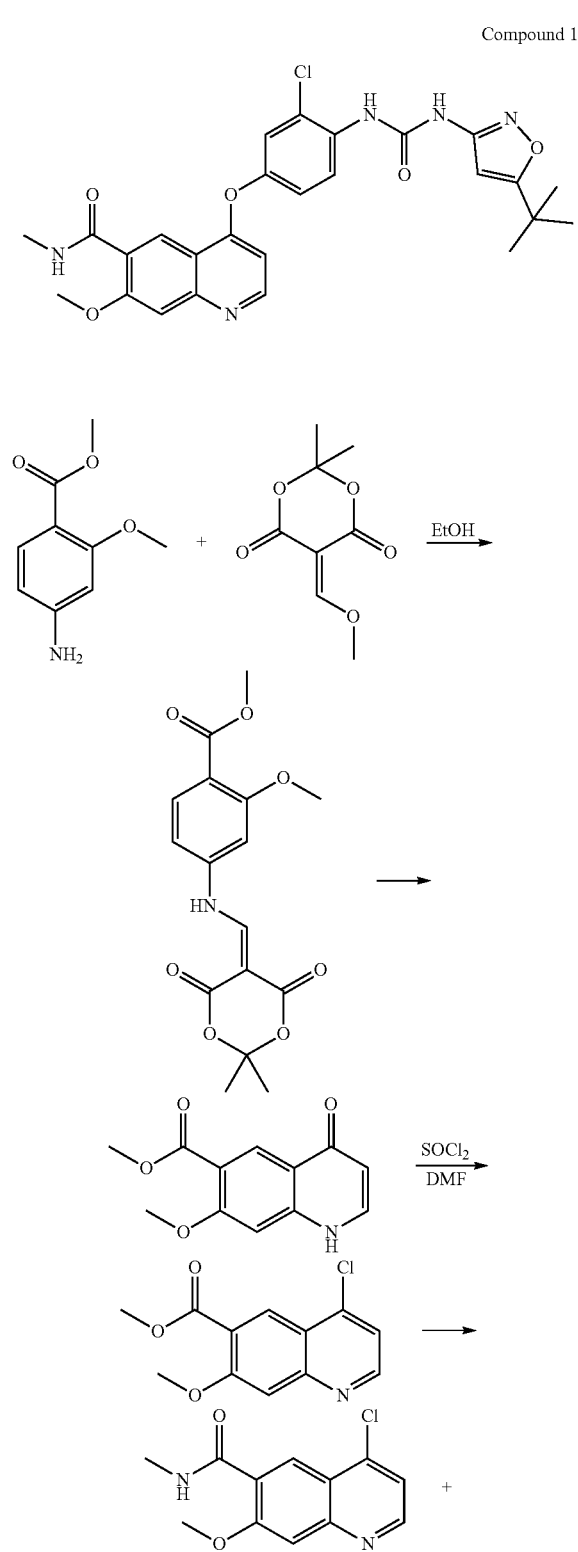

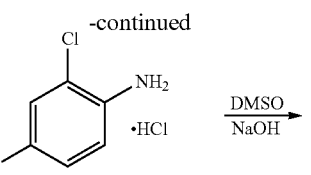

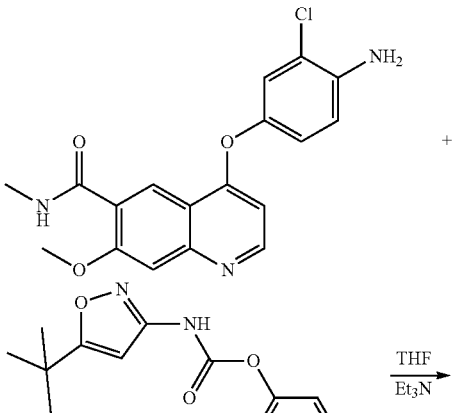

Step 1: Preparation of methyl 4-[(2,2-dimethyl-4,6-dioxo-[1,3]-diox-5-ylidenemethyl)-amino]-2-methoxy-carbamate At room temperature, methyl 4-amino-2-methoxybenzoate (purchased from Shanghai Darui) (3.62 g, 0.02 mol) and 5-methoxymethylene-2,2-dimethyl-[1,3]dioxane-4,6-dione (purchased from Shanghai Darui) (4.46 g, 0.024 mmol) were added to 50 ml of ethanol and reacted under reflux for 4 hours. The reaction solution was cooled to room temperature, filtered, and the filter cake was washed with a small amount of ethanol, and dried by air (60° C.) overnight to obtain 6.6 g of methyl 4-[(2,2-dimethyl-4,6-dioxo-[1,3]-diox-5-ylidenemethyl)-amino]-2-methoxy-carbamate, as a white solid.

Step 2: Preparation of methyl 7-methoxy-4-oxo-1,4-dihydro-quinolin-6-carboxylate Methyl 4-[(2,2-dimethyl-4,6-dioxo-[1,3]-diox-5-ylidenemethyl)-amino]-2-methoxy-carbamate (6.6 g, 0.019 mol) obtained in step 1 was added to 80 ml of diphenyl ether-biphenyl eutectic and heated to 250° C. under nitrogen protection (three times of gas exchange) and reacted for 0.5 h. The reaction solution was cooled to room temperature, and 80 ml of methyl tert-butyl ether was added and the reaction mixture was stirred at room temperature for 30 min. The mixture was filtered, and the filter cake was washed with a small amount of methyl tert-butyl ether, and dried by air (60° C.) overnight to obtain 4.0 g of 7-methoxy-4-oxo-1,4-dihydro-quinoline-6-carboxylate, as a nattierblue solid.

Step 3: Preparation of methyl 4-chloro-7-methoxy-quinolin-6-carboxylate

Methyl 7-methoxy-4-oxo-1,4-dihydro-quinolin-6-carboxylate (4.0 g, 0.016 mmol) obtained in step 2 was added to 40 ml of thionyl chloride, and 5 drops of DMF was added at room temperature. The mixture was heated to reflux for 2h. The reaction solution was cooled to room temperature, and the thionyl chloride was concentrated to obtain a crude yellow solid. 50 ml of water was added thereto under stirring. The mixture was adjusted to about pH 7-8 with saturated sodium bicarbonate aqueous solution, and extracted with ethyl acetate (80 ml×2). The organic phase was washed with saturated NaCl solution, dried over anhydrous sodium sulfate, filtered and the filtrate was concentrated under reduced pressure. The residues were purified via column chromatography (eluent: dichloromethane/methanol) to give 2.9 g of methyl 4-chloro-7-methoxy-quinolin-6-carboxylate, as a yellow solid.

Step 4: Preparation of 4-chloro-7-methoxy-quinolin-6-carboxylic acid methylamine Methyl 4-chloro-7-methoxy-quinolin-6-carboxylate (200 mg, 0.80 mmol) obtained in step 3 was added to 5 ml of an aqueous solution of methylamine, and then heated to 60° C. under nitrogen atmosphere and reacted for 0.5 h. The reaction solution was cooled to room temperature, and poured into 50 ml of water, and then extracted with ethyl acetate (50 ml×2). The organic phase was washed with saturated NaCl solution, dried over anhydrous sodium sulfate, filtered and the filtrate was concentrated under reduced pressure to obtain 228 mg of 4-chloro-7-methoxy-quinolin-6-carboxylic acid methylamine, as a solid.

Step 5: Preparation of 4-(4-amino-3-chloro-phenoxy)-7-methoxy-quinolin-6-carboxylic acid methylamine 4-Amino-3-chlorophenol hydrochloride (3.29 mg, 1.824 mmol) was dissolved in 10 ml DMSO at room temperature and sodium hydroxide (146 mg, 3.648 mmol) was added. The mixture was stirred at room temperature for 0.5 hours. 4-Chloro-7-methoxy-quinolin-6-carboxylic acid methylamine (228 mg, 0.912 mmol) (obtained in step 4) was added and the mixture was heated to 100° C. for 2 hours. The reaction solution was cooled to room temperature, and poured into 50 ml of water, and then extracted with ethyl acetate (50 ml×2). The organic phase was washed with saturated NaCl solution, dried over anhydrous sodium sulfate, filtered and the filtrate was concentrated under reduced pressure. The residues were purified via column chromatography (eluent: dichloromethane/methanol) to give 210 mg of 4-(4-amino-3-chloro-phenoxy)-7-methoxy-quinolin-6-carboxylic acid methylamine, as a solid.

Step 6: Preparation of 4-{4-[3-(5-tert-butyl-isoxazol-3-yl)-ureido]-3-chloro-phenoxy}-7-methoxy-quinolin-6-carboxylic acid methylamide The 4-(4-amino-3-chloro-phenoxy)-7-methoxy-quinolin-6-carboxylic acid methylamine (210 mg, 0.586 mmol) obtained in Step 5, phenyl (5-tert-butyl-isoxazol-3-yl)-carbamate (305 mg, 1.174 mmol) obtained in Step 2 of Example 1 and triethylamine (237 mg, 2.344 mmol) were dissolved in 10 ml of THF and the reaction mixture was refluxed overnight. The next day, the reaction solution was concentrated under a reduced pressure, and the residues were purified via column chromatography (eluent: dichloromethane/methanol) to give 35 mg of 4-{4-[3-(5-tert-butyl-isoxazol-3-yl)-ureido]-3-chloro-phenoxy}-7-methoxyquinolin-6-carboxylic acid methylamide, as a solid.

$^1$HNMR (DMSO-d6, 400 MHz) δ: 10.25 (s, 1H), 8.80 (s, 1H), 8.69-8.70 (d, 1H), 8.61 (s, 1H), 8.38 (d, 1H), 8.27-8.29 (d, 1H), 7.59 (s, 1H), 7.53 (s, 1H), 7.31-7.33 (dd, 1H), 6.58-6.60 (d, 1H), 6.48 (s, 1H), 4.04 (s, 3H), 2.85-2.86 (d, 3H), 1.31 (s, 9H).

LC-MS: ESI 524.1 (M+H)+.

Example 15

Preparation of 4-{4-[3-(3-tert-butyl-isoxazol-5-yl)-ureido]-3-chloro-phenoxy}-7-methoxyquinolin-6-carboxylic acid methylamide (Compound 15)

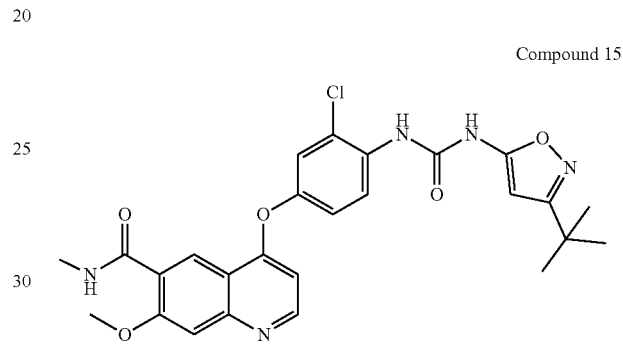

Compound 15

The preparation method was the same as step 6 of Example 14, except that phenyl (3-tert-butyl-isoxazol-5-yl)-carbamate obtained in Step 1 of Example 13 was used instead of phenyl (5-tert-butyl-isoxazol-3-yl)-carbamate obtained in Step 6 of Example 14.

$^1$HNMR (DMSO-d6, 400 MHz) δ: 10.78 (s, 1H), 8.69-8.70 (d, 1H), 8.60-8.61 (m, 1H), 8.37-8.38 (m, 1H), 8.23-8.25 (d, 1H), 7.59-7.60 (d, 1H), 7.53 (s, 1H), 7.31-7.34 (dd, 1H), 6.58-6.59 (d, 1H), 6.09 (s, 1H), 4.03 (s, 3H), 2.84-2.85 (d, 3H), 1.27 (s, 9H).

LC-MS: ESI 524.2 (M+H)+.

Example 16

Preparation of 4-{4-[3-(5-tert-butyl-isoxazol-3-yl)-ureido]-3-chloro-phenoxy}-7-methoxyquinolin-6-carboxylic acid diethyl amide (Compound 16)

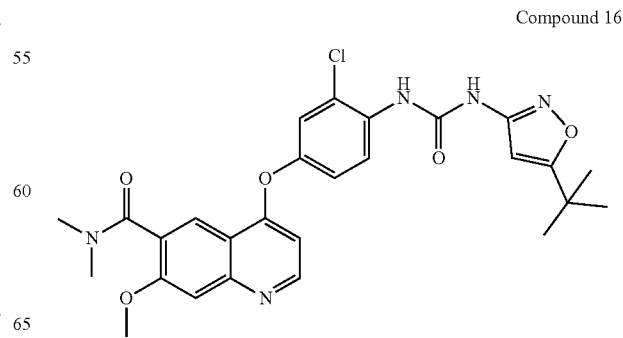

Compound 16

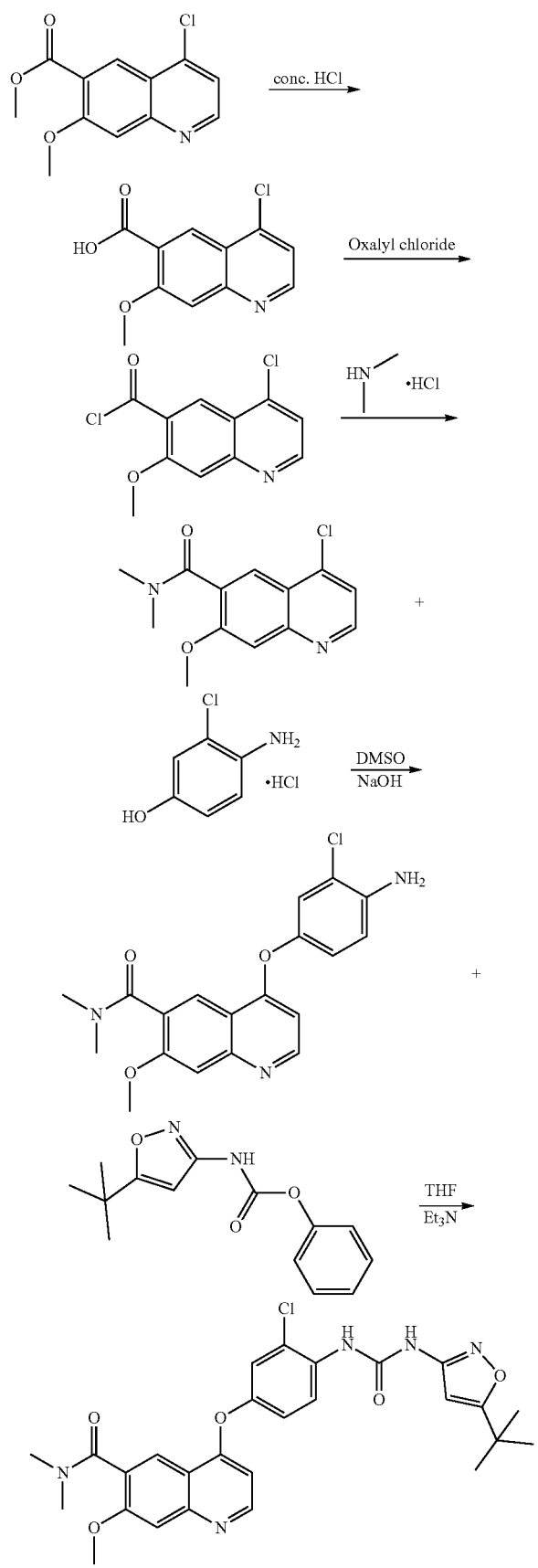

Step 1: Preparation of
4-chloro-7-methoxy-quinolin-6-carboxylic acid

Methyl 4-chloro-7-methoxy-quinolin-6-carboxylate (obtained in Step 3 of Example 14) (1.0 g, 3.97 mmol) was added to 10 mL of concentrated hydrochloric acid and heated to 90° C. for 0.5 hour under nitrogen atmosphere. The reaction mixture was cooled to room temperature and poured into 50 ml of water, and aqueous ammonia was added to adjust the PH to weak acidity. The mixture was filtered, and the filter cake was washed with water and dried (60° C.) overnight to give 1.08 g of 4-chloro-7-methoxy-quinolin-6-carboxylic acid as a solid.

Step 2: Preparation of
4-chloro-7-methoxy-quinolin-6-carbonyl chloride

4-Chloro-7-methoxy-quinolin-6-carboxylic acid (400 mg, 1.684 mmol) obtained in Step 1 was added to 15 ml of thionyl chloride, and 2 drops of DMF was added at room temperature. The mixture was heated to reflux for 2 hours. The reaction mixture was cooled to room temperature, and the thionyl chloride was concentrated to give a crude product as a yellow solid. The solid was added with 10 ml of toluene and then concentrated to give 300 mg of 4-chloro-7-methoxy-quinolin-6-carbonyl chloride (crude product) as a yellow solid.

Step 3: Preparation of
4-chloro-7-methoxy-quinolin-6-carboxylic acid diethylamide Dimethylamine hydrochloride (191 mg, 2.342 mmol), N,N-diisopropylethylamine (453 mg, 3.513 mmol) was added to 10 mL of dichloromethane. The mixture was stirred for 0.5 hours at room temperature. 4-Chloro-7-methoxy-quinolin-6-carbonyl chloride (300 mg, 1.171 mmol) (prepared in Step 2) was dissolved in 10 ml of dichloromethane, and then added dropwise to the above mixture. The mixture was allowed to react at room temperature for 2 hours. The reaction solution was poured into 50 ml of water and extracted with dichloromethane (50 ml×2). The organic phase was washed with saturated NaCl solution, dried over anhydrous sodium sulfate, filtered and the filtrate was concentrated under reduced pressure. The residues were purified via column chromatography (eluent: dichloromethane/methanol) to give 147 mg of 4-chloro-7-methoxy-quinolin-6-carboxylic acid diethylamide as a solid.

Step 4: Preparation of 4-(4-amino-3-chloro-phenoxy)-7-methoxy-quinolin-6-carboxylic acid diethylamide The preparation method was the same as step 5 of Example 14, except that 4-chloro-7-methoxy-quinolin-6-carboxylic acid diethylamide (obtained in Step 3 of Example 16) was used instead of 4-chloro-7-methoxy-quinolin-6-carboxylic acid methylamine obtained in Step 5 of Example 14.

Step 5: Preparation of 4-{4-[3-(5-tert-butyl-isoxazol-3-yl)-ureido]-3-chloro-phenoxy}-7-methoxy-quinolin-6-carboxylic acid diethyl amide The preparation method was the same as step 6 of Example 14, except that 4-(4-amino-3-chloro-phenoxy)-7-methoxy-quinolin-6-carboxylic acid diethylamide (obtained in Step 4 of Example 16) was used instead of 4-(4-amino-3-chloro-phenoxy)-7-methoxy-quinolin-6-carboxylic acid methylamine obtained in Step 6 of Example 14.

¹HNMR (DMSO-d6, 400 MHz) δ: 10.24 (s, 1H), 8.78 (s, 1H), 8.67-8.68 (d, 1H), 8.25-8.28 (d, 1H), 8.04 (s, 1H), 7.57-7.58 (d, 1H), 7.52 (s, 1H), 7.29-7.32 (dd, 1H), 6.58-6.59 (d, 1H), 6.47 (s, 1H), 3.98 (s, 3H), 3.03 (s, 3H), 2.80 (s, 3H), 1.31 (s, 9H).

LC-MS: ESI 538.1 (M+H)+.

Example 17

Preparation of 4-{4-[3-(5-tert-butyl-isoxazol-3-yl)-ureido]-3-chloro-phenoxy}-7-methoxyquinolin-6-carboxylic acid (2-methoxy-ethyl)-amide (Compound 17)

Compound 17

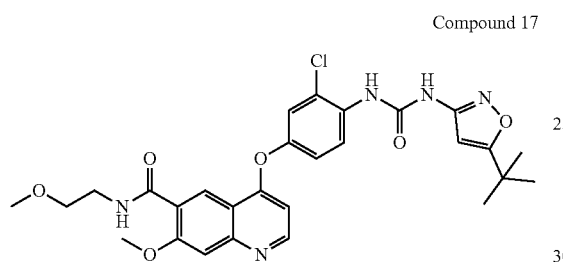

The preparation method was the same as Example 14, except that 2-methoxyethylamine (purchased from TCI) was used instead of methylamine aqueous solution in Step 4 to give 4-{4-[3-(5-tert-butyl-isoxazol-3-yl)-ureido]-3-chloro-phenoxy}-7-methoxyquinolin-6-carboxylic acid (2-methoxy-ethyl)-amide 1HNMR (DMSO-d6, 400 MHz) δ: 10.25 (s, 1H), 8.79 (s, 1H), 8.69-8.70 (d, 1H), 8.62 (s, 1H), 8.46 (d, 1H), 8.27-8.29 (d, 1H), 7.59-7.60 (d, 1H), 7.55 (s, 1H), 7.31-7.33 (dd, 1H), 6.58-6.59 (d, 1H), 6.48 (s, 1H), 4.04 (s, 3H), 3.50 (m, 4H), 3.31 (s, 3H), 1.31 (s, 9H).

LC-MS: ESI 568.1 (M+H)+.

Example 18

Preparation of 1-(5-tert-butyl-isoxazol-3-yl)-3-[2-chloro-4-(7-methoxy-6-nitro-quinolin-4-yloxy)-phenyl]-urea (Compound 18)

Compound 18

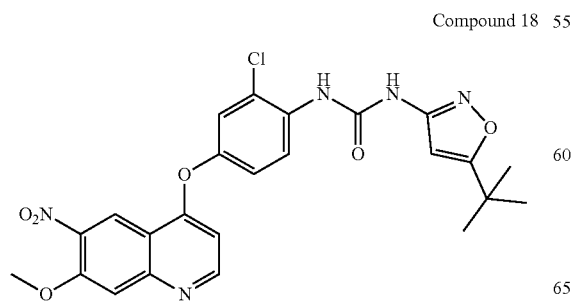

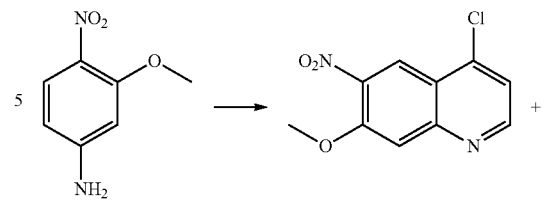

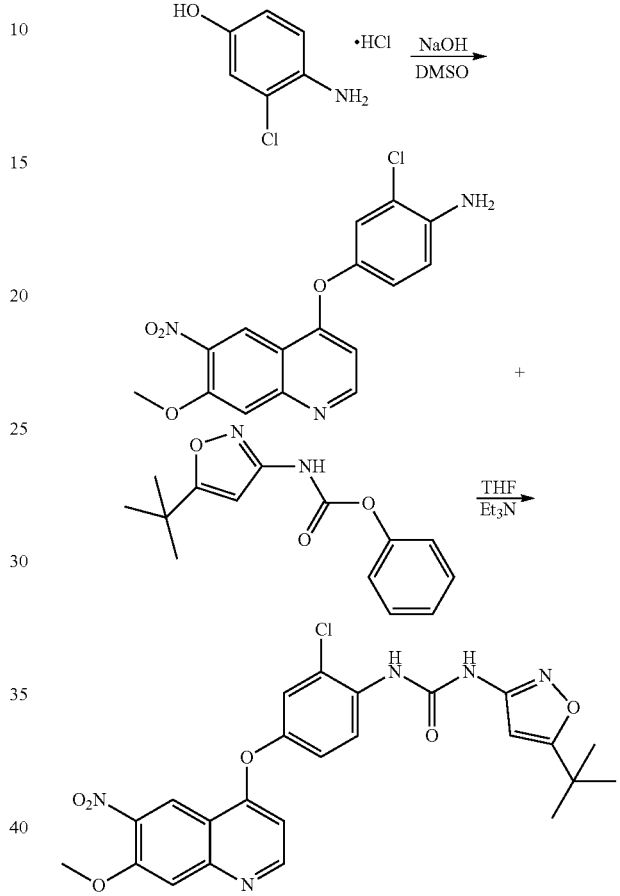

Step 1: Preparation of 4-chloro-7-methoxy-6-nitro-quinoline

The preparation method was the same as steps 1 to 3 of Example 14, except that 3-methoxy-4-nitrophenylamine (purchased from TCI) was used instead of methyl 4-amino-2-methoxybenzoate in Step 1 of Example 14 to give 4-chloro-7-methoxy-6-nitro-quinoline.

Step 2: Preparation of 2-chloro-4-(7-methoxy-6-nitro-quinolin-4-yloxy)-aniline

It was prepared in Step 1 of Example 63.

Step 3: Preparation of 1-(5-tert-butyl-isoxazol-3-yl)-3-[2-chloro-4-(7-methoxy-6-nitro-quinolin-4-yloxy)-phenyl]-urea The preparation method was the same as step 6 of Example 14, except that 2-chloro-4-(7-methoxy-6-nitro-quinolin-4-yloxy)-aniline was used instead of 4-(4-amino-3-chloro-phenoxy)-7-methoxy-quinolin-6-carboxylic acid methylamine in Step 6 of Example 14 to give 1-(5-tert-butyl-isoxazol-3-yl)-3-[2-chloro-4-(7-methoxy-6-nitro-quinolin-4-yloxy)-phen yl]-urea.

1HNMR (DMSO-d6, 400 MHz) δ: 10.25 (s, 1H), 879-8.80 (m, 3H), 8.28-8.31 (d, 1H), 7.75 (s, 1H), 7.63-7.64 (d, 1H), 7.34-7.37 (dd, 1H), 6.67-6.68 (d, 1H), 6.48 (s, 1H), 4.08 (s, 3H), 1.31 (s, 9H).

LC-MS: ESI 512.0 (M+H)+.

Example 19

Preparation of 1-(5-tert-butyl-isoxazol-3-yl)-3-[2-chloro-4-(6-cyano-7-methoxy-quinolin-4-yloxy)-phenyl]-urea (Compound 19)

Compound 19

The preparation method was the same as Example 18, except that 4-amino-2-methoxy-benzonitrile (purchased from TCI) was used instead of 3-methoxy-4-nitrophenylamine in Step 1 to give 1-(5-tert-butyl-isoxazol-3-yl)-3-[2-chloro-4-(6-cyano-7-methoxy-quinolin-4-yloxy)-phenyl]-urea.

1HNMR (DMSO-d6, 400 MHz) δ: 10.26 (s, 1H), 8.77-8.81 (m, 3H), 8.28-8.30 (d, 1H), 7.63 (s, 1H), 7.61-7.62 (d, 1H), 7.33-7.36 (dd, 1H), 6.64-6.65 (d, 1H), 6.47 (s, 1H), 4.08 (s, 3H), 1.31 (s, 9H).

LC-MS: ESI 492.2 (M+H)+.

Example 20

Preparation of N-(4-{4-[3-(5-tert-butyl-isoxazol-3-yl)-ureido]-3-chloro-phenoxy}-7-methoxyquinolin-6-acetamide (Compound 20)

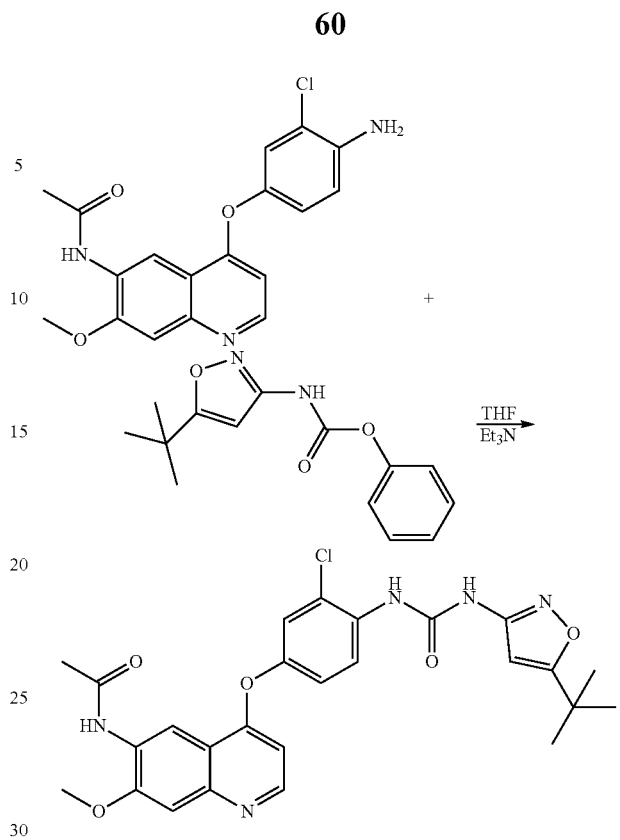

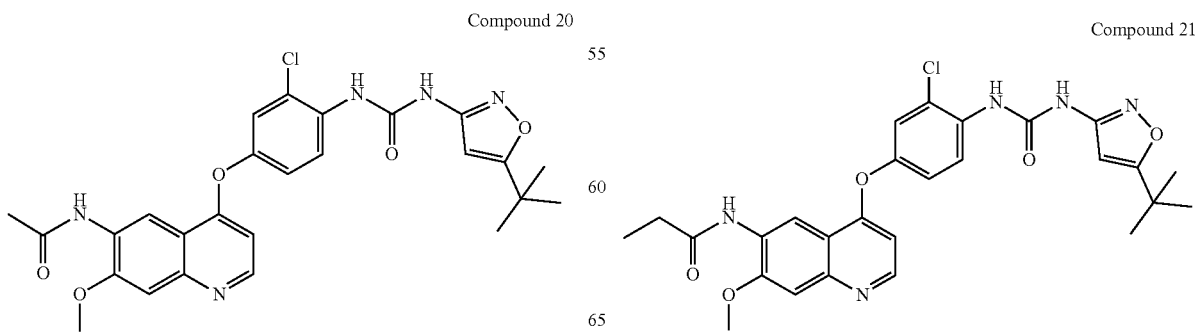

The preparation method was the same as Step 6 of Example 14, except that N-[4-(4-amino-3-chloro-phenoxy)-7-methoxy-quinolin-6-yl]-acetamide (prepared in step 5 of example 63) was used instead of 4-(4-amino-3-chloro-phenoxy)-7-methoxy-quinolin-6-carboxylic acid methylamine in Step 6 of Example 14 to give N-(4-{4-[3-(5-tert-butyl-isoxazol-3-yl)-ureido]-3-chloro-phenoxy}-7-methoxyquinolin-6-acetamide.

1HNMR (DMSO-d6, 400 MHz) δ: 10.23 (s, 1H), 9.47 (s, 1H), 8.98 (s, 1H), 8.77 (s, 1H), 8.54-8.55 (d, 1H), 8.24-8.27 (d, 1H), 7.52-7.53 (d, 1H), 7.47 (s, 1H), 7.25-7.28 (dd, 1H), 6.53-6.54 (d, 1H), 6.47 (s, 1H), 4.04 (s, 3H), 2.19 (s, 3H), 1.30 (s, 9H).

LC-MS: ESI 524.1 (M+H)+.

Example 21

Preparation of N-(4-{4-[3-(5-tert-butyl-isoxazol-3-yl)-ureido]-3-chloro-phenoxy}-7-methoxyquinolin-6-yl)-propionamide (Compound 21)

The preparation method was the same as Example 20, except that propionyl chloride (purchased from Shanghai Darui) was used instead of acetyl chloride in Step 3 of Example 20 to give N-(4-{4-[3-(5-tert-butyl-isoxazol-3-yl)-ureido]-3-chloro-phenoxy}-7-methoxyquinolin-6-yl)-propionamide.

$^1$HNMR (DMSO-d6, 400 MHz) δ: 10.23 (s, 1H), 9.38 (s, 1H), 9.02 (s, 1H), 8.77 (s, 1H), 8.54-8.55 (d, 1H), 8.24-8.26 (d, 1H), 7.53-7.54 (d, 1H), 7.47 (s, 1H), 7.25-7.28 (dd, 1H), 6.54-6.55 (d, 1H), 6.47 (s, 1H), 4.04s, 3H), 2.50 (m, 2H), 1.30 (s, 9H), 1.18-1.02 (t, 3H).

LC-MS: ESI 538.2 (M+H)+.

Example 22

Preparation of N-(4-{4-[3-(5-tert-butyl-isoxazol-3-yl)-ureido]-3-chloro-phenoxy}-7-methoxyquinolin-6-yl)-acrylamide (Compound 22)

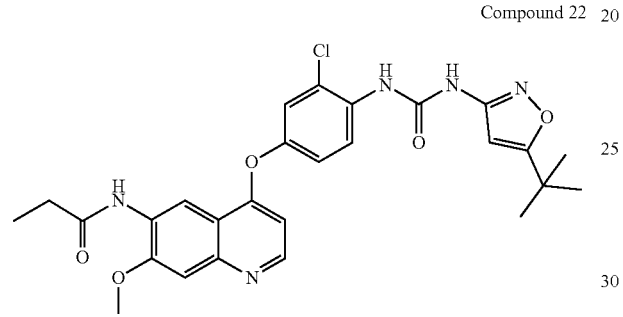

Compound 22

The preparation method was the same as Example 20, except that acryloyl chloride (purchased from Shanghai Darui) was used instead of acetyl chloride in Step 3 of Example 20 to give N-(4-{4-[3-(5-tert-butyl-isoxazol-3-yl)-ureido]-3-chloro-phenoxy}-7-methoxyquinolin-6-yl)-acrylamide.

$^1$HNMR (DMSO-d6, 400 MHz) δ: 10.24 (s, 1H), 9.73 (s, 1H), 9.12 (s, 1H), 8.79 (s, 1H), 8.56-8.57 (d, 1H), 8.25-8.27 (d, 1H), 7.54-7.55 (d, 1H), 7.50 (s, 1H), 7.27-7.30 (dd, 1H), 6.81-6.87 (m, 1H), 6.55-6.57 (d, 1H), 6.48 (s, 1H), 6.27-6.32 (m, 1H), 5.76-5.80 (m, 1H), 4.06 (s, 3H), 1.30 (s, 9H).

LC-MS: ESI 536.2 (M+H)+.

Example 23

Preparation of cyclopentane carboxylic acid (4-{4-[3-(5-tert-butyl-isoxazol-3-yl)-ureido]-3-chloro-phenoxy}-7-methoxyquinolin-6-yl)-amide (Compound 23)

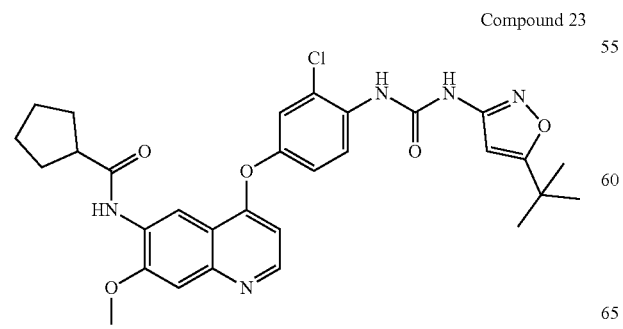

Compound 23

The preparation method was the same as Example 20, except that cyclopentane carbonyl chloride (purchased from TCI) was used instead of acetyl chloride in Step 3 of Example 20 to give cyclopentane carboxylic acid (4-{4-[3-(5-tert-butyl-isoxazol-3-yl)-ureido]-3-chloro-phenoxy}-7-methoxyquinolin-6-yl)-amide.

$^1$HNMR (DMSO-d6, 400 MHz) δ: 10.23 (s, 1H), 9.33 (s, 1H), 9.03 (s, 1H), 8.78 (s, 1H), 8.53-8.55 (d, 1H), 8.25-8.27 (d, 1H), 7.52-7.53 (d, 1H), 7.47 (s, 1H), 7.25-7.28 (dd, 1H), 6.53-6.54 (d, 1H), 6.48 (s, 1H), 4.04 (s, 3H), 3.08-3.09 (m, 1H), 1.54-1.89 (m, 8H), 1.30 (s, 9H).

LC-MS: ESI 578.2 (M+H)+.

Example 24

Preparation of 4-{5-[3-(5-tert-butyl-isoxazol-3-yl)-ureido]-pyridin-2-yloxy}-7-methoxyquinolin-6-carboxamide (Compound 24)

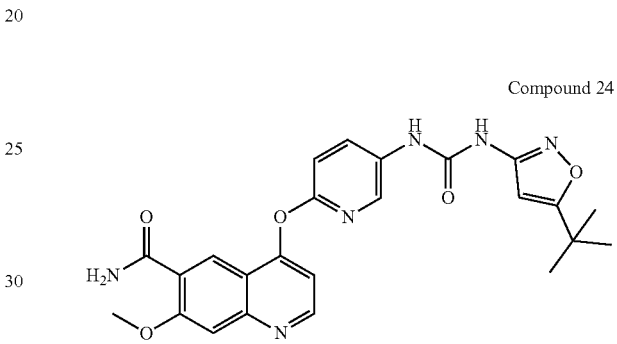

Compound 24

The preparation method was the same as Example 1, except that 5-amino-pyridine 2-ol (purchased from TCI) was used instead of 4-aminophenol in Step 1 of Example 1 to give 4-{5-[3-(5-tert-butyl-isoxazol-3-yl)-ureido]-pyridin-2-yloxy}-7-methoxy quinolin-6-carboxamide.

$^1$HNMR (DMSO-d6, 400 MHz) δ: 9.94 (s, 1H), 9.86 (s, 1H), 8.75-8.76 (d, 1H), 8.54 (s, 1H), 8.39 (d, 1H), 8.10-8.13 (dd, 1H), 7.87 (br, 1H), 7.73 (br, 1H), 7.54 (s, 1H), 7.33-7.35 (d, 1H), 6.86-6.88 (d, 1H), 6.52 (s, 1H), 4.03 (s, 3H), 1.30 (s, 9H).

LC-MS: ESI 477.1 (M+H)+.

Example 25

Preparation of 4-{4-[3-(5-tert-butyl-2H-pyrazol-3-yl)-ureido]-3-chloro-phenoxy}-7-methoxyquinolin-6-carboxamide (Compound 25)

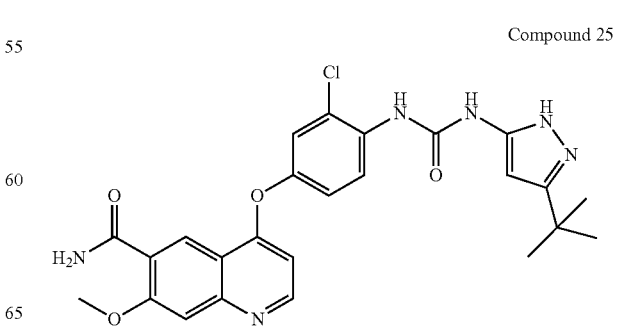

Compound 25

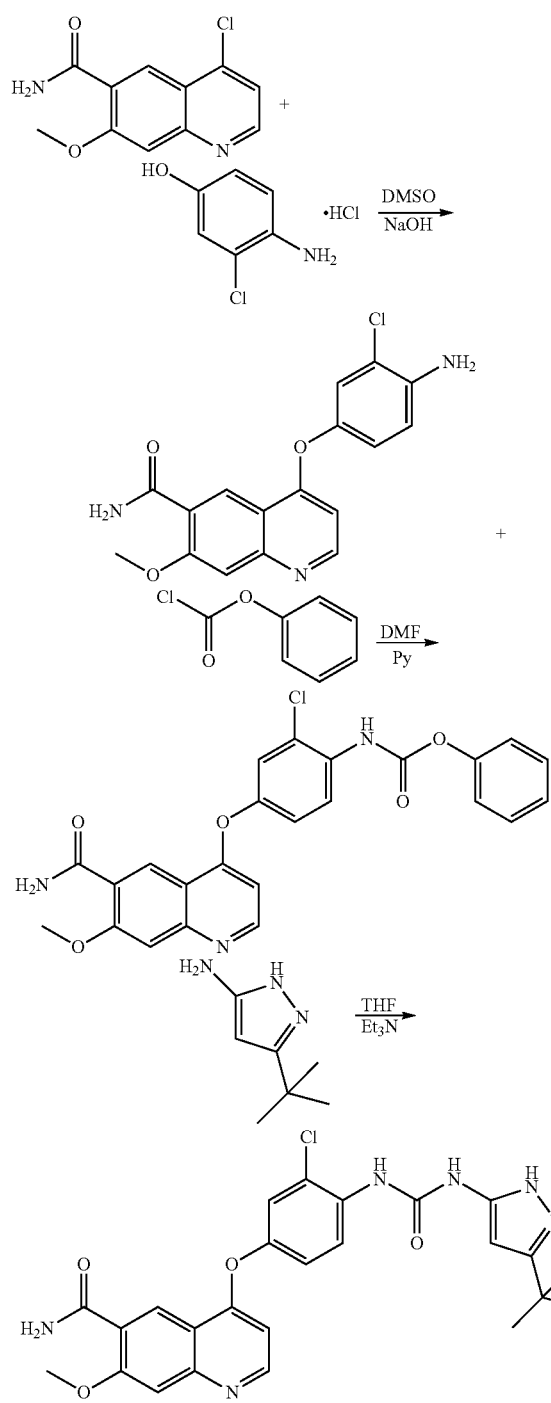

Step 1: Preparation of 4-(4-amino-3-chloro-phenoxy)-7-methoxy-quinolin-6-carboxamide At room temperature, 4-amino-3-chlorophenol hydrochloride (purchased from TCI) (30.6 g, 0.169 mol) was dissolved in 250 ml of DMSO, and sodium hydroxide (13.6 g, 0.338 mol) was added. The mixture was stirred at room temperature for 30 min. 4-Chloro-7-methoxy-quinolin-6-carboxamide (20 g, 0.0846 mmol) (purchased from Shanghai Titan) was added and the mixture was heated to 100° C. for 1 hour. The reaction solution was cooled to room temperature, was and then slowly poured into water. The resulted solid was filtered. The filtrate was extracted with ethyl acetate (80 ml*3). The organic phase was washed with saturated NaCl solution, dried over anhydrous sodium sulfate, filtered and the filtrate was concentrated under reduced pressure. The residues were purified via column chromatography (eluent: dichloromethane/methanol) to give 14.8 g of a yellow solid.

Step 2: Preparation of phenyl [4-(6-carbamoyl-7-methoxy-quinolin-4-yloxy)-2-chloro-phenyl]-carbamate 4-(4-Amino-3-chloro-phenoxy)-7-methoxy-quinolin-6-carboxamide (14.8 g, 43.1 mmol) (prepared in Example 1) was dissolved in 100 ml of DMF, and added with pyridine (10.2 g, 129.3 mmol) at room temperature. The mixture was cooled to 0-5° C. in an ice bath, and phenyl chloroformate (10.1 g, 64.7 mmol) was slowly added dropwise. The ice bath was removed and the mixture was slowly warmed to room temperature, and reacted for 4 hours. After the reaction was completed by TLC monitoring, the reaction solution was slowly poured into water (800 ml) to precipitate a solid, which was stirred at room temperature for 30 minutes, and then filtered. The filter cake was washed with water. The resulting solid was air-dried overnight (60° C.) to give 18.9 g of a yellow solid.

Step 3: Preparation of 4-{4-[3-(5-tert-butyl-2H-pyrazol-3-yl)-ureido]-3-chloro-phenoxy}-7-methoxyquinolin-6-carboxamide Phenyl [4-(6-carbamoyl-7-methoxy-quinolin-4-yloxy)-2-chloro-phenyl]-carbamate obtained in Step 2, 5-tert-butyl-2H-pyrazol-3-ylamine (purchased from TCI) (50 mg, 0.356 mmol) and triethylamine (72 mg, 0.712 mmol) were dissolved in 10 mL THF and refluxed overnight. The next day, the reaction mixture was concentrated under reduced pressure and the residues were purified by column chromatography (eluent: dichloromethane/methanol) to give 42 mg of 4-{4-[3-(5-tert-butyl-2H-pyrazol-3-yl)-ureido]-3-chloro-phenoxy}-7-methoxyquinolin-6-carboxamide as a solid.

$^1$HNMR (DMSO-d6, 400 MHz) δ: 12.11 (s, 1H), 9.60 (s, 1H), 8.68-8.69 (d, 1H), 8.68 (s, 1H), 8.40-8.42 (d, 1H), 7.87 (br, 1H), 7.75 (br, 1H), 7.56 (d, 1H), 7.53 (s, 1H), 7.28-7.31 (dd, 1H), 6.57-6.58 (d, 1H), 5.89 (br, 1H), 4.07 (s, 3H), 1.27 (s, 9H).

LC-MS: ESI 509.1 (M+H)+.

Example 26

Preparation of 4-{4-[3-(5-tert-butyl-2-methyl-2H-pyrazol-3-yl)-ureido]-3-chloro-phenoxy}-7-methoxyquinolin-6-carboxamide (Compound 26)

Compound 26

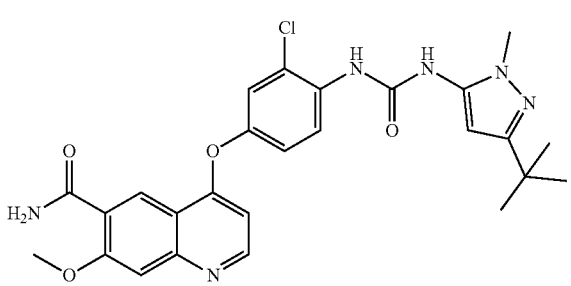

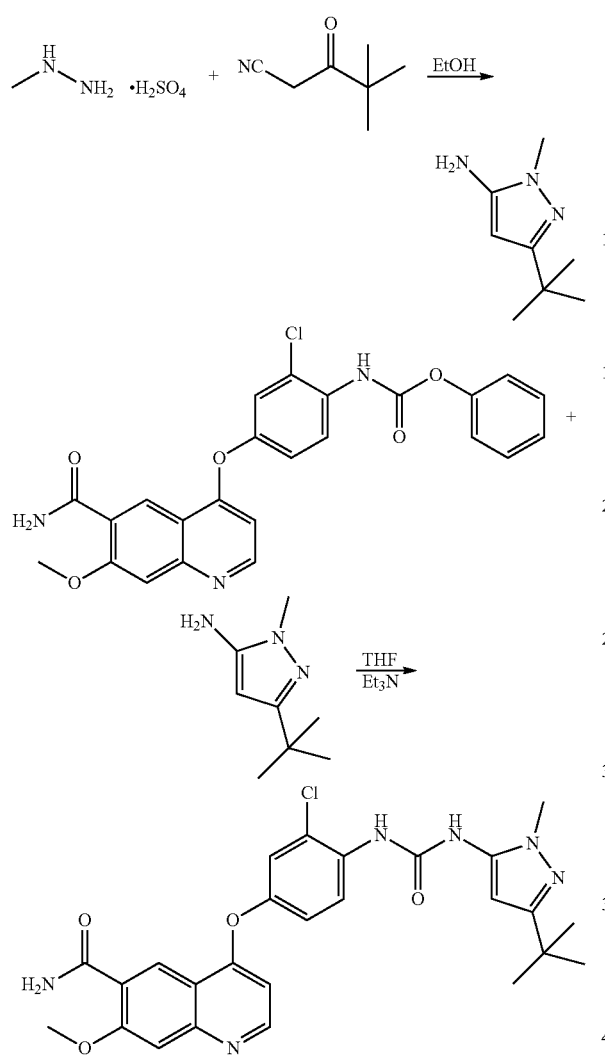

Step 1: Preparation of 5-tert-butyl-2-methyl-2H-pyrazol-3-ylamine

Methyl hydrazine sulfate (purchased from Shanghai Darui) (40 g, 0.278 mol) and pivaloylacetonitrile (purchased from TCI) (40 g, 0.320 mmol) were stirred at room temperature in 450 ml of ethanol. The mixture was added with 18 ml of concentrated hydrochloric acid and then heated to reflux and allowed to react overnight. The reaction solution was cooled to room temperature, and poured slowly into saturated aqueous solution of sodium bicarbonate, and then extracted with ethyl acetate (500 ml×2). The organic phase was washed twice with saturated NaCl solution, dried over anhydrous sodium sulfate, filtered and the filtrate was concentrated under reduced pressure to give 50 g of 5-tert-butyl-2-methyl-2H-pyrazol-3-ylamine as a yellow solid, which was used directly in the next step without purification.

Step 2: Preparation of 4-{4-[3-(5-tert-butyl-2-methyl-2H-pyrazol-3-yl)-ureido]-3-chloro-phenoxy}-7-methoxyquinolin-6-carboxamide The preparation method was the same as Step 3 of Example 12, except that 5-tert-butyl-2-methyl-2H-pyrazol-3-ylamine (prepared in Step 1) was used instead of (5-tert-butyl-isoxazol-3-yl)-methyl-amine in Step 3 of Example 12 to give 4-{4-[3-(5-tert-butyl-2-methyl-2H-pyrazol-3-yl)-ureido]-3-chloro-phenoxy}-7-methoxy quinolin-6-carboxamide.

$^1$HNMR (DMSO-d6, 400 MHz) δ: 9.37 (s, 1H), 8.72 (s, 1H), 8.69-8.70 (s, 1H), 8.67 (s, 1H), 8.24-8.27 (d, 1H), 7.87 (br, 1H), 7.75 (br, 1H), 7.57-7.58 (d, 1H), 7.53 (s, 1H), 7.29-7.31 (dd, 1H), 6.57-6.58 (d, 1H), 6.11 (s, 1H), 4.04 (s, 3H), 3.65 (s, 3H), 1.22 (s, 9H).

LC-MS: ESI 523.1 (M+H)+.

Example 27

Preparation of 4-{4-[3-(5-tert-butyl-2-ethyl-2H-pyrazol-3-yl)-ureido]-3-chloro-phenoxy}-7-methoxyquinolin-6-carboxamide (Compound 27)

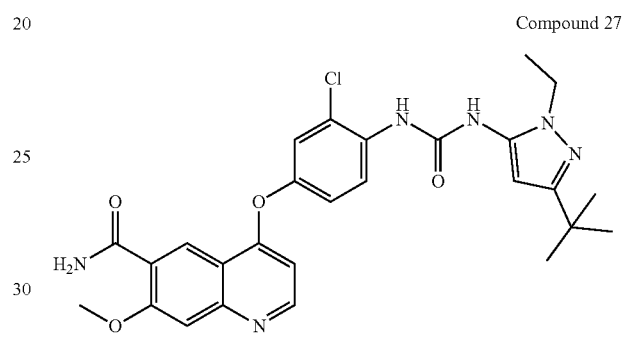

Compound 27

The preparation method was the same as Example 26, except that ethyl hydrazine (purchased from TCI) was used instead of methyl hydrazine in Step 1 of Example 26 to give 4-{4-[3-(5-tert-butyl-2-ethyl-2H-pyrazol-3-yl)-ureido]-3-chloro-phenoxy}-7-methoxyquinolin-6-carboxamide.

$^1$HNMR (DMSO-d6, 400 MHz) δ: 9.15 (s, 1H), 8.69-8.70 (d, 1H), 8.68 (s, 1H), 8.63 (s, 1H), 8.25-8.27 (d, 1H), 7.87 (br, 1H), 7.75 (br, 1H), 7.58-7.59 (d, 1H), 7.53 (s, 1H), 7.29-7.32 (dd, 1H), 6.57-6.58 (d, 1H), 6.12 (s, 1H), 4.04 (s, 3H), 3.95-4.01 (q, 2H), 1.29-1.33 (t, 3H), 1.23 (s, 9H).

LC-MS: ESI 537.2 (M+H)+.

Example 28

Preparation of 4-{4-[3-(2-acryloyl-5-tert-butyl-2H-pyrazol-3-yl)-ureido]-3-chloro-phenoxy}-7-methoxyquinolin-6-carboxamide (Compound 28)

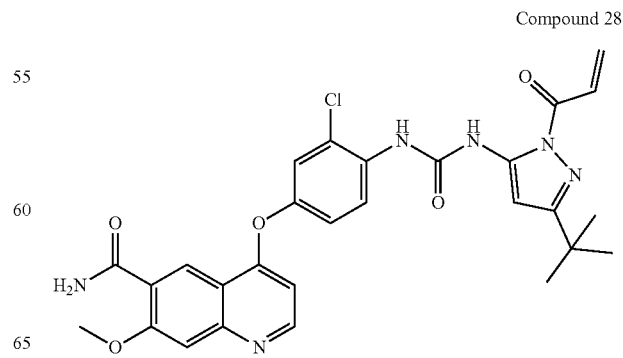

Compound 28

4-{4-[3-(5-tert-Butyl-2H-pyrazol-3-yl)-ureido]-3-chloro-phenoxy}-7-methoxyquinolin-6-carboxamide (prepared in Example 25) (300 mg, 0.591 mmol), N,N-dimethyl-ethylenediamine (228.7 mg, 1.773 mmol) were dissolved in 10 ml of DMF at room temperature. The mixture was cooled to 0-5° C. in an ice bath, and acryloyl chloride (80 mg, 0.886 mmol) was slowly added dropwise to the system. After addition, the mixture was heated to room temperature for 1 hour. The reaction solution was poured into water, and extracted with ethyl acetate (80 ml×2). The organic phase was washed twice with saturated NaCl solution, dried over anhydrous sodium sulfate, filtered and the filtrate was concentrated under reduced pressure. The residues were purified by column chromatography (eluent: dichloromethane/methanol) to give 138 mg of 4-{4-[3-(2-acryloyl-5-tert-butyl-2H-pyrazol-3-yl)-ureido]-3-chloro-phenoxy}-7-methoxyquinolin-6-carboxamide, as a white solid.

$^1$HNMR (DMSO-d6, 400 MHz) δ: 10.40 (s, 1H), 9.83 (s, 1H), 8.69-8.70 (d, 1H), 8.67 (s, 1H), 8.02-8.04 (d, 1H), 7.87 (br, 1H), 7.76 (br, 1H), 7.57-7.58 (d, 1H), 7.48-7.55 (m, 2H), 7.30-7.33 (dd, 1H), 6.70 (s, 1H), 6.59-6.64 (m, 2H), 6.19-6.22 (m, 1H), 4.04 (s, 3H), 1.27 (s, 9H).

LC-MS: ESI 563.1 (M+H)+.

Example 29

Preparation of 4-{4-[3-(5-tert-butyl-2-propanoyl-2H-pyrazol-3-yl)-ureido]-3-chloro-phenoxy}-7-methoxyquinolin-6-carboxamide (Compound 29)

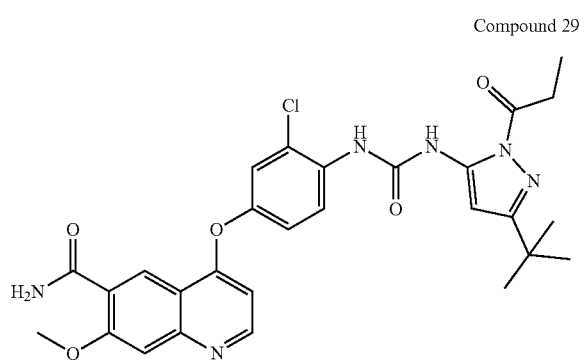 [SMILES: CCC(=O)n1nc(C(C)(C)C)cc1NC(=O)Nc1ccc(Oc2ccnc3cc(OC)c(C(N)=O)cc23)cc1Cl]

Compound 29

The preparation method was the same as Example 28, except that propionyl chloride was used instead of acryloyl chloride to give 4-{4-[3-(5-tert-butyl-2-propanoyl-2H-pyrazol-3-yl)-ureido]-3-chloro-phenoxy}-7-methoxyquinolin-6-carboxamide.

$^1$HNMR (DMSO-d6, 400 MHz) δ: 10.36 (s, 1H), 9.80 (s, 1H), 8.69-8.70 (d, 1H), 8.68 (s, 1H), 8.01-8.03 (d, 1H), 7.87 (br, 1H), 7.76 (br, 1H), 7.57-7.58 (d, 1H), 7.53 (s, 1H), 7.29-7.32 (dd, 1H), 6.64 (s, 1H), 6.58-6.59 (d, 1H), 4.04 (s, 3H), 3.07-3.13 (q, 2H), 1.26 (s, 9H), 1.14-1.18 (t, 3H).

LC-MS: ESI 565.1 (M+H)+.

Example 30

Preparation of 4-{4-[3-(5-tert-butyl-2-cyclopentyl-2H-pyrazol-3-yl)-ureido]-3-chloro-phenoxy}-7-methoxyquinolin-6-carboxamide (Compound 30)

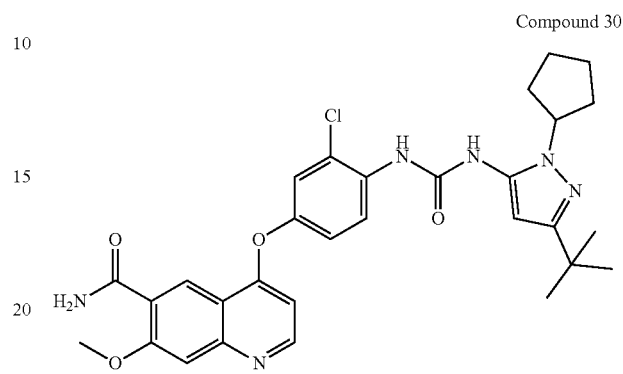

Compound 30

The preparation method was the same as Example 26, except that cyclopentyl hydrazine hydrochloride (purchased from TCI) was used instead of methyl hydrazine sulfate in step 1 of example 26 to give 4-{4-[3-(5-tert-butyl-2-cyclopentyl-2H-pyrazol-3-yl)-ureido]-3-chloro-phenoxy}-7-methoxyquinolin-6-carboxamide.

$^1$HNMR (DMSO-d6, 400 MHz) δ: 9.09 (s, 1H), 8.69-8.70 (d, 1H), 8.67 (s, 1H), 8.59 (s, 1H), 8.24-8.27 (d, 1H), 7.87 (br, 1H), 7.75 (br, 1H), 7.57-7.58 (d, 1H), 7.53 (s, 1H), 7.29-7.32 (dd, 1H), 6.57-6.58 (d, 1H), 6.09 (s, 1H), 4.54-4.57 (m, 1H), 4.04 (s, 3H), 1.61-2.03 (m, 8H), 1.22 (s, 9H).

LC-MS: ESI 577.3 (M+H)+.

Example 31

Preparation of 4-(4-{3-[5-tert-butyl-2-(2-morpholin-4-yl-ethyl)-2H-pyrazol-3-yl]-ureido}-3-chloro-phenoxy)-7-methoxyquinolin-6-carboxamide (Compound 31)

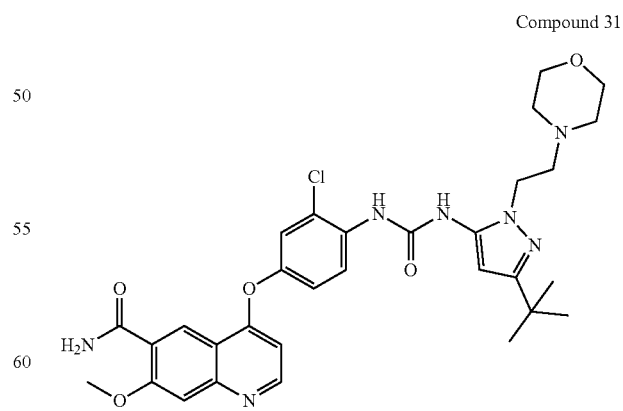

Compound 31

The preparation method was the same as Example 26, except that (2-morpholin-4-ethyl)-hydrazine (purchased from TCI) was used instead of methyl hydrazine sulfate in step 1 of example 26 to give 4-(4-{3-[5-tert-butyl-2-(2- morpholin-4-yl-ethyl)-2H-pyrazol-3-yl]-ureido}-3-chlorophe noxy)-7-methoxyquinolin-6-carboxamide.

¹HNMR (DMSO-d6, 400 MHz) δ: 9.15 (s, 1H), 8.69-8.70 (d, 1H), 8.68 (s, 1H), 8.59 (s, 1H), 8.22-8.25 (d, 1H), 7.85 (br, 1H), 7.72 (br, 1H), 7.56-7.57 (d, 1H), 7.53 (s, 1H), 7.29-7.32 (dd, 1H), 6.57-6.58 (d, 1H), 6.12 (s, 1H), 4.05-4.09 (t, 2H), 4.04 (s, 3H), 3.54-3.56 (t, 4H), 2.65-2.68 (t, 2H), 2.40-2.42 (t, 4H), 1.22 (s, 9H).

LC-MS: ESI 622.1 (M+H)+.

Example 32

Preparation of 4-(4-{3-[5-tert-butyl-2-(2-hydroxy-ethyl)-2H-pyrazol-3-yl]-ureido}-3-chloro-phenoxy)-7-methoxyquinolin-6-carboxamide (Compound 32)

Compound 32

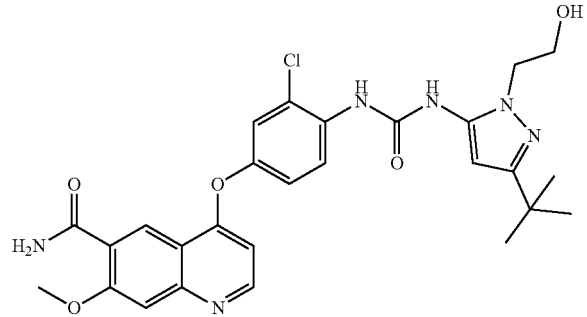

The preparation method was the same as Example 26, except that 2-hydrazino ethanol (purchased from TCI) was used instead of methyl hydrazine sulfate in step 1 of example 26 to give 4-(4-{3-[5-tert-butyl-2-(2-hydroxy-ethyl)-2H-pyrazol-3-yl]-ureido}-3-chloro-phenoxy)-7-methoxyquinolin-6-carboxamide.

¹HNMR (DMSO-d6, 400 MHz) δ: 9.32 (s, 1H), 8.84 (s, 1H), 8.69-8.70 (d, 1H), 8.68 (s, 1H), 8.22-8.24 (d, 1H), 7.87 (br, 1H), 7.74 (br, 1H), 7.56-7.57 (d, 1H), 7.53 (s, 1H), 7.28-7.31 (dd, 1H), 6.58-6.59 (d, 1H), 6.13 (s, 1H), 4.94 (br, 1H), 4.02-4.04 (m, 5H), 3.69-3.72 (t, 2H), 1.22 (s, 9H).

LC-MS: ESI 553.0 (M+H)+.

Example 33

Preparation of 4-{4-[3-(5-tert-butyl-2H-pyrazol-3-yl)-ureido]-3-trifluoromethyl-phenoxy}-7-methoxy-quinolin-6-carboxamide (Compound 33)

Compound 33

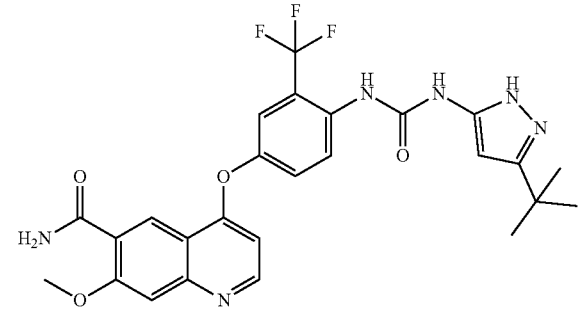

The preparation method was the same as Example 25, except that 4-amino-3-trifluoromethyl-phenol (purchased from TCI) was used instead of 4-amino-3-chlorophenol hydrochloride in step 1 of example 25 to give 4-{4-[3-(5-tert-butyl-2H-pyrazol-3-yl)-ureido]-3-trifluoromethyl-phenoxy}-7-methoxyquinolin-6-carboxamide.

¹HNMR (DMSO-d6, 400 MHz) δ: 12.10 (s, 1H), 9.61 (s, 1H), 8.69-8.70 (m, 2H), 8.17-8.19 (d, 1H), 7.88 (br, 1H), 7.76 (br, 1H), 7.67-7.68 (d, 1H), 7.60-7.63 (dd, 1H), 7.54 (s, 1H), 6.57-6.59 (d, 1H), 5.86 (br, 1H), 4.04 (s, 3H), 1.26 (s, 9H).

LC-MS: ESI 543.2 (M+H)+.

Example 34

Preparation of 4-{4-[3-(5-tert-butyl-2H-pyrazol-3-yl)-ureido]-3-methyl-phenoxy}-7-methoxyquinolin-6-carboxamide (Compound 34)

Compound 34

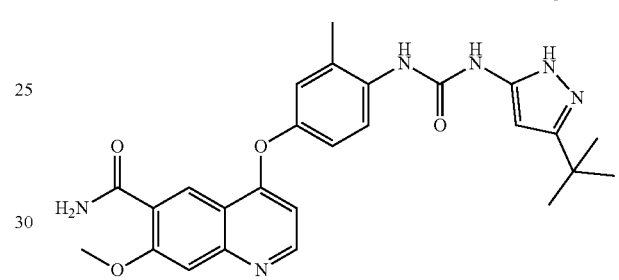

The preparation method was the same as Example 25, except that 4-amino-3-methyl-phenol (purchased from TCI) was used instead of 4-amino-3-chlorophenol hydrochloride in step 1 of example 25 to give 4-{4-[3-(5-tert-butyl-2H-pyrazol-3-yl)-ureido]-3-methyl-phenoxy}-7-methoxyquinolin-6-carboxamide.

¹HNMR (DMSO-d6, 400 MHz) δ: 12.05 (s, 1H), 9.32 (s, 1H), 8.69 (s, 1H), 8.65-8.67 (d, 1H), 8.14-8.16 (d, 1H), 7.87 (br, 1H), 7.74 (br, 1H), 7.51 (s, 1H), 7.17-7.18 (d, 1H), 7.09-7.11 (dd, 1H), 6.49-6.51 (d, 1H), 5.88 (br, 1H), 4.04 (s, 3H), 2.33 (s, 3H), 1.27 (s, 9H).

LC-MS: ESI 489.2 (M+H)+.

Example 35

Preparation of 4-{4-[3-(5-tert-butyl-2H-pyrazol-3-yl)-ureido]-2-methyl-phenoxy}-7-methoxyquinolin-6-carboxamide (Compound 35)

Compound 35

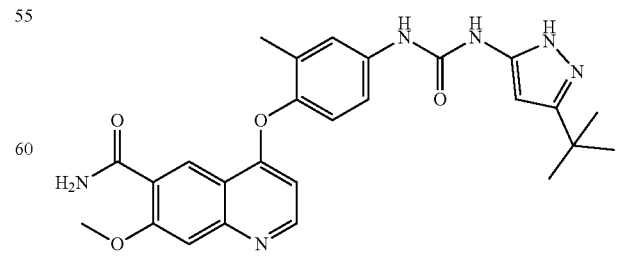

The preparation method was the same as Example 25, except that 4-amino-2-methyl-phenol (purchased from TCI)

was used instead of 4-amino-3-chlorophenol hydrochloride in step 1 of example 25 to give 4-{4-[3-(5-tert-butyl-2H-pyrazol-3-yl)-ureido]-2-methyl-phenoxy}-7-methoxyquinolin-6-carboxamide.

$^1$HNMR (DMSO-d6, 400 MHz) δ: 12.01 (s, 1H), 9.31 (s, 1H), 8.96 (s, 1H), 8.73 (s, 1H), 8.63-8.64 (d, 1H), 7.88 (br, 1H), 7.75 (br, 1H), 7.52 (m, 2H), 7.41-7.43 (dd, 1H), 7.14-7.16 (d, 1H), 6.33-6.34 (d, 1H), 6.01 (s, 1H), 4.04 (s, 3H), 2.10 (s, 3H), 1.27 (s, 9H).

LC-MS: ESI 489.0 (M+H)+.

Example 36

Preparation of 4-{4-[3-(5-tert-butyl-2H-pyrazol-3-yl)-ureido]-2-chloro-phenoxy}-7-methoxyquinolin-6-carboxamide (Compound 36)

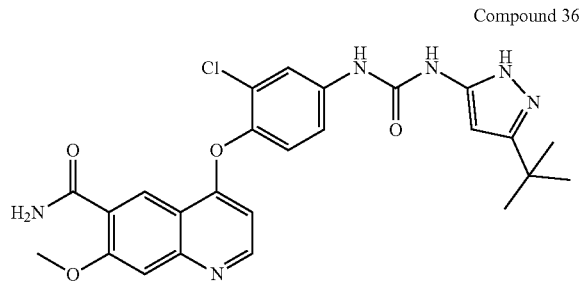 [SMILES: COc1cc2nccc(Oc3ccc(NC(=O)Nc4cc(C(C)(C)C)n[nH]4)cc3Cl)c2cc1C(N)=O]

Compound 36

The preparation method was the same as Example 25, except that 4-amino-2-chloro-phenol (purchased from TCI) was used instead of 4-amino-3-chlorophenol hydrochloride in step 1 of example 25 to give 4-{4-[3-(5-tert-butyl-2H-pyrazol-3-yl)-ureido]-2-chloro-phenoxy}-7-methoxyquinolin-6-carboxamide.

$^1$HNMR (DMSO-d6, 400 MHz) δ: 12.03 (s, 1H), 9.44 (s, 1H), 9.05 (s, 1H), 8.71 (s, 1H), 8.67-8.68 (d, 1H), 7.98 (d, 1H), 7.88 (br, 1H), 7.77 (br, 1H), 7.54 (s, 1H), 7.40-7.44 (m, 2H), 6.40-6.42 (d, 1H), 6.04 (s, 1H), 4.04 (s, 3H), 1.27 (s, 9H).

LC-MS: ESI 509.1 (M+H)+.

Example 37

Preparation of 4-{4-[3-(5-tert-butyl-2H-pyrazol-3-yl)-ureido]-2,3-dichloro-phenoxy}-7-methoxyquinolin-6-carboxamide (Compound 37)

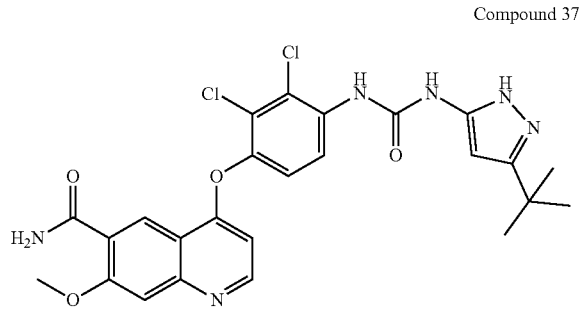 [SMILES: COc1cc2nccc(Oc3ccc(NC(=O)Nc4cc(C(C)(C)C)n[nH]4)c(Cl)c3Cl)c2cc1C(N)=O]

Compound 37

The preparation method was the same as Example 25, except that 4-amino-2,3-dichloro-phenol (purchased from TCI) was used instead of 4-amino-3-chlorophenol hydrochloride in step 1 of example 25 to give 4-{4-[3-(5-tert-butyl-2H-pyrazol-3-yl)-ureido]-2,3-dichloro-phenoxy}-7-methoxyquinolin-6-carboxamide.

$^1$HNMR (DMSO-d6, 400 MHz) δ: 12.14 (s, 1H), 9.71 (s, 1H), 8.71 (s, 1H), 8.66-8.68 (d, 1H), 8.46 (m, 1H), 7.89 (br, 1H), 7.86 (br, 1H), 7.55 (s, 1H), 7.50-7.52 (d, 1H), 6.47-6.48 (d, 1H), 5.85 (br, 1H), 4.04 (s, 3H), 1.27 (s, 9H).

LC-MS: ESI 543.0\545.0 (M+H)+.

Example 38

Preparation of 4-{4-[3-(5-tert-butyl-2-methyl-2H-pyrazol-3-yl)-ureido]-2,3-dichloro-phenoxy}-7-methoxyquinolin-6-carboxamide (Compound 38)

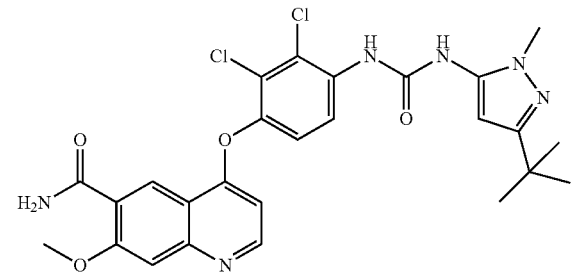

Compound 38

The preparation method was the same as Example 25, except that 4-amino-2,3-dichloro-phenol (purchased from TCI) was used instead of 4-amino-3-chlorophenol hydrochloride in step 1 of example 25, and 5-tert-butyl-2-methyl-2H-pyrazol-3-ylamine (prepared in Step 1 of Example 26) was used instead of 5-tert-butyl-2H-pyrazol-3-ylamine in Step 3 of Example 25 to give 4-{4-[3-(5-tert-butyl-2-methyl-2H-pyrazol-3-yl)-ureido]-2,3-dichloro-phenoxy}-7-methoxyquinolin-6-carboxamide.

$^1$HNMR (DMSO-d6, 400 MHz) δ: 9.31 (s, 1H), 8.80 (s, 1H), 8.70 (s, 1H), 8.67-8.68 (d, 1H), 8.28-8.30 (d, 1H), 7.89 (br, 1H), 7.78 (br, 1H), 7.55 (s, 1H), 7.51-7.53 (d, 1H), 6.47-6.48 (d, 1H), 6.12 (s, 1H), 4.05 (s, 3H), 3.66 (s, 3H), 1.22 (s, 9H).

LC-MS: ESI 557.0\559.0 (M+H)+.

Example 39

Preparation of 4-{4-[3-(5-tert-butyl-2-methyl-2H-pyrazol-3-yl)-ureido]-3-chloro-phenoxy}-2-chloro-7-methoxyquinolin-6-carboxamide (Compound 39)

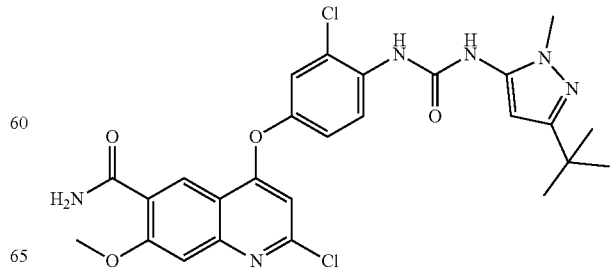

Compound 39

73

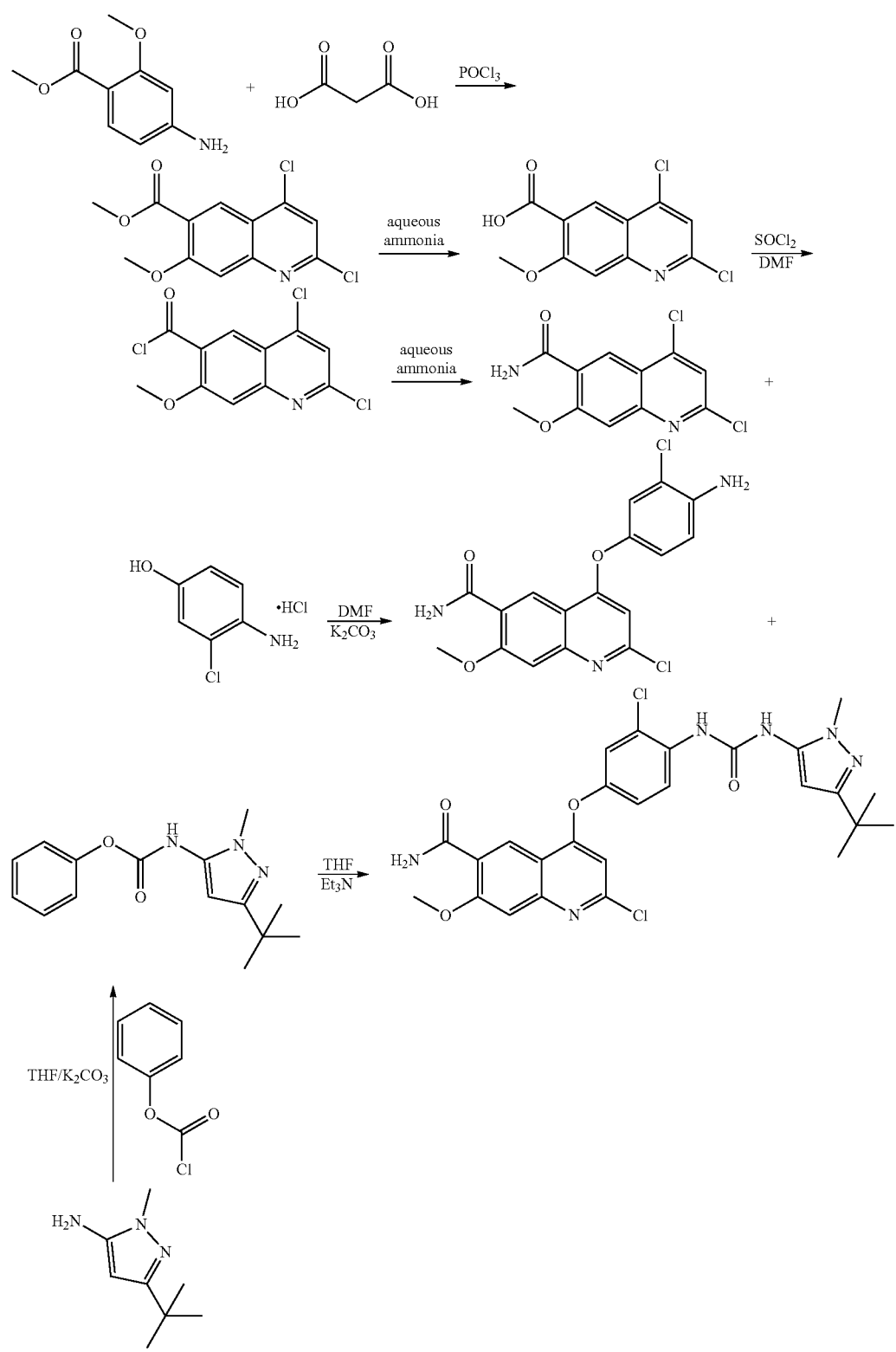

Step 1: Preparation of methyl 2,4-dichloro-7-methoxyl-quinolin-6-carboxylate

Methyl 4-amino-2-methoxy-benzoate (purchased from TCI) (1.81 g, 0.01 mol) and malonic acid (1.04 g, 0.01 mol)

74 were dissolved in 12 ml of phosphorus oxychloride and heated to 110° C., and then reacted for 3 hours. The reaction solution was cooled to room temperature, and slowly poured into ice water. The mixture was adjusted to pH 5-6 with aqueous ammonia, and then filtered. The filter cake was washed with water, and the resulted solid was purified by column chromatography (eluent: petroleum ether/ethyl acetate) to give 1.1 g of methyl 2,4-dichloro-7-methoxyl-quinolin-6-carboxylate as a white solid.

Step 2: Preparation of 2,4-dichloro-7-methoxy-quinolin-6-carboxylic acid

Methyl 4-amino-2-methoxy-benzoate (1.0 g, 3.50 mmol) obtained in the step 1 was added to 30 ml of aqueous ammonia under nitrogen atmosphere, and heated to 100° C. for 8 hours. The reaction solution was cooled to room temperature, and slowly poured into water (80 ml). The pH was adjusted to about 2 with 2N diluted hydrochloric acid, and then filtered. The filter cake was washed with water, and the resulted solid was air-dried (60° C.) to give 700 mg of 2,4-dichloro-7-methoxy-quinolin-6-carboxylic acid as a solid.

Step 3: Preparation of 2,4-dichloro-7-methoxy-quinolin-6-carbonyl chloride 2,4-Dichloro-7-methoxy-quinolin-6-carboxylic acid (700 mg, 2.57 mmol) obtained in the step 2 was dissolved in 10 ml of thionyl chloride, and two drops of DMF were added at room temperature. The reaction mixture was stirred at room temperature for 2 hours under nitrogen atmosphere, and then concentrated under reduced pressure to give 700 mg of 2,4-dichloro-7-methoxy-quinolin-6-carbonyl chloride as a white solid.

Step 4: Preparation of 2,4-dichloro-7-methoxy-quinolin-6-carboxamide

A mixture of 20 ml of aqueous ammonia and 20 ml of dichloromethane was quickly stirred in a 100 ml single-necked reaction flask and cooled to 0-5° C. in an ice bath. 2,4-Dichloro-7-methoxy-quinolin-6-carbonyl chloride (700 mg, 2.41 mmol) obtained in the step 3 was dissolved in 10 ml of dichloromethane and added dropwise to the reaction flask. The reaction mixture was stirred for 30 min at room temperature. The reaction solution was poured into water, and extracted with ethyl acetate (60 ml×2). The organic phase was washed with saturated NaCl solution, dried over anhydrous sodium sulfate, filtered and the filtrate was concentrated under reduced pressure. The residues were purified by column chromatography (eluent: dichloromethane/methanol) to give 470 mg of 2,4-dichloro-7-methoxy-quinolin-6-carboxamide as a solid.

Step 5: Preparation of 4-(4-amino-3-chloro-phenoxy)-2-chloro-7-methoxy-quinolin-6-carboxamide 4-Amino-3-chlorophenol hydrochloride (100 mg, 0.553 mmol) and potassium carbonate (229 mg, 1.659 mmol) were stirred for 30 min in 10 ml of DMF at room temperature. 2,4-Dichloro-7-methoxy-quinolin-6-carboxamide (150 mg, 0.553 mmol) obtained in the step 4 was added to the reaction system, and the mixture was heated to 90° C. for 3 hours. The reaction solution was poured into water, and extracted with ethyl acetate (60 ml×2). The organic phase was washed with saturated NaCl solution, dried over anhydrous sodium sulfate, filtered and the filtrate was concentrated under reduced pressure. The residues were purified by column chromatography (eluent: dichloromethane/methanol) to give 170 mg of 4-(4-amino-3-chloro-phenoxy)-2-chloro-7-methoxy-quinolin-6-carboxamide as a solid.

Step 6: Preparation of phenyl (5-tert-butyl-2-methyl-2H-pyrazol-3-yl)-carbamate 5-tert-Butyl-2-methyl-2H-pyrazol-3-ylamine (prepared in Step 1 of Example 26) (43 g, 0.281 mol) was dissolved in 400 ml of THF, and potassium carbonate (116 g, 0.843) was added at room temperature. The mixture was cooled to 0 to 5° C. in an ice bath, and added slowly with phenyl chloroformate (66 g, 0.421 mol) dropwise. The mixture was heated to room temperature for 1.5 hours. The reaction solution was poured into water, and extracted with ethyl acetate (500 ml×2). The organic phase was washed twice with saturated NaCl solution, dried over anhydrous sodium sulfate, filtered and the filtrate was concentrated under reduced pressure to give a sticky solid. The sticky solid was made slurry in 350 ml of methyl tert-butyl ether: petroleum ether=4:1 solution for 1 hour, and then filtered. The filter cake was washed with petroleum ether and air-dried (60° C.) to give 55 g of phenyl (5-tert-butyl-2-methyl-2H-pyrazol-3-yl)-carbamate as a white solid.

Step 7: Preparation of 4-{4-[3-(5-tert-butyl-2-methyl-2H-pyrazol-3-yl)-ureido]-3-chloro-phenoxy}-2-chloro-7-methoxyquinolin-6-carboxamide 4-(4-Amino-3-chloro-phenoxy)-2-chloro-7-methoxy-quinolin-6-carboxamide (70 mg, 0.19 mmol) obtained in Step 5, phenyl (5-tert-butyl-2-methyl-2H-pyrazol-3-yl)-carbamate (76 mg, 0.28 mmol) obtained in Step 6 and triethylamine (56 mg, 0.56 mmol) were dissolved in 10 mL THF and refluxed overnight. The next day, the reaction mixture was concentrated under reduced pressure and the residues were purified by column chromatography (eluent: dichloromethane/methanol) to give 5 mg of 4-{4-[3-(5-tert-butyl-2-methyl-2H-pyrazol-3-yl)-ureido]-3-chloro-phenoxy}-2-chloro-7-methoxyquinolin-6-carboxamide as a solid.

$^1$HNMR (DMSO-d6, 400 MHz) δ: 9.26 (s, 1H), 8.66 (s, 1H), 8.62 (s, 1H), 8.28-8.30 (d, 1H), 7.88 (br, 1H), 7.79 (br, 1H), 7.65 (d, 1H), 7.51 (s, 1H), 7.34-7.37 (dd, 1H), 6.50 (s, 1H), 6.12 (s, 1H), 4.04 (s, 3H), 3.65 (s, 3H), 1.22 (s, 9H).

LC-MS: ESI 557.1\559.1 (M+H)+.

Example 40

Preparation of 4-{3-chloro-4-[3-(5-isopropyl-2H-pyrazol-3-yl)-ureido]-phenoxy}-7-methoxyquinolin-6-carboxamide (Compound 40)

Compound 40

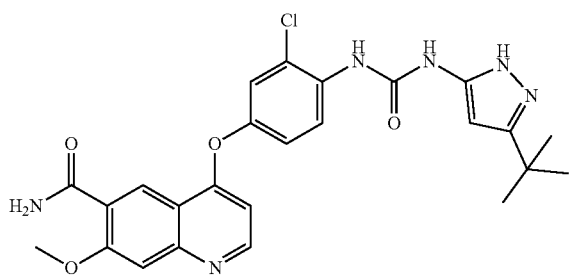

The preparation method was the same as Example 25, except that 5-isopropyl-2H-pyrazol-3-ylamine (purchased from TCI) was used instead of 5-tert-butyl-2H-pyrazol-3-ylamine in step 3 of example 25 to give 4-{3-chloro-4-[3-(5-isopropyl-2H-pyrazol-3-yl)-ureido]-phenoxy}-7-methoxyquinolin-6-carboxamide.

$^1$HNMR (DMSO-d6, 400 MHz) δ: 12.11 (s, 1H), 9.60 (s, 1H), 8.68-8.69 (m, 2H), 8.40-8.42 (d, 1H), 7.87 (br, 1H), 7.75 (br, 1H), 7.55-7.56 (d, 1H), 7.53 (s, 1H), 7.28-7.31 (dd, 1H), 6.57-6.58 (d, 1H), 5.90 (br, 1H), 4.04 (s, 3H), 2.88-2.95 (m, 1H), 1.21-1.23 (d, 6H).

LC-MS: ESI 495.1 (M+H)+.

Example 41

Preparation of 4-{3-chloro-4-[3-(5-cyclopropyl-2H-pyrazol-3-yl)-ureido]-phenoxy}-7-methoxyquinolin-6-carboxamide (Compound 41)

Compound 41

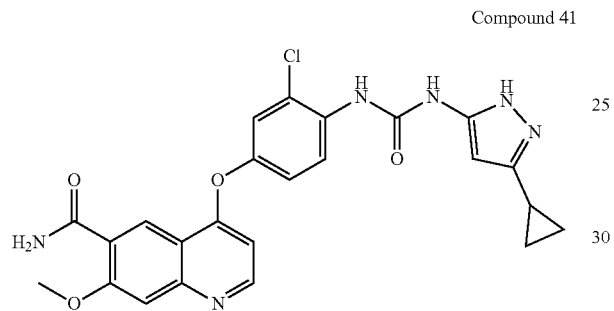

The preparation method was the same as Example 25, except that 5-cyclopropyl-2H-pyrazol-3-ylamine (purchased from TCI) was used instead of 5-tert-butyl-2H-pyrazol-3-ylamine in step 3 of example 25 to give 4-{3-chloro-4-[3-(5-cyclopropyl-2H-pyrazol-3-yl)-ureido]-phenoxy}-7-methoxyquinolin-6-carboxamide.

$^1$HNMR (DMSO-d6, 400 MHz) δ: 12.12 (s, 1H), 9.57 (s, 1H), 8.68-8.70 (m, 2H), 8.38-8.40 (d, 1H), 7.87 (br, 1H), 7.75 (br, 1H), 7.55-7.56 (d, 1H), 7.53 (s, 1H), 7.29-7.31 (dd, 1H), 6.58-6.59 (d, 1H), 5.78 (br, 1H), 4.04 (s, 3H), 1.85-1.89 (m, 1H), 0.92-0.94 (m, 2H), 0.68-0.69 (m, 2H).

LC-MS: ESI 493.0 (M+H)+.

Example 42

Preparation of 4-{4-[3-(5-tert-butyl-2H-pyrazol-3-yl)-ureido]-3-chloro-phenoxy}-7-(2-methoxy-ethoxy)-quinolin-6-carboxamide (Compound 42)

Compound 42

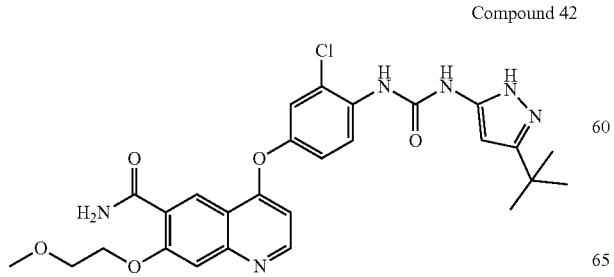

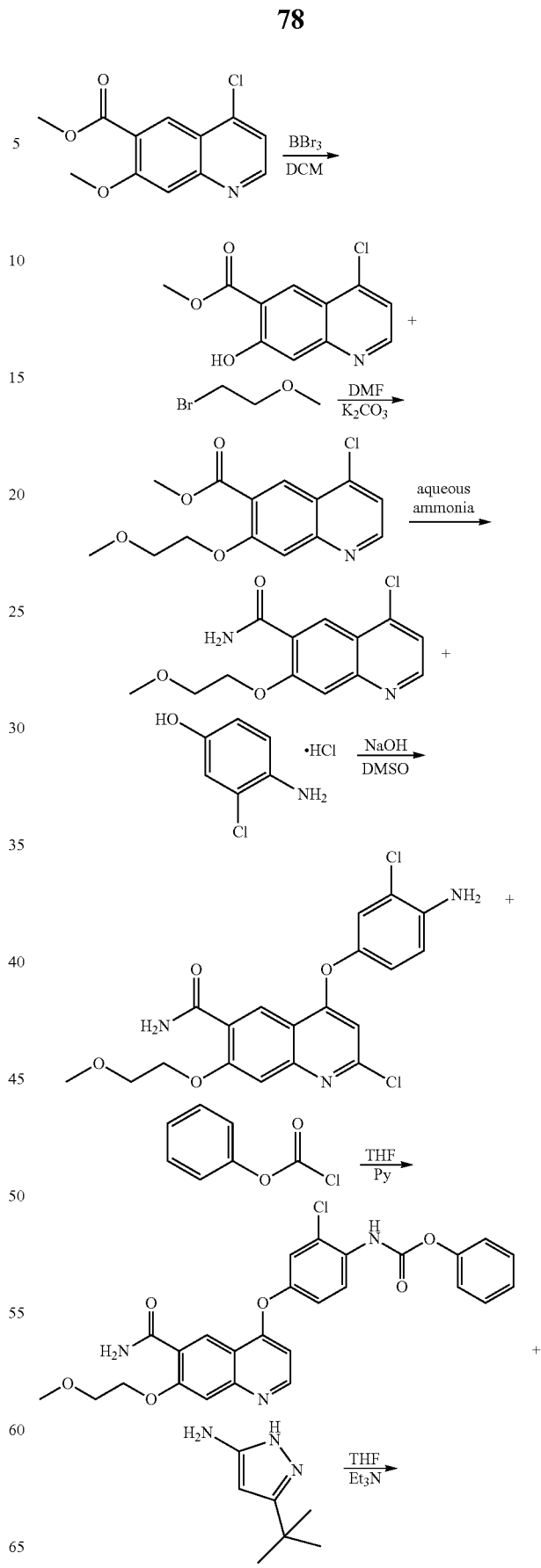

-continued

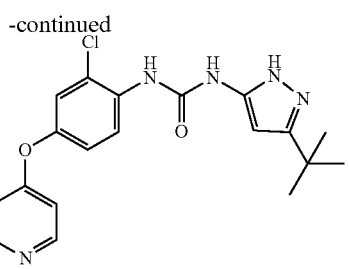

Step 1: Preparation of methyl 4-chloro-7-hydroxy-quinolin-6-carboxylate Methyl 4-chloro-7-methoxy-quinolin-6-carboxylate (prepared in Step 3 of Example 14) (8.0 g, 0.0361 mol) was dissolved in 80 ml of dichloromethane (three-necked flask) under nitrogen atmosphere (nitrogen exchange for three times), and the reaction system was cooled down to −15° C. to −20° C. A solution of boron tribromide in dichloromethane (65 ml, 1.66 mol/L) was added dropwise by a syringe. After addition, the reaction mixture was stirred for 30 min at low temperature. After the reaction was completed by TLC monitoring, the reaction was quenched by addition of methanol dropwise at a low temperature. The reaction solution was slowly poured into water, and adjusted to neutral pH by saturated aqueous solution of sodium bicarbonate. Then, it was extracted with dichloromethane (100 ml×3). The insoluble yellow solid resulted was filtered out, and the organic phase was washed with a saturated NaCl solution. The yellow solid in the filter cake was added with 150 ml of ethyl acetate, and stirred at room temperature for 30 min, and then filtered again. The organic phase (ethyl acetate) and the extracted organic phase (dichloromethane) were dried over anhydrous sodium sulfate and filtered. The filtrate was concentrated under reduced pressure to give 1.72 g of methyl 4-chloro-7-hydroxy-quinolin-6-carboxylate as a yellow solid.

Step 2: Preparation of methyl 4-chloro-7-(2-methoxy-ethoxy)-quinolin-6-carboxylate Methyl 4-chloro-7-hydroxy-quinolin-6-carboxylate (prepared in Step 1) (1.72 g, 7.24 mmol), 1-bromo-2-methoxy-ethane (purchased from Shanghai Darui) (2.01 g, 14.5 mmol) and potassium carbonate (4.0 g, 29.0 mmol) were dissolved in 30 ml of DMF and heated to 80° C. for 1.5 hours. The reaction solution was cooled to room temperature and poured into water, and then extracted with ethyl acetate (60 ml×2). The organic phase was washed twice with saturated NaCl solution, dried over anhydrous sodium sulfate, and filtered. The filtrate was concentrated under reduced pressure to give 1.63 g of methyl 4-chloro-7-(2-methoxy-ethoxy)-quinolin-6-carboxylate as a solid.

Step 3: Preparation of 4-chloro-7-(2-methoxy-ethoxy)-quinolin-6-carboxamide

Methyl 4-chloro-7-(2-methoxy-ethoxy)-quinolin-6-carboxylate prepared in Step 2 (500 mg, 1.78 mmol) was added to 20 ml of aqueous ammonia and heated to 50° C. under nitrogen atmosphere for 1 hour. The reaction solution was cooled to room temperature and poured slowly into water, and then extracted with ethyl acetate (50 ml×2). The organic phase was washed twice with saturated NaCl solution, dried over anhydrous sodium sulfate, and filtered. The filtrate was concentrated under reduced pressure to give 400 mg of 4-chloro-7-(2-methoxy-ethoxy)-quinolin-6-carboxamide as a solid.

Step 4: Preparation of 4-(4-amino-3-chloro-phenoxy)-7-(2-methoxy-ethoxy)-quinolin-6-carboxamide 4-Amino-3-chlorophenol hydrochloride (223 mg, 1.24 mmol) and sodium hydroxide (99 mg, 2.50 mmol) were dissolved in 10 ml of DMSO at room temperature and stirred for 30 min. 4-Chloro-7-(2-methoxy-ethoxy)-quinolin-6-carboxamide (240 mg, 0.823 mmol) prepared in Step 3 was added. The mixture was heated to 100° C. for 1 hour. The reaction solution was cooled to room temperature and poured slowly into water, and then stirred for 10 min at room temperature. The mixture was filtered, and the filter cake was washed with water and air-dried (60° C.) to give 280 mg of 4-(4-amino-3-chloro-phenoxy)-7-(2-methoxy-ethoxy)-quinolin-6-carboxamide as a solid.

Step 5: Preparation of phenyl {4-[6-carbamoyl-7-(2-methoxy-ethoxy)-quinolin-4-yloxy]-2-chloro-phenyl}-carbamate 4-(4-Amino-3-chloro-phenoxy)-7-(2-methoxy-ethoxy)-quinolin-6-carboxamide prepared in Step 4 (280 mg, 0.702 mmol) and pyridine (110 mg, 1.404 mmol) were dissolved in 10 ml of THF, and added with potassium carbonate (194 mg, 1.404 mmol) at room temperature. The reaction mixture was cooled to 0-5° C. in an ice bath, and then added with phenyl chloroformate (219 mg, 1.404 mmol) (dissolved in a small amount of THF) dropwise. The mixture was allowed to react at room temperature overnight. The reaction solution was poured slowly into water, and extracted with ethyl acetate (50 ml×3). The organic phase was washed twice with saturated NaCl solution, dried over anhydrous sodium sulfate, and filtered. The filtrate was concentrated under reduced pressure. The residues were purified by column chromatography (eluent: dichloromethane/methanol) to give 173 mg of phenyl {4-[6-carbamoyl-7-(2-methoxy-ethoxy)-quinolin-4-yloxy]-2-chloro-phenyl}-carbamate as a solid.

Step 6: Preparation of 4-{4-[3-(5-tert-butyl-2H-pyrazol-3-yl)-ureido]-3-chloro-phenoxy}-7-(2-methoxy-ethoxy)-quinolin-6-carboxamide Phenyl {4-[6-carbamoyl-7-(2-methoxy-ethoxy)-quinolin-4-yloxy]-2-chloro-phenyl}-carbamate prepared in Step 5 (44 mg, 0.087 mmol), 5-tert-butyl-2H-pyrazol-3-ylamine (24 mg, 0.174 mmol) and triethylamine (35 mg, 0.348 mmol) were dissolved in 10 ml of THF and refluxed overnight. The next day, the reaction solution was concentrated under reduced pressure, and the residues were purified by column chromatography (eluent: dichloromethane/methanol) to give 40 mg of 4-{4-[3-(5-tert-butyl-2H-pyrazol-3-yl)-ureido]-3-chloro-phenoxy}-7-(2-methoxy-ethoxy)-quinolin-6-carboxamide as a solid.

$^1$HNMR (DMSO-d6, 400 MHz) δ: 12.11 (s, 1H), 9.60 (s, 1H), 8.78 (s, 1H), 8.68-8.70 (d, 1H), 8.40-8.42 (d, 1H), 7.83-7.84 (m, 2H), 7.58 (s, 1H), 7.57-7.58 (d, 1H), 7.29-7.32 (dd, 1H), 6.57-6.58 (d, 1H), 5.85 (br, 1H), 4.42-4.43 (t, 2H), 3.81-3.83 (t, 2H), 3.37 (s, 3H), 1.27 (s, 9H).

LC-MS: ESI 553.2 (M+H)+.

Example 43

Preparation of 4-{4-[3-(5-tert-butyl-2H-pyrazol-3-yl)-ureido]-3-chloro-phenoxy}-7-isopropoxy-quinolin-6-carboxamide (Compound 43)

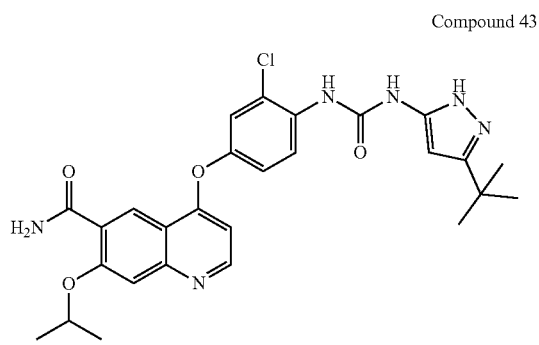 [SMILES: CC(C)Oc1cc2nccc(Oc3ccc(NC(=O)Nc4cc(C(C)(C)C)n[nH]4)c(Cl)c3)c2cc1C(N)=O]

Compound 43

The preparation method was the same as Example 42, except that 2-iodoisopropane (purchased from TCI) was used instead of 1-bromo-2-methoxyethane in step 2 of example 42 to give 4-{4-[3-(5-tert-butyl-2H-pyrazol-3-yl)-ureido]-3-chloro-phenoxy}-7-isopropoxy-quinolin-6-carboxamide.

$^1$HNMR (DMSO-d6, 400 MHz) δ: 12.10 (s, 1H), 9.60 (s, 1H), 8.71 (s, 1H), 8.67-8.68 (d, 1H), 8.40-8.42 (d, 1H), 7.77 (br, 1H), 7.74 (br, 1H), 7.55-7.56 (m, 2H), 7.27-7.30 (dd, 1H), 6.55-6.57 (d, 1H), 5.86 (br, 1H), 4.98-5.02 (m, 1H), 1.43-1.45 (d, 6H), 1.27 (s, 9H).

LC-MS: ESI 537.1 (M+H)+.

Example 44

Preparation of 4-{4-[3-(5-tert-butyl-2-methyl-2H-pyrazol-3-yl)-ureido]-3-chloro-phenoxy}-7-(2-methoxy-ethoxy)-quinolin-6-carboxamide (Compound 44)

Compound 44

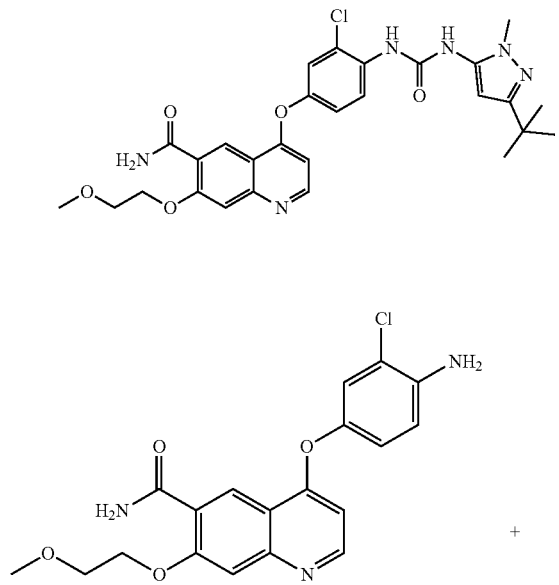

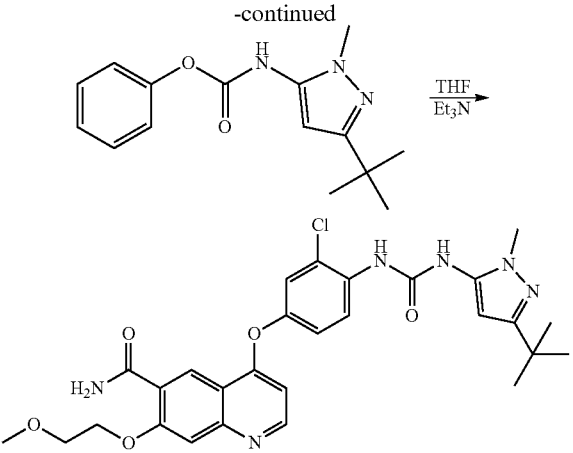

4-(4-Amino-3-chloro-phenoxy)-7-(2-methoxy-ethoxy)-quinolin-6-carboxamide (prepared in Step 4 of Example 42) (100 mg, 0.258 mmol), phenyl (5-tert-butyl-2-methyl-2H-pyrazol-3-yl)-carbamate (prepared in Step 6 of Example 39) (105 mg, 0.387 mmol) and triethylamine (77 mg, 0.774 mmol) were dissolved in 10 ml of THF and refluxed overnight. The next day, the reaction mixture was concentrated under reduced pressure and the residues were purified by column chromatography (eluent: dichloromethane/methanol) to give 66 mg of 4-{4-[3-(5-tert-butyl-2-methyl-2H-pyrazol-3-yl)-ureido]-3-chloro-phenoxy}-7-(2-methoxy-ethoxy)-quinolin-6-carboxamide as a solid.

$^1$HNMR (DMSO-d6, 400 MHz) δ: 9.24 (s, 1H), 8.78 (d, 1H), 8.69-8.70 (d, 1H), 8.65 (s, 1H), 8.26-8.28 (d, 1H), 7.83-7.84 (m, 2H), 7.58-7.59 (m, 2H), 7.30-7.33 (dd, 1H), 6.57-6.58 (d, 1H), 6.12 (s, 1H), 4.41-4.44 (t, 2H), 3.81-3.83 (t, 2H), 3.65 (s, 3H), 3.34 (s, 3H), 1.22 (s, 9H).

LC-MS: ESI 567.0 (M+H)+.

Example 45

Preparation of 4-{4-[3-(5-tert-butyl-2H-pyrazol-3-yl)-ureido]-3-chloro-phenoxy}-7-methoxyquinolin-6-carboxylic acid methylamide (Compound 45)

Compound 45

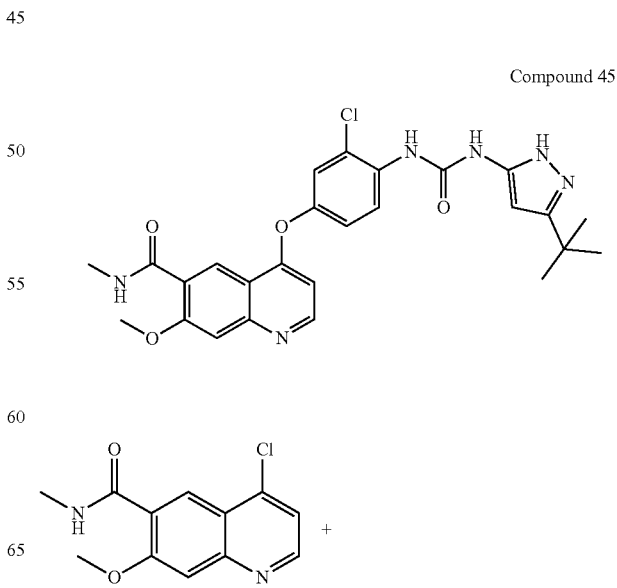

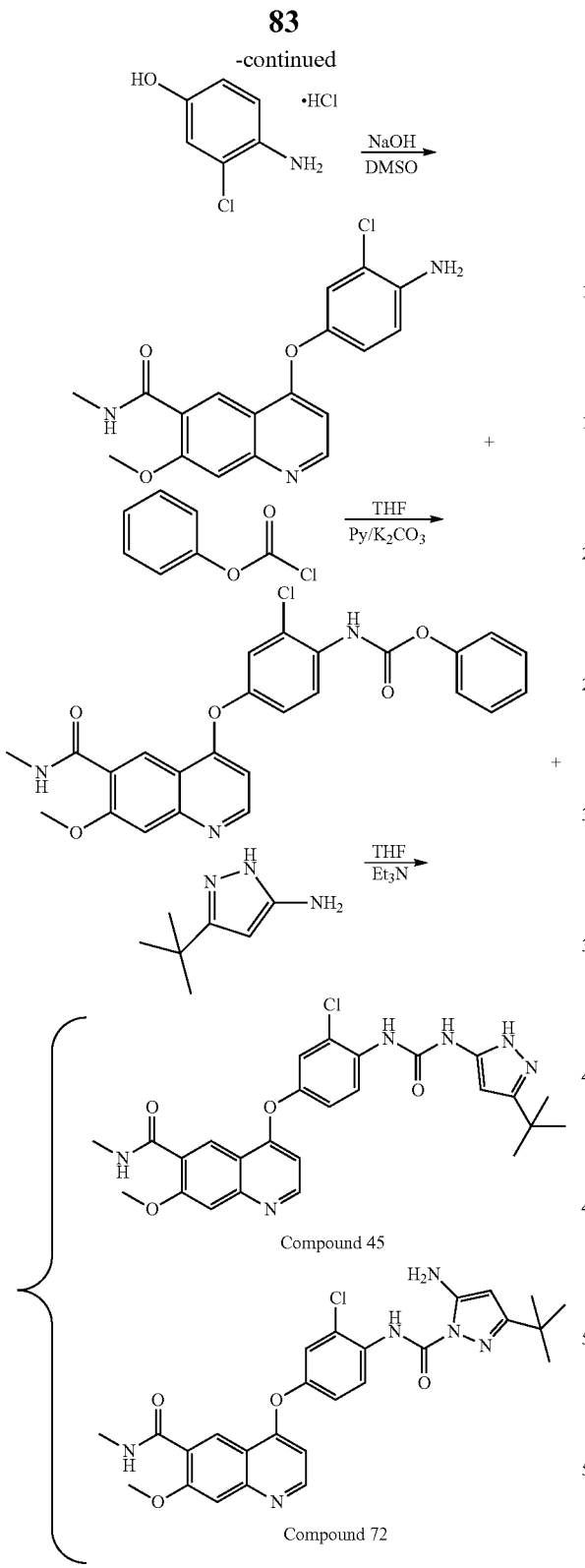

Step 1: Preparation of 4-(4-amino-3-chloro-phenoxy)-7-methoxy-quinolin-6-carboxylic acid methylamide The preparation method was the same as Step 5 of Example 14.

Step 2: Preparation of phenyl [2-chloro-4-(7-methoxy-6-methylcarbamoyl-quinolin-4-yloxy)-phenyl]-carbamate 4-(4-Amino-3-chloro-phenoxy)-7-methoxy-quinolin-6-carboxylic acid methylamide (500 mg, 1.40 mmol) prepared in Step 1 and pyridine (332 mg, 4.20 mmol) were dissolved in 20 ml of THF and added with potassium carbonate (193 mg, 1.40 mmol) at room temperature. The reaction mixture was cooled to 0 to 5° C. in an ice bath, and added with phenyl chloroformate (327 mg, 2.10 mmol) dropwise. The mixture was allowed to react at room temperature for 1 hour. The remaining starting material was detected by TLC, and phenyl chloroformate (327 mg, 2.10 mmol) was supplemented and the mixture was allowed to react at room temperature for another 2 hours. The reaction was completed by TLC monitoring, and the reaction mixture was poured into water, and then extracted with ethyl acetate (80 ml×2). The organic phase was washed twice with saturated NaCl solution, dried over anhydrous sodium sulfate, and filtered. The filtrate was concentrated under reduced pressure, and the residues were purified by column chromatography (eluent: dichloromethane/methanol) to give 400 mg of phenyl [2-chloro-4-(7-methoxy-6-methylcarbamoyl-quinolin-4-yloxy)-phenyl]-carbamate as a yellow solid.

Step 3: Preparation of 4-{4-[3-(5-tert-butyl-2H-pyrazol-3-yl)-ureido]-3-chloro-phenoxy}-7-methoxyquinolin-6-carboxylic acid methylamide Phenyl [2-chloro-4-(7-methoxy-6-methylcarbamoyl-quinolin-4-yloxy)-phenyl]-carbamate obtained in Step 2 (85 mg, 0.18 mmol), 5-tert-butyl-2H-pyrazol-3-ylamine (41 mg, 0.27 mmol) and triethylamine (55 mg, 0.54 mmol) were dissolved in 10 ml of THF and refluxed overnight. The next day, the reaction solution was concentrated under reduced pressure, and the residues were purified by column chromatography (eluent: dichloromethane/methanol) to give 45 mg of 4-{4-[3-(5-tert-butyl-2H-pyrazol-3-yl)-ureido]-3-chloro-phenoxy}-7-methoxyquinolin-6-carboxylic acid methylamide as a solid. Meanwhile, compound 72 was also obtained (Example 72).

$^1$HNMR (DMSO-d6, 400 MHz) δ: 12.11 (s, 1H), 9.60 (s, 1H), 8.68-8.69 (d, 1H), 8.61 (s, 1H), 8.37-8.42 (m, 2H), 7.55-7.569 (d, 1H), 7.53 (s, 1H), 7.27-7.30 (dd, 1H), 6.57-6.58 (d, 1H), 5.88 (br, 1H), 4.04 (s, 3H), 2.84-2.86 (d, 3H), 1.27 (s, 9H).

LC-MS: ESI 523.1 (M+H)+.

Example 46

Preparation of 4-{4-[3-(5-tert-butyl-2-methyl-2H-pyrazol-3-yl)-ureido]-3-chloro-phenoxy}-7-methoxy quinolin-6-carboxylic acid methylamide (Compound 46)

Compound 46

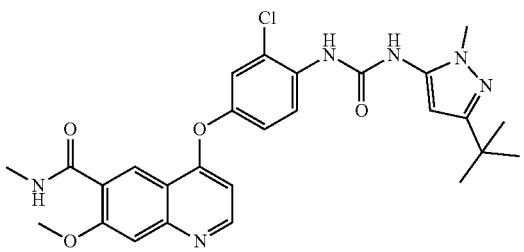

The preparation method was the same as Example 45, except that 5-tert-butyl-2-methyl-2H-pyrazol-3-ylamine (prepared in Step 1 of Example 26) was used instead of 5-tert-butyl-2H-pyrazol-3-ylamine in Step 3 of Example 45 to give 4-{4-[3-(5-tert-butyl-2-methyl-2H-pyrazol-3-yl)-ureido]-3-chloro-phenoxy}-7-methoxy quinolin-6-carboxylic acid methyl amide.

¹HNMR (DMSO-d6, 400 MHz) δ: 9.25 (s, 1H), 8.68-8.69 (d, 1H), 8.65 (s, 1H), 8.60 (s, 1H), 8.37-8.39 (d, 1H), 8.25-8.27 (d, 1H), 7.56-7.57 (d, 1H), 7.53 (s, 1H), 7.28-7.31 (dd, 1H), 6.57-6.58 (d, 1H), 6.11 (s, 1H), 4.03 (s, 3H), 3.65 (s, 3H), 2.84-2.85 (d, 3H), 1.22 (s, 9H).

LC-MS: ESI 537.3 (M+H)+.

Example 47

Preparation of 4-{4-[3-(5-tert-butyl-2-methyl-2H-pyrazol-3-yl)-ureido]-3-chloro-phenoxy}-7-methoxy quinolin-6-carboxylic acid methylamide (Compound 47)

Compound 47

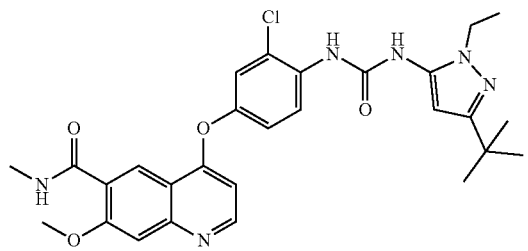

The preparation method was the same as Example 45, except that 5-tert-butyl-2-ethyl-2H-pyrazol-3-ylamine (prepared in Example 27) was used instead of 5-tert-butyl-2H-pyrazol-3-ylamine in Step 3 of Example 45 to give 4-{4-[3-(5-tert-butyl-2-methyl-2H-pyrazol-3-yl)-ureido]-3-chloro-phenoxy}-7-methoxy quinolin-6-carboxylic acid methyl amide.

¹HNMR (DMSO-d6, 400 MHz) δ: 9.14 (s, 1H), 8.68-8.69 (d, 1H), 8.63 (s, 1H), 8.60 (s, 1H), 8.37-8.38 (m, 1H), 8.25-8.27 (d, 1H), 7.57-7.58 (d, 1H), 7.53 (s, 1H), 7.28-7.31 (dd, 1H), 6.57-6.58 (d, 1H), 6.12 (s, 1H), 4.03 (s, 3H), 3.95-4.00 (q, 2H), 2.84-2.85 (d, 3H), 1.29-1.32 (t, 3H), 1.23 (s, 9H).

LC-MS: ESI 551.2 (M+H)+.

Example 48

Preparation of 4-{4-[3-(5-tert-butyl-2-cyclopentyl-2H-pyrazol-3-yl)-ureido]-3-chloro-phenoxy}-7-methoxyquinolin-6-carboxylic acid methylamide (Compound 48)

Compound 48

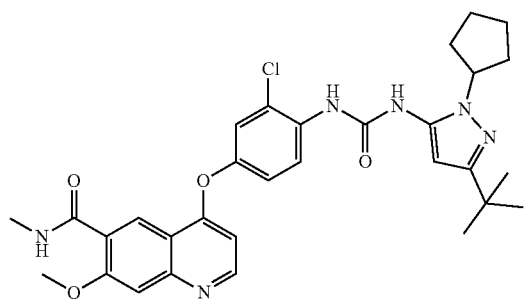

The preparation method was the same as Example 45, except that 5-tert-butyl-2-cyclopentyl-2H-pyrazol-3-ylamine (prepared in Example 30) was used instead of 5-tert-butyl-2H-pyrazol-3-ylamine in Step 3 of Example 45 to give 4-{4-[3-(5-tert-butyl-2-cyclopentyl-2H-pyrazol-3-yl)-ureido]-3-chloro-phenoxy}-7-methoxyquinolin-6-carboxylic acid methylamide.

¹HNMR (DMSO-d6, 400 MHz) δ: 9.10 (s, 1H), 8.69-8.70 (d, 1H), 8.59-8.60 (m, 2H), 8.37-8.38 (m, 1H), 8.25-8.27 (d, 1H), 7.57 (d, 1H), 7.53 (s, 1H), 7.28-7.31 (dd, 1H), 6.57-6.58 (d, 1H), 6.09 (s, 1H), 4.54-4.57 (m, 1H), 4.03 (s, 3H), 2.84-2.85 (d, 3H), 1.61-2.00 (m, 8H), 1.22 (s, 9H).

LC-MS: ESI 591.3 (M+H)+.

Example 49

Preparation of 4-{4-[3-(5-tert-butyl-2H-pyrazol-3-yl)-ureido]-3-methyl-phenoxy}-7-methoxyquinolin-6-carboxylate acid methylamide (Compound 49)

Compound 49

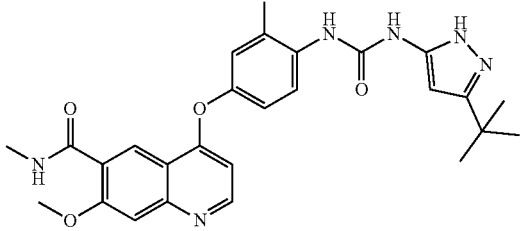

The preparation method was the same as Example 45, except that 4-amino-3-methylphenol was used instead of 4-amino-3-chlorophenol hydrochloride in Step 1 of Example 45 to give 4-{4-[3-(5-tert-butyl-2H-pyrazol-3-yl)-ureido]-3-methyl-phenoxy}-7-methoxyquinolin-6-carboxylate acid methylamide.

¹HNMR (DMSO-d6, 400 MHz) δ: 12.05 (s, 1H), 9.31 (s, 1H), 8.65-8.66 (d, 1H), 8.62 (s, 1H), 8.37-8.38 (m, 1H), 8.13-8.15 (d, 1H), 7.51 (s, 1H), 7.16-7.17 (d, 1H), 7.08-7.11 (dd, 1H), 6.49-6.51 (d, 1H), 5.88 (br, 1H), 4.03 (s, 3H), 2.85-2.86 (d, 3H), 2.33 (s, 3H), 1.27 (s, 9H).

LC-MS: ESI 503.2 (M+H)+.

Example 50

Preparation of 4-{4-[3-(5-tert-butyl-2-methyl-2H-pyrazol-3-yl)-ureido]-3-methyl-phenoxy}-7-methoxy quinolin-6-carboxylate acid methylamide (Compound 50)

Compound 50

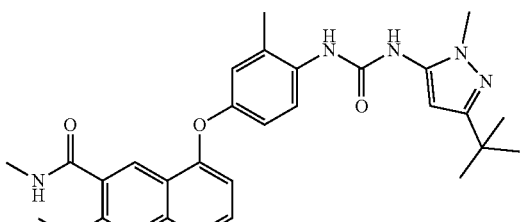

The preparation method was the same as Example 45, except that 4-amino-3-methylphenol was used instead of 4-amino-3-chlorophenol hydrochloride in Step 1 of Example 45, and 5-tert-butyl-2-methyl-2H-pyrazol-3-ylamine (prepared in Step 1 of Example 26) was used instead of 5-tert-butyl-2H-pyrazol-3-ylamine in Step 3 of Example 45 to give 4-{4-[3-(5-tert-butyl-2-methyl-2H-pyrazol-3-yl)-ureido]-3-methyl-phenoxy}-7-methoxy quinolin-6-carboxylate acid methylamide $^1$HNMR (DMSO-d6, 400 MHz) δ: 8.84 (s, 1H), 8.68 (s, 1H), 8.66-8.67 (d, 1H), 8.62 (s, 1H), 8.38-8.39 (m, 1H), 7.91-7.93 (d, 1H), 7.51 (s, 1H), 7.18-7.19 (d, 1H), 7.09-7.11 (dd, 1H), 6.49-6.51 (d, 1H), 6.08 (s, 1H), 4.03 (s, 3H), 3.64 (s, 3H), 2.84-2.86 (d, 3H), 2.30 (s, 3H), 1.22 (s, 9H).

LC-MS: ESI 517.2 (M+H)+.

Example 51

Preparation of 4-{4-[3-(5-tert-butyl-2H-pyrazol-3-yl)-ureido]-3-trifluoromethyl-phenoxy}-7-methoxy-quinolin-6-carboxylic acid methylamide (Compound 51)

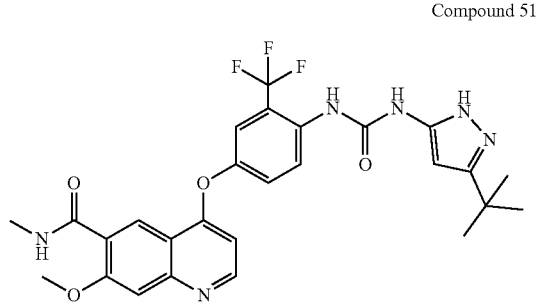 [SMILES: CNC(=O)c1cc2c(Oc3ccc(NC(=O)Nc4cc(C(C)(C)C)n[nH]4)c(C(F)(F)F)c3)ccnc2cc1OC]

Compound 51

The preparation method was the same as Example 45, except that 4-amino-3-trifluoromethylphenol (purchased from TCI) was used instead of 4-amino-3-chlorophenol hydrochloride in Step 1 of Example 45 to give 4-{4-[3-(5-tert-butyl-2H-pyrazol-3-yl)-ureido]-3-trifluoromethyl-phenoxy}-7-methoxyquinolin-6-carboxylic acid methylamide.

$^1$HNMR (DMSO-d6, 400 MHz) δ: 12.09 (s, 1H), 9.61 (s, 1H), 8.69-8.70 (d, 1H), 8.63 (s, 1H), 8.37-8.38 (m, 1H), 8.18-8.20 (d, 1H), 7.67-7.68 (d, 1H), 7.59-7.62 (dd, 1H), 7.54 (s, 1H), 6.58-6.59 (d, 1H), 5.85 (br, 1H), 4.04 (s, 3H), 2.85-2.86 (d, 3H), 1.27 (s, 9H).

LC-MS: ESI 557.1 (M+H)+.

Example 52

Preparation of 4-{4-[3-(5-tert-butyl-2H-pyrazol-3-yl)-ureido]-2-methyl-phenoxy}-7-methoxyquinolin-6-carboxylate acid methylamide (Compound 52)

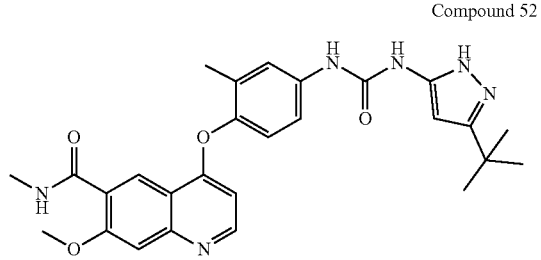 [SMILES: CNC(=O)c1cc2c(Oc3ccc(NC(=O)Nc4cc(C(C)(C)C)n[nH]4)cc3C)ccnc2cc1OC]

Compound 52

The preparation method was the same as Example 45, except that 4-amino-2-methylphenol (purchased from TCI) was used instead of 4-amino-3-chlorophenol hydrochloride in Step 1 of Example 45 to give 4-{4-[3-(5-tert-butyl-2H-pyrazol-3-yl)-ureido]-2-methyl-phenoxy}-7-methoxyquinolin-6-carboxylate acid methylamide.

$^1$HNMR (DMSO-d6, 400 MHz) δ: 12.01 (s, 1H), 9.28 (br, 1H), 8.95 (s, 1H), 8.66 (s, 1H), 8.62-8.64 (d, 1H), 8.37-8.39 (m, 1H), 7.51-7.52 (m, 2H), 7.40-7.43 (dd, 1H), 7.13-7.15 (d, 1H), 6.32-6.34 (d, 1H), 6.00 (br, 1H), 4.03 (s, 3H), 2.85-2.86 (d, 3H), 2.09 (s, 3H), 1.27 (s, 9H).

LC-MS: ESI 503.1 (M+H)+.

Example 53

Preparation of 4-{4-[3-(5-tert-butyl-2-methyl-2H-pyrazol-3-yl)-ureido]-2-methyl-phenoxy}-7-methoxy quinolin-6-carboxylate acid methylamide (Compound 53)

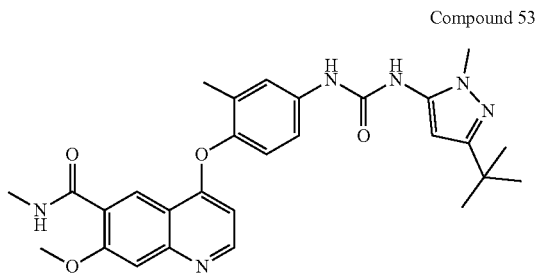 [SMILES: CNC(=O)c1cc2c(Oc3ccc(NC(=O)Nc4cc(C(C)(C)C)nn4C)cc3C)ccnc2cc1OC]

Compound 53

The preparation method was the same as Example 45, except that 4-amino-2-methylphenol (purchased from TCI) was used instead of 4-amino-3-chlorophenol hydrochloride in Step 1 of Example 45, and 5-tert-butyl-2-methyl-2H-pyrazol-3-ylamine (prepared in Step 1 of Example 26) was used instead of 5-tert-butyl-2H-pyrazol-3-ylamine in Step 3 of Example 45 to give 4-{4-[3-(5-tert-butyl-2-methyl-2H-pyrazol-3-yl)-ureido]-2-methyl-phenoxy}-7-methoxyquinolin-6-carboxylate acid methylamide.

$^1$HNMR (DMSO-d6, 400 MHz) δ: 9.01 (s, 1H), 8.66 (s, 1H), 8.63-8.64 (d, 1H), 8.56 (s, 1H), 8.38-8.39 (m, 1H), 7.54-7.55 (s, 1H), 7.52 (s, 1H), 7.39-7.42 (dd, 1H), 7.14-7.16 (d, 1H), 6.32-6.33 (d, 1H), 6.07 (br, 1H), 4.03 (s, 3H), 3.62 (s, 3H), 2.85-2.86 (d, 3H), 2.09 (s, 3H), 1.22 (s, 9H).

LC-MS: ESI 517.2 (M+H)+.

Example 54

Preparation of 4-{4-[3-(5-tert-butyl-2H-pyrazol-3-yl)-ureido]-2-chloro-phenoxy}-7-methoxyquinolin-6-carboxylic acid methylamide (Compound 54)

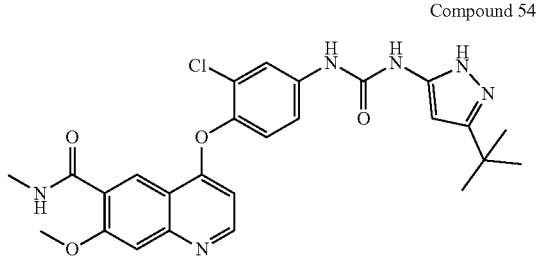 [SMILES: CNC(=O)c1cc2c(Oc3ccc(NC(=O)Nc4cc(C(C)(C)C)n[nH]4)cc3Cl)ccnc2cc1OC]

Compound 54

The preparation method was the same as Example 45, except that 4-amino-2-chlorophenol (purchased from TCI) was used instead of 4-amino-3-chlorophenol hydrochloride in Step 1 of Example 45 to give 4-{4-[3-(5-tert-butyl-2H-pyrazol-3-yl)-ureido]-2-chloro-phenoxy}-7-methoxyquinolin-6-carboxylic acid methylamide.

¹HNMR (DMSO-d6, 400 MHz) δ:12.04 (s, 1H), 9.43 (s, 1H), 9.04 (s, 1H), 8.66-8.67 (d, 1H), 8.64 (s, 1H), 8.39-8.41 (m, 1H), 7.97-7.98 (d, 1H), 7.53 (s, 1H), 7.38-7.41 (m, 2H), 6.39-6.41 (d, 1H), 6.04 (s, 1H), 4.03 (s, 3H), 2.85-2.86 (d, 3H), 1.27 (s, 9H).

LC-MS: ESI 523.2 (M+H)⁺.

Example 55

Preparation of 4-{4-[3-(5-tert-butyl-2-methyl-2H-pyrazol-3-yl)-ureido]-2-chloro-phenoxy}-7-methoxy quinolin-6-carboxylic acid methylamide (Compound 55)

Compound 55

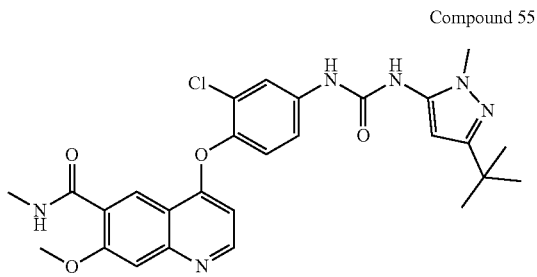 [SMILES: CNC(=O)c1cc2c(Oc3ccc(NC(=O)Nc4cc(C(C)(C)C)nn4C)cc3Cl)ccnc2cc1OC]

The preparation method was the same as Example 45, except that 4-amino-2-chlorophenol (purchased from TCI) was used instead of 4-amino-3-chlorophenol hydrochloride in Step 1 of Example 45, and 5-tert-butyl-2-methyl-2H-pyrazol-3-ylamine (prepared in Step 1 of Example 26) was used instead of 5-tert-butyl-2H-pyrazol-3-ylamine in Step 3 of Example 45 to give 4-{4-[3-(5-tert-butyl-2-methyl-2H-pyrazol-3-yl)-ureido]-2-chloro-phenoxy}-7-methoxyquinolin-6-carboxylic acid methylamide.

¹HNMR (DMSO-d6, 400 MHz) δ: 9.25 (s, 1H), 8.66-8.67 (d, 1H), 8.64 (s, 1H), 8.63 (s, 1H), 8.39-8.41 (m, 1H), 7.95-7.96 (d, 1H), 7.51 (s, 1H), 7.41-7.47 (m, 2H), 6.38-6.40 (d, 1H), 6.07 (s, 1H), 4.03 (s, 3H), 3.62 (s, 3H), 2.85-2.86 (d, 3H), 2.30 (s, 3H), 1.22 (s, 9H).

LC-MS: ESI 537.2 (M+H)⁺.

Example 56

Preparation of 4-{4-[3-(5-tert-butyl-2H-pyrazol-3-yl)-ureido]-2,3-dichloro-phenoxy}-7-methoxyquinolin-6-carboxylic acid methylamide (Compound 56)

Compound 56

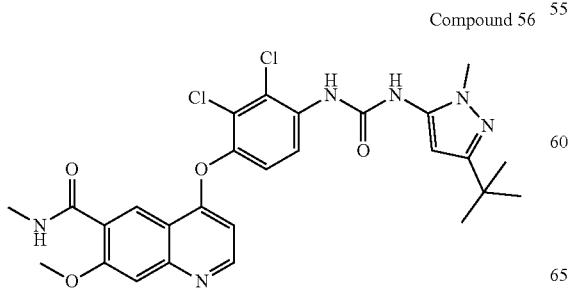

The preparation method was the same as Example 45, except that 4-amino-2,3-dichlorophenol (purchased from TCI) was used instead of 4-amino-3-chlorophenol hydrochloride in Step 1 of Example 45 to give 4-{4-[3-(5-tert-butyl-2H-pyrazol-3-yl)-ureido]-2,3-dichloro-phenoxy}-7-methoxyquinolin-6-carboxylic acid methylamide.

¹HNMR (DMSO-d6, 400 MHz) δ: 12.14 (s, 1H), 9.70 (s, 1H), 8.66-8.67 (d, 1H), 8.63 (s, 1H), 8.39-8.44 (m, 2H), 7.55 (s, 1H), 7.49-7.52 (d, 1H), 6.47-6.49 (d, 1H), 5.85 (br, 1H), 4.04 (s, 3H), 2.85-2.86 (d, 3H), 1.27 (s, 9H).

LC-MS: ESI 557.0\559.0 (M+H)+.

Example 57

Preparation of 4-{4-[3-(5-tert-butyl-2-methyl-2H-pyrazol-3-yl)-ureido]-2,3-dichloro-phenoxy}-7-methoxyquinolin-6-carboxylic acid methylamide (Compound 57)

Compound 57

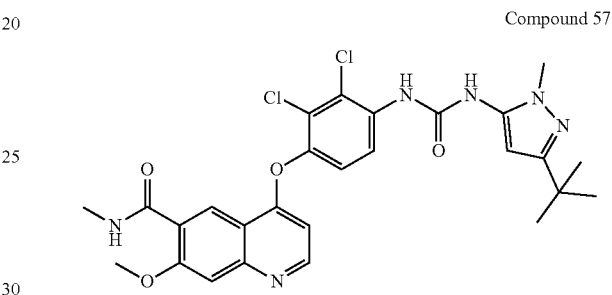

The preparation method was the same as Example 45, except that 4-amino-2,3-dichlorophenol (purchased from TCI) was used instead of 4-amino-3-chlorophenol hydrochloride in Step 1 of Example 45, and 5-tert-butyl-2-methyl-2H-pyrazol-3-ylamine (prepared in Step 1 of Example 26) was used instead of 5-tert-butyl-2H-pyrazol-3-ylamine in Step 3 of Example 45 to give 4-{4-[3-(5-tert-butyl-2-methyl-2H-pyrazol-3-yl)-ureido]-2,3-dichloro-phenoxy}-7-methoxyquinolin-6-carboxylic acid methylamide.

¹HNMR (DMSO-d6, 400 MHz) δ: 9.32 (s, 1H), 8.80 (s, 1H), 8.67-8.68 (d, 1H), 8.63 (s, 1H), 8.39-8.40 (m, 1H), 8.28-8.30 (d, 1H), 7.55 (s, 1H), 7.50-7.53 (d, 1H), 6.47-6.49 (d, 1H), 6.12 (s, 1H), 4.04 (s, 3H), 3.66 (s, 3H), 2.85-2.86 (d, 3H), 1.22 (s, 9H).

LC-MS: ESI 571.0\573.0 (M+H)⁺.

Example 58

Preparation of 4-{4-[3-(5-tert-butyl-2H-pyrazol-3-yl)-ureido]-3-chloro-phenoxy}-7-(2-methoxy-ethoxy)-quinolin-6-carboxylic acid methylamide (Compound 58)

Compound 58

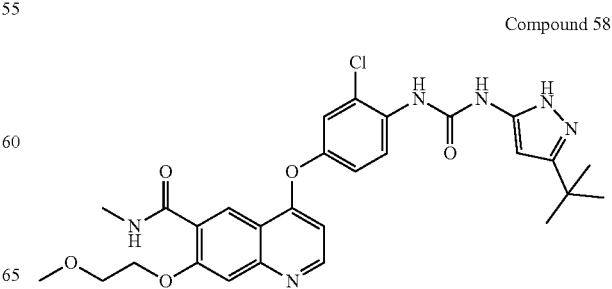

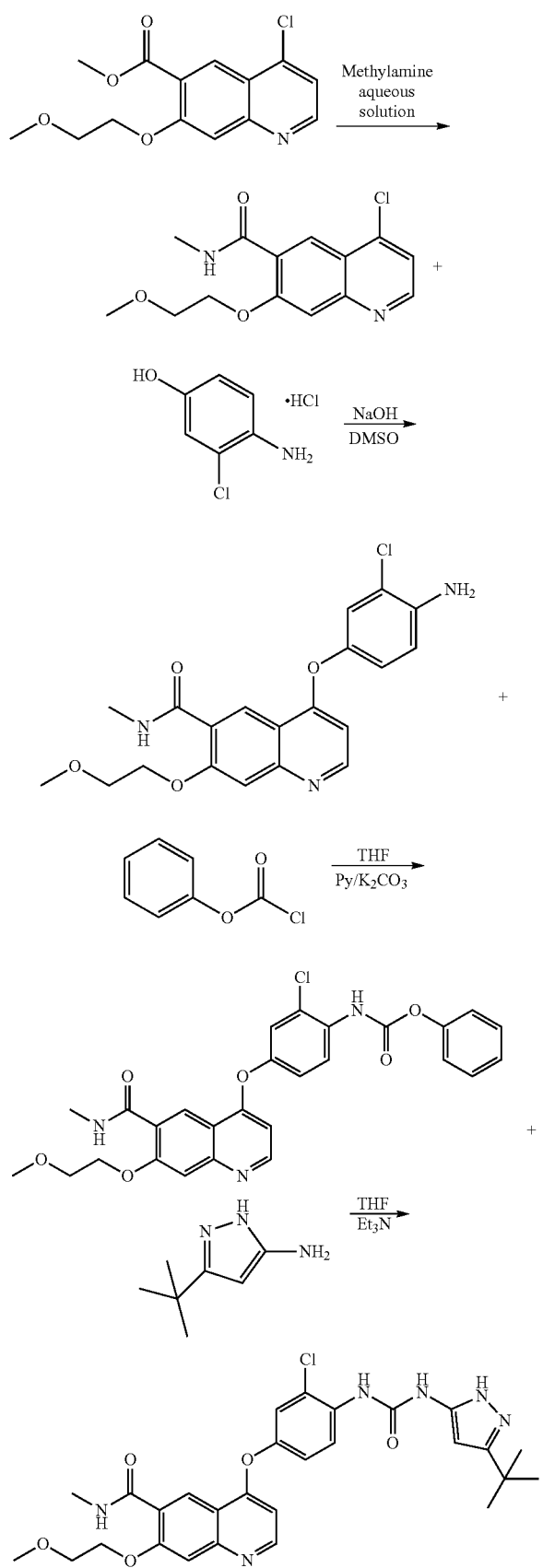

Step 1: Preparation of 4-chloro-7-(2-methoxy-ethoxy)-quinolin-6-carboxylic acid methylamide Methyl 4-chloro-7-(2-methoxy-ethoxy)-quinolin-6-carboxylate (prepared in step 2 of Example 42) (500 mg, 1.78 mmol) was dissolved in 20 ml of methylamine aqueous solution. The mixture was heated to 50° C. for 1 hour under nitrogen atmosphere. The reaction solution was cooled to room temperature, and poured slowly into water, and then extracted with ethyl acetate (50 ml×2). The organic phase was washed twice with saturated NaCl solution, dried over anhydrous sodium sulfate, and filtered. The filtrate was concentrated under reduced pressure to give 400 mg of 4-chloro-7-(2-methoxy-ethoxy)-quinolin-6-carboxylic acid methylamide as a solid.

Step 2: Preparation of 4-(4-amino-3-chloro-phenoxy)-7-(2-methoxy-ethoxy)-quinolin-6-carboxylic acid methylamide The preparation method was the same as Step 4 of Example 42, except that 4-chloro-7-(2-methoxy-ethoxy)-quinolin-6-carboxylic acid methyl prepared in Step 1 was used instead of 4-chloro-7-(2-methoxy-ethoxy)-quinolin-6-carboxamide in Step 4 of Example 42 to give 4-(4-amino-3-chloro-phenoxy)-7-(2-methoxy-ethoxy)-quinolin-6-carboxylic acid methylamide.

Step 3: Preparation of phenyl {2-chloro-4-[7-(2-methoxy-ethoxy)-6-methylcarbamoyl-quinolin-4-yloxy]-phenyl}-carbamate The preparation method was the same as Step 5 of Example 42, except that 4-(4-amino-3-chloro-phenoxy)-7-(2-methoxy-ethoxy)-quinolin-6-carboxylic acid methylamide prepared in Step 2 was used instead of 4-(4-amino-3-chloro-phenoxy)-7-(2-methoxy-ethoxy)-quinolin-6-carboxamide in Step 5 of Example 42 to give phenyl {2-chloro-4-[7-(2-methoxy-ethoxy)-6-methylcarbamoyl-quinolin-4-yloxy]-phenyl}-carbamate.

Step 4: Preparation of 4-{4-[3-(5-tert-butyl-2H-pyrazol-3-yl)-ureido]-3-chloro-phenoxy}-7-(2-methoxy-ethoxy)-quinolin-6-carboxylic acid methylamide Phenyl {2-chloro-4-[7-(2-methoxy-ethoxy)-6-meoxy-ethoxy)-6-methylcarbamoyl-quinolin-4-yloxy]-phenyl}-carbamate prepared in Step 3 (800 mg, 0.153 mmol), 5-tert-butyl-2H-pyrazol-3-ylamine (32 mg, 0.230 mmol) and triethylamine (46.3 mg, 0.459 mmol) were dissolved in 10 ml of THF and refluxed overnight. The next day, the reaction solution was concentrated under reduced pressure, and the residues were purified by column chromatography (eluent: dichloromethane/methanol) to give 55 mg of 4-{4-[3-(5-tert-butyl-2H-pyrazol-3-yl)-ureido]-3-chloro-phenoxy}-7-(2-methoxy-ethoxy)-quinolin-6-carboxylic acid methylamide as a solid.

$^1$HNMR (DMSO-d6, 400 MHz) δ: 12.11 (s, 1H), 9.60 (s, 1H), 8.70 (s, 1H), 8.68-8.69 (d, 1H), 8.37-8.42 (m, 2H), 7.59 (s, 1H), 7.56-7.57 (d, 1H), 7.28-7.31 (dd, 1H), 6.58-6.59 (d, 1H), 5.82 (br, 1H), 4.41-4.43 (t, 2H), 3.81-3.84 (t, 2H), 3.40 (s, 3H), 2.87-2.88 (d, 3H), 1.27 (s, 9H).

LC-MS: ESI 567.2 (M+H)$^+$.

Example 59

Preparation of 4-{4-[3-(5-tert-butyl-2-methyl-2H-pyrazol-3-yl)-ureido]-3-chloro-phenoxy}-7-(2-methoxy-ethoxy)-quinolin-6-carboxylic acid methylamide (Compound 59)

Compound 59

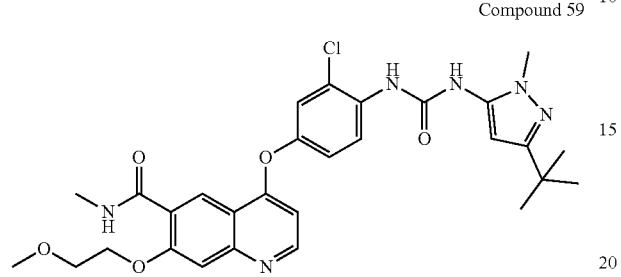

The preparation method was the same as Example 58, except that 5-tert-butyl-2-methyl-2H-pyrazol-3-ylamine was used instead of 5-tert-butyl-2H-pyrazol-3-ylamine in Step 4 of Example 58 to give 4-{4-[3-(5-tert-butyl-2-methyl-2H-pyrazol-3-yl)-ureido]-3-chloro-phenoxy}-7-(2-methoxy-ethoxy)-quinolin-6-carboxylic acid methylamide.

$^1$HNMR (DMSO-d6, 400 MHz) δ: 9.22 (s, 1H), 8.69-8.70 (m, 2H), 8.63 (s, 1H), 8.36-8.37 (m, 1H), 8.25-8.27 (d, 1H), 7.59 (s, 1H), 7.57-7.58 (d, 1H), 7.29-7.32 (dd, 1H), 7.58-7.59 (d, 1H), 6.11 (s, 1H), 4.41-4.43 (t, 2H), 3.81-3.84 (t, 2H), 3.65 (s, 3H), 3.40 (s, 3H), 2.87-2.88 (d, 3H), 1.22 (s, 9H).

LC-MS: ESI 581.0 (M+H)$^+$.

Example 60

Preparation of 4-{4-[3-(5-tert-butyl-2-methyl-2H-pyrazol-3-yl)-ureido]-2,3-dichloro-phenoxy}-7-(2-methoxy-ethoxy)-quinolin-6-carboxylic acid methylamide (Compound 60)

Compound 60

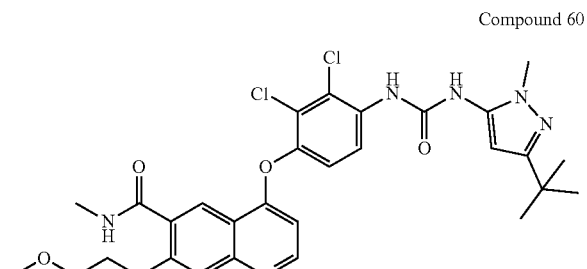

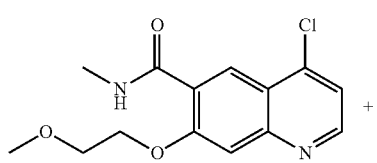

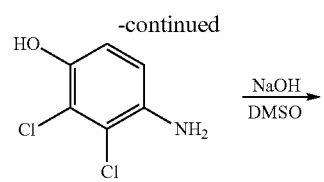

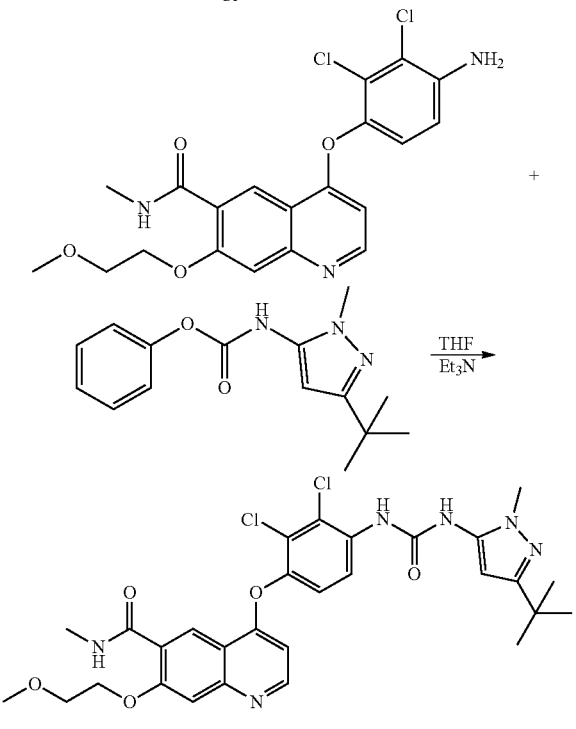

Step 1: Preparation of 4-(4-amino-2,3-dichloro-phenoxy)-7-(2-methoxy-ethoxy)-quinolin-6-carboxylic acid methylamide 4-Amino-2,3-dichlorophenol (272 mg, 1.52 mmol) and sodium hydroxide (61 mg, 1.52 mmol) were dissolved in 10 mL DMSO and stirred for 30 min at room temperature. 4-Chloro-7-(2-methoxy-ethoxy)-quinolin-6-carboxylic acid methylamide (300 mg, 1.02 mmol) (prepared in Step 1 of Example 58) was added and the mixture was heated to 100° C. for 1 hour. The reaction solution was cooled to room temperature, and poured slowly into water, and then extracted with ethyl acetate (60 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 280 mg of the product.

Step 2: Preparation of 4-{4-[3-(5-tert-butyl-2-methyl-2H-pyrazol-3-yl)-ureido]-2,3-dichloro-phenoxy}-7-(2-methoxy-ethoxy)-quinolin-6-carboxylic acid methylamide 4-(4-Amino-2,3-dichloro-phenoxy)-7-(2-methoxy-ethoxy)-quinolin-6-carboxylic acid methylamide obtained in Step 1, phenyl (5-tert-butyl-2-methyl-2H-pyrazol-3-yl)-carbamate (prepared in Step 6 of Example 39) (132 mg, 0.482 mmol) and triethylamine (97 mg, 0.963 mmol) were dissolved in 12 ml of THF and refluxed overnight. The next day, the reaction solution was concentrated under reduced pressure, and the residues were purified by column chromatography (eluent: dichloromethane/methanol) to give 42 mg of 4-{4-[3-(5-tert-butyl-2-methyl-2H-pyrazol-3-yl)-ureido]-2,3-dichloro-phenoxy}-7-(2-m ethoxy-ethoxy)-quinolin-6-carboxylic acid methylamide as a solid.

¹HNMR (DMSO-d6, 400 MHz) δ: 9.29 (s, 1H), 8.78 (s, 1H), 8.73 (s, 1H), 8.67-8.69 (d, 1H), 8.37-8.38 (m, 1H), 8.27-8.29 (d, 1H), 7.61 (s, 1H), 7.50-7.53 (d, 1H), 6.48-6.49 (d, 1H), 6.12 (s, 1H), 4.42-4.44 (t, 2H), 3.82-3.84 (t, 2H), 3.66 (s, 3H), 3.40 (s, 3H), 2.88-2.89 (d, 3H), 1.22 (s, 9H).

LC-MS: ESI 615.0\617.0 (M+H)+.

Example 61

Preparation of 4-{4-[3-(5-tert-butyl-2H-pyrazol-3-yl)-ureido]-3-chloro-phenoxy}-7-methoxyquinolin-6-carboxylic acid diethylamide (Compound 61)

Compound 61

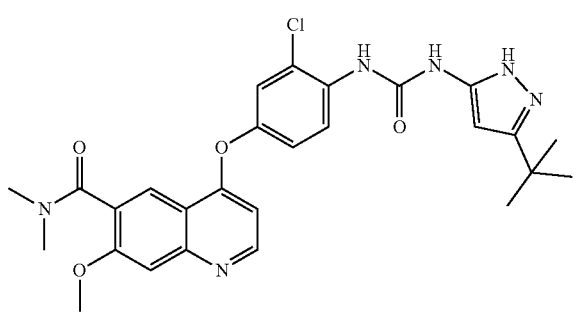

The preparation method was the same as Example 45, except that 4-chloro-7-methoxy-quinolin-6-carboxylic acid diethylamide (prepared in Step 3 of Example 16) was used instead of 4-chloro-7-methoxy-quinolin-6-carboxylic acid methylamine in Step 1 of Example 45 to give 4-{4-[3-(5-tert-butyl-2H-pyrazol-3-yl)-ureido]-3-chloro-phenoxy}-7-methoxyquinolin-6-carboxylic acid diethylamide.

¹HNMR (DMSO-d6, 400 MHz) δ: 12.11 (s, 1H), 9.59 (s, 1H), 8.66-8.67 (d, 1H), 8.38-8.40 (d, 1H), 8.05 (s, 1H), 7.54-7.55 (d, 1H), 7.52 (s, 1H), 7.27-7.30 (dd, 1H), 7.58-7.59 (d, 1H), 5.85 (br, 1H), 3.98 (s, 3H), 3.03 (s, 3H), 2.81 (s, 3H), 1.27 (s, 9H).

LC-MS: ESI 537.1 (M+H)+.

Example 62

Preparation of 4-{4-[3-(5-tert-butyl-2H-pyrazol-3-yl)-ureido]-3-chloro-phenoxy}-7-methoxyquinolin-6-carboxylic acid (2-methoxy-ethyl)-amide (Compound 62)

Compound 62

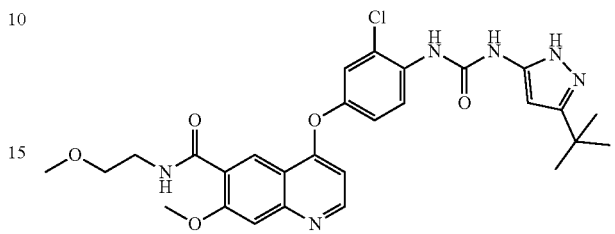

The preparation method was the same as Example 45, except that 4-chloro-7-methoxy-quinolin-6-carboxylic acid (2-methoxy-ethyl)-amide (prepared in Example 17) was used instead of 4-chloro-7-methoxy-quinolin-6-carboxylic acid methylamine in Step 1 of Example 45 to give 4-{4-[3-(5-tert-butyl-2H-pyrazol-3-yl)-ureido]-3-chloro-phenoxy}-7-methoxyquinolin-6-carboxylic acid (2-methoxy-ethyl)-amide.

¹HNMR (DMSO-d6, 400 MHz) δ: 12.11 (s, 1H), 9.60 (s, 1H), 8.68-8.70 (d, 1H), 8.63 (s, 1H), 8.40-8.48 (m, 2H), 7.55-7.56 (d, 1H), 7.54 (s, 1H), 7.28-7.31 (dd, 1H), 7.57-7.59 (d, 1H), 5.90 (br, 1H), 4.04 (s, 3H), 3.48-3.50 (m, 4H), 3.31 (s, 3H), 1.27 (s, 9H).

LC-MS: ESI 567.1 (M+H)+.

Example 63

Preparation of N-(4-{4-[3-(5-tert-butyl-2H-pyrazol-3-yl)-ureido]-3-chloro-phenoxy}-7-methoxyquinolin-6-yl)-acetamide (Compound 63)

Compound 63

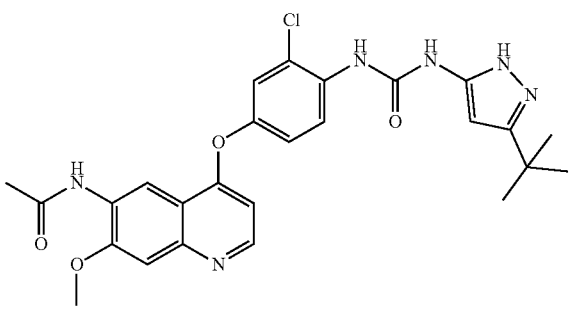

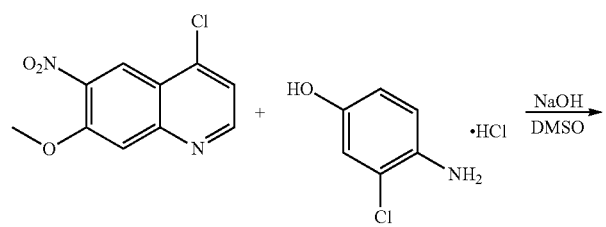

-continued
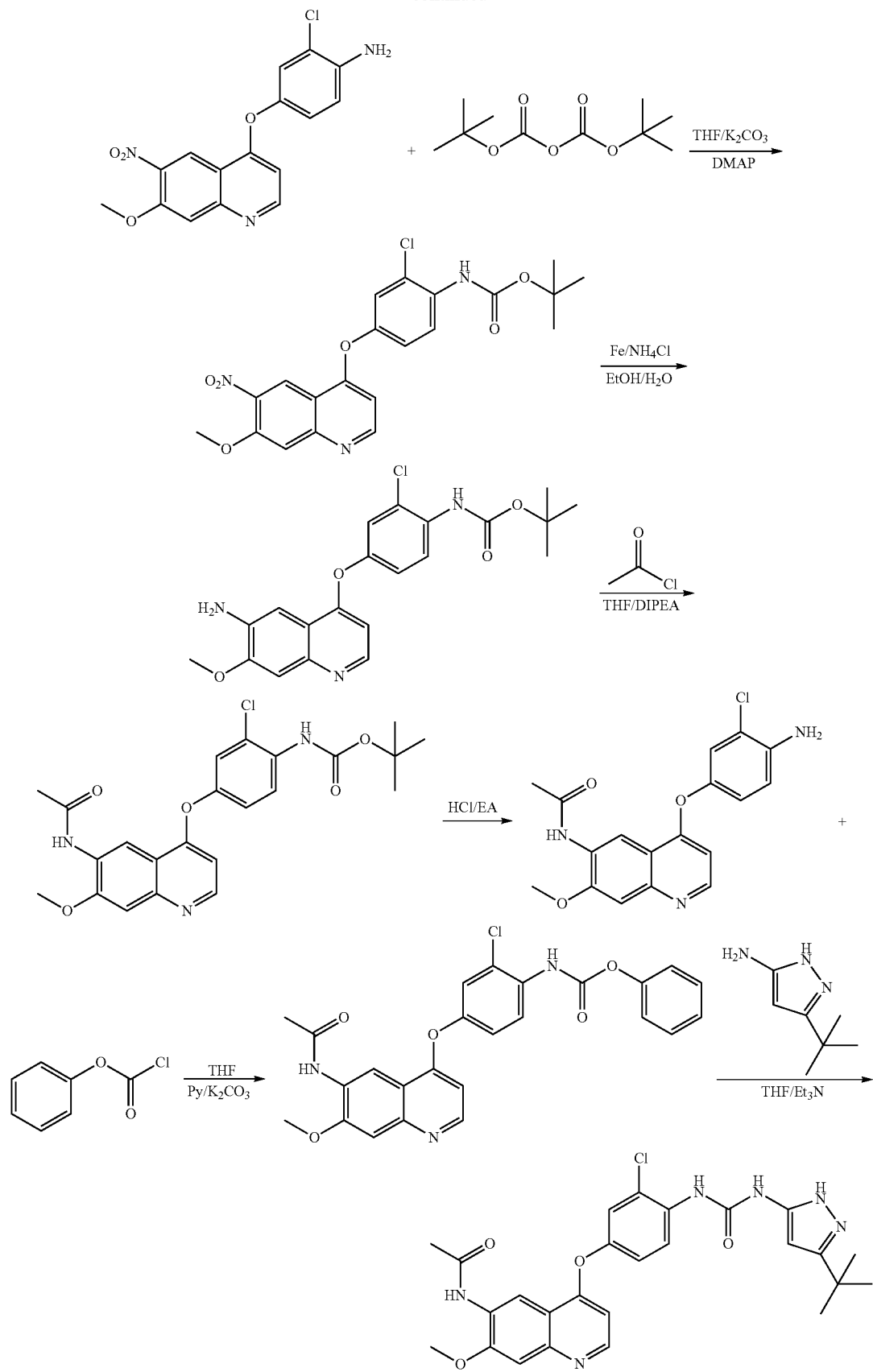

Step 1: Preparation of 2-chloro-4-(7-methoxy-6-nitro-quinolin-4-yloxy)-aniline 4-Amino-3-chlorophenol hydrochloride (1.44 g, 8.0 mmol) was dissolved in 30 ml of DMSO at room temperature, and added with sodium hydroxide (640 mg, 16.0 mmol). The mixture was stirred at room temperature for 0.5 hour. 4-Chloro-7-methoxy-6-nitro-quinoline (prepared in Step 1 of Example 18) (954 mg, 4 mmol) (dissolved in 30 ml DMSO) was added and the mixture was heated to 100° C. for 1 hour. The reaction solution was cooled to room temperature, and poured slowly into 200 ml of water, and then extracted with ethyl acetate (100 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 1.10 g of 2-chloro-4-(7-methoxy-6-nitro-quinolin-4-yloxy)-aniline as a solid.

Step 2: Preparation of tert-butyl [2-chloro-4-(7-methoxyl-6-nitro-quinolin-4-yloxy)-phenyl]-carbamate At room temperature, 2-chloro-4-(7-methoxy-6-nitro-quinolin-4-yloxy)-aniline (prepared in Step 1) (1 g, 2.90 mmol), di-tert-butyl dicarbonate (5 g, 23.20 mmol) and DMAP (18 mg, 0.145 mmol) were dissolved in 40 ml of THF and added with potassium carbonate (800 mg, 5.80 mmol). The mixture was stirred at room temperature for 1 hour.

The reaction solution was poured slowly into 100 ml of water, and extracted with ethyl acetate (60 ml×2). The organic phase was washed twice with saturated NaCl solution, dried over anhydrous sodium sulfate, and filtered. The filtrate was concentrated under reduced pressure to give 1.30 g crude product, which was used directly in the next step without purification.

Step 3: Preparation of tert-butyl [4-(6-amino-7-methoxy-quinolin-4-yloxy)-2-chloro-phenyl]-carbamate

[2-chloro-4-(7-methoxyl-6-nitro-quinolin-4-yloxy)-phenyl]-t carbamate (1.30 g, 2.90 mmol) obtained in Step 2, reduced iron powder (812 mg, 14.5 mmol) and ammonium chloride (1.24 g, 23.2 mmol) were added to ethanol (24 ml) and water (6 ml). The mixture was refluxed for 1 hour. The reaction solution was cooled to room temperature, and poured slowly into 100 ml of saturated aqueous solution of sodium bicarbonate, and then extracted with ethyl acetate (80 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 620 mg of tert-butyl [4-(6-amino-7-methoxy-quinolin-4-yloxy)-2-chloro-phenyl]-carbamate.

Step 4: Preparation of tert-butyl [4-(6-acetylamino-7-methoxy-quinolin-4-yloxy)-2-chloro-phenyl]-carbamate tert-Butyl [4-(6-amino-7-methoxy-quinolin-4-yloxy)-2-chloro-phenyl]-carbamate obtained in Step 3 (400 mg, 0.96 mmol) and N,N-diisopropylethylamine (186 mg, 1.44 mmol) were dissolved in 20 ml of THF at room temperature. Acetyl chloride (90 mg, 1.15 mmol) (diluted in 2 ml of THF) was added dropwise under ice bath. The mixture was stirred at room temperature for 0.5 hour. The reaction solution was poured slowly into water, and extracted with ethyl acetate (50 ml×2). The organic phase was washed twice with saturated NaCl solution, dried over anhydrous sodium sulfate, and filtered. The filtrate was concentrated under reduced pressure to give 500 mg of crude tert-butyl [4-(6-acetylamino-7-methoxy-quinolin-4-yloxy)-2-chloro-phenyl]-carbamate, which was used directly in the next step without purification.

Step 5: Preparation of N-[4-(4-amino-3-chloro-phenoxy)-7-methoxy-quinolin-6-yl]-acetamide tert-Butyl [4-(6-acetylamino-7-methoxy-quinolin-4-yloxy)-2-chloro-phenyl]-carbamate obtained in Step 4 (500 mg, 1.09 mmol) was dissolved in 10 ml of ethyl acetate, and added with a solution of hydrochloric acid in ethyl acetate (10 ml, 4.7 mol/L) dropwise at room temperature. The mixture was reacted at room temperature for 1 hour. The reaction solution was poured slowly into 100 ml of saturated aqueous solution of sodium bicarbonate, and extracted with ethyl acetate (50 ml×2). The organic phase was washed twice with saturated NaCl solution, dried over anhydrous sodium sulfate, and filtered. The filtrate was concentrated under reduced pressure to give 320 mg of crude N-[4-(4-amino-3-chloro-phenoxy)-7-methoxy-quinolin-6-yl]-acetamide, which was used directly in the next step without any purification.

Step 6: Preparation of phenyl [4-(6-acetylamino-7-methoxy-quinolin-4-yloxy)-2-chloro-phenyl]-carbamate N-[4-(4-amino-3-chloro-phenoxy)-7-methoxy-quinolin-6-yl]-acetamide (320 mg, 0.90 mmol) obtained in Step 5 and pyridine (213 mg, 2.70 mmol) were dissolved in 20 ml of THF, and added with potassium carbonate (138 mg, 1 mmol) at room temperature. The reaction solution was cooled to 0-5° C. in an ice bath, and added with phenyl chloroformate (211 mg, 1.35 mmol) (diluted with 2 ml of THF) dropwise. The mixture was allowed to react at room temperature for 2 hours and poured slowly into water, and then extracted with ethyl acetate (50 ml×2). The organic phase was washed with saturated NaCl solution, dried over anhydrous sodium sulfate, and filtered. The filtrate was concentrated under reduced pressure and the residues were purified by column chromatography (eluent: dichloromethane/methanol) to give 400 mg of phenyl [4-(6-acetylamino-7-methoxy-quinolin-4-yloxy)-2-chloro-phenyl]-carbamate as a solid.

Step 7: Preparation of N-(4-{4-[3-(5-tert-butyl-2H-pyrazol-3-yl)-ureido]-3-chloro-phenoxy}-7-methoxyquinolin-6-yl)-acetamide Phenyl [4-(6-acetylamino-7-methoxy-quinolin-4-yloxy)-2-chloro-phenyl]-carbamate (100 mg, 0.21 mmol) obtained in Step 6, 5-tert-butyl-2H-pyrazol-3-ylamine (purchased from TCI) (40.3 mg, 0.29 mmol) and triethylamine (63.6 mg, 0.63 mmol) were dissolved in 10 ml of THF. The mixture was heated to 70° C. and allowed to react overnight. The next day, the reaction solution was concentrated under reduced pressure, and the residues were purified by column chromatography (eluent: dichloromethane/methanol) to give 67 mg of N-(4-{4-[3-(5-tert-butyl-2H-pyrazol-3-yl)-ureido]-3-chloro-phenoxy}-7-methoxyquinol in-6-yl)-acetamide as a solid.

$^1$HNMR (DMSO-d6, 400 MHz) δ: 12.10 (s, 1H), 9.59 (s, 1H), 9.48 (s, 1H), 8.99 (s, 1H), 8.54-8.55 (d, 1H), 8.38-8.40 (d, 1H), 7.74 (br, 1H), 7.50-7.51 (d, 1H), 7.47 (s, 1H), 7.23-7.26 (dd, 1H), 6.53-6.54 (d, 1H), 5.85 (br, 1H), 4.04 (s, 3H), 2.19 (s, 3H), 1.27 (s, 9H).

LC-MS: ESI 523.1 (M+H)+.

Example 64

Preparation of N-(4-{4-[3-(5-tert-butyl-2H-pyrazol-3-yl)-ureido]-3-chloro-phenoxy}-7-methoxyquinol in-6-yl)-propionamide (Compound 64)

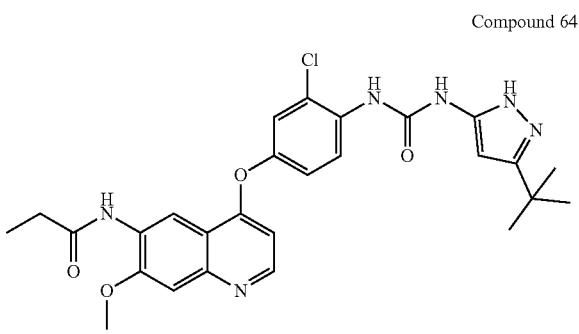 [SMILES: CCC(=O)Nc1cc2c(Oc3ccc(NC(=O)Nc4cc(C(C)(C)C)n[nH]4)c(Cl)c3)ccnc2cc1OC]

Compound 64

The preparation method was the same as Steps 2 to 3 of Example 45, except that N-[4-(4-amino-3-chloro-phenoxy)-7-methoxy-quinolin-6-yl]-propanamide (prepared in Example 21) was used instead of 4-(4-amino-3-chloro-phenoxy)-7-methoxy-quinolin-6-carboxylic acid methylamide in Step 2 of Example 45 to give N-(4-{4-[3-(5-tert-butyl-2H-pyrazol-3-yl)-ureido]-3-chloro-phenoxy}-7-methoxyquinol in-6-yl)-propionamide.

$^1$HNMR (DMSO-d6, 400 MHz) δ: 12.11 (s, 1H), 9.59 (s, 1H), 9.38 (s, 1H), 9.02 (s, 1H), 8.53-8.54 (d, 1H), 8.38-8.40 (m, 1H), 7.49-7.50 (d, 1H), 7.47 (s, 1H), 7.23-7.26 (dd, 1H), 6.53-6.54 (d, 1H), 5.87 (br, 1H), 4.04 (s, 3H), 2.48-2.53 (m, 2H), 1.27 (s, 9H), 1.08-1.12 (t, 3H).

LC-MS: ESI 537.2 (M+H)+.

Example 65

Preparation of cyclopentane carboxylic acid (4-{4-[3-(5-tert-butyl-2H-pyrazol-3-yl)-ureido]-3-chloro-phenoxy}-7-methoxy-quinolin-6-yl)-amide (Compound 65)

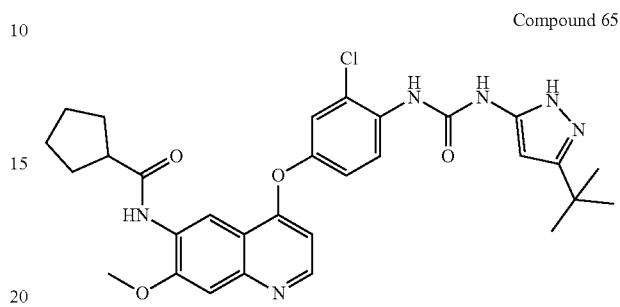

Compound 65

The preparation method was the same as Steps 2 to 3 of Example 45, except that cyclopentane carboxylic acid [4-(4-amino-3-chloro-phenoxy)-7-methoxy-quinolin-6-yl]-amide (prepared in Example 23) was used instead of 4-(4-amino-3-chloro-phenoxy)-7-methoxy-quinolin-6-carboxylic acid methylamide in Step 2 of Example 45 to give cyclopentane carboxylic acid (4-{4-[3-(5-tert-butyl-2H-pyrazol-3-yl)-ureido]-3-chloro-phenoxy}-7-methoxy-quinolin-6-yl)-amide.

$^1$HNMR (DMSO-d6, 400 MHz) δ: 12.10 (s, 1H), 9.59 (s, 1H), 9.33 (s, 1H), 9.03 (s, 1H), 8.53-8.55 (d, 1H), 8.38-8.40 (d, 1H), 7.50 (d, 1H), 7.47 (s, 1H), 7.23-7.26 (dd, 1H), 6.52-6.54 (d, 1H), 5.85 (br, 1H), 4.04 (s, 3H), 3.08-3.12 (m, 1H), 1.54-1.92 (m, 8H), 1.27 (s, 9H).

LC-MS: ESI 577.1 (M+H)+.

Example 66

Preparation of N-[4-{4-[3-(5-tert-butyl-2H-pyrazol-3-yl)-ureido]-3-chloro-phenoxy}-7-(2-methoxy-ethoxy)-quinolin-6-yl]-acetamide (Compound 66)

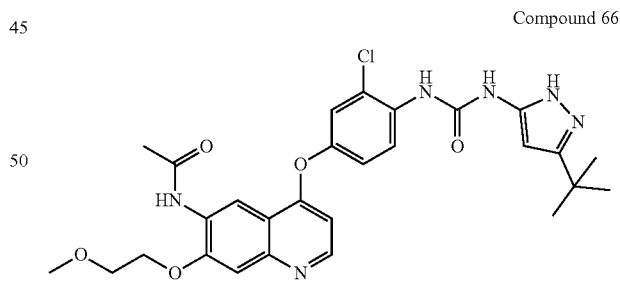

Compound 66

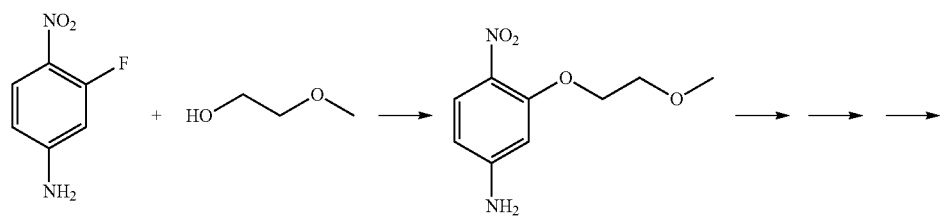

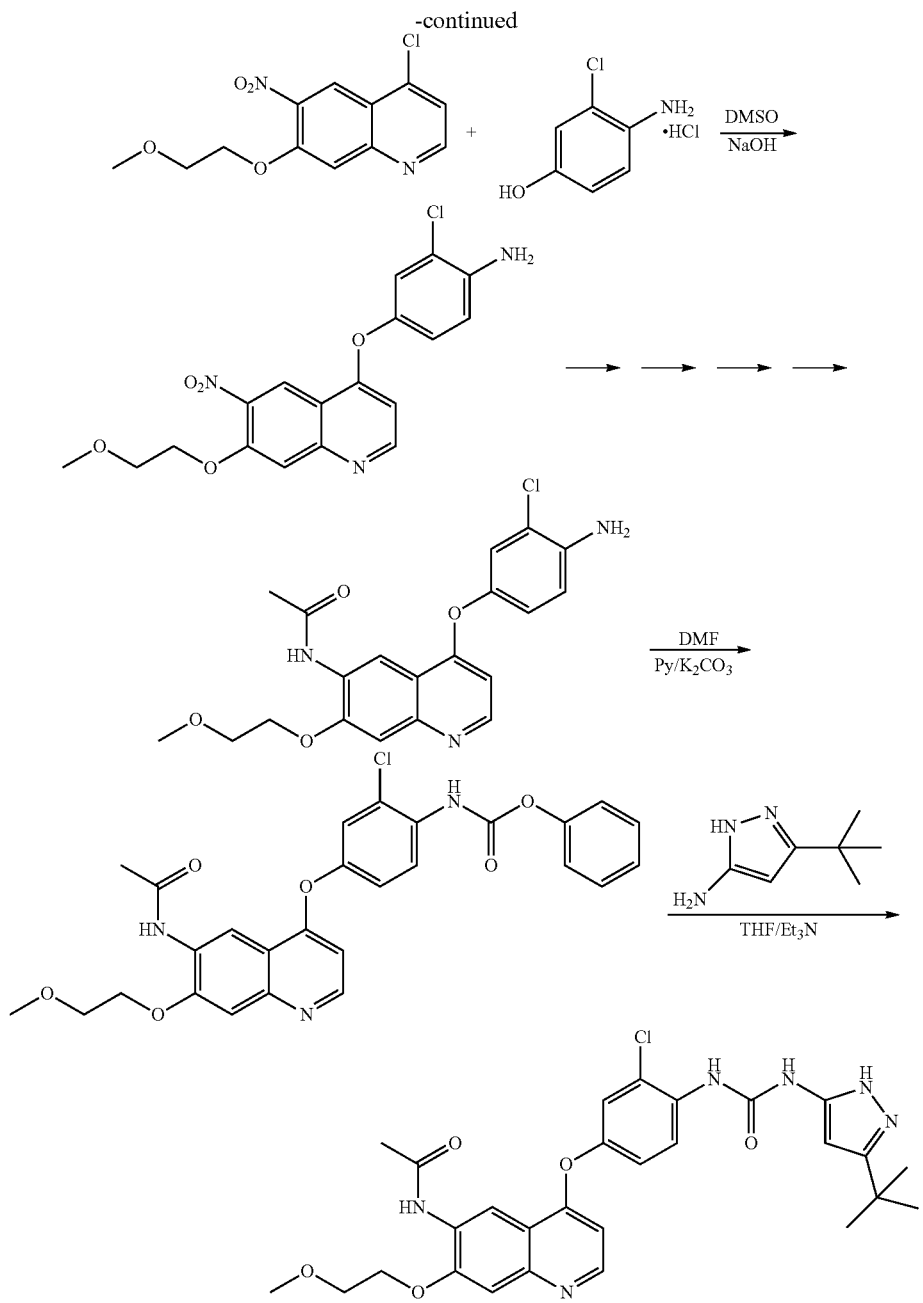

Step 1: Preparation of 3-(2-methoxy-ethoxy)-4-nitro-aniline

2-Methoxy-ethanol (purchased from TCI) (15.2 g, 0.2 mol) was dissolved in 50 ml of THF at room temperature. The solution was cooled to 0-5° C. in an ice bath, and added with 60% sodium hydrogen (2.4 g, 0.06 mol) slowly. The mixture was allowed to react at room temperature for 1 hour. 3-Fluoro-4-nitro-aniline (3.12 g, 0.02 mol) was slowly added and the reaction mixture was stirred at room temperature overnight. The reaction solution was poured slowly into water, and then extracted with ethyl acetate (100 ml×2). The organic phase was washed twice with saturated NaCl solution, dried over anhydrous sodium sulfate, and filtered. The filtrate was concentrated under reduced pressure to give 4.30 g of 3-(2-methoxy-ethoxy)-4-nitro-aniline as a solid.

Step 2: Preparation of 4-chloro-7-(2-methoxy-ethoxy)-6-nitro-quinoline

The preparation method was the same as Steps 1 to 3 of Example 14, except that 3-(2-methoxy-ethoxy)-4-nitro-aniline obtained in Step 1 was used instead of methyl 4-amino-2-methoxybenzoate in Step 1 of Example 14 to give 4-chloro-7-(2-methoxy-ethoxy)-6-nitro-quinoline.

Step 3: Preparation of 2-chloro-4-[7-(2-methoxy-ethoxy)-6-nitro-quinolin-4-yloxy]-aniline The preparation method was the same as Step 5 of Example 14, except that 4-chloro-7-(2-methoxy-ethoxy)-6- nitro-quinoline obtained in Step 2 was used instead of 4-chloro-7-methoxy-quinolin-6-carboxylic acid methylamine in Step 5 of Example 14 to give 2-chloro-4-[7-(2-methoxy-ethoxy)-6-nitro-quinolin-4-yloxy]-aniline.

Step 4: Preparation of N-[4-(4-amino-3-chloro-phenoxy)-7-(2-methoxy-ethoxy)-quinolin-6-yl]-acetamide The preparation method was the same as Steps 1 to 4 of Example 20, except that 2-chloro-4-[7-(2-methoxy-ethoxy)-6-nitro-quinolin-4-yloxy]-aniline obtained in Step 3 was used instead of 2-chloro-4-(7-methoxy-6-nitro-quinolin-4-yloxy)-aniline in Step 1 of Example 20 to give N-[4-(4-amino-3-chloro-phenoxy)-7-(2-methoxy-ethoxy)-quinolin-6-yl]-acetamide.

Step 5: Preparation of phenyl {4-[6-acetylamino-7-(2-methoxy-ethoxy)-quinolin-4-yloxy]-2-chloro-phenyl}-carbamate The preparation method was the same as Step 5 of Example 42, except that N-[4-(4-amino-3-chloro-phenoxy)-7-(2-methoxy-ethoxy)-quinolin-6-yl]-acetamide obtained in Step 4 was used instead of 4-(4-amino-3-chloro-phenoxy)-7-(2-methoxy-ethoxy)-quinolin-6-carboxamide in Step 5 of Example 42 to give phenyl {4-[6-acetylamino-7-(2-methoxy-ethoxy)-quinolin-4-yloxy]-2-chloro-phenyl}-carbamat e.

Step 6: Preparation of N-[4-{4-[3-(5-tert-butyl-2H-pyrazol-3-yl)-ureido]-3-chloro-phenoxy}-7-(2-methoxy-ethoxy)-quinolin-6-yl]-acetamide The preparation method was the same as Step 3 of Example 25, except that phenyl {4-[6-acetylamino-7-(2-methoxy-ethoxy)-quinolin-4-yloxy]-2-chloro-phenyl}-carbamate obtained in Step 5 was used instead of phenyl [4-(6-carbamoyl-7-methoxy-quinolin-4-yloxy)-2-chloro-phenyl]-carbamate in Step 3 of Example 25 to give N-[4-{4-[3-(5-tert-butyl-2H-pyrazol-3-yl)-ureido]-3-chloro-phenoxy}-7-(2-methoxy-ethoxy)-quinolin-6-yl]-acetamide ¹HNMR (DMSO-d6, 400 MHz) δ: 12.10 (s, 1H), 9.59 (s, 1H), 9.26 (s, 1H), 8.97 (s, 1H), 8.53-8.55 (d, 1H), 8.38-8.40 (m, 1H), 7.50-7.51 (m, 2H), 7.23-7.26 (dd, 1H), 6.53-6.54 (d, 1H), 5.85 (br, 1H), 4.38-4.40 (t, 2H), 3.83-3.86 (t, 2H), 3.38 (s, 3H), 2.20 (s, 3H), 1.27 (s, 9H).

LC-MS: ESI 567.2 (M+H)+.

Example 67

Preparation of 1-(5-tert-butyl-2H-pyrazol-3-yl)-3-[2-chloro-4-(6-cyano-7-methoxy-quinolin-4-yloxy)-phenyl]-urea (Compound 67)

The preparation method was the same as Steps 2 to 3 of Example 25, except that 4-(4-amino-3-chloro-phenoxy)-7-methoxy-quinolin-6-carbonitrile (prepared in Example 19) was used instead of 4-(4-amino-3-chloro-phenoxy)-7-methoxy-quinolin-6-carboxamide in Step 2 of Example 25 to give 1-(5-tert-butyl-2H-pyrazol-3-yl)-3-[2-chloro-4-(6-cyano-7-methoxy-quinolin-4-yloxy)-phenyl]-urea.

¹HNMR (DMSO-d6, 400 MHz) δ: 12.10 (s, 1H), 9.61 (s, 1H), 8.76-8.77 (m, 2H), 8.41-8.43 (d, 1H), 7.62 (s, 1H), 7.57-7.58 (d, 1H), 7.30-7.33 (dd, 1H), 6.64-6.65 (d, 1H), 4.08 (s, 3H) 1.27 (s, 9H).

LC-MS: ESI 491.1 (M+H)+.

Example 68

Preparation of N-(4-{4-[3-(5-tert-butyl-2H-pyrazol-3-yl)-ureido]-3-chloro-phenoxy}-3-cyano-7-ethoxy-quinolin-6-yl) acetamide (Compound 68)

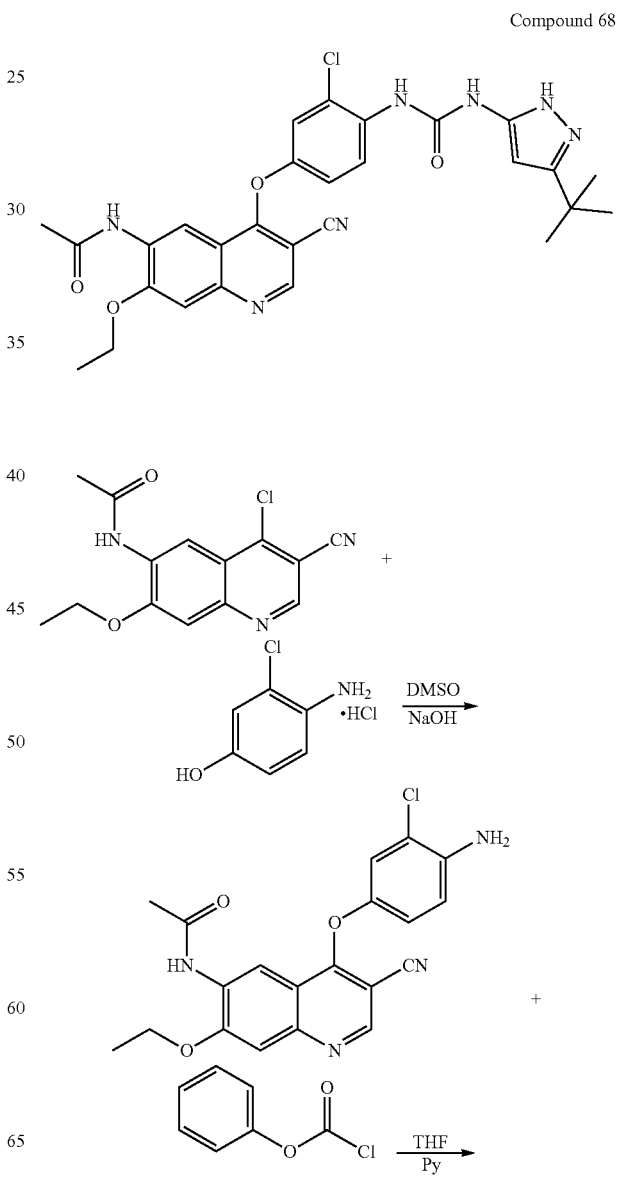

Compound 68

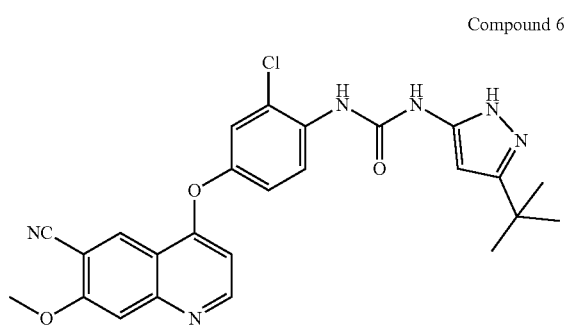

Compound 67

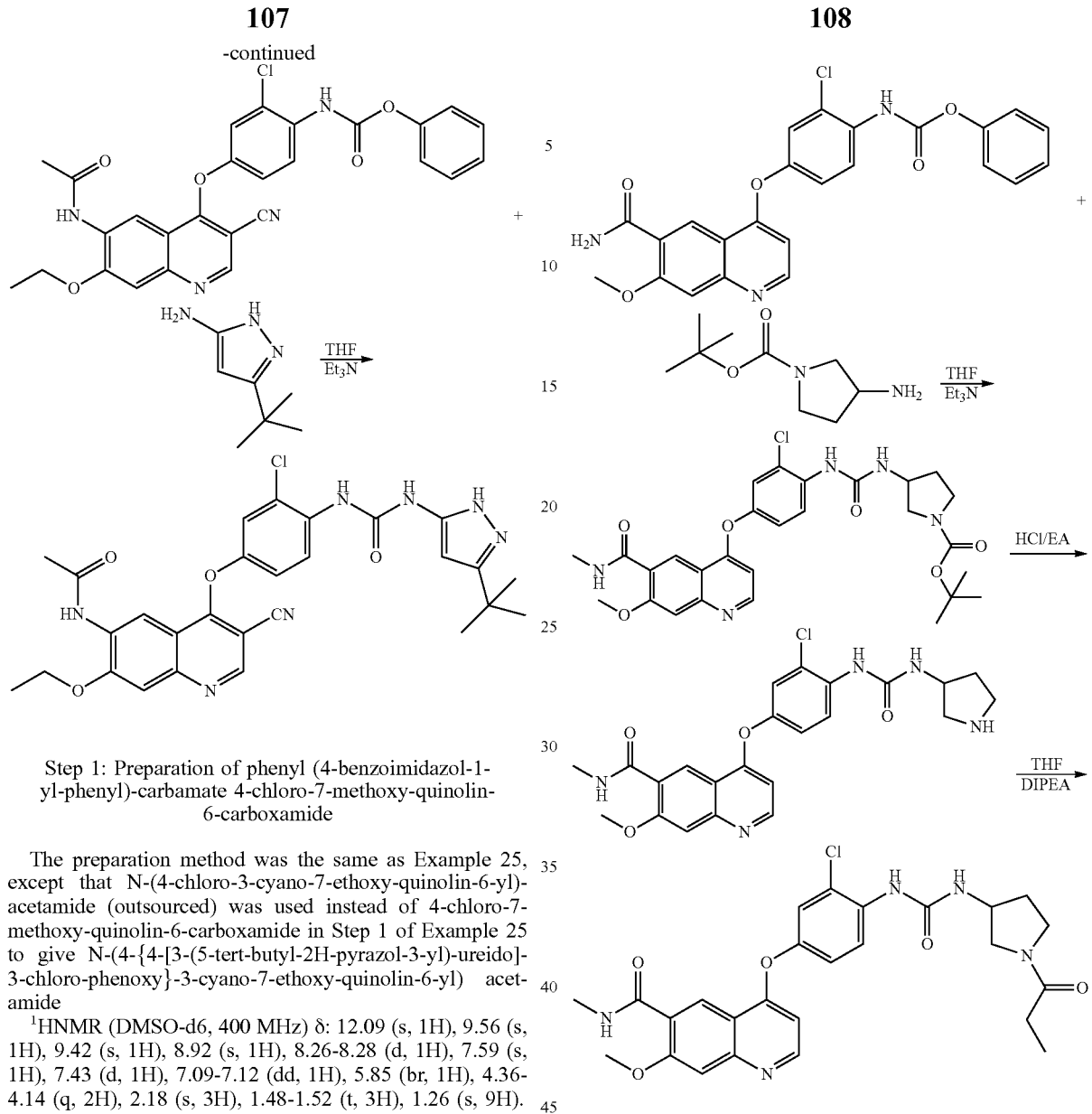

Step 1: Preparation of phenyl (4-benzoimidazol-1-yl-phenyl)-carbamate 4-chloro-7-methoxy-quinolin-6-carboxamide The preparation method was the same as Example 25, except that N-(4-chloro-3-cyano-7-ethoxy-quinolin-6-yl)-acetamide (outsourced) was used instead of 4-chloro-7-methoxy-quinolin-6-carboxamide in Step 1 of Example 25 to give N-(4-{4-[3-(5-tert-butyl-2H-pyrazol-3-yl)-ureido]-3-chloro-phenoxy}-3-cyano-7-ethoxy-quinolin-6-yl) acetamide ¹HNMR (DMSO-d6, 400 MHz) δ: 12.09 (s, 1H), 9.56 (s, 1H), 9.42 (s, 1H), 8.92 (s, 1H), 8.26-8.28 (d, 1H), 7.59 (s, 1H), 7.43 (d, 1H), 7.09-7.12 (dd, 1H), 5.85 (br, 1H), 4.36-4.14 (q, 2H), 2.18 (s, 3H), 1.48-1.52 (t, 3H), 1.26 (s, 9H). LC-MS: ESI 562.1 (M+H)+.

Example 69

Preparation of 4-{3-chloro-4-[3-(1-propionyl-pyrrolidin-3-yl)-ureido]-phenoxy}-7-methoxyquinolin-6-carboxamide (Compound 69)

Compound 69

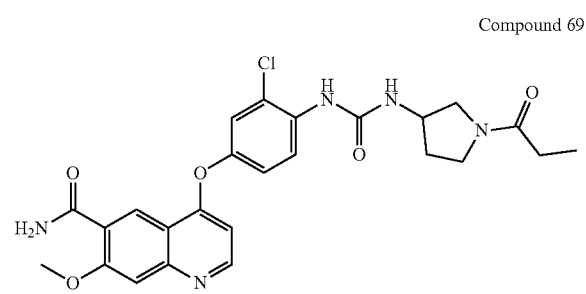 [SMILES: CCC(=O)N1CCC(NC(=O)Nc2ccc(Oc3ccnc4cc(OC)c(C(N)=O)cc34)cc2Cl)C1]

Step 1: Preparation of tert-butyl 3-{3-[4-(6-carbamoyl-7-methoxy-quinolin-4-yloxy)-2-chloro-phenyl]-ureido}-pyrrolidin-1-carboxylate Phenyl [4-(6-carbamoyl-7-methoxy-quinolin-4-yloxy)-2-chloro-phenyl]-carbamate (prepared in Step 2 of Example 12) (500 mg, 1.08 mmol), tert-butyl 3-amino-pyrrolidine-1-carboxylate (purchased from TCI) (300 mg, 1.62 mmol) and triethylamine (327 mg, 3.24 mmol) were dissolved in 15 ml of THF at room temperature and then refluxed overnight. The next day, the reaction solution was cooled to room temperature and concentrated under reduced pressure. The residues were purified by column chromatography (eluent: dichloromethane/methanol) to give 630 mg of tert-butyl 3-{3-[4-(6-carbamoyl-7-methoxy-quinolin-4-yloxy)-2-chloro-phenyl]-ureido}-pyrrolidin-1-carboxylate.

Step 2: Preparation of 4-[3-chloro-4-(3-pyrrolidin-3-yl-ureido)-phenoxy]-7-methoxy-quinolin-6-carboxamide Tert-Butyl 3-{3-[4-(6-carbamoyl-7-methoxy-quinolin-4-yloxy)-2-chloro-phenyl]-ureido}-pyrrolidin-1-carboxylate (prepared in Step 1) (630 mg, 1.13 mmol) was added to 20 ml of ethyl acetate/hydrochloric acid (3.0 mol/L). The reaction was carried out at room temperature for 2 hours. Then the reaction solution was poured into 100 ml of saturated aqueous solution of sodium bicarbonate, and filtered. The filter cake was washed with water and air-dried (60° C.) to give 410 mg of 4-[3-chloro-4-(3-pyrrolidin-3-yl-ureido)-phenoxy]-7-methoxy-quinolin-6-carboxamide as a solid.

Step 3: Preparation of 4-{3-chloro-4-[3-(1-propionyl-pyrrolidin-3-yl)-ureido]-phenoxy}-7-methoxy-quinolin-6-carboxamide 4-[3-Chloro-4-(3-pyrrolidin-3-yl-ureido)-phenoxy]-7-methoxy-quinolin-6-carboxamide (prepared in Step 2) (210 mg, 0.461 mmol) and N,N-diisopropylethylamine (178 mg, 1.383 mmol) were dissolved in 10 ml of DMF at room temperature, and the mixture was cooled to 0-5° C. in an ice bath. Propionyl chloride (64 mg, 0.691 mmol) was dissolved in a small amount of THF and added to the reaction system dropwise. The mixture was allowed to react at room temperature for 0.5 hour. The reaction solution was poured slowly into water, and extracted with ethyl acetate (60 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 120 mg of 4-{3-chloro-4-[3-(1-propionyl-pyrrolidin-3-yl)-ureido]-phenoxy}-7-methoxyquinolin-6-carboxamide as a solid.

$^{1}$HNMR (DMSO-d6, 400 MHz) δ: 8.67-8.68 (m, 2H), 8.29-8.31 (d, 1H), 8.06-8.09 (d, 1H), 7.86 (br, 1H), 7.74 (br, 1H), 7.52 (s, 1H), 7.50-7.51 (m, 1H), 7.33-7.38 (m, 1H), 7.24-7.27 (dd, 1H), 6.53-6.54 (d, 1H), 4.15-4.30 (m, 1H), 4.04 (s, 3H), 3.24-3.69 (m, 4H), 2.22-2.31 (m, 2H), 2.02-2.19 (m, 1H), 1.75-1.94 (m, 1H), 0.97-1.03 (m, 3H).

LC-MS: ESI 512.2 (M+H)+.

Example 70

Preparation of 4-{3-chloro-4-[3-(1-acryloylpyrrolidin-3-yl)-ureido]-phenoxy}-7-methoxyquinolin-6-carboxamide (Compound 70)

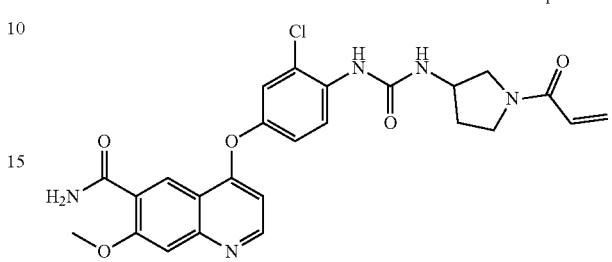

Compound 70

The preparation method was the same as Example 69, except that acryloyl chloride was used instead of propionyl chloride in Step 3 of Example 69 to give 4-{3-chloro-4-[3-(1-acryloylpyrrolidin-3-yl)-ureido]-phenoxy}-7-methoxyquinolin-6-carboxamide.

$^{1}$HNMR (DMSO-d6, 400 MHz) δ: 8.67-8.68 (m, 2H), 8.29-8.31 (m, 1H), 8.07-8.10 (d, 1H), 7.86 (br, 1H), 7.74 (br, 1H), 7.52 (s, 1H), 7.50-7.51 (m, 1H), 7.36-7.41 (m, 1H), 7.24-7.27 (dd, 1H), 6.56-6.67 (m, 1H), 6.53-6.54 (d, 1H), 6.14-6.20 (m, 1H), 5.67-5.73 (m, 1H), 4.18-4.34 (m, 1H), 4.04 (s, 3H), 3.41-3.81 (m, 4H), 2.05-2.22 (m, 1H), 1.78-2.01 (m, 1H).

LC-MS: ESI 510.1 (M+H)+.

Example 71

Preparation of 4-[2,3-dichloro-4-(3-{6-[4-(4-ethyl-piperazin-1-yl)-phenylamino]-pyrimidin-4-yl}-ureido)-phenoxy]-6-methoxy-quinolin-6-carboxamide (Compound 71)

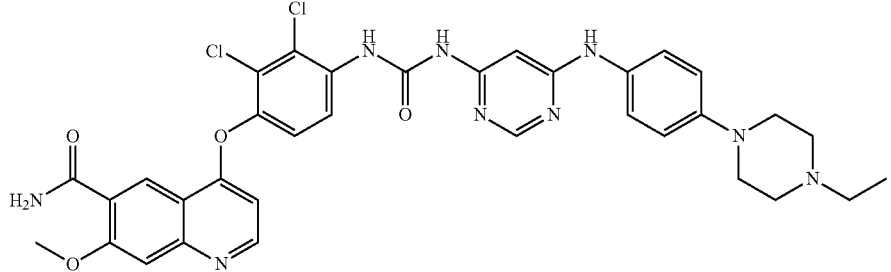

Compound 71

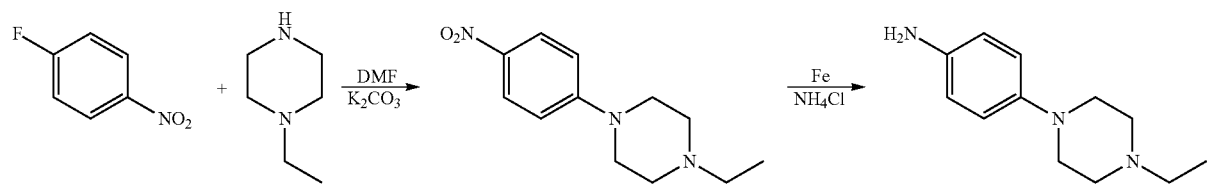

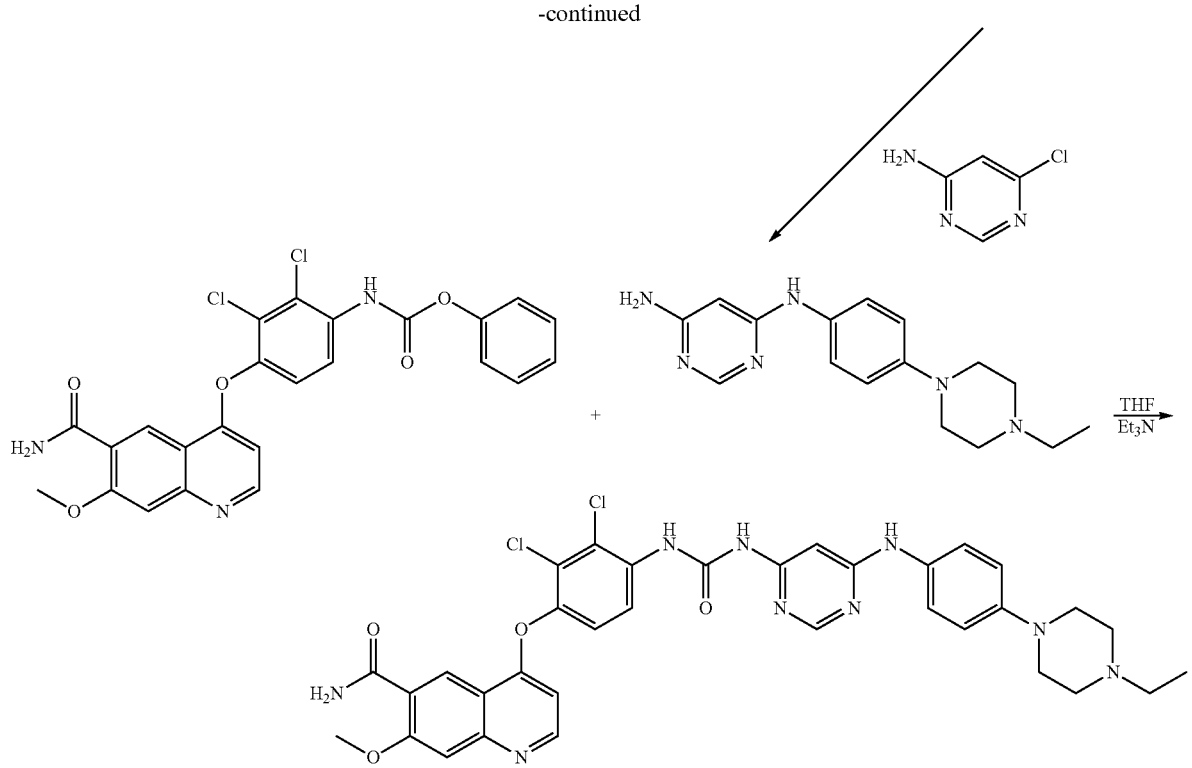

Step 1: Preparation of 1-ethyl-4-(4-nitro-phenyl)-piperazine

4-Fluoro-nitrobenzene (purchased from Shanghai Darui) (1.41 g, 0.01 mol), 1-ethyl-piperazine (purchased from Shanghai Darui) (1.25 g, 0.011 mol) and potassium carbonate (4.14 g, 0.03 mol) were dissolved in 20 ml of DMF and stirred at room temperature for 30 min. The reaction solution was heated to 90° C. for 2 hours, and poured into water, and then extracted with ethyl acetate (60 ml×2). The organic phase was washed twice with saturated NaCl solution, dried over anhydrous sodium sulfate, and filtered. The filtrate was concentrated under reduced pressure to give 2.20 g of 1-ethyl-4-(4-nitro-phenyl)-piperazine.

Step 2: Preparation of 4-(4-ethyl-piperazin-1-yl)-aniline 4-(4-Ethyl-piperazin-1-yl)-aniline (prepared in Step 1) (2.20 g, 9.36 mmol), reduced iron powder (2.62 g, 46.80 mmol) and ammonium chloride (4.0 g, 74.88 mmol) were added to a mixture of 40 ml of ethanol and 10 ml of water. The reaction solution was heated to 80° C. for 2 hours, and poured into 150 ml of saturated aqueous solution of sodium bicarbonate, and then extracted with ethyl acetate (60 ml×2). The organic phase was washed twice with saturated NaCl solution, dried over anhydrous sodium sulfate, and filtered. The filtrate was concentrated under reduced pressure to give 1.7 g of 4-(4-ethyl-piperazin-1-yl)-aniline as a solid.

Step 3: Preparation of N-[4-(4-ethyl-piperazin-1-yl)-phenyl]-pyrimidine-4,6-diamine At room temperature, 4-(4-ethyl-piperazin-1-yl)-aniline (prepared in Step 2) (801 mg, 6.18 mmol) and 4-amino-6-chloropyrimidine (purchased from Shanghai Darui) (788 mg, 4.12 mmol) were dissolved in 10 ml of acetic acid and 2 ml of water. The reaction solution was heated to 100° C. for 5 hours, and poured into 100 ml of saturated aqueous solution of sodium bicarbonate, and then extracted with ethyl acetate (60 ml×2). The organic phase was washed twice with saturated NaCl solution, dried over anhydrous sodium sulfate, and filtered. The filtrate was concentrated under reduced pressure to give 700 mg of N-[4-(4-ethyl-piperazin-1-yl)-phenyl]-pyrimidine-4,6-diamine as a brown solid.

Step 4: Preparation of 4-[2,3-dichloro-4-(3-{6-[4-(4-ethyl-piperazin-1-yl)-phenylamino]-pyrimidin-4-yl}-ureido)-phenoxy]-6-methoxy-quinolin-6-carboxamide Phenyl [4-(6-carbamoyl-7-methoxy-quinolin-4-yloxy)-2,3-dichloro-phenyl]-carbamate (prepared in Example 37) (150 mg, 0.302 mmol), N-[4-(4-ethyl-piperazin-1-yl)-phenyl]-pyrimidin-4,6-diamine (prepared in Step 3) (180 mg, 0.604 mmol) and triethylamine (122 mg, 1.208 mmol) were dissolved in 15 ml of THF and refluxed overnight. The next day, the reaction solution was concentrated under reduced pressure, and the residues were purified by column chromatography (eluent: dichloromethane/methanol) to give 30 mg of 4-[2,3-dichloro-4-(3-{6-[4-(4-ethyl-piperazin-1-yl)-phenylamino]-pyrimidin-4-yl}-ureido)-phenoxy]-6-methoxy-quinolin-6-carboxamide as a solid.

$^1$HNMR (DMSO-d6, 400 MHz) δ: 14.24 (s, 1H), 8.70 (s, 1H), 8.66-8.68 (d, 1H), 8.40-8.42 (m, 2H), 7.89 (br, 1H), 7.77 (br, 1H), 7.55 (s, 1H), 7.50-7.52 (d, 1H), 7.18-7.20 (d, 2H), 7.09-7.11 (d, 2H), 6.97 (s, 1H), 6.97 (s, 1H), 6.47-6.48 (d, 1H), 5.28 (s, 1H), 4.04 (s, 3H), 3.37 (m, 8H), 2.43 (m, 2H), 1.09 (m, 3H).

LC-MS: ESI 702.2 (M+H)+.

Example 72

Preparation of 4-{4-[(5-amino-3-tert-butyl-pyrazol-1-carbonyl)-amino]-3-chloro-phenoxy}-7-methoxy quinolin-6-carboxamide (Compound 72)

Compound 72

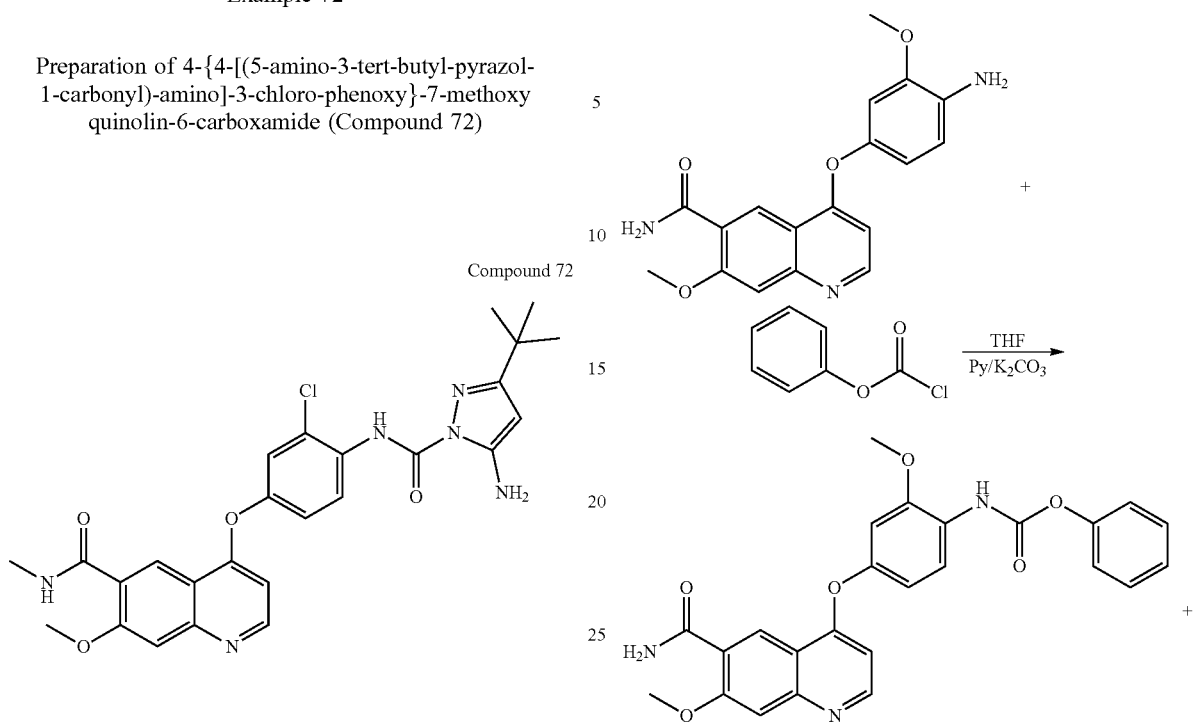

It was prepared in Example 45.

¹HNMR (DMSO-d6, 400 MHz) δ: 9.80 (s, 1H), 8.69-8.71 (d, 1H), 8.59 (s, 1H), 8.36-8.37 (m, 1H), 8.19-8.21 (d, 1H), 7.66-7.67 (d, 1H), 7.53 (s, 1H), 7.37-7.40 (dd, 1H), 6.60-6.61 (d, 1H), 6.44-6.46 (s, 2H), 5.33 (s, 1H), 4.02 (s, 3H), 2.83-2.84 (d, 3H), 1.24 (s, 9H).

LC-MS: ESI 523.2 (M+H)+.

Example 73

Preparation of 4-{4-[(5-amino-3-tert-butyl-pyrazol-1-carbonyl)-amino]-3-methoxy-phenoxy}-7-methoxyquinolin-6-carboxamide (Compound 73)

Compound 73

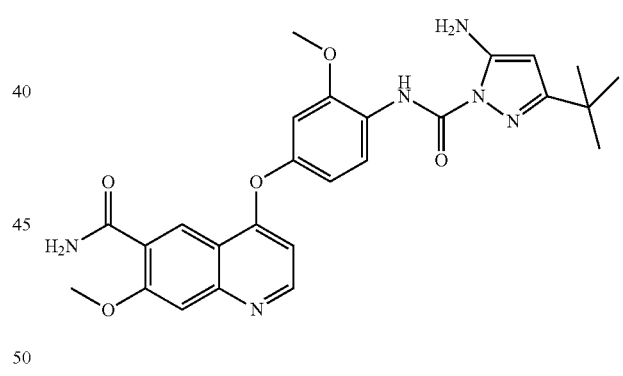

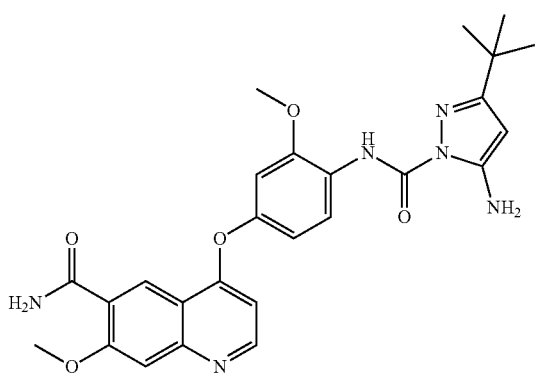

The preparation method was the same as Steps 2 to 3 of Example 45, except that 4-(4-amino-3-methoxy-phenoxy)-7-methoxy-quinolin-6-carboxamide was used instead of 4-(4-amino-3-chloro-phenoxy)-7-methoxy-quinolin-6-carboxylic acid methylamide in Step 2 of Example 45 to give 4-{4-[(5-amino-3-tert-butyl-pyrazol-1-carbonyl)-amino]-3-methoxy-phenoxy}-7-methoxyquinolin-6-carboxamide.

¹HNMR (DMSO-d6, 400 MHz) δ: 9.61 (s, 1H), 8.72 (s, 1H), 8.68-8.70 (d, 1H), 8.16-8.18 (d, 1H), 7.87 (br, 1H), 7.75 (br, 1H), 7.53 (s, 1H), 7.17-7.18 (d, 1H), 6.93-6.96 (dd, 1H), 6.58-6.59 (d, 1H), 6.43 (br, 2H), 5.32 (s, 1H), 4.04 (s, 3H), 3.91 (s, 3H), 1.25 (s, 9H).

LC-MS: ESI 505.2 (M+H)+.

Example 74

Preparation of 4-{3-chloro-4-[(4,7-dihydro-5H-thieno[2,3-c]pyridin-6-carbonyl)-amino]-phenoxy}-7-methoxyquinolin-6-carboxamide (Compound 74)

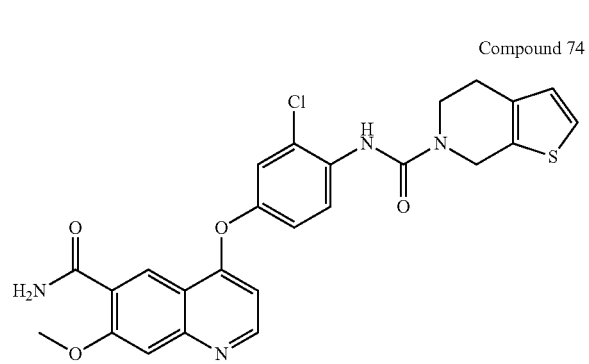 [SMILES: COc1cc2nccc(Oc3ccc(NC(=O)N4CCc5ccsc5C4)c(Cl)c3)c2cc1C(N)=O]

Compound 74

At room temperature, 4-[3-chloro-4-(3-pyrrolidin-3-yl-uneido)-phenoxy]-7-methoxy-quinolin-6-carbamate (prepared in Step 2) (317 mg, 0.683 mmol), 4,5,6,7-tetrahydro-thieno[3,2-c]pyridine hydrochloride (purchased from TCI) (100 mg, 0.569 mmol) and triethylamine (230 mg, 2.276 mmol) were dissolved in 15 ml of THF and refluxed overnight. The next day, the reaction solution was concentrated under reduced pressure, and the residues were purified by column chromatography (eluent: dichloromethane/methanol) to give 50 mg of 4-{3-chloro-4-[(4,7-dihydro-5H-thieno[2,3-c]pyridin-6-carbonyl)-amino]-phenoxy}-7-methoxyquinolin-6-carboxamide as a solid.

$^1$HNMR (DMSO-d6, 400 MHz) δ: 8.70-8.71 (d, 1H), 8.66 (s, 1H), 8.45 (s, 1H), 7.87 (br, 1H), 7.76 (br, 1H), 7.61-7.64 (d, 1H), 7.53 (m, 2H), 7.36-7.37 (d, 1H), 7.26-7.29 (dd, 1H), 6.91-6.92 (d, 1H), 6.56-6.57 (d, 1H), 4.06 (s, 2H), 3.80-3.82 (t, 2H), 2.89 (t, 2H).

LC-MS: ESI 509.0 (M+H)+.

Example 75

Preparation of 4-{2,3-dichloro-4-[(4-methyl-piperazin-1-carbonyl)-amino]-phenoxy}-7-(2-methoxy-ethoxy)-quinolin-6-carboxylic acid methylamide (Compound 75)

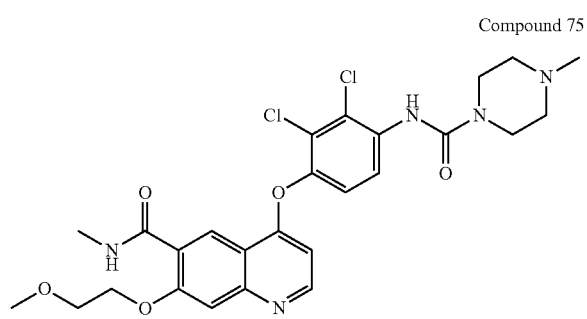

Compound 75

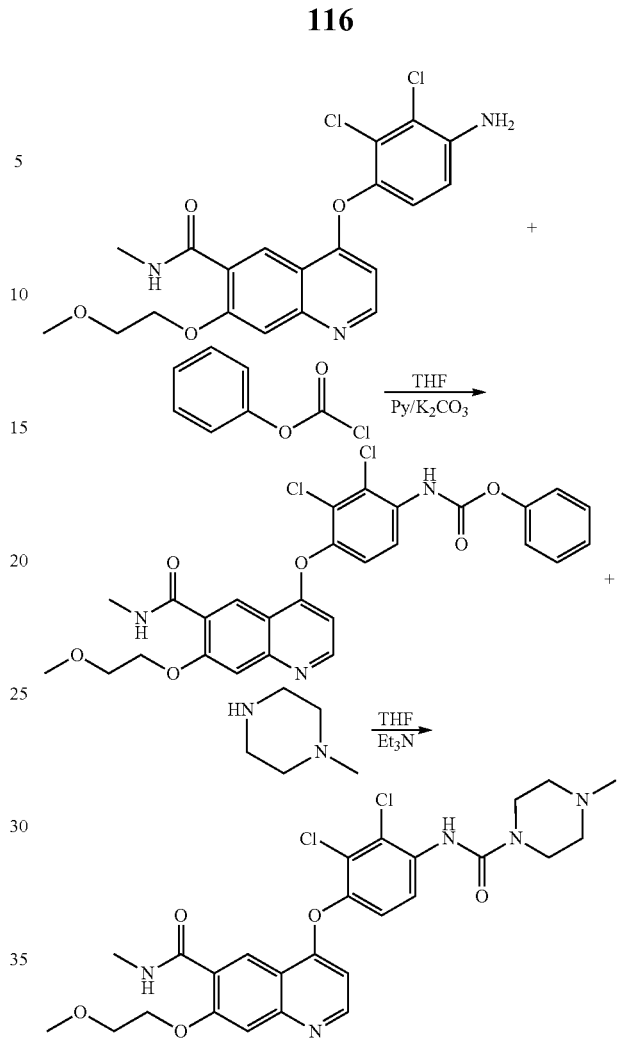

Step 1: Preparation of phenyl {2,3-dichloro-4-[7-(2-methoxy-ethoxy)-6-methylcarbamoyl-quinolin-4-yloxy]-phenyl}-carbamate The preparation method was the same as Step 5 of Example 42, except that 4-(4-amino-2,3-dichloro-phenoxy)-7-(2-methoxy-ethoxy)-quinolin-6-carboxylic acid methylamide (prepared in Step 1 of Example 60) was used instead of 4-(4-amino-3-chloro-phenoxy)-7-(2-methoxy-ethoxy)-quinolin-6-carboxamide in Step 5 of Example 42 to give phenyl {2,3-dichloro-4-[7-(2-methoxy-ethoxy)-6-methylcarbamoyl-quinolin-4-yloxy]-phenyl}-carbamate.

Step 2: Preparation of 4-{2,3-dichloro-4-[(4-methyl-piperazin-1-carbonyl)-amino]-phenoxy}-7-(2-methoxy-ethoxy)-quinolin-6-carboxylic acid methylamide Phenyl {2,3-dichloro-4-[7-(2-methoxy-ethoxy)-6-methylcarbamoyl-quinolin-4-yloxy]-phenyl}-carbamate obtained in Step 1 (100 mg, 0.180 mmol), 1-methyl-piperazine (36 mg, 0.360 mmol) and triethylamine (73 mg, 0.720 mmol) were dissolved in 15 ml of THF and refluxed overnight. The next day, the reaction solution was cooled, and concentrated under reduced pressure. The residues were purified by column chromatography (eluent: dichloromethane/methanol) to give 105 mg of 4-{2,3-dichloro-4-[(4- methyl-piperazine-1-carbonyl)-amino]-phenoxy}-7-(2-methoxy-ethoxy)-quinolin-6-carboxylic acid methylamide as a solid.

¹HNMR (DMSO-d6, 400 MHz) δ: 8.72 (s, 1H), 8.69-8.70 (d, 1H), 8.50 (s, 1H), 8.39-8.40 (m, 1H), 7.61-7.64 (m, 2H), 7.47-7.50 (d, 1H), 6.43-6.44 (d, 1H), 4.42-4.44 (t, 2H), 3.81-3.83 (t, 2H), 3.47-3.49 (t, 4H), 3.40 (s, 3H), 2.87-2.88 (d, 3H), 2.34-2.36 (t, 4H), 2.22 (s, 3H).

LC-MS: ESI 562.0/564.0 (M+H)+.

Example 76

Preparation of 4-{2,3-dichloro-4-[(pyrrolidin-1-carbonyl)-amino]-phenoxy}-7-(2-methoxy-ethoxy)-quinolin-6-carboxylic acid methylamide (Compound 76)

Compound 76

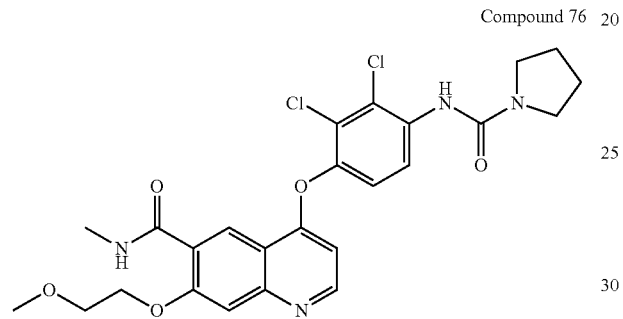

The preparation method was the same as Example 75, except that pyrrolidine (purchased from Shanghai Darui) was used instead of 1-methyl-piperazine in Step 2 of Example 75 to give 4-{2,3-dichloro-4-[(pyrrolidin-1-carbonyl)-amino]-phenoxy}-7-(2-methoxy-ethoxy)-quinolin-6-carboxylic acid methylamide.

1HNMR (DMSO-d6, 400 MHz) δ: 8.72 (s, 1H), 8.68-8.70 (d, 1H), 8.39-8.40 (m, 1H), 7.89 (s, 1H), 7.85-7.87 (d, 1H), 7.61 (s, 1H), 7.48-7.51 (d, 1H), 6.42-6.44 (d, 1H), 4.42-4.44 (t, 2H), 3.81-3.83 (t, 2H), 3.38-3.43 (m, 4H), 3.40 (s, 3H), 2.85-2.87 (d, 3H), 1.90 (m, 4H).

LC-MS: ESI 533.0/534.9 (M+H)+.

Example 77

Preparation of 4-{4-[3-(5-tert-butyl-isoxazol-3-yl)-ureido]-3-chlorophenylamino}-7-methoxyquinolin-6-carboxamide (Compound 77)

Compound 77

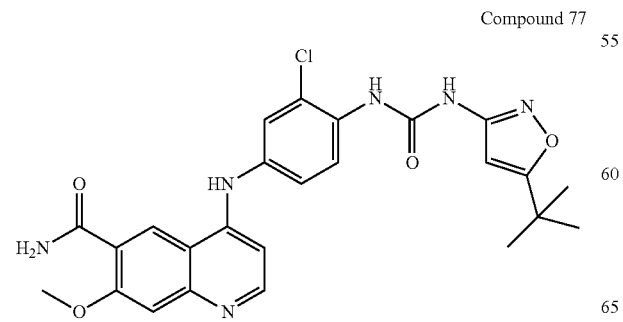

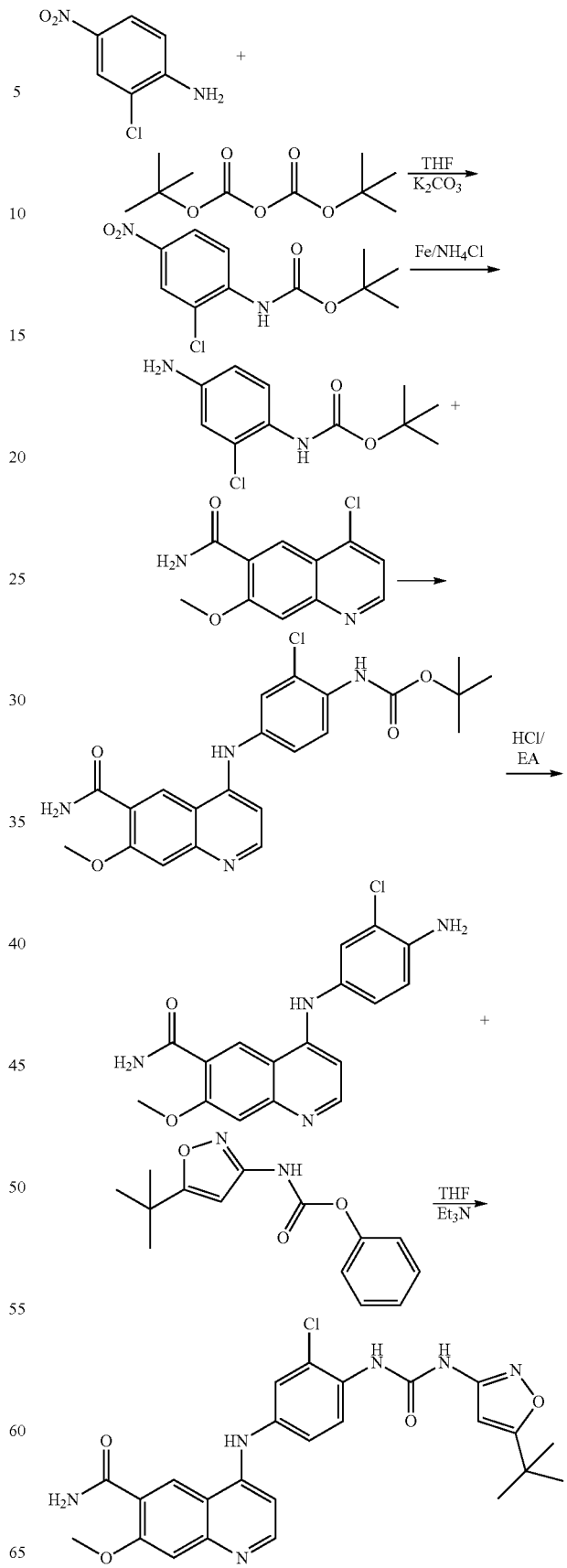

Step 1: Preparation of tert-butyl (2-chloro-4-nitro-phenyl)-carbamate

2-Chloro-4-nitroaniline (purchased from Shanghai Darui) (3.45 g, 0.02 mol) and di-tert-butyl dicarbonate (purchased from Shanghai Darui) (8.72 g, 0.04 mol) were dissolved in 50 ml of THF, and added with potassium carbonate (8.28 g, 0.06 mol) and DMAP (122 mg, 0.001 mol). The mixture was stirred at room temperature a under nitrogen atmosphere. The reaction solution was poured into water, and extracted with ethyl acetate (100 ml×2). The organic phase was washed twice with saturated NaCl solution, dried over anhydrous sodium sulfate, and filtered. The filtrate was concentrated under reduced pressure to give 6.0 g crude product, which was used in the next step without purification.

Step 2: Preparation of tert-butyl (4-amino-2-chloro-phenyl)-carbamate

Tert-butyl (2-chloro-4-nitro-phenyl)-carbamate (prepared in Step 1) (6.0 g, 0.022 mol), reduced iron powder (7.6 g, 0.135 mol) and ammonium chloride (11.6 g, 0.216 mol) were added to a mixture of 48 ml of ethanol and 12 ml of water at room temperature. The reaction solution was heated to 80° C. for 1 hour, and poured into saturated aqueous solution of sodium bicarbonate, and then extracted with ethyl acetate (100 ml×2). The organic phase was washed twice with saturated NaCl solution, dried over anhydrous sodium sulfate, and filtered. The filtrate was concentrated under reduced pressure to give 3.8 g of crude product, which was used in the next step without purification.

Step 3: Preparation of tert-butyl [4-(6-carbamoyl-7-methoxy-quinolin-4-ylamino)-2-chloro-phenyl]-carbamate 4-Chloro-7-methoxy-quinolin-6-carboxamide (473 mg, 2 mmol) and tert-butyl (4-amino-2-chloro-phenyl)-carbamate (prepared in step 2) (485 mg, 2 mmol) were added to 10 ml of isopropanol and stirred at 100° C. for 3 hours under nitrogen atmosphere. The reaction solution was cooled to room temperature, and poured into saturated aqueous solution of sodium bicarbonate, and then extracted with ethyl acetate (50 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 200 mg of tert-butyl [4-(6-carbamoyl-7-methoxy-quinolin-4-ylamino)-2-chloro-phenyl]-carbamate as a solid.

Step 4: Preparation of 4-(4-amino-3-chloro-phenylamino)-7-methoxy-quinolin-6-carboxamide Tert-butyl [4-(6-carbamoyl-7-methoxy-quinolin-4-ylamino)-2-chloro-phenyl]-carbamate (prepared in Step 3) (200 mg, 0.450 mmol) was added to 15 ml of hydrochloric acid/ethyl acetate solution (3.0 mol/L) and stirred at room temperature for 1 hour under nitrogen atmosphere. The reaction solution was poured into saturated aqueous solution of sodium bicarbonate (100 ml), and extracted with ethyl acetate (50 ml×2). The organic phase was washed twice with saturated NaCl solution, dried over anhydrous sodium sulfate, and filtered. The filtrate was concentrated under reduced pressure to give 100 mg of 4-(4-amino-3-chloro-phenylamino)-7-methoxy-quinolin-6-carboxamide.

Step 5: Preparation of 4-{4-[3-(5-tert-butyl-isoxazol-3-yl)-ureido]-3-chlorophenylamino}-7-methoxyquinolin-6-carboxamide The preparation method was the same as Step 3 of Example 1, except that 4-(4-amino-3-chloro-phenylamino)-7-methoxy-quinolin-6-carboxamide (prepared in Step 4) was used instead of 4-(4-aminophenoxy)-7-methoxy-quinolin-6-carboxamide in Step 3 of Example 1 to give 4-{4-[3-(5-tert-butyl-isoxazol-3-yl)-ureido]-3-chlorophenylamino}-7-methoxyquinolin-6-carboxamide.

$^1$HNMR (DMSO-d6, 400 MHz) δ: 10.15 (s, 1H), 9.30 (s, 1H), 8.80 (s, 1H), 8.68 (s, 1H), 8.44-8.45 (d, 1H), 8.10-8.12 (d, 1H), 7.80 (br, 1H), 7.68 (br, 1H), 7.46-7.47 (d, 1H), 7.33-7.36 (m, 2H), 6.83-6.84 (d, 1H), 6.46 (s, 1H), 4.00 (s, 3H), 1.30 (s, 9H).

LC-MS: ESI 509.1 (M+H)+.

Example 78

Preparation of 4-{4-[3-(5-tert-butyl-isoxazol-3-yl)-ureido]-phenylamino}-7-methoxyquinolin-6-carboxamide (Compound 78)

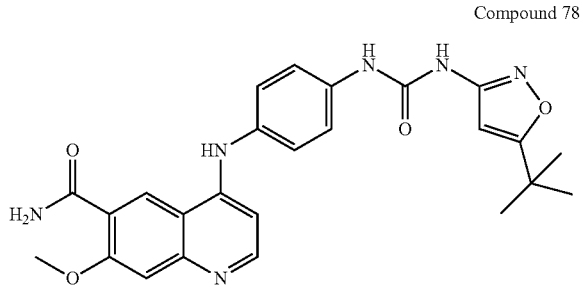 [SMILES: COc1cc2nccc(Nc3ccc(NC(=O)Nc4cc(C(C)(C)C)on4)cc3)c2cc1C(N)=O]

Compound 78

The preparation method was the same as steps 3 to 5 of example 77, except that tert-butyl (4-amino-phenyl)-carbamate was used instead of tert-butyl (4-amino-2-chloro-phenyl)-carbamate in Step 3 of Example 77 to give 4-{4-[3-(5-tert-butyl-isoxazol-3-yl)-ureido]-phenylamino}-7-methoxyquinolin-6-carboxamide.

$^1$HNMR (DMSO-d6, 400 MHz) δ: 9.51 (s, 1H), 9.17 (s, 1H), 8.84 (s, 1H), 8.82 (s, 1H), 8.37-8.38 (d, 1H), 7.78 (br, 1H), 7.66 (br, 1H), 7.48-7.51 (d, 2H), 7.33 (s, 1H), 7.28-7.30 (d, 2H), 6.69-6.71 (d, 1H), 6.51 (s, 1H), 3.99 (s, 3H), 1.30 (s, 9H).

LC-MS: ESI 475.1 (M+H)+.

Example 79

Preparation of 4-{4-[3-(5-tert-butyl-2H-pyrazol-3-yl)-ureido]-3-chlorophenylamino}-7-methoxyquinolin-6-carboxamide (Compound 79)

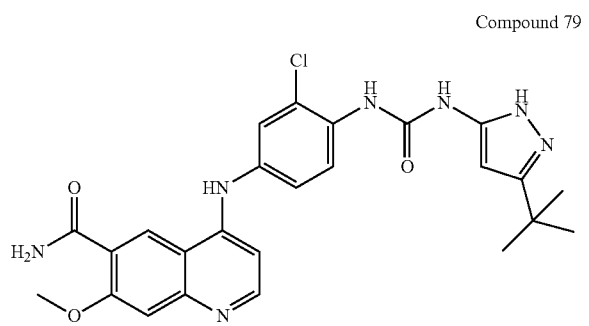 [SMILES: COc1cc2nccc(Nc3ccc(NC(=O)Nc4cc(C(C)(C)C)n[nH]4)c(Cl)c3)c2cc1C(N)=O]

Compound 79

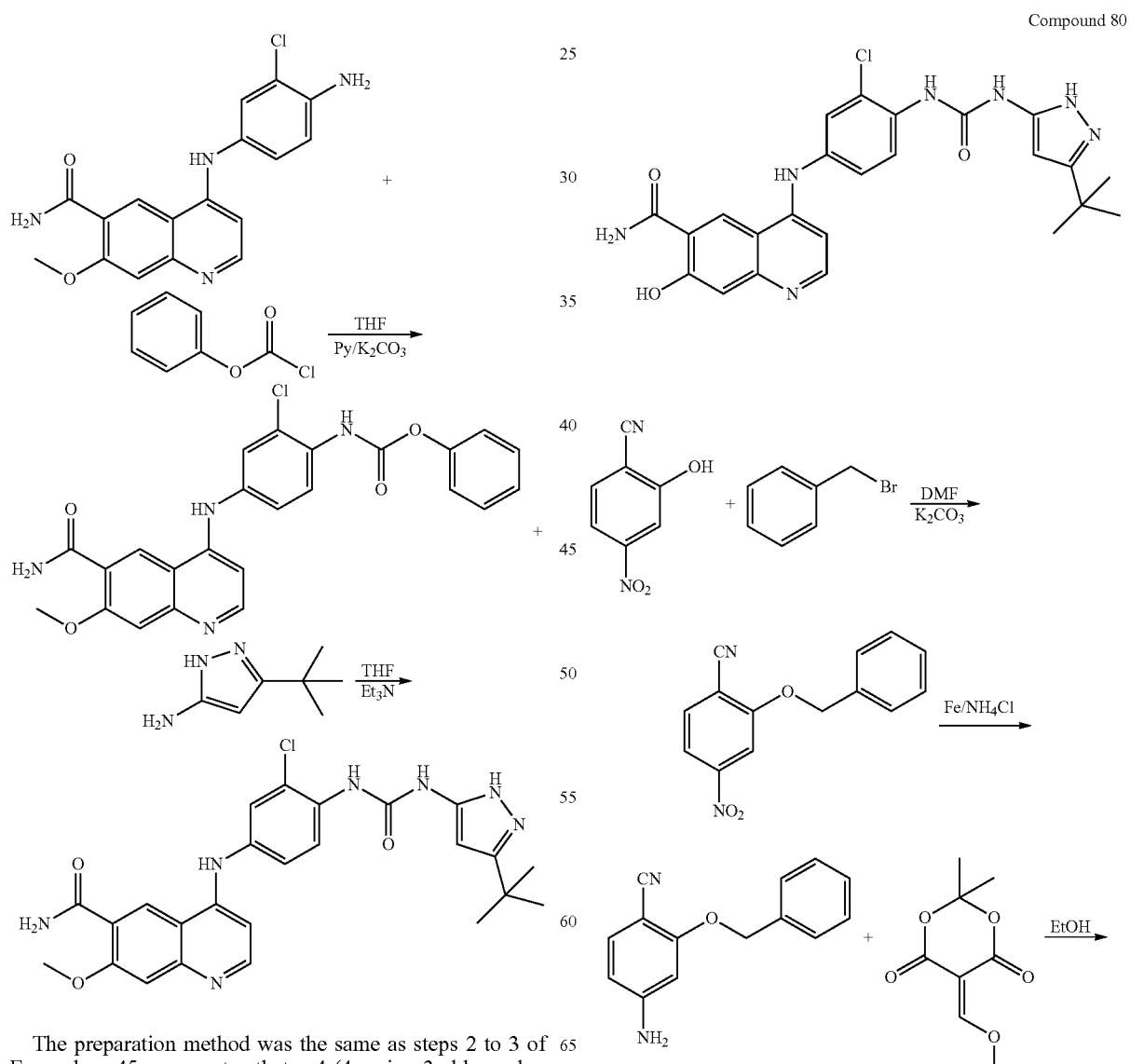

The preparation method was the same as steps 2 to 3 of Example 45, except that 4-(4-amino-3-chloro-phenylamino)-7-methoxy-quinolin-6-carboxamide (prepared in step 4 of example 77) was used instead of 4-(4-amino-3-chloro-phenoxy)-7-methoxy-quinolin-6-carboxylic acid methylamide in step 2 of example 45 to give 4-{4-[3-(5-tert-butyl-2H-pyrazol-3-yl)-ureido]-3-chlorophenylamino}-7-methoxyquinolin-6-carboxamide.

$^1$HNMR (DMSO-d6, 400 MHz) δ: 12.11 (s, 1H), 9.57 (br, 2H), 8.85 (s, 1H), 8.42-8.43 (d, 1H), 8.25-8.27 (d, 1H), 7.82 (br, 1H), 7.70 (br, 1H), 7.47 (d, 1H), 7.40 (s, 1H), 7.32-7.35 (dd, 1H), 6.78-6.80 (d, 1H), 5.88 (br, 1H), 4.00 (s, 3H), 1.27 (s, 9H).

LC-MS: ESI 508.1 (M+H)+.

Example 80

Preparation of 4-{4-[3-(5-tert-butyl-2H-pyrazol-3-yl)-ureido]-3-chloro-phenoxy}-7-hydroxy-quinolin-6-carboxamide (Compound 80)

Compound 80

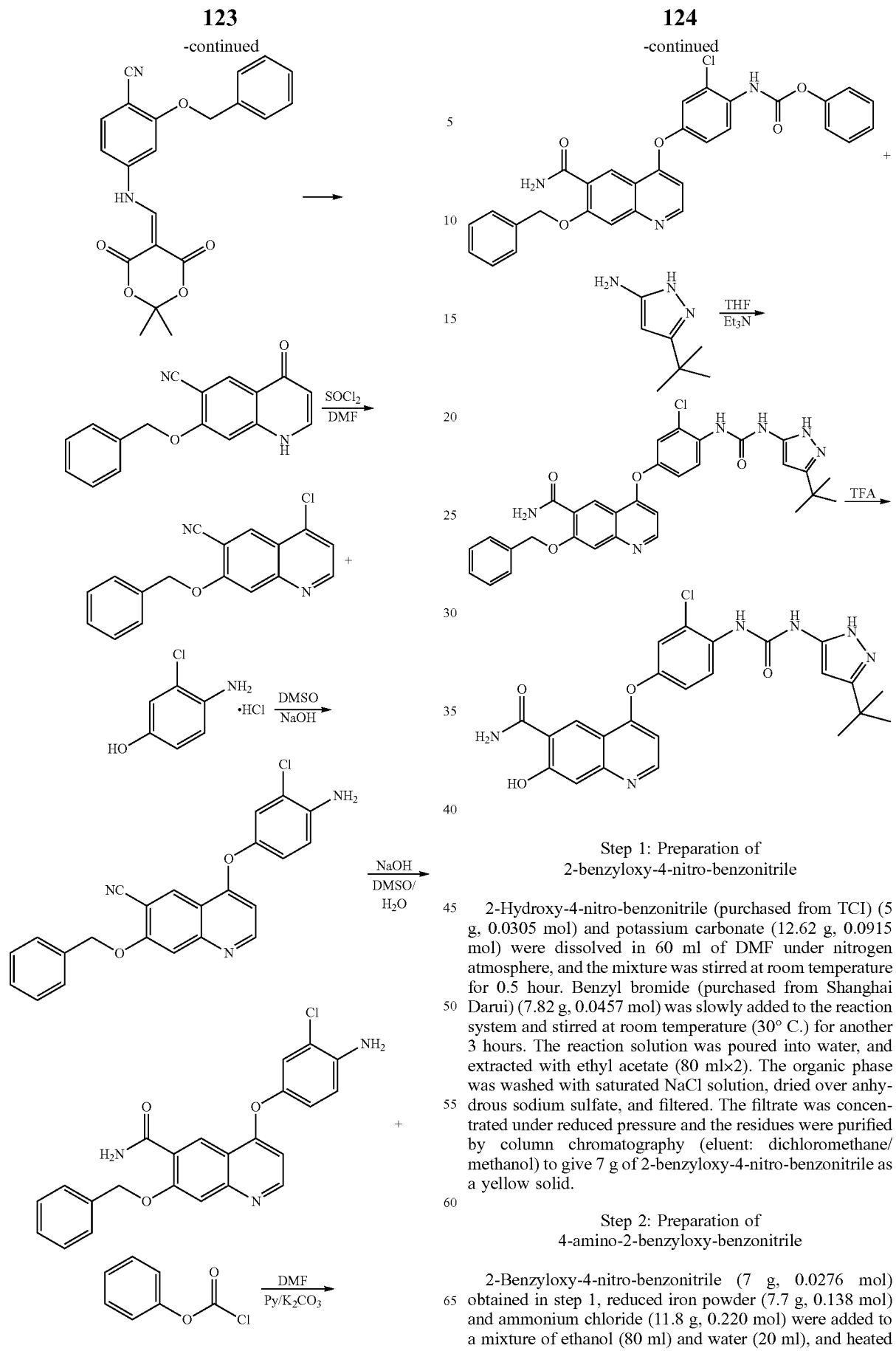

Step 1: Preparation of 2-benzyloxy-4-nitro-benzonitrile

2-Hydroxy-4-nitro-benzonitrile (purchased from TCI) (5 g, 0.0305 mol) and potassium carbonate (12.62 g, 0.0915 mol) were dissolved in 60 ml of DMF under nitrogen atmosphere, and the mixture was stirred at room temperature for 0.5 hour. Benzyl bromide (purchased from Shanghai Darui) (7.82 g, 0.0457 mol) was slowly added to the reaction system and stirred at room temperature (30° C.) for another 3 hours. The reaction solution was poured into water, and extracted with ethyl acetate (80 ml×2). The organic phase was washed with saturated NaCl solution, dried over anhydrous sodium sulfate, and filtered. The filtrate was concentrated under reduced pressure and the residues were purified by column chromatography (eluent: dichloromethane/methanol) to give 7 g of 2-benzyloxy-4-nitro-benzonitrile as a yellow solid.

Step 2: Preparation of 4-amino-2-benzyloxy-benzonitrile

2-Benzyloxy-4-nitro-benzonitrile (7 g, 0.0276 mol) obtained in step 1, reduced iron powder (7.7 g, 0.138 mol) and ammonium chloride (11.8 g, 0.220 mol) were added to a mixture of ethanol (80 ml) and water (20 ml), and heated to 70° C. for 1 h. The reaction solution was cooled to room temperature, and poured into saturated aqueous solution of sodium bicarbonate, and then extracted with ethyl acetate (100 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 4.2 g of 4-amino-2-benzyloxy-benzonitrile as a yellow solid.

Step 3: Preparation of 2-benzyloxy-4-[(2,2-dimethyl-4,6-dioxo-[1,3]dioxan-5-ylidenemethyl)-amino]-benzonitrile 4-Amino-2-benzyloxy-benzonitrile obtained in Step 2 (4.2 g, 18.75 mmol) and 5-(methoxy-methylene)-2,2-dimethyl-[1,3]dioxane-4,6-dione (4.2 g, 22.50 mmol) were added to 50 ml of ethanol at room temperature and then refluxed for 1 hour. The reaction solution was cooled to room temperature, and filtered. The filter cake was washed with a little amount of ethanol, and air-dried overnight to give 5.4 g of 2-benzyloxy-4-[(2,2-dimethyl-4,6-dioxo-[1,3]-dioxane-5-ylidenemethyl)-amino]-benzo nitrile, as a yellow-white solid.

Step 4: Preparation of 7-benzyloxy-4-oxo-1,4-dihydro-quinolin-6-carbonitrile

2-Benzyloxy-4-[(2,2-dimethyl-4,6-dioxo-[1,3]dioxan-5-ylidenemethyl)-amino]-benzonitrile obtained in Step 3 (5.4 g, 0.0143 mol) was added to 50 ml of diphenyl ether-biphenyl eutectic and heated to 250° C. under nitrogen atmosphere (nitrogen exchange for three times) for 0.5 h. The reaction solution was cooled to room temperature, and added with 50 ml of methyl tert-butyl ether. The reaction mixture was stirred at room temperature for 30 min and filtered. The filter cake was washed with a small amount of methyl tert-butyl ether, and air-dried (60° C.) overnight to give 4.0 g of 7-benzyloxy-4-oxo-1,4-dihydro-quinolin-6-carbonitrile, as a brown-yellow solid.

Step 5: Preparation of 7-benzyloxy-4-chloro-quinolin-6-carbonitrile

7-Benzyloxy-4-oxo-1,4-dihydro-quinolin-6-carbonitrile (4.0 g, 0.0145 mol) obtained in step 4 was added to 30 ml of thionyl chloride, and added with 3 drops of DMF at room temperature. The mixture was heated to reflux for 2h. The reaction solution was cooled to room temperature, and the thionyl chloride was concentrated to obtain a crude yellow solid. The solid was added with 50 ml of water, and adjusted to about pH 7-8 by saturated sodium bicarbonate aqueous solution under stirring, and then extracted with ethyl acetate (80 ml×2). The organic phase was washed with saturated NaCl solution, dried over anhydrous sodium sulfate, and filtered. The filtrate was concentrated under reduced pressure, and the residues were purified via column chromatography (eluent: dichloromethane/methanol) to give 1.6 g of 7-benzyloxy-4-chloro-quinolin-6-carbonitrile, as a yellow solid.

Step 6: Preparation of 4-(4-amino-3-chloro-phenoxy)-7-benzyloxy-quinolin-6-carbonitrile 4-Amino-3-chlorophenol hydrochloride (612 mg, 3.40 mmol) was dissolved in 40 ml of DMSO at room temperature and added with sodium hydroxide (146 mg, 3.648 mmol). The mixture was stirred at room temperature for 0.5 hour. 7-Benzyloxy-4-chloro-quinolin-6-carbonitrile (500 mg, 1.70 mmol) (obtained in step 5) was added and the mixture was heated to 100° C. for 1 hour. The reaction solution was cooled to room temperature, and poured into 100 ml of water, and extracted with ethyl acetate (80 ml×2). The organic phase was washed with saturated NaCl solution, dried over anhydrous sodium sulfate, and filtered. The filtrate was concentrated under reduced pressure, and the residues were purified via column chromatography (eluent: dichloromethane/methanol) to give 390 mg of 4-(4-amino-3-chloro-phenoxy)-7-benzyloxy-quinolin-6-carbonitrile, as a solid.

Step 7: Preparation of 4-(4-amino-3-chloro-phenoxy)-7-benzyloxy-quinolin-6-carboxamide 4-(4-Amino-3-chloro-phenoxy)-7-benzyloxy-quinolin-6-carbonitrile obtained in Step 6 (2.9 g, 7.22 mmol) was dissolved in 40 ml of DMSO at room temperature and added with sodium hydroxide (1.6 g, 0.04 mol) (dissolved in 10 ml of water). The mixture was heated to 80° C. for 1 hour. The reaction solution was cooled to room temperature, and poured into water, and then extracted with ethyl acetate (100 ml×2). The organic phase was washed with saturated NaCl solution, dried over anhydrous sodium sulfate, and filtered. The filtrate was concentrated under reduced pressure, and the residues were purified via column chromatography (eluent: dichloromethane/methanol) to give 1.1 g of 4-(4-amino-3-chloro-phenoxy)-7-benzyloxy-quinolin-6-carboxamide, as a yellow solid.

Step 8: Preparation of phenyl [4-(7-benzyloxy-6-carbamoyl-quinolin-4-yloxy)-2-chloro-phenyl]-carbamate 4-(4-Amino-3-chloro-phenoxy)-7-benzyloxy-quinolin-6-carboxamide (1.1 g, 2.60 mmol) (obtained in Step 7) and pyridine (610 mg, 7.0 mmol) were dissolved in 20 ml of DMF, and added with potassium carbonate (360 mg, 2.60 mmol) at room temperature. The mixture was cooled in an ice bath to 0-5° C. and added with phenyl chloroformate (Shanghai Dari) (609 mg, 3.50 mmol) (dissolved in a small amount of THF) dropswise. The reaction was warmed to room temperature and stirred overnight. The reaction solution was poured into water and extracted with ethyl acetate (50 ml×3). The organic phase was washed twice with saturated NaCl solution, dried over anhydrous sodium sulfate, and filtered. The filtrate was concentrated under a reduced pressure and the residues were purified via column chromatography (eluent: dichloromethane/methanol) to give 890 mg of phenyl [4-(7-benzyloxy-6-carbamoyl-quinolin-4-yloxy)-2-chloro-phenyl]-carbamate as a solid.

Step 9: Preparation of 7-benzyloxy-4-{4-[3-(5-tert-butyl-2H-pyrazol-3-yl)-ureido]-3-chloro-phenoxy}-quinoline-6-carboxamide The preparation method was the same as Step 3 of Example 25, except that phenyl [4-(7-benzyloxy-6-carbamoyl-quinolin-4-yloxy)-2-chloro-phenyl]-carbamate (prepared in Step 8) was used instead of phenyl [4-(6-carbamoyl-7-methoxy-quinolin-4-yloxy)-2-chloro-phenyl]-carbamate in Step 3 of Example 25 to give 7-benzyloxy-4-{4-[3-(5-tert-butyl-2H-pyrazol-3-yl)-ureido]-3-chloro-phenoxy}-quinolin-6-carboxamide Step 10: Preparation of 4-{4-[3-(5-tert-butyl-2H-pyrazol-3-yl)-ureido]-3-chloro-phenoxy}-7-hydroxy-quinolin-6-carboxamide 7-Benzyloxy-4-{4-[3-(5-tert-butyl-2H-pyrazol-3-yl)-ureido]-3-chloro-phenoxy}-quinolin-6-carboxamide obtained in step 9 (140 mg, 0.24 mmol) and thioanisole (purchased from Shanghai Darui) (149 mg, 1.2 mmol) were dissolved in 5 ml of trifluoroacetic acid at room temperature and heated to 70° C. for 3 hours. The reaction solution was cooled to room temperature and concentrated under a reduced pressure to give a brown-yellow solid. The crude product was added to 60 ml of 5% sodium bicarbonate, and extracted with ethyl acetate (60 ml×3). The organic phase was washed twice with saturated NaCl solution, dried over anhydrous sodium sulfate, and filtered. The filtrate was concentrated under a reduced pressure to remove most of the solvent and then added with 15 ml of methyl t-butyl ether and stirred at room temperature for 10 min. The mixture was filtered, and the filter cake was washed with a small amount of methyl tert-butyl ether, and air-dried (60° C.) for 1 hour to give 50 mg of 4-{4-[3-(5-tert-butyl-2H-pyrazol-3-yl)-ureido]-3-chloro-phenoxy}-7-hydroxy-quinolin-6-carboxamide, as a yellow solid.

$^1$HNMR (DMSO-d6, 400 MHz) δ: 12.96 (s, 1H), 12.11 (s, 1H), 9.62 (s, 1H), 8.98 (s, 1H), 8.81 (s, 1H), 8.64-8.65 (d, 1H), 8.42-8.44 (m, 1H), 8.14 (s, 1H), 7.57-7.58 (d, 1H), 7.30-7.33 (m, 2H), 6.47-6.49 (d, 1H), 5.77 (br, 1H), 1.27 (s, 9H).

LC-MS: ESI 495.1 (M+H)+.

Example 81

Preparation of 4-{4-[3-(5-tert-butyl-2H-pyrazol-3-yl)-ureido]-3-chloro-phenoxy}-7-(2-morpholin-4-yl-ethoxy) pyridine-6-carboxamide (Compound 81)

Compound 81

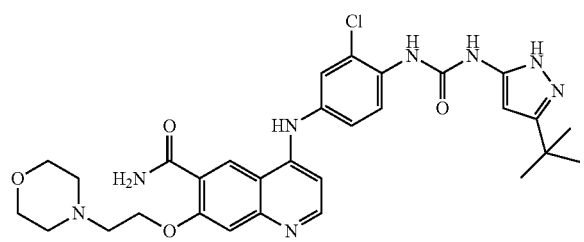

4-{4-[3-(5-tert-Butyl-2H-pyrazol-3-yl)-ureido]-3-chloro-phenoxy}-7-hydroxy-quinolin-6-carboxamide (Compound 80) (50 mg, 0.10 mmol), N-(2-chloroethyl) morpholine hydrochloride (purchased from TCI) (28.2 mg, 0.15 mmol) and cesium carbonate (98 mg, 0.30 mmol) were added to 6 ml of DMF and stirred at room temperature for 0.5 hour. The mixture was then heated to 80° C. for 3 hours. The reaction solution was poured into water, and extracted with ethyl acetate (50 ml×3). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 35 mg of 4-{4-[3-(5-tert-butyl-2H-pyrazol-3-yl)-ureido]-3-chloro-phenoxy}-7-(2-morpholin-4-yl-ethoxy) pyridin-6-carboxamide as a solid.

$^1$HNMR (DMSO-d6, 400 MHz) δ: 11.94 (s, 1H), 9.40 (s, 1H), 8.81 (s, 1H), 8.67-8.68 (d, 1H), 8.35-8.38 (d, 1H), 8.20 (br, 1H), 7.64 (br, 1H), 7.57 (s, 1H), 7.47 (d, 1H), 7.32-7.26 (dd, 1H), 6.58-6.59 (d, 1H), 5.89 (br, 1H), 4.40-4.43 (t, 2H), 3.59-3.61 (t, 4H), 2.82 (m, 2H), 2.50 (m, 4H), 1.27 (s, 9H).

LC-MS: ESI 608.2 (M+H)+.

Example 82

Preparation of 4-{4-[3-(5-tert-butyl-2H-pyrazol-3-yl)-ureido]-3-chloro-phenoxy}-7-[3-(4-methyl-piperazin-1-yl)-propoxy]-quinolin-6-carboxamide (Compound 82)

Compound 82

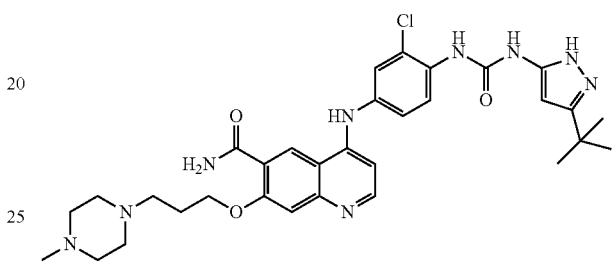

The preparation method was the same as Example 81, except that 1-(3-chloropropyl)-4-methylpiperazine dihydrochloride (purchased from TCI) was used instead of N-(2-chloroethyl) morpholine hydrochloride in Example 81 to give 4-{4-[3-(5-tert-butyl-2H-pyrazol-3-yl)-ureido]-3-chloro-phenoxy}-7-[3-(4-methyl-piperazin-1-yl)-propoxy]-quinolin-6-carboxamide.

$^1$HNMR (DMSO-d6, 400 MHz) δ: 12.09 (s, 1H), 9.61 (s, 1H), 8.66-8.68 (m, 2H), 8.39-8.41 (m, 1H), 7.79 (s, 2H), 7.55-7.56 (d, 1H), 7.52 (s, 1H), 7.27-7.30 (dd, 1H), 6.56-6.57 (d, 1H), 5.89 (br, 1H), 4.28-4.31 (t, 2H), 2.41-2.54 (m, 10H), 2.31 (s, 3H), 1.99-2.04 (m, 2H), 1.26 (s, 9H).

LC-MS: ESI 635.1 (M+H)+.

Example 83

Preparation of 4-{4-[3-(5-tert-butyl-2H-pyrazol-3-yl)-ureido]-3-chloro-phenoxy}-7-(2-dimethylamino-ethoxy-quinolin-6-carboxamide (Compound 83)

Compound 83

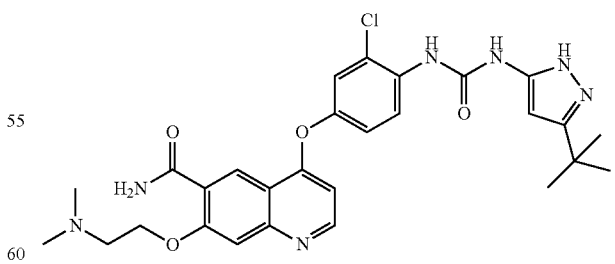

The preparation method was the same as Example 81, except that 2-dimethylaminoethyl chloride hydrochloride (purchased from TCI) was used instead of N-(2-chloroethyl) morpholine hydrochloride in Example 81 to give 4-{4-[3-(5-tert-butyl-2H-pyrazol-3-yl)-ureido]-3-chloro-phenoxy}-7-(2-dimethylamino-ethoxy-quinolin-6-carboxamide.

¹HNMR (DMSO-d6, 400 MHz) δ: 12.11 (s, 1H), 9.61 (s, 1H), 8.79 (s, 1H), 8.68-8.69 (d, 1H), 8.42 (m, 1H), 8.23 (br, 1H), 7.76 (br, 1H), 7.58 (s, 1H), 7.56-7.57 (d, 1H), 7.28-7.31 (dd, 1H), 6.55-6.57 (d, 1H), 5.87 (br, 1H), 4.36-4.39 (t, 2H), 2.74-2.76 (t, 2H), 2.25 (s, 6H), 1.26 (s, 9H).
LC-MS: ESI 566.1 (M+H)+.

Example 84

Preparation of 4-{4-[3-(5-tert-butyl-2H-pyrazol-3-yl)-ureido]-3-chloro-phenoxy}-7-(2-piperidin-1-yl-ethoxy)-quinolin-pyridine-6-carboxamide (Compound 84)

Compound 84

The preparation method was the same as Example 81, except that 1-(2-chloroethyl) piperidine hydrochloride (purchased from TCI) was used instead of N-(2-chloroethyl) morpholine hydrochloride in Example 81 to give 4-{4-[3-(5-tert-butyl-2H-pyrazol-3-yl)-ureido]-3-chloro-phenoxy}-7-(2-piperidin-1-yl-ethoxy)-quinolin-pyridine-6-carboxamide.

¹HNMR (DMSO-d6, 400 MHz) δ: 12.11 (s, 1H), 9.61 (s, 1H), 8.84 (s, 1H), 8.67-8.69 (d, 1H), 8.40-8.44 (m, 2H), 7.86 (s, 1H), 7.56-7.58 (m, 2H), 7.28-7.32 (dd, 1H), 6.56-6.57 (d, 1H), 5.88 (br, 1H), 4.39-4.41 (t, 2H), 2.74 (m, 2H), 2.43 (m, 4H), 1.49-1.51 (m, 6H), 1.26 (s, 9H).
LC-MS: ESI 606.1 (M+H)+.

Example 85

Preparation of 4-{4-[3-(5-tert-butyl-2H-pyrazol-3-yl)-ureido]-3-chloro-phenoxy}-7-{3-[4-(2-methoxy-ethyl)-piperazin-1-yl]-propoxy}-quinolin-6-carboxamide (Compound 85)

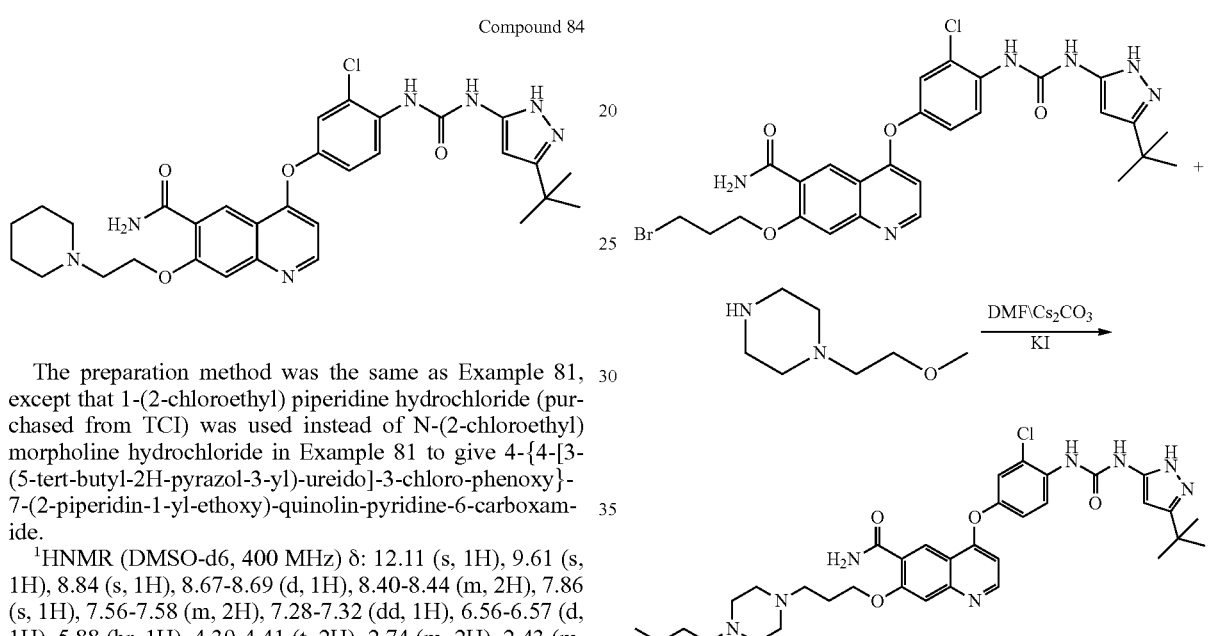

Step 1: Preparation of 7-(3-bromo-propoxy)-4-{4-[3-(5-tert-butyl-2H-pyrazol-3-yl)-ureido]-3-chloro-phenoxy}-quinolin-6-carboxamide 4-{4-[3-(5-tert-Butyl-2H-pyrazol-3-yl)-ureido]-3-chloro-phenoxy}-7-hydroxy-quinolin-6-carboxamide (Compound

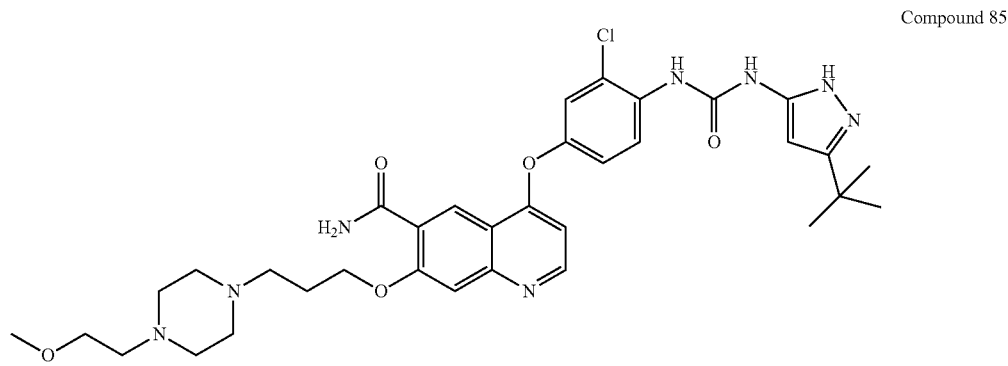 [SMILES: COCCN1CCN(CCCOc2cc3nccc(Oc4ccc(NC(=O)Nc5cc(C(C)(C)C)n[nH]5)c(Cl)c4)c3cc2C(N)=O)CC1]

Compound 85

80) (400 mg, 0.809 mmol) and 1,3-dibromopropane (809 mg, 4.045 mmol) were dissolved in 10 ml of DMF, and added with cesium carbonate (792 mg, 2.43 mmol) and a catalytic amount of potassium iodide at room temperature. The mixture was heated to 60° C. and stirred overnight. The reaction solution was cooled to room temperature, and poured into water, and then extracted with ethyl acetate (50 ml×3). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 170 mg of 7-(3-bromo-propoxy)-4-{4-[3-(5-tert-butyl-2H-pyrazol-3-yl)-ureido]-3-chloro-phenoxy}-quinolin-6-carboxamide as a solid.

Step 2: Preparation of 4-{4-[3-(5-tert-butyl-2H-pyrazol-3-yl)-ureido]-3-chloro-phenoxy}-7-{3-[4-(2-methoxy-ethyl)-piperazin-1-yl]-propoxy}-quinolin-6-carboxamide 7-(3-Bromo-propoxy)-4-{4-[3-(5-tert-butyl-2H-pyrazol-3-yl)-ureido]-3-chloro-phenoxy}-quinolin-6-carboxamide obtained in Step 1 (50 mg, 0.081 mmol) and 1-(2-methoxy-ethyl)piperazine (purchased from TCI) (58.6 mg, 0.407 mmol) were dissolved in 2 ml of DMF, and added with cesium carbonate (80 mg, 0.243 mmol) and a catalytic amount of potassium iodide at room temperature. The mixture was heated to 70° C. and stirred overnight. The reaction solution was cooled to room temperature, and poured into water, and then extracted with ethyl acetate (50 ml×3). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 20 mg of 4-{4-[3-(5-tert-butyl-2H-pyrazol-3-yl)-ureido]-3-chloro-phenoxy}-7-{3-[4-(2-methoxy-ethyl)-piperazin-1-yl]-propoxy}-quinolin-6-carboxamide as a solid.

$^1$HNMR (DMSO-d6, 400 MHz) δ: 12.11 (s, 1H), 9.61 (s, 1H), 8.67-8.69 (m, 1H), 8.40-8.42 (m, 1H), 7.79 (s, 2H), 7.55-7.56 (d, 1H), 7.52 (s, 1H), 7.27-7.30 (dd, 1H), 6.56-6.58 (d, 1H), 5.90 (br, 1H), 4.29-4.32 (t, 2H), 3.42-3.45 (t, 2H), 3.23 (s, 3H), 2.35-2.55 (m, 12H), 1.96-2.03 (m, 2H), 1.26 (s, 9H).

LC-MS: ESI 679.3 (M+H)+.

Example 86

Preparation of 4-{4-[3-(5-tert-butyl-2H-pyrazol-3-yl)-ureido]-3-chloro-phenoxy}-7-[3-(4-phenyl-piperazin-1-yl)-propoxy]-quinolin-6-carboxamide (Compound 86)

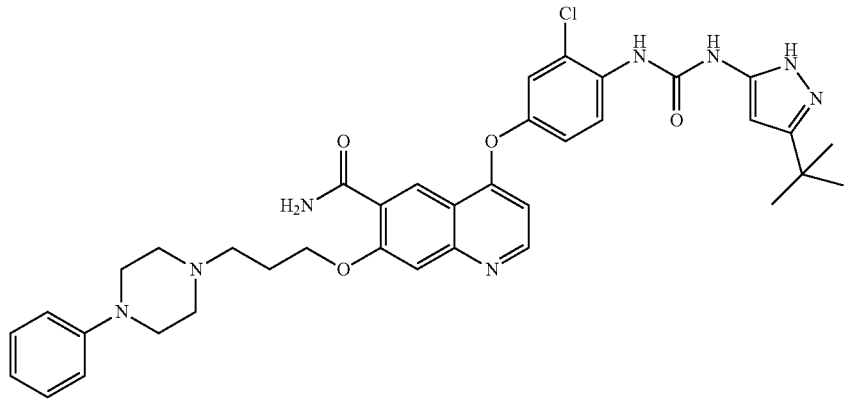

Compound 86

The preparation method was the same as Example 85, except that 1-phenylpiperazine (purchased from TCI) was used instead of 1-(2-methoxyethyl)-piperazine in Step 2 of Example 85 to give 4-{4-[3-(5-tert-butyl-2H-pyrazol-3-yl)-ureido]-3-chloro-phenoxy}-7-[3-(4-phenyl-piperazin-1-yl)-propoxy]-quinolin-6-carboxamide.

$^1$HNMR (DMSO-d6, 400 MHz) δ: 12.11 (s, 1H), 9.61 (s, 1H), 8.67-8.69 (m, 2H), 8.40-8.42 (m, 1H), 7.82 (s, 2H), 755-7.56 (d, 1H), 7.54 (s, 1H), 7.28-7.31 (dd, 1H), 7.19-7.23 (t, 1H), 6.92-6.94 (d, 2H), 6.75-6.79 (t, 1H), 6.56-6.57 (d, 1H), 5.89 (br, 1H), 4.33-4.45 (t, 2H), 3.15 (m, 4H), 2.56 (m, 6H), 2.06-2.09 (m, 2H), 1.27 (s, 9H).

LC-MS: ESI 696.7 (M+H)+.

Example 87

Preparation of 7-[3-(4-tert-butyl-piperazin-1-yl)-propoxy]-4-{4-[3-(5-tert-butyl-2H-pyrazol-3-yl)-ureido]-3-chlorophenoxy}-quinolin-6-carboxamide (Compound 87)

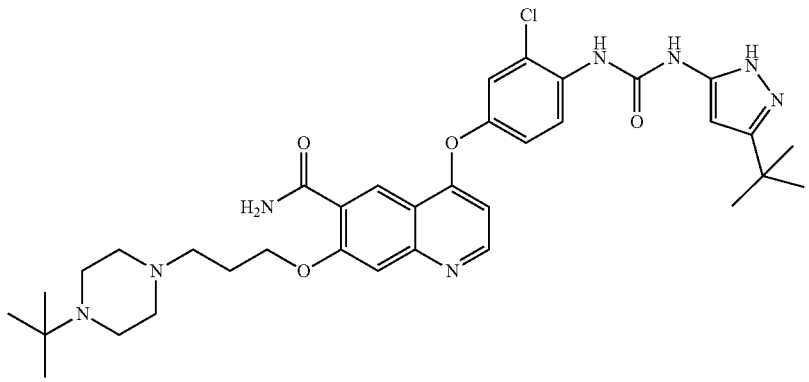

Compound 87

The preparation method was the same as Example 85, except that 1-tert-butylpiperazine (purchased from TCI) was used instead of 1-(2-methoxyethyl)piperazine in Step 2 of Example 85 to give 7-[3-(4-tert-butyl-piperazin-1-yl)-propoxy]-4-{4-[3-(5-tert-butyl-2H-pyrazol-3-yl)-ureido]-3-chlorophenoxy}-quinolin-6-carboxamide.

$^1$HNMR (DMSO-d6, 400 MHz) δ: 12.10 (s, 1H), 9.60 (s, 1H), 8.67-8.71 (m, 2H), 8.40-8.42 (m, 1H), 7.77-7.78 (m, 2H), 7.55-7.56 (d, 1H), 7.52 (s, 1H), 7.27-7.30 (dd, 1H), 6.56-6.57 (d, 1H), 5.88 (br, 1H), 4.28-4.31 (t, 2H), 2.34-2.52 (m, 10H), 1.98-2.04 (m, 2H), 2.06-2.09 (m, 2H), 1.27 (s, 9H), 0.99 (s, 9H).

LC-MS: ESI 677.3 (M+H)$^+$.

Example 88

Preparation of 4-{4-[3-(5-tert-butyl-2H-pyrazol-3-yl)-ureido]-3-chloro-phenoxy}-7-[3-(4-methyl-[1,4]-1-yl)-propoxy]-quinolin-6-carboxamide (Compound 88)

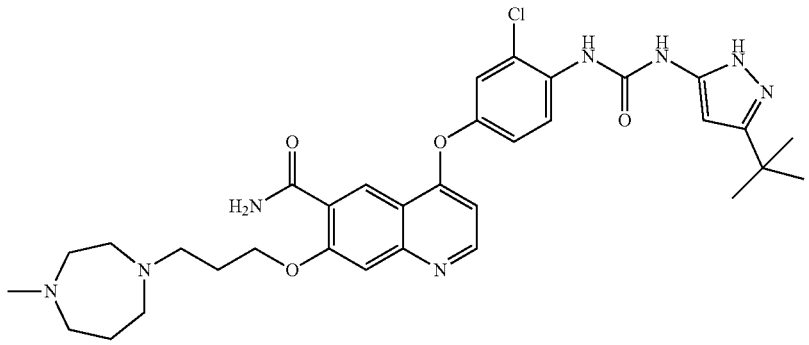

Compound 88

The preparation method was the same as Example 85, except that N-methylhomopiperazine (purchased from TCI) was used instead of 1-(2-methoxyethyl)piperazine in Step 2 of Example 85 to give 4-{4-[3-(5-tert-butyl-2H-pyrazol-3-yl)-ureido]-3-chloro-phenoxy}-7-[3-(4-methyl-[1,4]-1-yl)-propoxy]-quinolin-6-carboxamide.

$^1$HNMR (DMSO-d6, 400 MHz) δ: 12.11 (s, 1H), 9.61 (s, 1H), 8.67-8.70 (m, 2H), 8.40-8.42 (m, 1H), 7.79 (s, 1H), 7.82 (s, 1H), 7.55-7.56 (d, 1H), 7.52 (s, 1H), 7.28-7.32 (dd, 1H), 6.56-6.57 (d, 1H), 5.88 (br, 1H), 4.29-4.32 (t, 2H), 2.56-2.70 (m, 10H), 2.27 (s, 3H), 1.97-2.01 (m, 2H), 1.71-1.74 (m, 2H), 1.27 (s, 9H).

LC-MS: ESI 649.3 (M+H)+.

Example 89

Preparation of 4-{4-[3-(5-tert-butyl-2H-pyrazol-3-yl)-ureido]-3-chloro-phenoxy}-7-[3-(4-isobutyl-piperazin-1-yl)-propoxy]-quinolin-6-carboxamide (Compound 89)

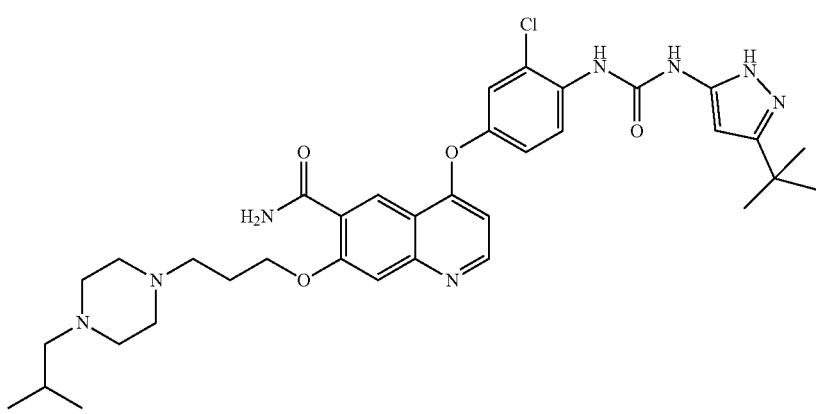

Compound 89

The preparation method was the same as Example 85, except that N-isobutylpiperazine (purchased from TCI) was used instead of 1-(2-methoxyethyl)piperazine in Step 2 of Example 85 to give 4-{4-[3-(5-tert-butyl-2H-pyrazol-3-yl)-ureido]-3-chloro-phenoxy}-7-[3-(4-isobutyl-piperazin-1-yl)-propoxy]-quinolin-6-carboxamide.

$^1$HNMR (DMSO-d6, 400 MHz) δ: 12.11 (s, 1H), 9.61 (s, 1H), 8.67-8.68 (m, 2H), 8.40-8.42 (m, 1H), 7.79 (s, 1H), 7.79 (s, 1H), 7.55-7.56 (d, 1H), 7.54 (s, 1H), 7.28-7.30 (dd, 1H), 6.56-6.57 (d, 1H), 5.88 (br, 1H), 4.28-4.31 (t, 2H), 2.25-2.51 (m, 12H), 1.97-2.02 (m, 2H), 1.69-1.78 (m, 1H), 1.27 (s, 9H), 0.84-0.85 (d, 6H).

LC-MS: ESI 676.8 (M+H)+.

Example 90

Preparation of 4-{4-[3-(5-tert-butyl-2H-pyrazol-3-yl)-ureido]-3-chloro-phenoxy}-7-[3-(4-cyclohexylmethyl)-piperazin-1-yl)-propoxy]-quinolin-6-carboxamide (Compound 90)

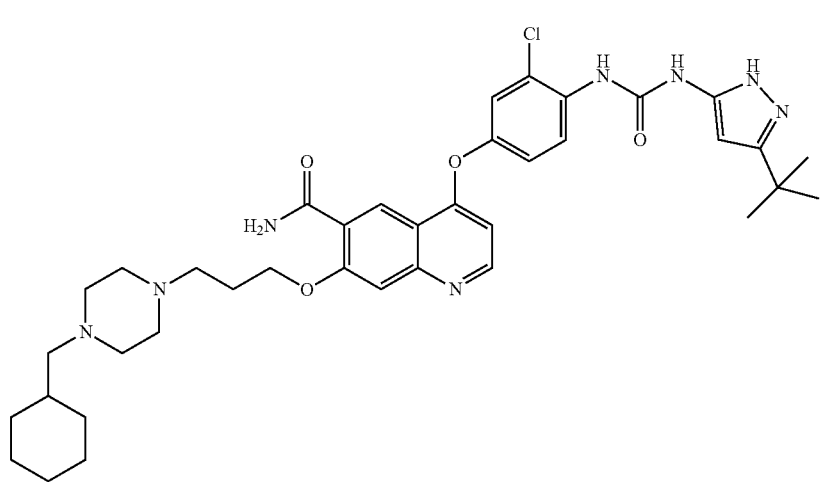

Compound 90

The preparation method was the same as Example 85, except that 1-(cyclohexylmethyl)piperazine (purchased from TCI) was used instead of 1-(2-methoxyethyl)piperazine in Step 2 of Example 85 to give 4-{4-[3-(5-tert-butyl-2H-pyrazol-3-yl)-ureido]-3-chloro-phenoxy}-7-[3-(4-cyclohexylmethyl)-piperazin-1-yl)-propoxy]-quinolin-6-carboxamide.

$^1$HNMR (DMSO-d6, 400 MHz) δ: 12.11 (s, 1H), 9.61 (s, 1H), 8.67-8.73 (m, 2H), 8.40-8.42 (m, 1H), 7.78 (m, 2H), 7.55-7.56 (d, 1H), 7.51 (s, 1H), 7.27-7.30 (dd, 1H), 6.56-

6.57 (d, 1H), 5.88 (br, 1H), 4.28-4.31 (t, 2H), 2.20-2.51 (m, 12H), 2.01-2.05 (m, 2H), 1.42-1.69 (m, 5H), 1.27 (s, 9H), 1.10-1.20 (m, 4H), 0.76-0.87 (m, 2H).

LC-MS: ESI 716.8 (M+H)+.

Example 91

Preparation of 7-[3-(4-acetyl-piperazin-1-yl)-propoxy]-4-{4-[3-(5-tert-butyl-2H-pyrazol-3-yl)-ureido]-3-chloro-phenoxy}-quinolin-6-carboxamide (Compound 91)

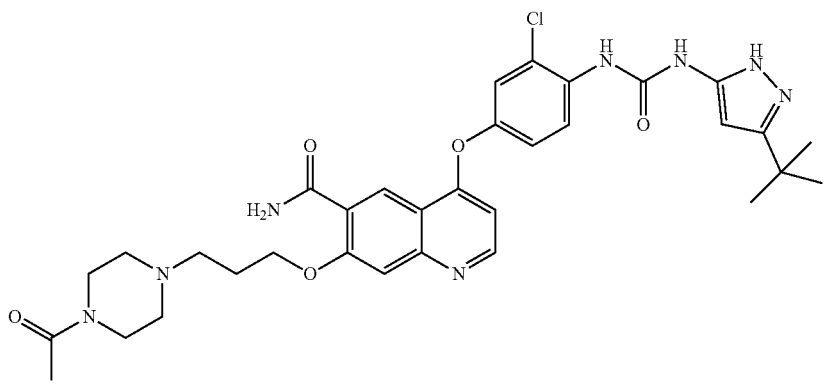

Compound 91

The preparation method was the same as Example 85, except that 1-acetylpiperazine (purchased from TCI) was used instead of 1-(2-methoxyethyl)piperazine in Step 2 of Example 85 to give 7-[3-(4-acetyl-piperazin-1-yl)-propoxy]-4-{4-[3-(5-tert-butyl-2H-pyrazol-3-yl)-ureido]-3-chloro-phenoxy}-quinolin-6-carboxamide.

$^1$HNMR (DMSO-d6, 400 MHz) δ: 12.10 (s, 1H), 9.60 (s, 1H), 8.68-8.69 (m, 2H), 8.40-8.42 (m, 1H), 7.79-7.80 (m, 2H), 7.55-7.56 (d, 1H), 7.54 (s, 1H), 7.28-7.31 (dd, 1H), 6.56-6.58 (d, 1H), 5.88 (br, 1H), 4.31-4.34 (t, 2H), 3.42-3.45 (m, 4H), 2.34-2.54 (m, 6H), 2.01-2.06 (m, 2H), 1.99 (s, 3), 1.27 (s, 9H).

LC-MS: ESI 662.7 (M+H)+.

Example 92

Preparation of 4-{4-[3-(5-tert-butyl-2H-pyrazol-3-yl)-ureido]-2,3-dichloro-phenoxy}-7-hydroxy-quinolin-6-carboxamide (Compound 92)

Compound 92

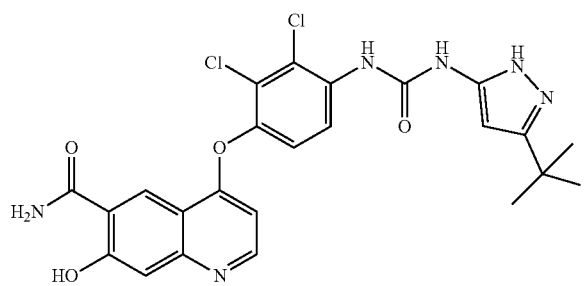

The preparation method was the same as Example 80, except that 4-amino-2,3-dichlorophenol (purchased from TCI) was used instead of 4-amino-3-chlorophenol hydrochloride in Step 6 of Example 80 to give 4-{4-[3-(5-tert-butyl-2H-pyrazol-3-yl)-ureido]-2,3-dichloro-phenoxy}-7-hydroxy-quinolin-6-carboxamide.

$^1$HNMR (DMSO-d6, 400 MHz) δ: 13.03 (s, 1H), 12.14 (s, 1H), 9.71 (s, 1H), 9.04 (s, 1H), 8.82 (s, 1H), 8.65-8.66 (d, 1H), 8.46-8.47 (m, 1H), 8.16 (s, 1H), 7.52-7.54 (d, 1H), 7.37 (s, 1H), 6.43-6.44 (d, 1H), 5.88 (br, 1H), 1.27 (s, 9H).

LC-MS: ESI 529.1\531.1 (M+H)+.

Example 93

Preparation of 4-{4-[3-(5-tert-butyl-2H-pyrazol-3-yl)-ureido]-2,3-dichloro-phenoxy}-7-(2-dimethyl-amino-ethoxy)carboxamide (Compound 93)

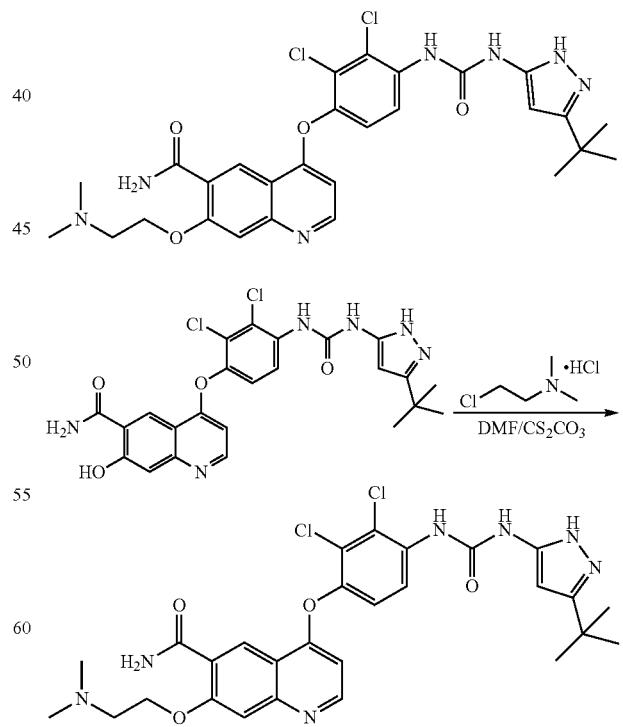

Compound 93

4-{4-[3-(5-tert-Butyl-2H-pyrazol-3-yl)-ureido]-2,3-dichloro-phenoxy}-7-hydroxy-quinolin-6-carboxamide (Compound 92) (100 mg, 0.189 mmol), dimethylaminoethyl chloride hydrochloride (purchased from TCI) (54 mg, 0.378 mmol) and cesium carbonate (185 mg, 0.567 mmol) were stirred in 10 ml of DMF at room temperature for 0.5 hour. The mixture was heated to 70° C. and stirred overnight. The reaction solution was poured into water, and extracted with ethyl acetate (50 ml×3). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 20 mg of 4-{4-[3-(5-tert-butyl-2H-pyrazol-3-yl)-ureido]-2,3-dichloro-phenoxy}-7-(2-dimethylamino-ethoxy)-carboxamide as a solid.

¹HNMR (DMSO-d6, 400 MHz) δ: 12.14 (s, 1H), 9.70 (s, 1H), 8.82 (s, 1H), 8.67-8.68 (d, 1H), 8.45-8.46 (m, 1H), 8.24 (s, 1H), 7.78 (s, 1H), 7.61 (s, 1H), 7.50-7.53 (d, 1H), 6.47-6.49 (d, 1H), 5.88 (br, 1H), 4.38-4.41 (t, 2H), 2.79 (t, 2H), 2.28 (s, 6H), 1.27 (s, 9H).

LC-MS: ESI 600.2\602.2 (M+H)+.

Example 94

Preparation of 4-{4-[3-(5-tert-butyl-2H-pyrazol-3-yl)-ureido]-2,3-dichloro-phenoxy}-7-(2-morpholin-4-yl-ethoxy)-quinolin-6-carboxamide (Compound 94)

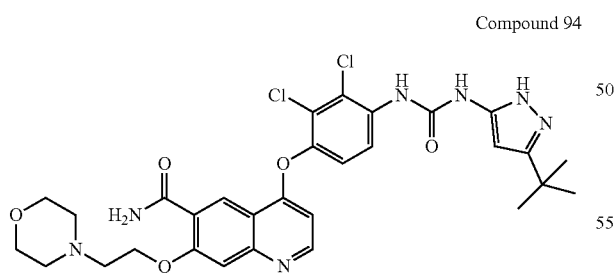

Compound 94

The preparation method was the same as Example 93, except that N-(2-chloroethyl)-morpholine hydrochloride (purchased from TCI) was used instead of dimethylaminoethyl chloride hydrochloride in Example 93 to give 4-{4-[3-(5-tert-butyl-2H-pyrazol-3-yl)-ureido]-2,3-dichloro-phenoxy}-7-(2-morpholin-4-yl-ethoxy)-quinolin-6-carboxamide.

¹HNMR (DMSO-d6, 400 MHz) δ: 12.14 (s, 1H), 9.70 (s, 1H), 8.88 (s, 1H), 8.67-8.68 (d, 1H), 8.42-8.50 (m, 2H), 7.91 (s, 1H), 7.62 (s, 1H), 7.50-7.53 (d, 1H), 6.47-6.48 (d, 1H), 5.88 (br, 1H), 4.42-4.44 (t, 2H), 3.59-3.61 (t, 4H), 2.80-2.82 (t, 2H), 2.46-2.50 (m, 4H), 1.27 (s, 9H).

LC-MS: ESI 642.2\644.2 (M+H)+.

Example 95

Preparation of 4-{4-[3-(5-tert-butyl-2H-pyrazol-3-yl)-ureido]-2,3-dichloro-phenoxy}-7-[3-(4-methyl-pyridin-3-yl)-propoxy]-quinolin-6-carboxamide (Compound 95)

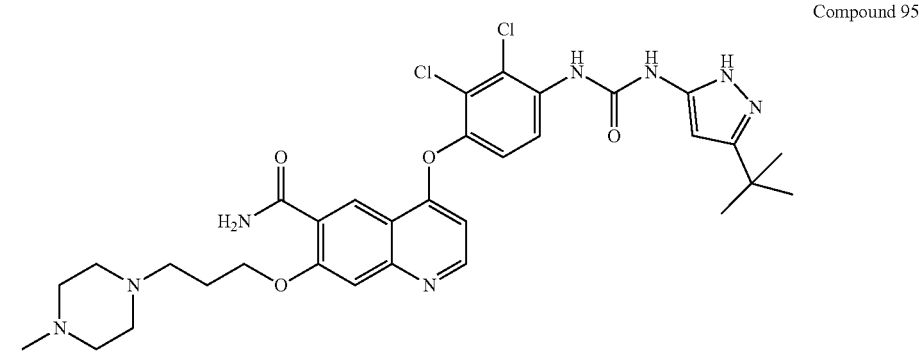 [SMILES: CN1CCN(CCCOc2cc3nccc(Oc4ccc(NC(=O)Nc5cc(C(C)(C)C)n[nH]5)c(Cl)c4Cl)c3cc2C(N)=O)CC1]

Compound 95

The preparation method was the same as Example 93, except that 1-(3-chloropropyl)-4-methylpiperazine dihydrochloride (purchased from TCI) was used instead of dimethylaminoethyl chloride hydrochloride in Example 93 to give 4-{4-[3-(5-tert-butyl-2H-pyrazol-3-yl)-ureido]-2,3-dichloro-phenoxy}-7-[3-(4-methyl-pyridin-3-yl)-propoxy]-quinolin-6-carboxamide.

¹HNMR (DMSO-d6, 400 MHz) δ: 12.15 (s, 1H), 9.71 (s, 1H), 8.70 (s, 1H), 8.66-8.67 (d, 1H), 8.43-8.45 (m, 1H), 7.80 (s, 2H), 7.54 (s, 1H), 7.50-7.52 (d, 1H), 6.46-6.48 (d, 1H), 5.89 (br, 1H), 4.29-4.32 (t, 2H), 2.32-2.49 (m, 10H), 2.20 (s, 3H), 2.00-2.04 (m, 2H), 1.27 (s, 9H).

LC-MS: ESI 669.2\671.2 (M+H)⁺.

Example 96

Preparation of 4-{4-[3-(5-tert-butyl-2H-pyrazol-3-yl)-ureido]-2,3-dichloro-phenoxy}-7-(2-piperidin-1-yl-ethoxy)-quinolin-6-carboxamide (Compound 96)

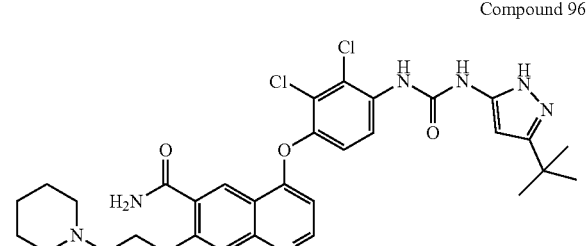

Compound 96

The preparation method was the same as Example 93, except that 1-(2-chloroethyl)-piperidine hydrochloride (purchased from TCI) was used instead of dimethylaminoethyl chloride hydrochloride in Example 93 to give 4-{4-[3-(5-tert-butyl-2H-pyrazol-3-yl)-ureido]-2,3-dichloro-phenoxy}-7-(2-piperidin-1-yl-ethoxy)-quinolin-6-carboxamide.

¹HNMR (DMSO-d6, 400 MHz) δ: 12.14 (s, 1H), 9.70 (s, 1H), 8.88 (s, 1H), 8.67-8.68 (d, 1H), 8.43-8.46 (m, 2H), 7.88 (s, 1H), 7.61 (s, 1H), 7.50-7.53 (d, 1H), 6.47-6.48 (d, 1H), 5.89 (br, 1H), 4.40-4.43 (t, 2H), 2.75 (t, 2H), 2.44 (m, 4H), 1.34-1.52 (m, 6H), 1.27 (s, 9H).

LC-MS: ESI 640.2\642.2 (M+H)+.

Example 97

Preparation of 4-{4-[3-(5-tert-butyl-2H-pyrazol-3-yl)-ureido]-2-chloro-phenylamino}-7-methoxy-quinolin-6-carboxamide (Compound 97)

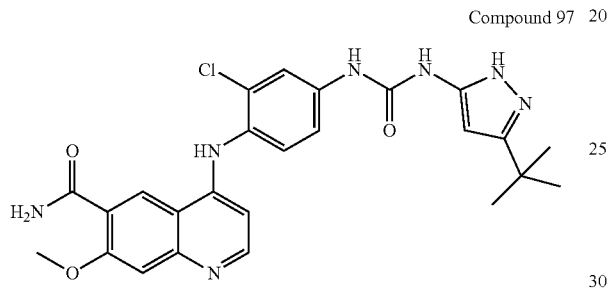

Compound 97

The preparation method was the same as Example 77 and Example 79, except that 3-chloro-4-nitroaniline (purchased from Shanghai Darui) was used instead of 2-chloro-4-nitroaniline in step 1 of Example 77 to give 4-{4-[3-(5-tert-butyl-2H-pyrazol-3-yl)-ureido]-2-chloro-phenylamino}-7-methoxy-quinolin-6-carboxamide.

¹HNMR (DMSO-d6, 400 MHz) δ: 12.02 (s, 1H), 9.47 (br, 1H), 9.23 (br, 1H), 9.05 (s, 1H), 8.86 (s, 1H), 8.31-8.32 (d, 1H), 7.92 (m, 1H), 7.80 (s, 1H), 7.67 (s, 1H), 7.34-7.35 (m, 3H), 6.04 (s, 1H), 6.00-6.01 (d, 1H), 4.00 (s, 3H), 1.27 (s, 9H).

LC-MS: ESI 507.8 (M+H)+.

Example 98

Preparation of 4-{4-[3-(5-tert-butyl-2H-pyrazol-3-yl)-ureido]-2-methyl-phenylamino}-7-methoxy-quinolin-6-carboxamide (Compound 98)

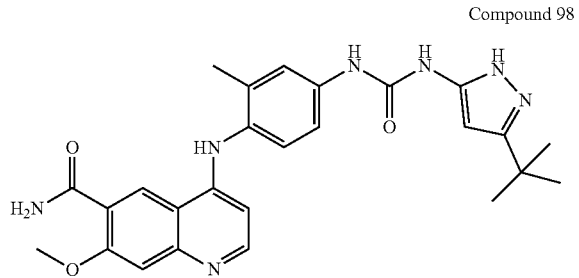 [SMILES: COc1cc2nccc(Nc3ccc(NC(=O)Nc4cc(C(C)(C)C)n[nH]4)cc3Cl)c2cc1C(N)=O]

Compound 98

The preparation method was the same as Example 77 and Example 79, except that 3-methyl-4-nitroaniline (purchased from Shanghai Darui) was used instead of 2-chloro-4-nitroaniline in step 1 of Example 77 to give 4-{4-[3-(5-tert-butyl-2H-pyrazol-3-yl)-ureido]-2-methyl-phenylamino}-7-methoxy-quinolin-6-carboxamide.

¹HNMR (DMSO-d6, 400 MHz) δ: 12.01 (s, 1H), 9.74 (br, 1H), 9.35 (br, 1H), 9.00 (s, 1H), 8.94 (s, 1H), 8.31-8.33 (d, 1H), 7.84 (s, 1H), 7.75 (s, 1H), 7.50 (d, 1H), 7.40-7.43 (dd, 1H), 7.36 (s, 1H), 7.17-7.19 (d, 1H), 6.04-6.06 (d, 1H), 6.01 (s, 1H), 4.01 (s, 3H), 2.14 (s, 3H), 1.27 (s, 9H).

LC-MS: ESI 487.8 (M+H)+.

Example 99

Preparation of 4-{4-[3-(5-tert-butyl-isoxazol-3-yl)-ureido]-2-methyl-phenylamino}-7-methoxy-quinolin-6-carboxamide (Compound 99)

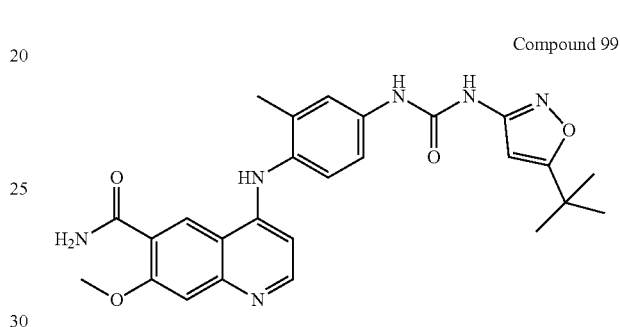

Compound 99

The preparation method was the same as Example 77, except that 3-methyl-4-nitroaniline (purchased from Shanghai Darui) was used instead of 2-chloro-4-nitroaniline in step 1 of Example 77 to give 4-{4-[3-(5-tert-butyl-isoxazol-3-yl)-ureido]-2-methyl-phenylamino}-7-methoxy-quinolin-6-carboxamide.

¹HNMR (DMSO-d6, 400 MHz) δ: 9.54 (s, 1H), 8.92 (s, 1H), 8.85 (m, 2H), 8.27-8.28 (d, 1H), 7.78 (s, 1H), 7.65 (s, 1H), 7.47-7.48 (d, 1H), 7.35-7.37 (dd, 1H), 7.31 (s, 1H), 7.15-7.17 (d, 1H), 6.52 (s, 1H), 5.92-5.93 (d, 1H), 3.99 (s, 3H), 2.13 (s, 3H), 1.30 (s, 9H).

LC-MS: ESI 489.2 (M+H)+.

Example 100

Preparation of 4-{4-[3-(5-tert-butyl-isoxazol-3-yl)-ureido]-2-chloro-phenylamino}-7-methoxy-quinolin-6-carboxamide (Compound 100)

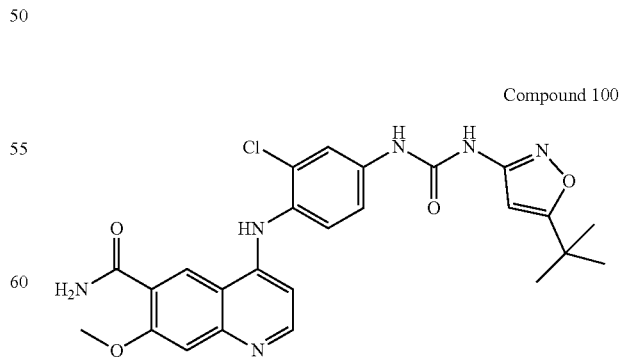

Compound 100

The preparation method was the same as Example 77, except that 3-chloro-4-nitroaniline (purchased from Shanghai Darui) was used instead of 2-chloro-4-nitroaniline in step 1 of Example 77 to give 4-{4-[3-(5-tert-butyl-isoxazol-3-yl)-ureido]-2-chloro-phenylamino}-7-methoxy-quinolin-6-carboxamide.

¹HNMR (DMSO-d6, 400 MHz) δ: 10.08 (br, 1H), 9.92 (s, 1H), 9.90 (s, 1H), 8.96 (s, 1H), 8.38-8.39 (d, 1H), 7.95 (d, 1H), 7.87 (s, 1H), 7.78 (s, 1H), 7.42-7.47 (m, 3H), 6.55 (s, 1H), 6.15-6.15 (d, 1H), 4.02 (s, 3H), 1.31 (s, 9H).

LC-MS: ESI 509.1 (M+H)+.

Example 101

Preparation of N-(4-{4-[3-(5-tert-butyl-2H-pyrazol-3-yl)-ureido]-2-chloro-phenoxy}-7-methoxy-quinolin-6-yl)-acetamide (Compound 101)

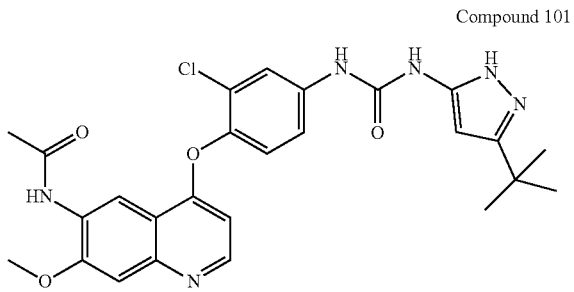 [SMILES: COc1cc2nccc(Oc3ccc(NC(=O)Nc4cc(C(C)(C)C)n[nH]4)cc3Cl)c2cc1NC(C)=O]

Compound 101

The preparation method was the same as Example 63, except that 4-amino-2-chlorophenol (purchased from Shanghai Darui) was used instead of 4-amino-3-chlorophenol hydrochloride in step 1 of Example 63 to give N-(4-{4-[3-(5-tert-butyl-2H-pyrazol-3-yl)-ureido]-2-chloro-phenoxy}-7-methoxy-quinolin-6-yl)-acetamide.

¹HNMR (DMSO-d6, 400 MHz) δ: 12.03 (s, 1H), 9.49 (s, 1H), 9.41 (br, 1H), 9.05 (s, 1H), 9.05 (s, 1H), 8.51-8.52 (d, 1H), 7.96 (m, 1H), 7.47 (s, 1H), 7.39 (m, 2H), 6.34-6.35 (d, 1H), 6.04 (s, 1H), 4.09 (s, 3H), 2.20 (s, 3H), 1.27 (s, 9H).

LC-MS: ESI 523.2 (M+H)+.

Example 102

Preparation of N-(4-{4-[3-(5-tert-butyl-2H-pyrazol-3-yl)-ureido]-2-fluoro-phenoxy}-7-methoxy-quinolin-6-yl)-acetamide (Compound 102)

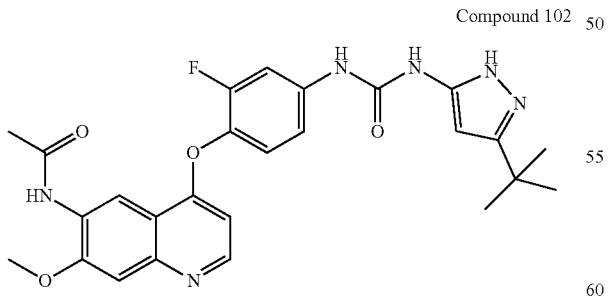

Compound 102

The preparation method was the same as Example 63, except that 4-amino-2-fluorophenol (purchased from Shanghai Darui) was used instead of 4-amino-3-chlorophenol hydrochloride in step 1 of Example 63 to give N-(4-{4-[3-(5-tert-butyl-2H-pyrazol-3-yl)-ureido]-2-fluoro-phenoxy}-7-methoxy-quinolin-6-yl)-acetamide.

¹HNMR (DMSO-d6, 400 MHz) δ: 12.03 (s, 1H), 9.50 (s, 1H), 9.03 (s, 1H), 9.03 (s, 1H), 9.9.52-9.53 (d, 1H), 7.68-7.80 (dd, 1H), 7.47 (s, 1H), 7.36-7.41 (t, 1H), 7.20-7.22 (m, 1H), 6.45-6.46 (d, 1H), 6.03 (s, 1H), 4.09 (s, 3H), 2.20 (s, 3H), 1.27 (s, 9H).

LC-MS: ESI 507.1 (M+H)+.

Example 103

Preparation of N-(4-{4-[3-(5-tert-butyl-2H-pyrazol-3-yl)-ureido]-2-methyl-phenoxy}-7-methoxy-quinolin-6-yl)-acetamide (Compound 103)

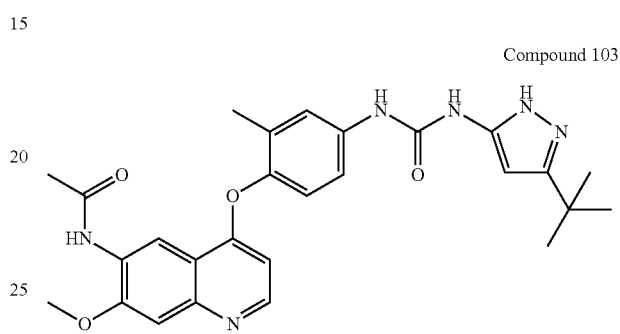

Compound 103

The preparation method was the same as Example 63, except that 4-amino-2-methylphenol (purchased from Shanghai Darui) was used instead of 4-amino-3-chlorophenol hydrochloride in step 1 of Example 63 to give N-(4-{4-[3-(5-tert-butyl-2H-pyrazol-3-yl)-ureido]-2-methyl-phenoxy}-7-methoxy-quinolin-6-yl)-acetamide.

¹HNMR (DMSO-d6, 400 MHz) δ: 12.00 (s, 1H), 9.48 (s, 1H), 9.28 (br, 1H), 9.06 (s, 1H), 8.96 (s, 1H), 8.49-8.50 (d, 1H), 7.50-7.51 (d, 1H), 7.46 (s, 1H), 7.39-7.42 (dd, 1H), 7.11-7.13 (d, 1H), 6.29-6.31 (d, 1H), 6.00 (s, 1H), 4.04 (s, 3H), 2.20 (s, 3H), 2.07 (s, 3H), 1.27 (s, 9H).

LC-MS: ESI 502.8 (M+H)+.

Example 104

Preparation of N-(4-{5-[3-(5-tert-butyl-2H-pyrazol-3-yl)-ureido]-pyridin-2-yloxy}-7-methoxy-quinolin-6-yl)-acetamide (Compound 104)

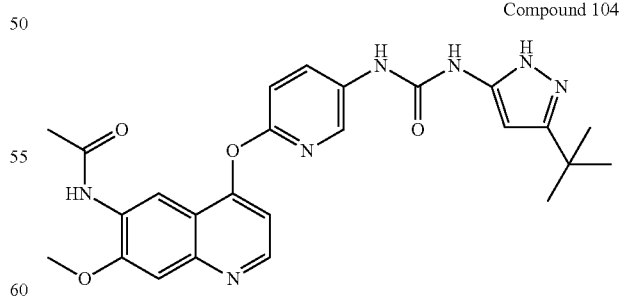

Compound 104

The preparation method was the same as Example 63, except that 5-amino-2-hydroxypyridine (purchased from Shanghai Darui) was used instead of 4-amino-3-chlorophenol hydrochloride in step 1 of Example 63 to give N-(4-{5-[3-(5-tert-butyl-2H-pyrazol-3-yl)-ureido]-pyridin-2-yloxy}-7-methoxy-quinolin-6-yl)-acetamide.

¹HNMR (DMSO-d6, 400 MHz) δ: 12.03 (s, 1H), 9.46 (s, 1H), 9.35 (br, 1H), 9.06 (s, 1H), 8.88 (s, 1H), 8.60-8.61 (d, 1H), 8.30-8.31 (d, 1H), 8.13-8.15 (dd, 1H), 7.48 (s, 1H), 7.26-7.28 (d, 1H), 6.78-6.80 (d, 1H), 6.01 (s, 1H), 4.04 (s, 3H), 2.17 (s, 3H), 1.26 (s, 9H).
LC-MS: ESI 490.2 (M+H)+.

Example 105

Preparation of N-(4-{4-[3-(5-tert-butyl-2H-pyrazol-3-yl)-ureido]-2-chloro-phenoxy}-7-methoxy-quinolin-6-yl)-acrylamide (Compound 105)

Compound 105

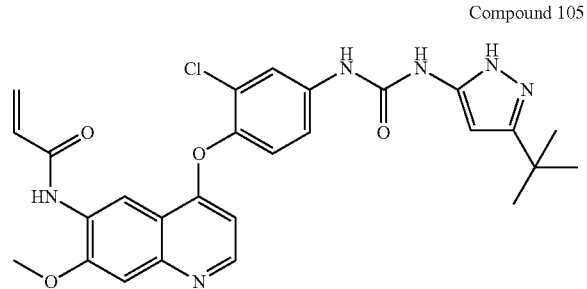 [SMILES: C=CC(=O)Nc1cc2c(Oc3ccc(NC(=O)Nc4cc(C(C)(C)C)n[nH]4)cc3Cl)ccnc2cc1OC]

The preparation method was the same as Example 63, except that 4-amino-2-chlorophenol (purchased from Shanghai Darui) was used instead of 4-amino-3-chlorophenol hydrochloride in step 1 of Example 63, and acryloyl chloride was used instead of acetyl chloride in step 4 of Example 63 to give N-(4-{4-[3-(5-tert-butyl-2H-pyrazol-3-yl)-ureido]-2-chloro-phenoxy}-7-methoxy-quinolin-6-yl)-acrylamide.
¹HNMR (DMSO-d6, 400 MHz) δ: 12.03 (s, 1H), 9.74 (s, 1H), 9.41 (br, 1H), 9.19 (s, 1H), 9.05 (s, 1H), 8.53-8.54 (d, 1H), 7.97 (m, 1H), 7.50 (s, H), 7.40 (m, 2H), 6.84-6.89 (m, 1H), 6.35-6.36 (d, 1H), 6.28-6.33 (m, 1H), 6.04 (s, 1H), 5.78-5.81 (m, 1H), 4.06 (s, 3H), 1.27 (s, 9H).
LC-MS: ESI 535.2 (M+H)+.

Example 106

Preparation of 4-{4-[3-(5-tert-butyl-2H-pyrazol-3-yl)-ureido]-2-ethyl-phenoxy}-7-methoxy-quinolin-6-carboxamide (Compound 106)

Compound 106

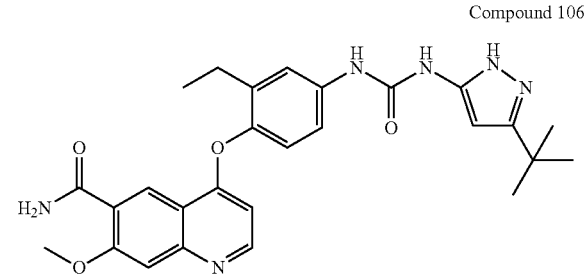 [SMILES: CCc1cc(NC(=O)Nc2cc(C(C)(C)C)n[nH]2)ccc1Oc1ccnc2cc(OC)c(C(N)=O)cc12]

The preparation method was the same as Example 25, except that 4-amino-2-ethylphenol (purchased from Shanghai Darui) was used instead of 4-amino-3-chlorophenol hydrochloride in step 1 of Example 25 to give {4-[3-(5-tert-butyl-2H-pyrazol-3-yl)-ureido]-2-ethyl-phenoxy}-7-methoxy-quinolin-6-carboxamide.
¹HNMR (DMSO-d6, 400 MHz) δ: 12.01 (s, 1H), 9.30 (br, 1H), 8.95 (s, 1H), 8.73 (s, 1H), 8.63-8.65 (d, 1H), 7.87 (s, 1H), 7.75 (s, 1H), 7.53-7.54 (d, 1H), 7.52 (s, H), 7.42-7.44 (dd, 1H), 7.13-7.15 (d, 1H), 6.36-6.37 (d, 1H), 6.01 (s, 1H), 4.04 (s, 3H), 2.44-2.52 (q, 2H), 1.27 (s, 9H), 1.08-1.12 (t, 3H).
LC-MS: ESI 503.2 (M+H)+.

Example 107

Preparation of 4-{4-[3-(5-tert-butyl-2H-pyrazol-3-yl)-ureido]-2-isopropyl-phenoxy}-7-methoxy-quinolin-6-carboxamide (Compound 107)

Compound 107

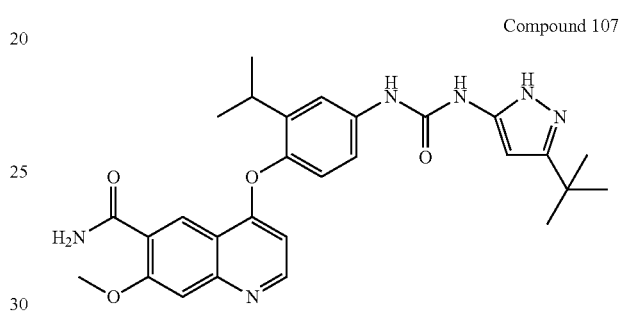

The preparation method was the same as Example 25, except that 4-amino-2-isopropyl phenol (purchased from Shanghai Darui) was used instead of 4-amino-3-chlorophenol hydrochloride in step 1 of Example 25 to give 4-{4-[3-(5-tert-butyl-2H-pyrazol-3-yl)-ureido]-2-isopropyl-phenoxy}-7-methoxy-quinolin-6-carboxamide.
¹HNMR (DMSO-d6, 400 MHz) δ: 12.01 (s, 1H), 9.35 (br, 1H), 8.94 (s, 1H), 8.74 (s, 1H), 8.63-8.65 (d, 1H), 7.88 (s, 1H), 7.76 (s, 1H), 7.58 (d, 1H), 7.53 (s, H), 7.42-7.44 (dd, 1H), 7.11-7.13 (d, 1H), 6.37-6.38 (d, 1H), 6.01 (s, 1H), 4.04 (s, 3H), 2.95-2.98 (m, 1H), 1.27 (s, 9H), 1.14-1.15 (d, 6H).
LC-MS: ESI 517.3 (M+H)+.

Example 108

Preparation of 4-{5-[3-(5-tert-butyl-2H-pyrazol-3-yl)-ureido]-pyridin-2-yloxy}-7-methoxy-quinolin-6-carboxamide (Compound 108)

Compound 108

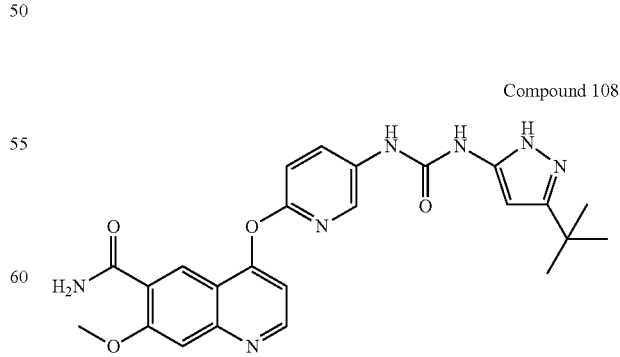

The preparation method was the same as Example 25, except that 5-amino-2-hydroxypyridine (purchased from Shanghai Darui) was used instead of 4-amino-3-chlorophenol hydrochloride in step 1 of Example 25 to give 4-{5-[3-(5-tert-butyl-2H-pyrazol-3-yl)-ureido]-pyridin-2-yloxy}-7-methoxy-quinolin-6-carboxamide.

¹HNMR (DMSO-d6, 400 MHz) δ: 12.03 (s, 1H), 9.40 (br, 1H), 9.08 (s, 1H), 8.75-8.76 (d, 1H), 8.56 (s, 1H), 8.34-8.35 (d, 1H), 8.15-8.18 (dd, 1H), 7.87 (s, 1H), 7.74 (s, 1H), 7.54 (s, 1H), 7.31-7.34 (d, 1H), 6.86-6.87 (d, 1H), 6.01 (s, 1H), 4.04 (s, 3H), 1.26 (s, 9H).

LC-MS: ESI 475.8 (M+H)+.

Example 109

Preparation of 4-{4-[3-(5-tert-butyl-2H-pyrazol-3-yl)-ureido]-2,3-dimethyl-phenoxy}-7-methoxy-quinolin-6-carboxamide (Compound 109)

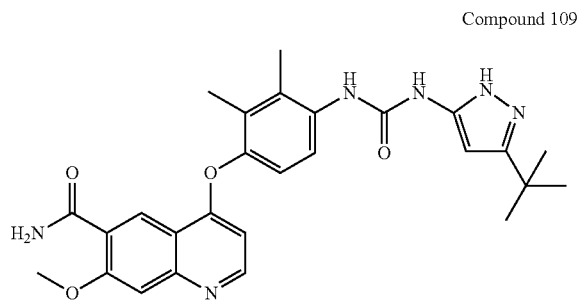 [SMILES: COc1cc2nccc(Oc3ccc(NC(=O)Nc4cc(C(C)(C)C)n[nH]4)c(C)c3C)c2cc1C(N)=O]

Compound 109

The preparation method was the same as Example 25, except that 4-amino-2,3-dimethylphenol (purchased from TCI) was used instead of 4-amino-3-chlorophenol hydrochloride in step 1 of Example 25 to give {4-[3-(5-tert-butyl-2H-pyrazol-3-yl)-ureido]-2,3-dimethyl-phenoxy}-7-methoxy-quinolin-6-carboxamide.

¹HNMR (DMSO-d6, 400 MHz) δ: 12.05 (s, 1H), 9.25 (s, 1H), 8.75 (s, 1H), 8.62-8.63 (d, 1H), 7.88 (m, 2H), 7.76 (s, 1H), 7.52 (s, 1H), 7.04-7.06 (d, 1H), 6.28-6.29 (d, 1H), 5.88 (br, 1H), 4.04 (s, 3H), 2.27 (s, 3H), 2.07 (s, 3H), 1.26 (s, 9H).

LC-MS: ESI 503.2 (M+H)+.

Example 110

Preparation of 4-{4-[3-(5-tert-butyl-2-methyl-2H-pyrazol-3-yl)-ureido]-2,3-dimethyl-phenoxy}-7-methoxy-quinolin-6-carboxamide (Compound 110)

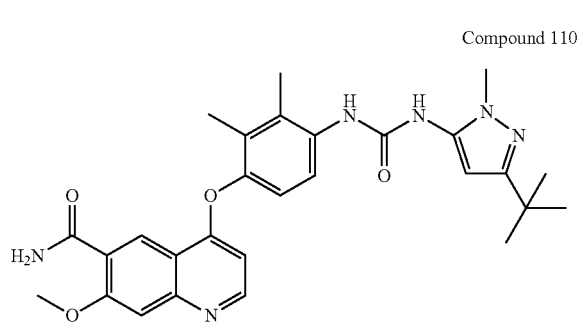 [SMILES: COc1cc2nccc(Oc3ccc(NC(=O)Nc4cc(C(C)(C)C)nn4C)c(C)c3C)c2cc1C(N)=O]

Compound 110

The preparation method was the same as Example 25, except that 4-amino-2,3-dimethylphenol (purchased from TCI) was used instead of 4-amino-3-chlorophenol hydrochloride in step 1 of Example 25, and 5-tert-butyl-2-methyl-2H-pyrazol-3-ylamine (prepared in Step 1 of Example 26) was used instead of 5-tert-butyl-2H-pyrazol-3-ylamine in step 3 of Example 25 to give 4-{4-[3-(5-tert-butyl-2-methyl-2H-pyrazol-3-yl)-ureido]-2,3-dimethyl-phenoxy}-7-methoxy-quinolin-6-carboxamide.

¹HNMR (DMSO-d6, 400 MHz) δ: 8.82 (s, 1H), 8.74 (s, 1H), 8.63-8.64 (d, 1H), 8.33 (s, 1H), 7.88 (s, 1H), 7.76 (s, 1H), 7.64-7.66 (d, 1H), 7.53 (s, 1H), 7.05-7.07 (d, 1H), 6.28-6.30 (d, 1H), 6.07 (s, 1H), 4.04 (s, 3H), 3.64 (s, 3H), 2.24 (s, 3H), 2.07 (s, 3H), 1.21 (s, 9H).

LC-MS: ESI 517.2 (M+H)+.

Example 111

Preparation of 4-{4-[3-(5-tert-butyl-2-methyl-2H-pyrazol-3-yl)-ureido]-3-chloro-2-methyl-phenoxy}-7-methoxy-carboxamide (Compound 111)

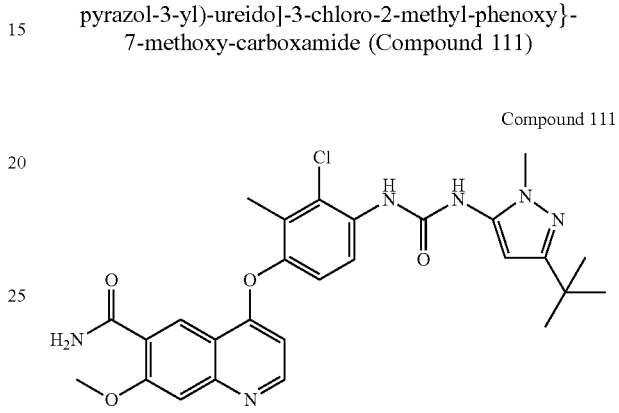

Compound 111

The preparation method was the same as Example 25, except that 4-amino-3-chloro-2-methylphenol (purchased from TCI) was used instead of 4-amino-3-chlorophenol hydrochloride in step 1 of Example 25, and 5-tert-butyl-2-methyl-2H-pyrazol-3-ylamine (prepared in Step 1 of Example 26) was used instead of 5-tert-butyl-2H-pyrazol-3-ylamine in step 3 of Example 25 to give 4-{4-[3-(5-tert-butyl-2-methyl-2H-pyrazol-3-yl)-ureido]-3-chloro-2-methyl-phenoxy}-7-methoxy-quinolin-6-carboxamide.

¹HNMR (DMSO-d6, 400 MHz) δ: 9.39 (s, 1H), 8.73 (s, 1H), 8.70 (s, 1H), 8.64-8.65 (d, 1H), 8.12-8.15 (d, 1H), 7.89 (s, 1H), 7.77 (s, 1H), 7.54 (s, 1H), 725-7.27 (d, 1H), 6.37-6.38 (d, 1H), 6.11 (s, 1H), 4.04 (s, 3H), 3.66 (s, 3H), 2.19 (s, 3H), 1.22 (s, 9H).

LC-MS: ESI 537.2 (M+H)+.

Example 112

Preparation of 4-{4-[3-(5-tert-butyl-2H-pyrazol-3-yl)-ureido]-3-chloro-2-methyl-phenoxy}-7-methoxy-quinolin-6-carboxamide (Compound 112)

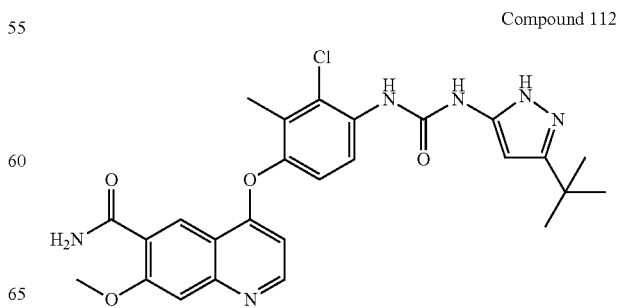

Compound 112

The preparation method was the same as Example 25, except that 4-amino-3-chloro-2-methylphenol (purchased from TCI) was used instead of 4-amino-3-chlorophenol hydrochloride in step 1 of Example 25 to give 4-{4-[3-(5-tert-butyl-2H-pyrazol-3-yl)-ureido]-3-chloro-2-methyl-phenoxy}-7-methoxy-quinolin-6-carboxamide.

¹HNMR (DMSO-d6, 400 MHz) δ: 12.11 (s, 1H), 9.61 (s, 1H), 8.73 (s, 1H), 8.65 (m, 1H), 8.29 (m, 1H), 7.89 (s, 1H), 7.77 (s, 1H), 7.54 (s, 1H), 7.25-7.26 (m, 1H), 6.38 (m, 1H), 5.88 (br, 1H), 4.05 (s, 3H), 2.19 (s, 3H), 1.27 (s, 9H).

LC-MS: ESI 523.1 (M+H)+.

Example 113

Preparation of 1-(5-tert-butyl-isoxazol-3-yl)-3-[2-chloro-4-(8-fluoro-quinolin-4-yloxy)-phenyl]-urea (Compound 113)

Compound 113

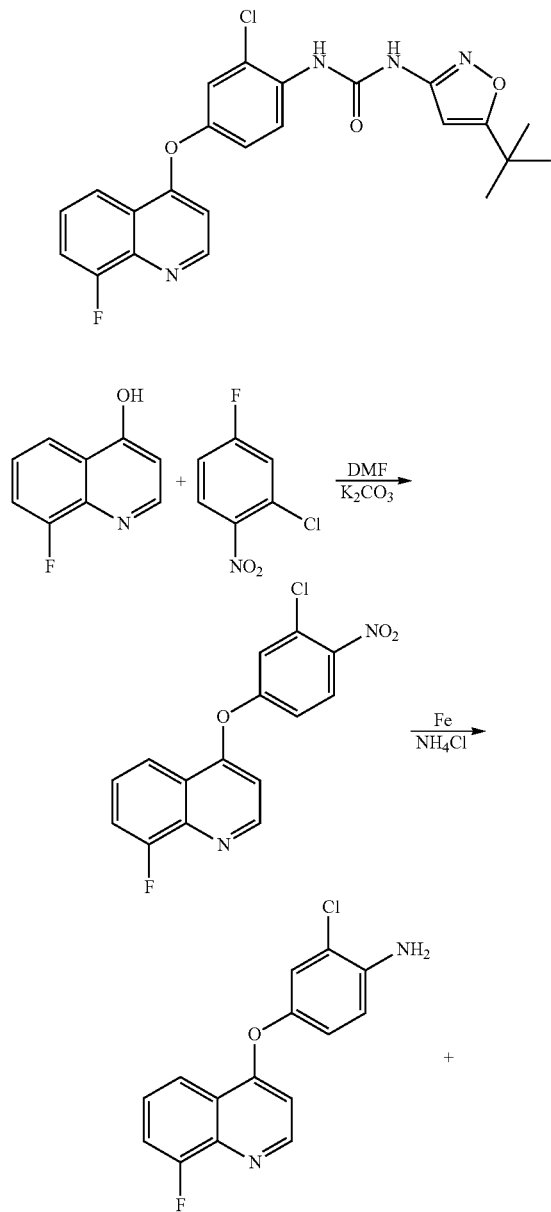

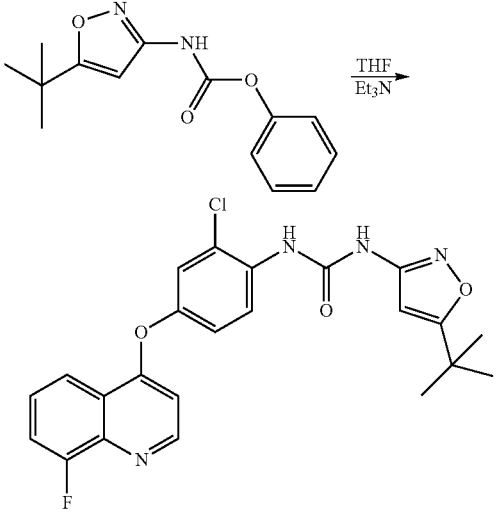

Step 1: Preparation of 4-(3-chloro-4-nitro-phenoxy)-8-fluoro-quinoline

4-Hydroxy-8-fluoroquinoline (purchased from TCI) (500 mg, 3.06 mmol), 2-chloro-4-fluoronitrobenzene (purchased from Shanghai Darui) (592 mg, 3.37 mmol) and potassium carbonate (1.27 g, 9.20 mmol) were added to 6 ml of DMF and heated to 90° C. for 1 hour. The reaction solution was cooled to room temperature, and poured into water, and then extracted with ethyl acetate (40 ml×2). The organic phase was washed twice with saturated NaCl solution, dried over anhydrous sodium sulfate, and filtered. The filtrate was concentrated under reduced pressure to give 890 mg of 4-(3-chloro-4-nitro-phenoxy)-8-fluoro-quinoline as a yellow solid.

Step 2: Preparation of 2-chloro-4-(8-fluoro-quinolin-4-yloxy)-aniline 4-(3-Chloro-4-nitro-phenoxy)-8-fluoro-quinoline obtained in Step 1 (890 mg, 2.79 mmol), reduced iron powder (625 mg, 11.17 mmol) and ammonium chloride (1.04 g, 19.53 mmol) were added to a mixture of ethanol (16 ml) and water (4 ml), and then heated to 80° C. for 1 h. The reaction solution was cooled to room temperature, and poured into saturated aqueous solution of sodium bicarbonate (100 ml), and then extracted with ethyl acetate (50 ml×2). The organic phase was washed twice with saturated NaCl solution, dried over anhydrous sodium sulfate, and filtered. The filtrate was concentrated under reduced pressure and the residues were purified by column chromatography (eluent: dichloromethane/methanol) to give 460 mg of 2-chloro-4-(8-fluoro-quinolin-4-yloxy)-aniline as a yellow solid.

Step 3: Preparation of 1-(5-tert-butyl-isoxazol-3-yl)-3-[2-chloro-4-(8-fluoro-quinolin-4-yloxy)-phenyl]-urea 2-Chloro-4-(8-fluoro-quinolin-4-yloxy)-aniline obtained in Step 2 (200 mg, 0.693 mmol), phenyl (5-tert-butyl-isoxazol-3-yl)-carbamate (prepared in Step 2 of Example 1) (360 mg, 1.386 mmol) and triethylamine (280 mg, 2.772 mmol) were dissolved in 10 ml of THF and refluxed overnight. The next day, the reaction solution was concentrated under reduced pressure, and the residues were purified by column chromatography (eluent: dichloromethane/methanol) to give 130 mg of 1-(5-tert-butyl-isoxazol-3-yl)-3-[2-chloro-4-(8-fluoro-quinolin-4-yloxy)-phenyl]-urea, as a white solid.

¹HNMR (DMSO-d6, 400 MHz) δ: 10.25 (s, 1H), 8.80 (s, 1H), 8.75-8.77 (d, 1H), 8.28-8.30 (d, 1H), 8.11-8.13 (m, 1H), 7.64-7.69 (m, 2H), 7.61 (d, 1H), 7.32-7.35 (dd, 1H), 6.79-6.80 (d, 1H), 6.47 (s, 1H), 1.31 (s, 9H).

LC-MS: ESI 455.1 (M+H)+.

Example 114

Preparation of 1-(5-tert-butyl-isoxazol-3-yl)-3-[2-chloro-4-(8-trifluoromethyl-quinolin-4-yloxy)-phenyl]-urea (Compound 114)

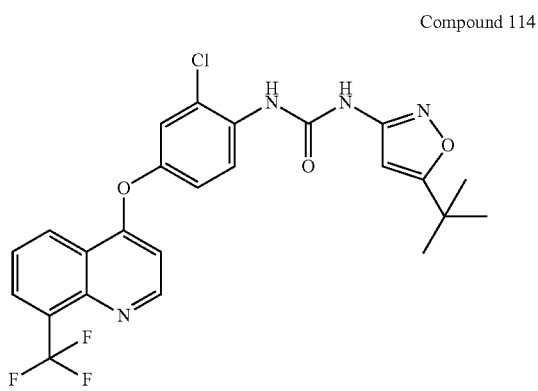 [SMILES: CC(C)(C)c1cc(NC(=O)Nc2ccc(Oc3ccnc4c(C(F)(F)F)cccc34)cc2Cl)no1]

Compound 114

The preparation method was the same as Example 113, except that 4-hydroxy-8-trifluoromethylquinoline (purchased from TCI) was used instead of 4-hydroxy-8-fluoroquinoline in step 1 of Example 113 to give 1-(5-tert-butyl-isoxazol-3-yl)-3-[2-chloro-4-(8-trifluoromethyl-quinolin-4-yloxy)-phenyl]-urea.

¹HNMR (DMSO-d6, 400 MHz) δ: 10.28 (s, 1H), 8.83-8.86 (m, 2H), 8.62-8.64 (d, 1H), 8.27-8.30 (m, 2H), 7.79-7.83 (m, 1H), 7.63 (d, 1H), 7.34-7.37 (dd, 1H), 6.84-6.86 (d, 1H), 6.48 (s, 1H), 1.31 (s, 9H).

LC-MS: ESI 505.1 (M+H)+.

Example 115

Preparation of 1-(5-tert-butyl-isoxazol-3-yl)-3-[2-chloro-4-(2-trifluoromethyl-quinolin-4-yloxy)-phenyl]-urea (Compound 115)

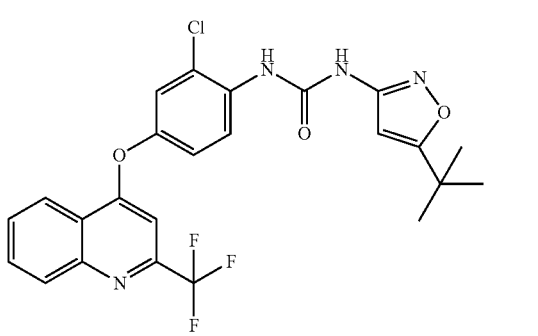

Compound 115

The preparation method was the same as Example 113, except that 4-hydroxy-2-trifluoromethylquinoline (purchased from TCI) was used instead of 4-hydroxy-8-fluoroquinoline in step 1 of Example 113 to give 1-(5-tert-butyl-isoxazol-3-yl)-3-[2-chloro-4-(2-trifluoromethyl-quinolin-4-yloxy)-phenyl]-urea.

¹HNMR (DMSO-d6, 400 MHz) δ: 10.28 (s, 1H), 8.82 (s, 1H), 8.42-8.44 (d, 1H), 8.30-8.32 (d, 1H), 8.20-8.22 (d, 1H), 7.99-8.04 (m, 1H), 7.85-7.89 (m, 1H), 7.70-7.71 (d, 1H), 7.39-7.42 (dd, 1H), 6.53 (s, 1H), 6.48 (s, 1H), 1.31 (s, 9H).

LC-MS: ESI 505.0 (M+H)+.

Example 116

Preparation of N-[4-{4-[3-(5-tert-butyl-2H-pyrazol-3-yl)-ureido]-phenoxy}-7-(2-methoxy-ethoxy)-quinolin-6-yl]-acetamide (Compound 116)

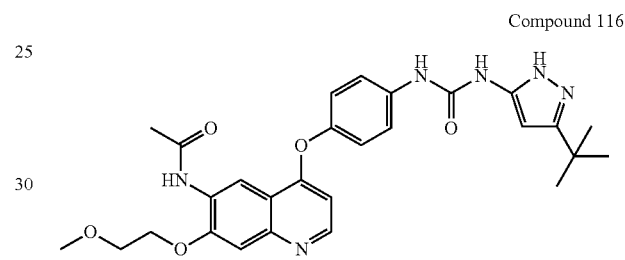

Compound 116

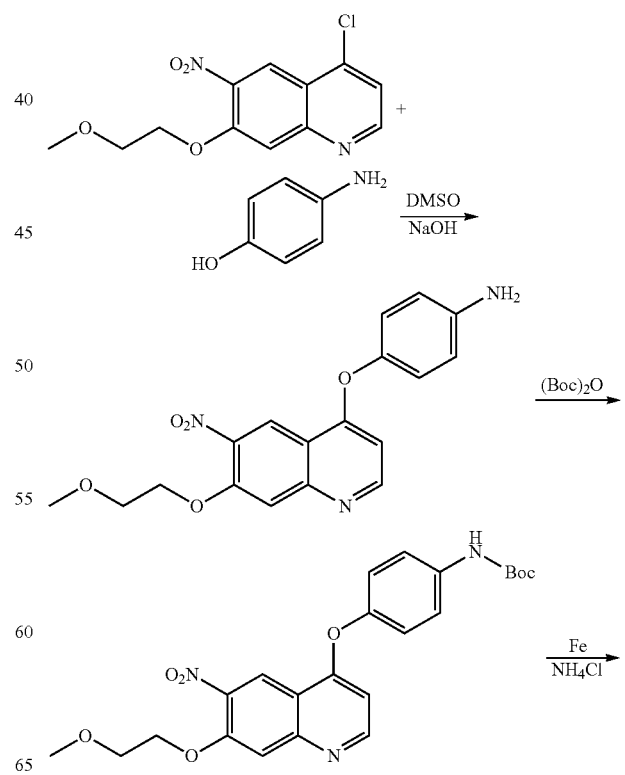

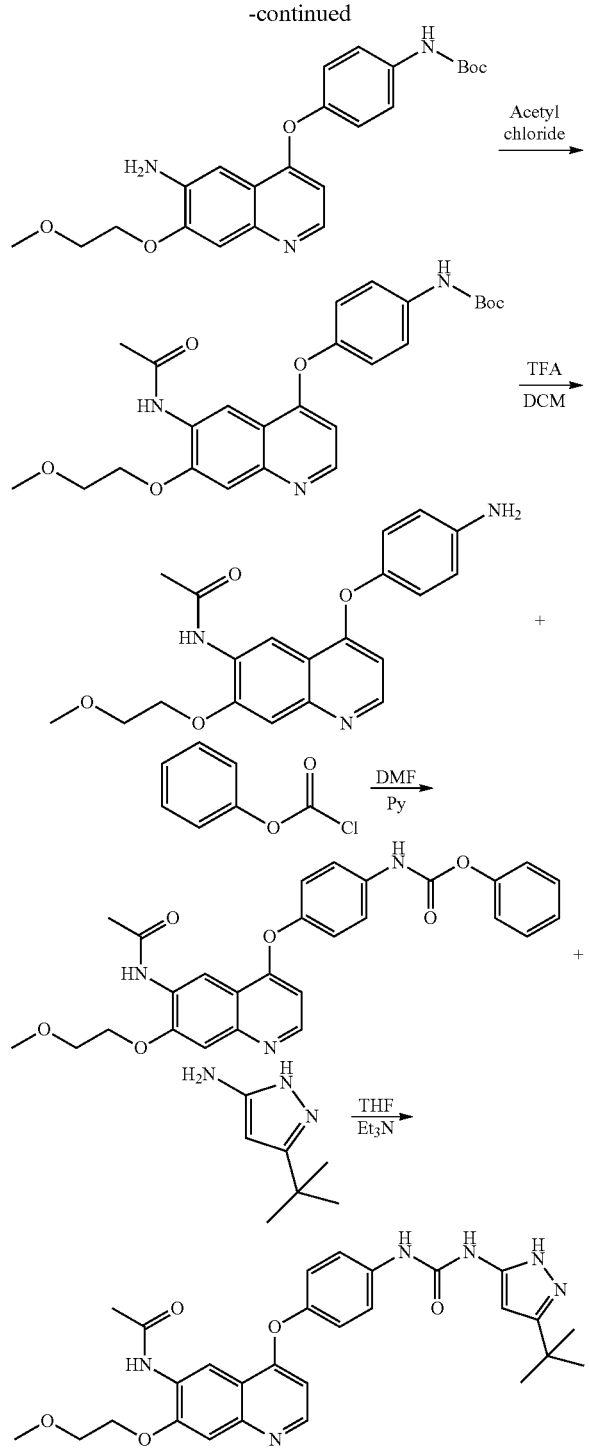

Step 1: Preparation of 4-[7-(2-methoxy-ethoxy)-6-nitro-quinolin-4-yloxy]-aniline 4-Aminophenol (774 mg, 7.1 mmol) was dissolved in 30 ml of DMSO at room temperature and added with sodium hydroxide (284 mg, 7.1 mmol). The mixture was stirred at room temperature for 0.5 hour, and added with 4-chloro-7-(2-methoxy-ethoxy)-6-nitro-quinoline (prepared in Step 2 of Example 66) (1 g, 3.55 mmol). The mixture was heated to 100° C. for 1 hour. The reaction solution was cooled to room temperature, and poured into 100 ml of water, and then extracted with ethyl acetate (80 ml×2). The organic phase was washed with saturated NaCl solution, dried over anhydrous sodium sulfate, and filtered. The filtrate was concentrated under reduced pressure, and the residues were purified via column chromatography (eluent: dichloromethane/methanol) to give 1.10 g of 4-[7-(2-methoxy-ethoxy)-6-nitro-quinolin-4-yloxy]-aniline as a solid.

Step 2: Preparation of tert-butyl {4-[7-(2-methoxy-ethoxy)-6-nitro-quinolin-4-yloxy]-phenyl}-carbamate 4-[7-(2-Methoxy-ethoxy)-6-nitro-quinolin-4-yloxy]-aniline (1.1 g, 3.09 mmol) di-tert-butyl decarbonate (6.2 g, 28.4 mmol) and DMAP (22 mg, 0.175 mmol) were dissolved in 40 ml of THF at room temperature, and added with potassium carbonate (980 mg, 7.10 mmol). The reaction mixture was stirred at room temperature for 1 hour. The reaction solution was poured slowly into 100 ml of water, and extracted with ethyl acetate (60 ml×2). The organic phase was washed with saturated NaCl solution, dried over anhydrous sodium sulfate, and filtered. The filtrate was concentrated under reduced pressure and the residues were purified via column chromatography (eluent: dichloromethane/methanol) to give 770 mg of tert-butyl {4-[7-(2-methoxy-ethoxy)-6-nitro-quinolin-4-yloxy]-phenyl}-carbamate as a solid.

Step 3: Preparation of tert-butyl {4-[6-amino-7-(2-methoxy-ethoxy)-quinolin-4-yloxy]-phenyl}-carbamate Tert-butyl {4-[7-(2-methoxy-ethoxy)-6-nitro-quinolin-4-yloxy]-phenyl}-carbamate obtained in step 2 (770 mg, 1.69 mmol), reduced iron powder (421 mg, 7.5 mmol) and ammonium chloride (704 mg, 13.4 mmol) were added to the mixture of ethanol (30 ml) and water (10 ml), and heated to reflux for 1 hour. The reaction solution was cooled to room temperature, and poured into 100 ml of saturated aqueous solution of sodium bicarbonate, and extracted with ethyl acetate (80 ml×2). The organic phase was washed with saturated NaCl solution, dried over anhydrous sodium sulfate, and filtered. The filtrate was concentrated under reduced pressure to give 500 mg of tert-butyl {4-[6-amino-7-(2-methoxy-ethoxy)-quinolin-4-yloxy]-phenyl}-carbamate.

Step 4: Preparation of tert-butyl {4-[6-acetylamino-7-(2-methoxy-ethoxy)-quinolin-4-yloxy]-phenyl}-carbamate Tert-butyl {4-[6-amino-7-(2-methoxy-ethoxy)-quinolin-4-yloxy]-phenyl}-carbamate (500 mg, 1.18 mmol) obtained in Step 3 and N,N-diisopropylethylamine (252 mg, 1.95 mmol) were dissolved in 30 ml of THF and added with potassium carbonate (90 ml, 0.65 mmol) at room temperature. The mixture was added with acetyl chloride (122 mg, 1.56 mmol) (diluted with 2 ml of THF) dropwise under ice bath, and the mixture was warmed to room temperature and stirred for 0.5 hour. The reaction solution was poured slowly into water, and extracted with ethyl acetate (50 ml×2). The organic phase was washed with saturated NaCl solution, dried over anhydrous sodium sulfate, and filtered. The filtrate was concentrated under reduced pressure and the residues were purified via column chromatography (eluent: dichloromethane/methanol) to give 380 mg of tert-butyl {4-[6-acetylamino-7-(2-methoxy-ethoxy)-quinolin-4-yloxy]-phenyl}-carbamate as a solid.

Step 5: Preparation of N-[4-(4-amino-phenoxy)-7-(2-methoxy-ethoxy)-quinolin-6-yl]-acetamide Tert-butyl {4-[6-acetylamino-7-(2-methoxy-ethoxy)-quinolin-4-yloxy]-phenyl}-carbamate obtained in Step 4 (380 mg, 0.813 mmol) was dissolved in 5 ml of dichloromethane, and added with trifluoroacetic acid (2 ml) dropwise at room temperature. The mixture was stirred at room temperature for 1 hour. The reaction solution was poured slowly into 100 ml of saturated aqueous solution of sodium bicarbonate, and extracted with ethyl acetate (50 ml×2). The organic phase was washed with saturated NaCl solution, dried over anhydrous sodium sulfate, and filtered. The filtrate was concentrated under reduced pressure to give 140 mg of N-[4-(4-amino-phenoxy)-7-(2-methoxy-ethoxy)-quinolin-6-yl]-acetamide, which was used directly in the next step without purification.

Step 6: Preparation of phenyl {4-[6-acetylamino-7-(2-methoxy-ethoxy)-quinolin-4-yloxy]-phenyl}-carbamate N-[4-(4-Amino-phenoxy)-7-(2-methoxy-ethoxy)-quinolin-6-yl]-acetamide obtained in Step 5 (140 mg, 0.381 mmol) and pyridine (102 mg, 1.29 mmol) were dissolved in 10 ml of DMF. The mixture was cooled to 0-5° C. in an ice bath, and added with phenyl chloroformate (101 mg, 0.65 mmol) dropwise. The reaction mixture was stirred at room temperature for 1 hour. The reaction solution was poured slowly into water, and extracted with ethyl acetate (50 ml×2). The organic phase was washed with saturated NaCl solution, dried over anhydrous sodium sulfate, and filtered. The filtrate was concentrated under reduced pressure and the residues were purified via column chromatography (eluent: dichloromethane/methanol) to give 130 mg of phenyl {4-[6-acetylamino-7-(2-methoxy-ethoxy)-quinolin-4-yloxy]-phenyl}-carbamate as a solid.

Step 7: Preparation of N-[4-{4-[3-(5-tert-butyl-2H-pyrazol-3-yl)-ureido]-phenoxy}-7-(2-methoxy-ethoxy)-quinolin-6-yl]-acetamide Phenyl {4-[6-acetylamino-7-(2-methoxy-ethoxy)-quinolin-4-yloxy]-phenyl}-carbamate obtained in Step 6 (130 mg, 0.27 mmol), 5-tert-butyl-2H-pyrazol-3-ylamine (purchased from TCI) (61 mg, 0.438 mmol) and triethylamine (89 mg, 0.876 mmol) were dissolved in 10 ml of THF and stirred at 70° C. overnight. The next day, the reaction solution was cooled to room temperature, and then concentrated under reduced pressure. The residues were purified by column chromatography (eluent: dichloromethane/methanol) to give 20 mg of N-[4-{4-[3-(5-tert-butyl-2H-pyrazol-3-yl)-ureido]-phenoxy}-7-(2-methoxy-ethoxy)-quinolin-6-yl]-acetamide as a solid.

$^1$HNMR (DMSO-d$_6$, 400 MHz) δ: 12.01 (br, 1H), 9.29 (br, 1H), 9.28 (s, 1H), 9.00 (s, 1H), 8.97 (s, 1H), 8.51-8.53 (d, 1H), 7.58-7.60 (d, 2H), 7.50 (s, 1H), 7.20-7.22 (d, 2H), 6.44-6.45 (d, 1H), 6.00 (s, 1H), 4.38-4.40 (t, 2H), 3.83-3.86 (t, 2H), 3.38 (s, 3H), 2.20 (s, 3H), 1.26 (s, 9H).

LC-MS: ESI 533.2 (M+H)$^+$.

Example 117

Preparation of N-[4-{4-[3-(5-tert-butyl-2-methyl-2H-pyrazol-3-yl)-ureido]-phenoxy}-7-(2-methoxy-ethoxy)-quinolin-6-yl]-acetamide (Compound 117)

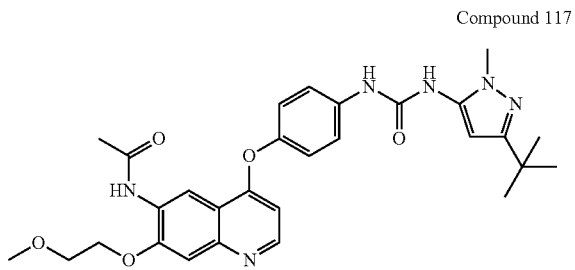 [SMILES: COCCOc1cc2nccc(Oc3ccc(NC(=O)Nc4cc(C(C)(C)C)nn4C)cc3)c2cc1NC(C)=O]

Compound 117

The preparation method was the same as Example 116, except that 5-tert-butyl-2-methyl-2H-pyrazol-3-ylamine was used instead of 5-tert-butyl-2H-pyrazol-3-ylamine in step 7 to give N-[4-{4-[3-(5-tert-butyl-2-methyl-2H-pyrazol-3-yl)-ureido]-phenoxy}-7-(2-methoxy-ethoxy)-quinolin-6-yl]-acetamide.

$^1$HNMR (DMSO-d$_6$, 400 MHz) δ: 9.27 (s, 1H), 9.07 (s, 1H), 8.99 (s, 1H), 8.75 (s, 1H), 8.56 (s, 1H), 8.51-8.52 (d, 1H), 7.58-7.60 (d, 2H), 7.50 (s, 1H), 7.20-7.22 (d, 2H), 6.43-6.44 (d, 1H), 6.07 (s, 1H), 4.37-4.39 (t, 2H), 3.83-3.85 (t, 2H), 3.62 (s, 3H), 3.38 (s, 3H), 2.20 (s, 3H), 1.22 (s, 9H).

LC-MS: ESI 547.2 (M+H)$^+$.

Example 118

Preparation of N-[4-{4-[3-(5-tert-butyl-2-cyclopropylmethyl-2H-pyrazol-3-yl)-ureido]-phenoxy}-7-(2-methoxy-ethoxy)-quinolin-6-yl]-acetamide (Compound 118)

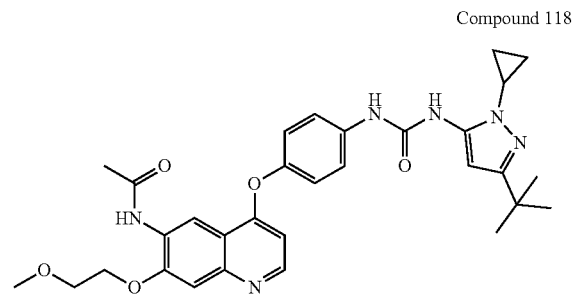 [SMILES: COCCOc1cc2nccc(Oc3ccc(NC(=O)Nc4cc(C(C)(C)C)nn4C4CC4)cc3)c2cc1NC(C)=O]

Compound 118

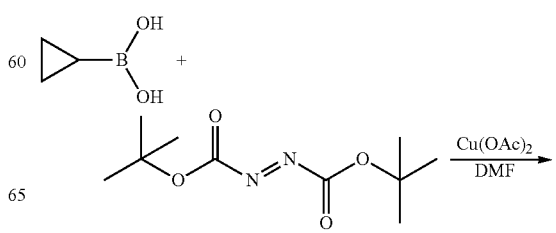

157

-continued

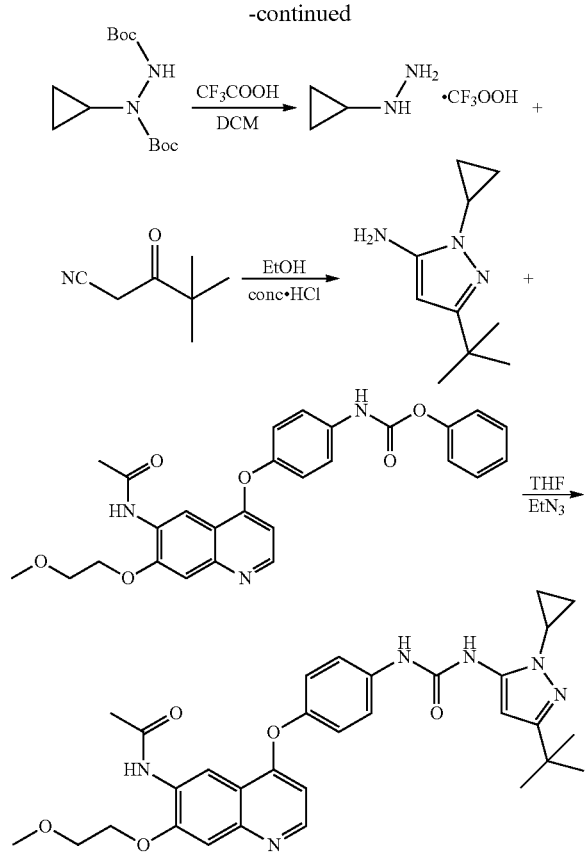

Step 1: Preparation of tert-butyl 1-cyclopropyl hydrazino-1,2-dicarboxylate

Cyclopropylboronic acid (3 g, 0.035 mol) and di-tert-butyl azodicarboxylate (4 g, 0.0175 mol) were dissolved in 40 ml of DMF at room temperature under nitrogen atmosphere, and added with copper acetate (315 mg, 1.75 mmol). The reaction mixture was heated to 90° C. for 12 hours, and then cooled to room temperature. The reaction mixture was poured slowly into 120 ml of water, and extracted with ethyl acetate (60 ml×2). The organic phase was washed with saturated NaCl solution, dried over anhydrous sodium sulfate, and filtered. The filtrate was concentrated under reduced pressure and the residues were purified via column chromatography (eluent: petroleum ether/ethyl acetate) to give 3.3 g of tert-butyl 1-cyclopropyl hydrazino-1,2-dicarboxylate as a solid.

Step 2: Preparation of cyclopropyl hydrazine trifluoroacetate

Tert-butyl 1-cyclopropyl hydrazino-1,2-dicarboxylate obtained in Step 1 (3.3 g, 0.012 mol) was dissolved in 20 ml of dichloromethane at room temperature, and added with 10 ml of trifluoroacetic acid. The reaction mixture was stirred at room temperature for 16 hours. The reaction was completed by TLC monitoring, and then concentrated under reduced pressure to give cyclopropyl hydrazine trifluoroacetate as an oil.

Step 3: Preparation of 5-tert-butyl-2-cyclopropyl-2H-pyrazol-3-ylamine

Cyclopropyl hydrazine trifluoroacetate obtained in step 2 (0.0121 mol) and pivaloylacetonitrile (1.53 g, 0.0121 mol)

158 were dissolved in 50 ml of ethanol at room temperature, and added with 5 drops of concentrated hydrochloric acid. The reaction mixture was heated to 90° C. for 12 hours. The reaction was completed by TLC monitoring, and then cooled to room temperature. The reaction mixture was poured into 150 ml of saturated aqueous solution of sodium bicarbonate, and extracted with ethyl acetate (60 ml×2). The organic phase was washed with saturated NaCl solution, dried over anhydrous sodium sulfate, and filtered. The filtrate was concentrated under reduced pressure and the residues were purified via column chromatography (eluent: petroleum ether/ethyl acetate) to give 1 g of 5-tert-butyl-2-cyclopropyl-2H-pyrazol-3-ylamine as a solid.

Step 4: Preparation of N-[4-{4-[3-(5-tert-butyl-2-cyclopropylmethyl-2H-pyrazol-3-yl)-ureido]-phenoxy}-7-(2-methoxy-ethoxy)-quinolin-6-yl]-acetamide The preparation method was the same as Step 7 of Example 116, except that 5-tert-butyl-2-cyclopropyl-2H-pyrazol-3-ylamine was used instead of 5-tert-butyl-2H-pyrazol-3-ylamine in step 7 of Example 116 to give N-[4-{4-[3-(5-tert-butyl-2-cyclopropylmethyl-2H-pyrazol-3-yl)-ureido]-phenoxy}-7-(2-methoxy-ethoxy)-quinolin-6-yl]-acetamide.

$^1$HNMR (DMSO-$d_6$, 400 MHz) δ: 9.32 (s, 1H), 9.26 (s, 1H), 8.99 (s, 1H), 8.51-8.53 (m, 2H), 7.60-7.62 (d, 2H), 7.50 (s, 1H), 7.20-7.23 (d, 2H), 6.44-6.45 (d, 1H), 6.12 (s, 1H), 4.38-4.40 (t, 2H), 3.83-3.86 (t, 2H), 3.38 (s, 3H), 2.20 (s, 3H), 2.00 (m, 1H), 1.00-1.01 (d, 4H), 1.20 (s, 9H).

LC-MS: ESI 573.2 (M+H)$^+$.

Example 119

Preparation of N-[4-(4-{3-[5-tert-butyl-2-(2-dimethylamino-ethyl)-2H-pyrazol-3-yl]-ureido}-phenoxy)-7-(2-methoxyethoxy)-quinolin-6-yl]-acetamide (Compound 119)

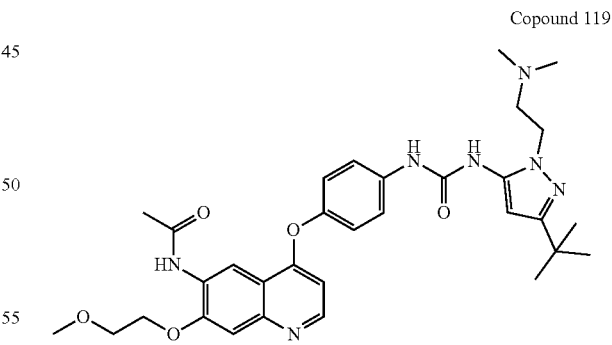

Copound 119

The preparation method was the same as Example 122, except that 2-dimethylaminoethyl chloride hydrochloride was used instead of N-(2-chloroethyl)-morpholine hydrochloride in step 1 of Example 122 to give N-[4-(4-{3-[5-tert-butyl-2-(2-dimethylamino-ethyl)-2H-pyrazol-3-yl]-ureido}-phenoxy)-7-(2-methoxyethoxy)-quinolin-6-yl]-acetamide $^1$HNMR (DMSO-$d_6$, 400 MHz) δ: 9.46 (s, 1H), 9.27 (s, 1H), 9.07 (s, 1H), 8.99 (s, 1H), 8.51-8.52 (d, 1H), 7.59-7.61 (d, 2H), 7.51 (s, 1H), 7.20-7.22 (d, 2H), 6.43-6.44 (d, 1H), 6.08 (s, 1H), 4.39 (m, 2H), 4.03-4.06 (t, 2H), 3.85 (m, 2H), 3.38 (s, 3H), 2.60-2.63 (t, 2H), 2.20 (s, 6H), 2.18 (s, 3H), 1.22 (s, 9H).
LC-MS: ESI 621.3 (M+H)+.

Example 120

Preparation of N-[4-{4-[3-(5-tert-butyl-2-piperidin-4-yl-2H-pyrazol-3-yl)-ureido]-phenoxy}-7-(2-methoxy-ethoxy)-quinolin-6-yl]-acetamide (Compound 120)

Compound 120

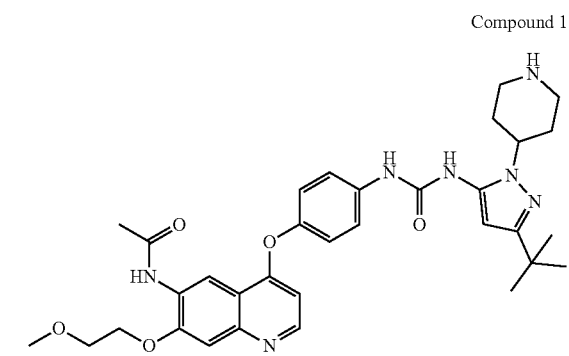

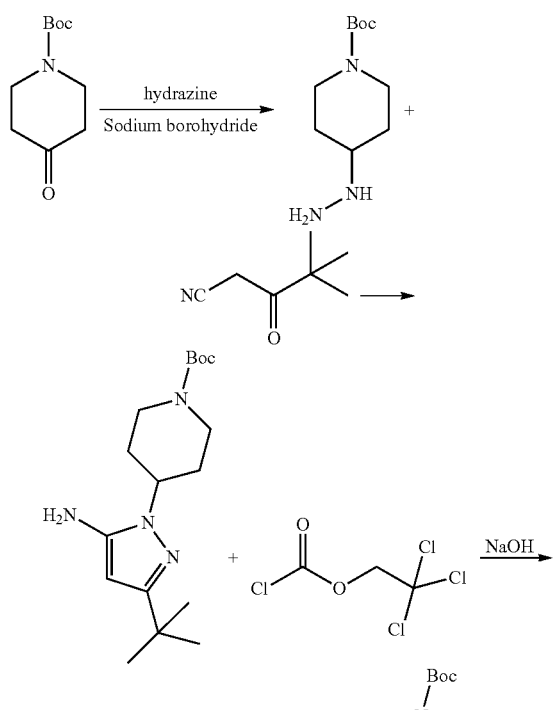

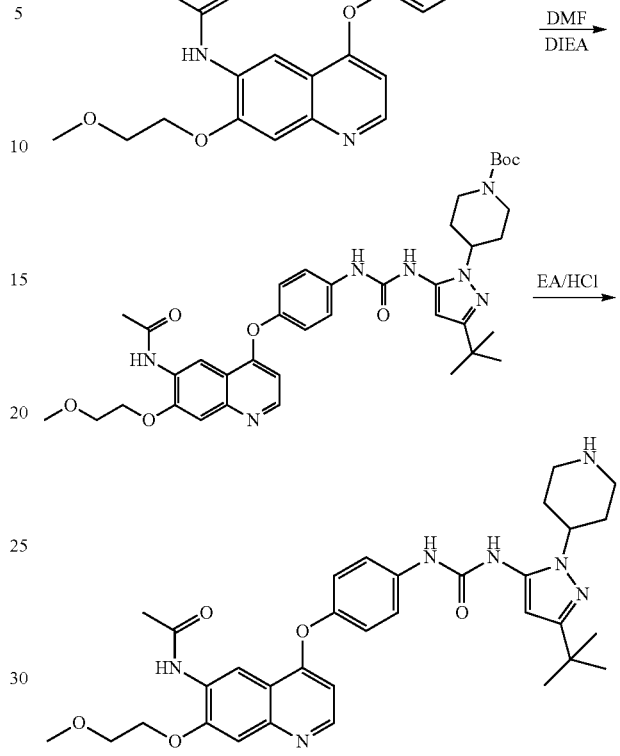

Step 1: Preparation of tert-butyl 4-hydrazino-piperidin-1-carboxylate

1-Boc-4-piperidone (20 g, 0.1 mol) was dissolved in methanol (200 ml), and added with hydrazine hydrate (5.28 g, 0.105 mmol) at room temperature. The reaction mixture was heated to 65° C. for 2 hours. The mixture was cooled to room temperature, and added with sodium borohydride (10 g, 0.264 mol) slowly and then 1 ml of acetic acid dropwise. The mixture was heated to 60° C. for 12 hours. After the reaction is completed by TLC monitoring, the reaction solution was concentrated and added with 100 ml of water, and then extracted with ethyl acetate (100 ml×3). The organic phase was washed with saturated NaCl solution, dried over anhydrous sodium sulfate, and filtered. The filtrate was concentrated under reduced pressure to give 11.2 g of 4-hydrazino-piperidine-1-carboxylate as a oil.

Step 2: Preparation of tert-butyl 4-(5-amino-3-tert-butyl-pyrazol-1-yl)-piperidin-1-carboxylate Tert-butyl 4-hydrazino-piperidin-1-carboxylate (11.2 g, 0.052 mmol) obtained in step 1 and pivaloylacetonitrile (purchased from TCI) (11.68 g, 0.063 mol) were dissolved in 150 ml of ethanol, and added with 1.3 g of concentrated hydrochloric acid at room temperature. The mixture was heated to 90° C. for 8 hours. After the reaction is completed by TLC monitoring, the reaction solution was cooled to 0 to 5° C. The solid resulted was filter out and the filtrate was concentrated under reduced pressure. The residues were purified via column chromatography (eluent: dichloromethane/methanol) to give 3 g of tert-butyl 4-(5-amino-3-tert-butyl-pyrazol-1-yl)-piperidin-1-carboxylate as a solid.

Step 3: Preparation of tert-butyl 4-[3-tert-butyl-5-(2,2,2-trichloro-ethoxycarbonylamino)-pyrazol-1-yl]-piperidine-1-carboxylate Tert-butyl 4-(5-amino-3-tert-butyl-pyrazol-1-yl)-piperidin-1-carboxylate (210 mg, 0.652 mmol) obtained in step 2 was dissolved in 3 ml of ethyl acetate, and added with sodium hydroxide (65 mg, 1.63 mmol, dissolved in 2 ml of water) at room temperature. The mixture was added with 2,2,2-trichloroethyl chloroformate (207 mg, 0.978 mmol) dropwise, and then stirred at room temperature for 30 minutes. After the reaction is completed by TLC monitoring, the reaction solution was poured into 50 ml of water, and extracted with ethyl acetate (50 ml×3). The organic phase was washed with saturated NaCl solution, dried over anhydrous sodium sulfate, and filtered. The filtrate was concentrated under reduced pressure to give 350 mg of tert-butyl 4-[3-tert-butyl-5-(2,2,2-trichloro-ethoxycarbonylamino)-pyrazol-1-yl]-piperidin-1-carboxylate.

Step 4: Preparation of tert-butyl 4-[5-(3-{4-[6-acetylamino-7-(2-methoxy-ethoxy)-quinolin-4-yloxy]-phenyl}-ureido)-3-tert-butyl-pyrazol-1-yl]-piperidin-1-carboxylate Tert-butyl 4-[3-tert-butyl-5-(2,2,2-trichloro-ethoxycarbonylamino)-pyrazol-1-yl]-piperidin-1-carboxylate (277 mg, 0.557 mmol) obtained in step 3, N-[4-(4-amino-phenoxy)-7-(2-methoxy-ethoxy)-quinolin-6-yl]-acetamide (prepared in Step 5 of Example 116) (170 mg, 0.464 mmol) and N,N-diisopropylethylamine (75 mg, 0.581 mmol) were dissolved in 8 ml of DMF. The mixture was heated to 100° C. for 2 hours. After the reaction is completed by TLC monitoring, the reaction solution was cooled to room temperature, and poured into 50 ml of water, and then extracted with ethyl acetate (50 ml×3). The organic phase was washed with saturated NaCl solution, dried over anhydrous sodium sulfate, and filtered. The filtrate was concentrated under reduced pressure, and the residues were purified via column chromatography (eluent: dichloromethane/methanol) to give 100 mg of tert-butyl 4-[5-(3-{4-[6-acetylamino-7-(2-methoxy-ethoxy)-quinolin-4-yloxy]-phenyl}-ureido)-3-tert-butyl-pyrazol-1-yl]-piperidin-1-carboxylate as a solid.

Step 5: Preparation of N-[4-{4-[3-(5-tert-butyl-2-piperidin-4-yl-2H-pyrazol-3-yl)-ureido]-phenoxy}-7-(2-methoxy-ethoxy)-quinolin-6-yl]-acetamide Tert-butyl 4-[5-(3-{4-[6-acetylamino-7-(2-methoxy-ethoxy)-quinolin-4-yloxy]-phenyl}-ureido)-3-tert-butyl-pyrazol-1-yl]-piperidin-1-carboxylate (100 mg, 0.14 mmol) obtained in step 4 was dissolved in 5 ml of ethyl acetate, and added with ethyl acetate/hydrochloric acid (3 ml, 2 mol/L) at room temperature. The reaction mixture was stirred at room temperature for 1 hour. After the reaction is completed by TLC monitoring, the reaction solution was filtered, and the resulting solid was washed with a small amount of ethyl acetate and dissolved in 20 ml of water. 20 ml of saturated sodium bicarbonate solution was added, and extracted with ethyl acetate (50 ml×3). The organic phase was washed with saturated NaCl solution, dried over anhydrous sodium sulfate, and filtered. the filtrate was concentrated under reduced pressure to give 70 mg of N-[4-{4-[3-(5-tert-butyl-2-piperidin-4-yl-2H-pyrazol-3-yl)-ureido]-phenoxy}-7-(2-methoxy-ethoxy)-quinolin-6-yl]-acetamide as a solid.

¹HNMR (DMSO-d₆, 400 MHz) δ: 9.52 (s, 1H), 9.27 (s, 1H), 8.99 (s, 1H), 8.95 (s, 1H), 8.51-8.52 (d, 1H), 7.59-7.61 (d, 2H), 7.50 (s, 1H), 7.20-7.22 (d, 2H), 6.42-6.43 (d, 1H), 6.07 (s, 1H), 4.33-4.40 (m, 3H), 3.83-3.86 (t, 2H), 3.38 (s, 3H), 2.86-2.92 (m, 2H), 2.20 (s, 3H), 1.93-2.12 (m, 6H), 1.23 (s, 9H).

LC-MS: ESI 616.3 (M+H)⁺.

Example 121

Preparation of N-[4-(4-{3-[5-tert-butyl-2-(1-methyl-piperidin-4-yl)-2H-pyrazol-3-yl]-ureido}-phenoxy-7-(2-methoxy-ethoxy)-quinolin-6-yl]-acetamide (Compound 121)

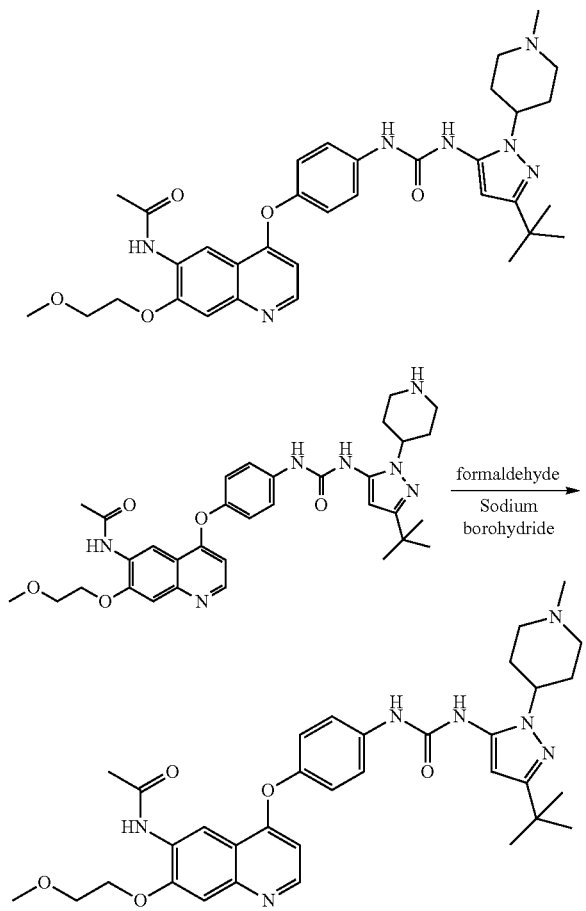

Compound 121

Compound 120 (70 mg, 0.114 mmol) was dissolved in a mixture of dichloromethane (5 ml) and methanol (1 ml), and added with aqueous solution of formaldehyde (314 mg, 37% aqueous solution). The mixture was stirred at room temperature for 30 minutes, and added successively with 14 mg of acetic acid and 8.6 mg of sodium borohydride gradually. The reaction mixture was stirred at room temperature for 1 hour. The reaction was completed by TLC monitoring, and then concentrated under reduced pressure. The residues were purified via column chromatography (eluent: dichloromethane/methanol) to give 50 mg of N-[4-(4-{3-[5-tert-butyl-2-(1-methyl-piperidin-4-yl)-2H-pyrazol-3-yl]-ureido}-phenoxy-7-(2-methoxy-ethoxy)-quinolin-6-yl]-acetamide.

1HNMR (DMSO-d6, 400 MHz) δ: 9.44 (s, 1H), 9.26 (s, 1H), 8.99 (s, 1H), 8.84 (s, 1H), 8.51-8.52 (d, 1H), 7.59-7.61 (d, 2H), 7.50 (s, 1H), 7.20-7.22 (d, 2H), 6.42-6.44 (d, 1H), 6.06 (s, 1H), 4.38-4.40 (t, 2H), 4.14 (m, 1H), 3.83-3.86 (t, 2H), 3.38 (s, 3H), 3.05-3.08 (m, 2H), 2.32-2.37 (m, 4H), 2.20 (s, 3H), 2.07-2.18 (m, 2H), 1.87-1.91 (m, 4H), 1.23 (s, 9H).

LC-MS: ESI 630.3 (M+H)+.

Example 122

Preparation of N-[4-(4-{3-[5-tert-butyl-2-(2-morpholin-4-yl-ethyl)-2H-pyrazol-3-yl]-ureido}-phenoxy-7-(2-methoxy-ethoxy)-quinolin-6-yl]-acetamide (Compound 122)

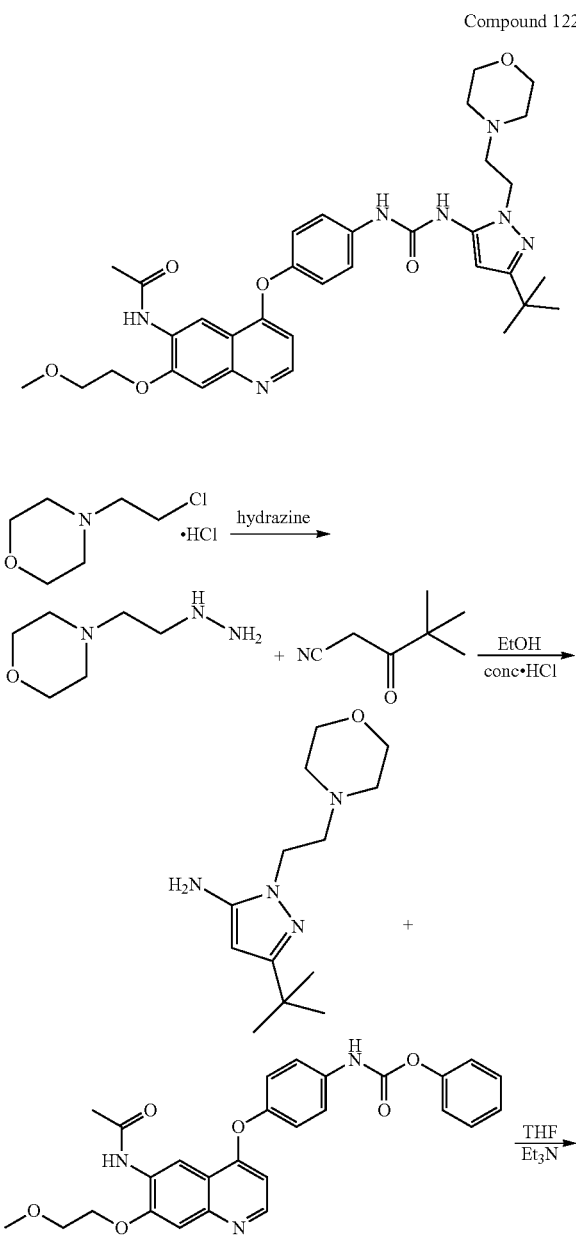

Compound 122

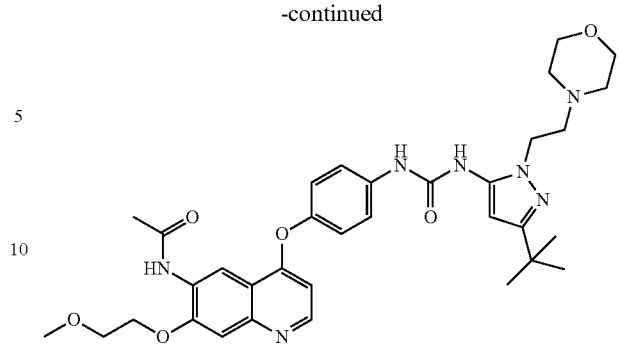

Step 1: Preparation of 2-morpholin-4-yl-ethyl)-hydrazine

N-(2-Chloroethyl)-morpholine hydrochloride (14.8 g, 0.08 mol) and hydrazine hydrate (20 g, 0.4 mol) were dissolved in 250 ml of ethanol at room temperature, and the reaction system was heated to 90° C. for 4 hours. The reaction was completed by TLC monitoring, and then concentrated under reduced pressure. The residues were added with 100 ml of water and concentrated again under reduced pressure (repeated for three times) to give crude (2-morpholin-4-yl-ethyl)-hydrazine.

Step 2: Preparation of 5-tert-butyl-2-(2-morpholin-4-yl-ethyl)-2H-pyrazol-3-ylamine 2-Morpholin-4-yl-ethyl)-hydrazine obtained in step 1 (0.08 mol) and pivaloylacetonitrile (10 g, 0.08 mol) were dissolved in 200 ml of ethanol at room temperature, and added with 0.2 ml of concentrated hydrochloric acid. The reaction system was heated to 90° C. for 12 hours. The reaction was completed by TLC monitoring, and concentrated under reduced pressure. The residues were purified via column chromatography (eluent: dichloromethane/methanol) to give 8 g crude product, which was stirred in 40 ml of methyl tert-butyl ether for 4 hours, and then filtered. The resulting solid was washed with a small amount of methyl t-butyl ether, and air-dried (60° C.) for 1 hour to give 3 g of 5-tert-butyl-2-(2-morpholin-4-yl-ethyl)-2H-pyrazol-3-ylamine as a solid.

Step 3: Preparation of N-[4-(4-{3-[5-tert-butyl-2-(2-morpholin-4-yl-ethyl)-2H-pyrazol-3-yl]-ureido}-phenoxy-7-(2-methoxy-ethoxy)-quinolin-6-yl]-acetamide The preparation method was the same as Step 7 of Example 116, except that 5-tert-butyl-2-(2-morpholin-4-yl-ethyl)-2H-pyrazol-3-ylamine was used instead of 5-tert-butyl-2H-pyrazol-3-ylamine in step 7 to give N-[4-(4-{3-[5-tert-butyl-2-(2-morpholin-4-yl-ethyl)-2H-pyrazol-3-yl]-ureido}-phenoxy-7-(2-methoxy-ethoxy)-quinolin-6-yl]-acetamide.

1HNMR (DMSO-d6, 400 MHz) δ: 9.26 (s, 1H), 9.06 (s, 1H), 8.99 (s, 1H), 8.55 (s, 1H), 8.51-8.52 (d, 1H), 7.58-7.61 (d, 2H), 7.50 (s, 1H), 7.20-7.22 (d, 2H), 6.43-6.44 (d, 1H), 6.08 (s, 1H), 4.39 (m, 2H), 4.04 (m, 2H), 3.83 (m, 2H), 3.56 (m, 4H), 3.38 (s, 3H), 2.66 (m, 2H), 2.41 (m, 4H), 2.20 (s, 3H), 1.22 (s, 9H).

LC-MS: ESI 646.3 (M+H)+.

Example 123

Preparation of N-[4-(4-{3-[5-tert-butyl-2-(2-morpholin-4-yl-ethyl)-2H-pyrazol-3-yl]-ureido}-3-chloro-phenoxy)-7-(2-methoxy-ethoxy)-quinolin-6-yl]-acetamide (Compound 123)

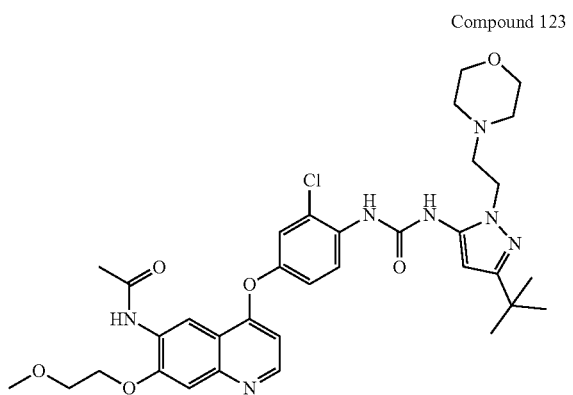 [SMILES: COCCOc1cc2nccc(Oc3ccc(NC(=O)Nc4cc(C(C)(C)C)nn4CCN4CCOCC4)c(Cl)c3)c2cc1NC(C)=O]

Compound 123

The preparation method was the same as Example 66, except that 5-tert-butyl-2-(2-morpholin-4-yl-ethyl)-2H-pyrazol-3-ylamine was used instead of 5-tert-butyl-2H-pyrazol-3-ylamine in step 6 to give N-[4-(4-{3-[5-tert-butyl-2-(2-morpholin-4-yl-ethyl)-2H-pyrazol-3-yl]-ureido}-3-chloro-phenoxy)-7-(2-methoxy-ethoxy)-quinolin-6-yl]-acetamide.

$^1$HNMR (DMSO-d$_6$, 400 MHz) δ: 9.27 (s, 1H), 9.27 (s, 1H), 8.98 (s, 1H), 8.66 (s, 1H), 8.54-8.55 (d, 1H), 8.21-8.23 (d, 1H), 7.52 (m, 2H), 7.25-7.27 (dd, 1H), 6.53-6.54 (d, 1H), 6.13 (s, 1H), 4.39 (m, 2H), 4.11 (m, 2H), 3.85 (m, 2H), 3.57 (m, 4H), 3.38 (s, 3H), 2.72 (m, 2H), 2.49 (m, 4H), 2.20 (s, 3H), 1.22 (s, 9H).
LC-MS: ESI 680.3 (M+H)$^+$.

Example 124

Preparation of N-[4-{4-[3-(5-tert-butyl-2-methyl-2H-pyrazol-3-yl)-ureido]-3-chloro-phenoxy}-7-(2-methoxy-ethoxy)-quinolin-6-yl]-acetamide (Compound 124)

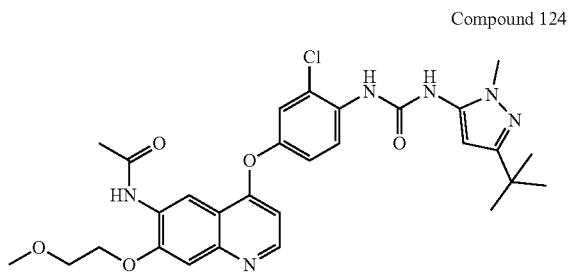 [SMILES: COCCOc1cc2nccc(Oc3ccc(NC(=O)Nc4cc(C(C)(C)C)nn4C)c(Cl)c3)c2cc1NC(C)=O]

Compound 124

The preparation method was the same as Example 66, except that 5-tert-butyl-2-methyl-2H-pyrazol-3-ylamine was used instead of 5-tert-butyl-2H-pyrazol-3-ylamine in step 6 to give N-[4-{4-[3-(5-tert-butyl-2-methyl-2H-pyrazol-3-yl)-ureido]-3-chloro-phenoxy}-7-(2-methoxy-ethoxy)-quinolin-6-yl]-acetamide.

$^1$HNMR (DMSO-d$_6$, 400 MHz) δ: 9.28 (s, 1H), 9.24 (s, 1H), 8.98 (s, 1H), 8.64 (s, 1H), 8.54-8.55 (d, 1H), 8.24-8.26 (d, 1H), 7.53-7.54 (d, 1H), 7.52 (s, 1H), 7.25-7.28 (dd, 1H), 6.53-6.54 (d, 1H), 6.12 (s, 1H), 4.38-4.40 (t, 2H), 3.84-3.86 (t, 2H), 3.65 (m, 3H), 3.38 (s, 3H), 2.20 (s, 3H), 1.22 (s, 9H).
LC-MS: ESI 581.2 (M+H)$^+$.

Example 125

Preparation of N-[4-{4-[3-(5-tert-butyl-2-cyclopropylmethyl-2H-pyrazol-3-yl)-ureido]-3-chloro-phenoxy}-7-(2-methoxy-ethoxy)-quinolin-6-yl]-acetamide (Compound 125)

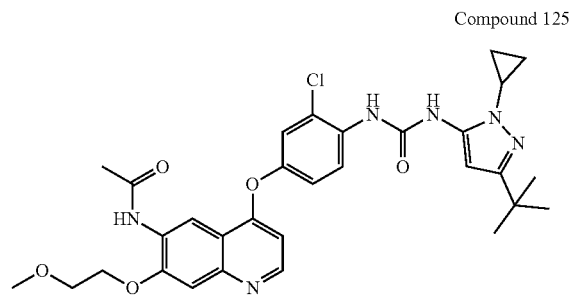 [SMILES: COCCOc1cc2nccc(Oc3ccc(NC(=O)Nc4cc(C(C)(C)C)nn4C4CC4)c(Cl)c3)c2cc1NC(C)=O]

Compound 125

The preparation method was the same as Example 66, except that 5-tert-butyl-2-cyclopropyl-2H-pyrazol-3-ylamine was used instead of 5-tert-butyl-2H-pyrazol-3-ylamine in step 6 to give N-[4-{4-[3-(5-tert-butyl-2-cyclopropylmethyl-2H-pyrazol-3-yl)-ureido]-3-chloro-phenoxy}-7-(2-methoxy-ethoxy)-quinolin-6-yl]-acetamide.

$^1$HNMR (DMSO-d$_6$, 400 MHz) δ: 9.27 (s, 1H), 9.25 (s, 1H), 8.98 (s, 1H), 8.87 (s, 1H), 8.55-8.56 (d, 1H), 8.22-8.24 (d, 1H), 7.53-7.54 (d, 1H), 7.52 (s, 1H), 7.25-7.28 (dd, 1H), 6.54-6.55 (d, 1H), 6.14 (s, 1H), 4.38-4.41 (t, 2H), 3.84-3.86 (t, 2H), 3.38 (s, 3H), 2.20 (s, 3H), 2.00 (m, 1H), 1.20 (s, 9H), 1.01-1.02 (d, 4H).
LC-MS: ESI 607.2 (M+H)$^+$.

Example 126

Preparation of N-[4-(4-{3-[5-tert-butyl-2-(1-methyl-piperidin-4-yl)-2H-pyrazol-3-yl]-ureido}-3-chloro-phenoxy)-7-(2-methoxy-ethoxy)-quinolin-6-yl]-acetamide (Compound 126)

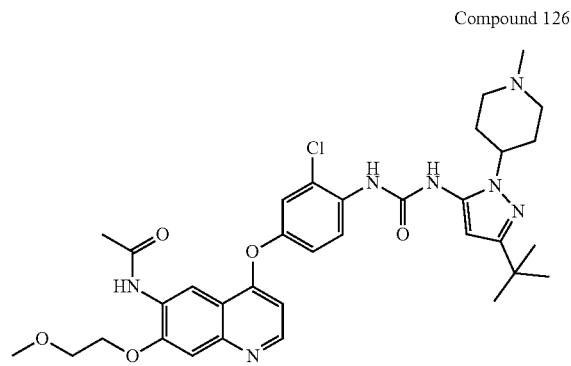 [SMILES: COCCOc1cc2nccc(Oc3ccc(NC(=O)Nc4cc(C(C)(C)C)nn4C4CCN(C)CC4)c(Cl)c3)c2cc1NC(C)=O]

Compound 126

The preparation method was the same as Example 120 and 121, except that N-[4-(4-amino-3-chloro-phenoxy)-7-(2-methoxy-ethoxy)-quinolin-6-yl]-acetamide (prepared in Step 4 of Example 66) was used instead of N-[4-(4-amino-phenoxy)-7-(2-methoxy-ethoxy)-quinolin-6-yl]-acetamide in step 4 of Example 120 to give N-[4-(4-{3-[5-tert-butyl-2-(1-methyl-piperidin-4-yl)-2H-pyrazol-3-yl]-ureido}-3-chloro-phenoxy)-7-(2-methoxy-ethoxy)-quinolin-6-yl]-acetamide.

$^1$HNMR (DMSO-$d_6$, 400 MHz) δ: 9.32 (s, 1H), 9.27 (s, H), 8.97 (s, H), 8.70 (s, 1H), 8.54-8.55 (d, 1H), 8.18-8.20 (d, H), 7.53 (d, H), 7.52 (s, 1H), 7.24-7.27 (dd, 1H), 6.52-6.54 (d, 1H), 6.09 (s, 1H), 4.38-4.40 (t, 2H), 4.15 (m, 1H), 3.83-3.86 (t, 2H), 3.38 (s, 3H), 3.06-3.08 (m, 2H), 2.33-2.38 (m, 4H), 2.20 (s, 3H), 2.00 (m, 1H), 2.06-2.17 (m, 2H), 1.87-1.91 (m, 4H), 1.23 (s, 9H).

LC-MS: ESI 664.3 (M+H)$^+$.

Example 127

Preparation of N-[4-{4-[3-(5-tert-butyl-2-dimethyl-amino-ethyl-2H-pyrazol-3-yl)-ureido]-3-chloro-phenoxy}-7-(2-methoxy-ethoxy)-quinolin-6-yl]-acetamide (Compound 127)

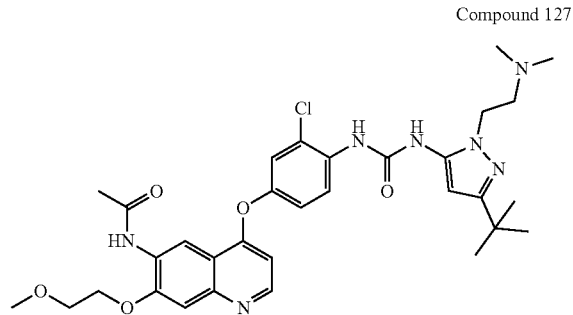

Compound 127

The preparation method was the same as Example 66, except that 5-tert-butyl-2-(2-dimethylamino-ethyl)-2H-pyrazol-3-ylamine was used instead of 5-tert-butyl-2H-pyrazol-3-ylamine in step 6 to give N-[4-{4-[3-(5-tert-butyl-2-dimethylamino-ethyl-2H-pyrazol-3-yl)-ureido]-3-chloro-phenoxy}-7-(2-methoxy-ethoxy)-quinolin-6-yl]-acetamide.

$^1$HNMR (DMSO-$d_6$, 400 MHz) δ: 9.88 (s, H), 9.28 (s, 1H), 8.97 (s, H), 8.89 (s, 1H), 8.54-8.55 (d, 1H), 8.18-8.20 (d, 1H), 7.51 (m, 2H), 7.24-7.27 (dd, 1H), 6.52-6.54 (d, 1H), 6.14 (s, 1H), 4.38-4.40 (t, 2H), 4.22-4.25 (t, 2H), 3.83-3.85 (t, 2H), 3.38 (s, 3H), 2.99 (m, 2H), 2.46 (s, 6H), 2.20 (s, 3H), 1.23 (s, 9H).

LC-MS: ESI 638.2 (M+H)$^+$.

Example 128

Preparation of N-[4-{4-[3-(5-tert-butyl-2H-pyrazol-3-yl)-ureido]-3-fluoro-phenoxy}-7-(2-methoxy-ethoxy)-quinolin-6-yl]-acetamide (Compound 128)

Compound 128

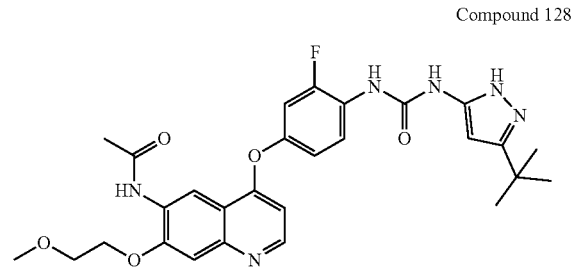

The preparation method was the same as Example 66, except that 4-amino-3-fluorophenol was used instead of 4-amino-3-chlorophenol hydrochloride in step 1 to give N-[4-{4-[3-(5-tert-butyl-2H-pyrazol-3-yl)-ureido]-3-fluoro-phenoxy}-7-(2-methoxy-ethoxy)-quinolin-6-yl]-acetamide.

$^1$HNMR (DMSO-$d_6$, 400 MHz) δ: 12.09 (s, 1H), 9.36 (s, 1H), 9.27 (s, 1H), 8.89 (s, 1H), 8.53-8.54 (d, 1H), 8.31-8.35 (t, 1H), 7.51 (s, 1H), 7.33-7.36 (dd, 1H), 7.08-7.10 (d, 1H), 6.53-6.55 (d, 1H), 5.86 (br, 1H), 4.38-4.40 (t, 2H), 3.83-3.85 (t, 2H), 3.38 (s, 3H), 2.20 (s, 3H), 1.26 (s, 9H).

LC-MS: ESI 551.2 (M+H)$^+$.

Example 129

Preparation of N-[4-{4-[3-(5-tert-butyl-2H-pyrazol-3-yl)-ureido]-3-chloro-phenoxy}-7-(3-methoxy-propoxy)-quinolin-6-yl]-acetamide (Compound 129)

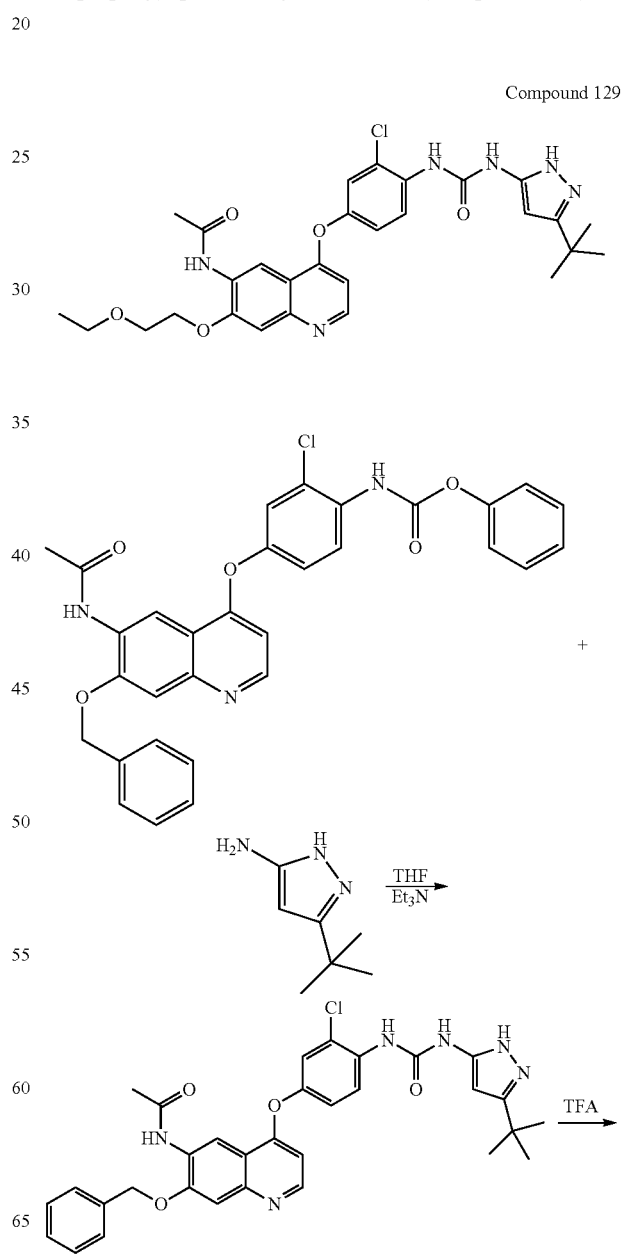

Compound 129

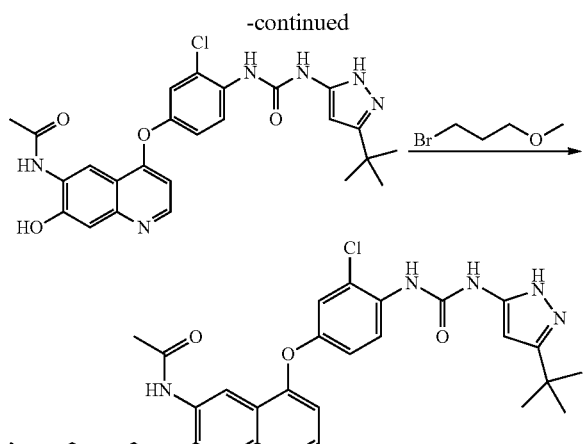

Step 1: Preparation of N-(7-benzyloxy-4-{4-[3-(5-tert-butyl-2H-pyrazol-3-yl)-ureido]-3-chloro-phenoxy}-quinolin-6-yl)-acetamide (M-129)

The preparation method was the same as Example 66 (compound 66), except that benzyl alcohol was used instead of 2-methoxy-ethanol in step 1 of example 66 to give the intermediate N-(7-benzyloxy-4-{4-[3-(5-tert-butyl-2H-pyrazol-3-yl)-ureido]-3-chloro-phenoxy}-quinolin-6-yl)-acetamide (M-129).

Step 2: Preparation of N-(4-{4-[3-(5-tert-butyl-2H-pyrazol-3-yl)-ureido]-3-chloro-phenoxy}-7-hydroxy-quinolin-6-yl)-acetamide N-(7-Benzyloxy-4-{4-[3-(5-tert-butyl-2H-pyrazol-3-yl)-ureido]-3-chloro-phenoxy}-quinolin-6-yl)-acetamide obtained in Step 1 (310 mg, 0.52 mmol) was dissolved in 10 ml of trifluoroacetic acid, and added with thioanisole (320 mg, 2.58 mmol) at room temperature. The mixture was heated to 60° C. for 12 hours. After the reaction was completed by TLC monitoring, the reaction solution was concentrated and added with 20 ml of water. The solution was adjusted to about pH 8 with a saturated aqueous solution of sodium bicarbonate, and then extracted with ethyl acetate (50 ml×3). The organic phase was washed with saturated NaCl solution, dried over anhydrous sodium sulfate, and filtered. The filtrate was concentrated under reduced pressure and the residues were purified via column chromatography (eluent: dichloromethane/methanol) to give 100 mg of N-(4-{4-[3-(5-tert-butyl-2H-pyrazol-3-yl)-ureido]-3-chloro-phenoxy}-7-hydroxy-quinolin-6-yl)-acetamide as a solid.

Step 3: Preparation of N-[4-{4-[3-(5-tert-butyl-2H-pyrazol-3-yl)-ureido]-3-chloro-phenoxy}-7-(3-methoxy-propoxy)-quinolin-6-yl]-acetamide N-(4-{4-[3-(5-Tert-butyl-2H-pyrazol-3-yl)-ureido]-3-chloro-phenoxy}-7-hydroxy-quinolin-6-yl)-acetamide obtained in Step 2 (100 mg, 0.196 mmol) was dissolved in 10 ml of DMF, and added with 1-bromo-3-methoxypropane (46 mg, 0.295 mmol), cesium carbonate (192 mg, 0.59 mmol) and a catalytic amount of potassium iodide at room temperature. The mixture was stirred at room temperature for 30 minutes, was and then heated to 60° C. for 2 hours. The reaction was completed by TLC monitoring, and then poured into water, and extracted with ethyl acetate (50 ml×3). The organic phase was washed with saturated NaCl solution, dried over anhydrous sodium sulfate, and filtered. The filtrate was concentrated under reduced pressure and the residues were purified via column chromatography (eluent: dichloromethane/methanol) to give 18 mg of N-[4-{4-[3-(5-tert-butyl-2H-pyrazol-3-yl)-ureido]-3-chloro-phenoxy}-7-(3-methoxy-propoxy)-quinolin-6-yl]-acetamide as a solid.

$^1$HNMR (DMSO-$d_6$, 400 MHz) δ: 12.12 (s, 1H), 9.60 (s, 1H), 9.26 (s, 1H), 8.97 (s, 1H), 8.53-8.54 (d, 1H), 8.38-8.40 (d, 1H), 7.50-7.51 (d, 1H), 7.45 (s, 1H), 7.23-7.26 (dd, 1H), 6.52-6.53 (d, 1H), 5.88 (br, 1H), 4.28-4.31 (t, 2H), 3.56-3.59 (t, 2H), 3.29 (s, 3H), 2.21 (s, 3H), 1.27 (s, 9H).

LC-MS: ESI 581.2 (M+H)$^+$.

Example 130

Preparation of N-{4-{4-[3-(5-tert-butyl-2H-pyrazol-3-yl)-ureido]-3-chloro-phenoxy}-7-[3-(4-methy-piperazin-1-yl)-propoxy]-quinolin-6-yl}-acetamide (Compound 130)

Compound 130

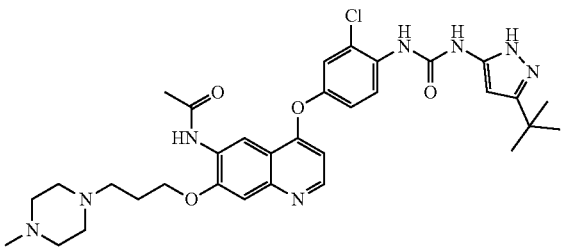

The preparation method was the same as Example 129, except that 1-(3-chloropropyl)-4-methylpiperazine dihydrochloride was used instead of 1-bromo-3-methoxypropane in step 3 to give N-{4-{4-[3-(5-tert-butyl-2H-pyrazol-3-yl)-ureido]-3-chloro-phenoxy}-7-[3-(4-methy-piperazin-1-yl)-propoxy]-quinolin-6-yl}-acetamide.

$^1$HNMR (DMSO-$d_6$, 400 MHz) δ: 12.11 (s, 1H), 9.60 (s, 1H), 9.27 (s, 1H), 8.94 (s, 1H), 8.53-8.54 (d, 1H), 8.37-8.39 (d, 1H), 7.50-7.51 (d, 1H), 7.46 (s, 1H), 7.23-7.26 (dd, 1H), 6.52-6.53 (d, 1H), 5.88 (br, 1H), 4.26-4.29 (t, 2H), 2.50 (m, 10H), 2.28 (s, 3H), 2.20 (s, 3H), 2.05 (m, 2H), 1.27 (s, 9H).

LC-MS: ESI 649.2 (M+H)$^+$.

Example 131

Preparation of N-[4-{4-[3-(5-tert-butyl-2H-pyrazol-3-yl)-ureido]-3-chloro-phenoxy}-7-(2-hydroxy-ethoxy-quinolin-6-yl]-acetamide (Compound 131)

Compound 131

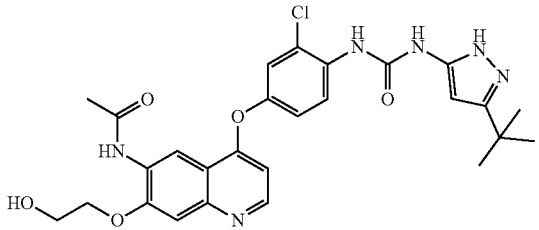

The preparation method was the same as Example 129, except that 2-bromoethanol was used instead of 1-bromo-3-methoxypropane in step 3 to give N-[4-{4-[3-(5-tert-butyl-2H-pyrazol-3-yl)-ureido]-3-chloro-phenoxy}-7-(2-hydroxy-ethoxy-quinolin-6-yl]-acetamide.

¹HNMR (DMSO-d₆, 400 MHz) δ: 12.10 (s, 1H), 9.68 (s, 1H), 9.36 (s, 1H), 9.10 (s, 1H), 8.54-8.55 (d, 1H), 8.35 (m, 1H), 7.52 (d, 1H), 7.51 (s, 1H), 7.30-7.33 (dd, 1H), 6.52-6.54 (d, 1H), 5.89 (br, 1H), 4.38-4.40 (t, 2H), 3.83-3.85 (t, 2H), 2.20 (s, 3H), 1.24 (s, 9H).
LC-MS: ESI 553.2 (M+H)⁺.

Example 132

Preparation of N-[4-{4-[3-(5-tert-butyl-2H-pyrazol-3-yl)-ureido]-3-chloro-phenoxy}-7-(2-morpholin-4-yl-ethoxy)-quinolin-6-yl]-acetamide (Compound 132)

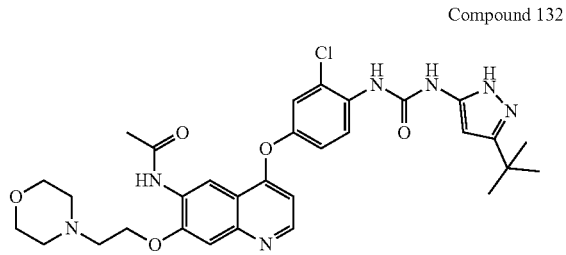 [SMILES: CC(=O)Nc1cc2c(Oc3ccc(NC(=O)Nc4cc(C(C)(C)C)n[nH]4)c(Cl)c3)ccnc2cc1OCCN1CCOCC1]

Compound 132

The preparation method was the same as Example 129, except that 4-(2-chloroethyl)-morpholine hydrochloride was used instead of 1-bromo-3-methoxypropane in step 3 to give N-[4-{4-[3-(5-tert-butyl-2H-pyrazol-3-yl)-ureido]-3-chloro-phenoxy}-7-(2-morpholin-4-yl-ethoxy)-quinolin-6-yl]-acetamide.

¹HNMR (DMSO-d₆, 400 MHz) δ: 12.11 (s, 1H), 9.60 (s, 1H), 9.31 (s, 1H), 8.95 (s, 1H), 8.53-8.54 (d, 1H), 8.38-8.39 (d, 1H), 7.52 (s, 1H), 7.50-7.51 (d, 1H), 7.23-7.26 (dd, 1H), 6.52-6.54 (d, 1H), 5.88 (br, 1H), 4.36-4.39 (t, 2H), 3.62 (m, 4H), 2.89 (m, 2H), 2.55 (m, 4H), 2.20 (s, 3H), 1.27 (s, 9H).
LC-MS: ESI 622.1 (M+H)⁺.

Example 133

Preparation of N-[4-{4-[3-(5-tert-butyl-2H-pyrazol-3-yl)-ureido]-3-methyl-phenoxy}-7-(2-methoxy-ethoxy)-quinolin-6-yl]-acetamide (Compound 133)

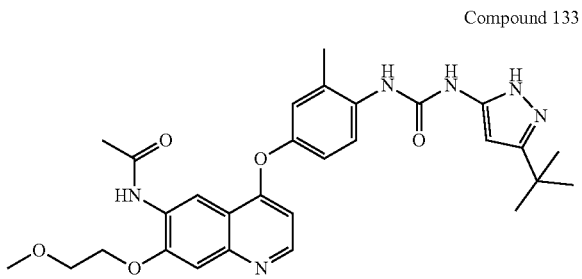 [SMILES: COCCOc1cc2nccc(Oc3ccc(NC(=O)Nc4cc(C(C)(C)C)n[nH]4)c(C)c3)c2cc1NC(C)=O]

Compound 133

The preparation method was the same as Example 66, except that 4-amino-3-methylphenol was used instead of 4-amino-3-chlorophenol hydrochloride in step 3 to give N-[4-{4-[3-(5-tert-butyl-2H-pyrazol-3-yl)-ureido]-3-methyl-phenoxy}-7-(2-methoxy-ethoxy)-quinolin-6-yl]-acetamide.

¹HNMR (DMSO-d₆, 400 MHz) δ: 12.06 (s, 1H), 9.32 (s, 1H), 9.26 (s, 1H), 8.99 (s, 1H), 8.50-8.52 (d, 1H), 8.12-8.14 (d, 1H), 7.50 (s, 1H), 7.14-7.15 (d, 1H), 7.05-7.08 (dd, 1H), 6.44-6.46 (d, 1H), 5.88 (br, 1H), 4.38-4.40 (t, 2H), 3.83-3.85 (t, 2H), 3.38 (s, 3H), 2.32 (s, 3H), 2.20 (s, 3H), 1.26 (s, 9H).
LC-MS: ESI 547.3 (M+H)⁺.

Example 134

Preparation of N-[4-{4-[3-(5-tert-butyl-2-cyclopropylmethyl-2H-pyrazol-3-yl)-ureido]-2-fluoro-phenoxy}-7-(2-methoxy-ethoxy)-quinolin-6-yl]-acetamide (Compound 134)

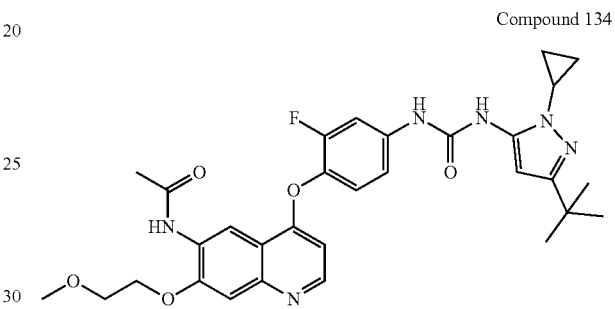

Compound 134

The preparation method was the same as Example 66, except that 4-amino-2-fluorophenol was used instead of 4-amino-3-chlorophenol hydrochloride in step 3, and 5-tert-butyl-2-cyclopropyl-2H-pyrazol-3-ylamine (prepared in Example 118) was used instead of 5-tert-butyl-2H-pyrazol-3-ylamine in step 6 to give N-[4-{4-[3-(5-tert-butyl-2-cyclopropylmethyl-2H-pyrazol-3-yl)-ureido]-2-fluoro-phenoxy}-7-(2-methoxy-ethoxy)-quinolin-6-yl]-acetamide.

¹HNMR (DMSO-d₆, 400 MHz) δ: 9.53 (s, 1H), 9.29 (s, 1H), 9.02 (s, 1H), 8.62 (s, 1H), 8.53-8.54 (d, 1H), 7.76-7.79 (m, 1H), 7.52 (s, 1H), 7.39-7.43 (t, 1H), 7.26-7.28 (m, 1H), 6.45-6.46 (d, 1H), 6.13 (s, 1H), 4.40 (m, 2H), 3.85 (m, 2H), 3.38 (s, 3H), 2.21 (s, 3H), 2.20 (s, 3H), 1.21 (s, 9H), 1.00-1.01 (d, 4H).
LC-MS: ESI 591.2 (M+H)⁺.

Example 135

Preparation of N-[4-{4-[3-(5-tert-butyl-2-methyl-2H-pyrazol-3-yl)-ureido]-2-chloro-phenoxy}-7-(2-methoxy-ethoxy)-quinolin-6-yl]-acetamide (Compound 135)

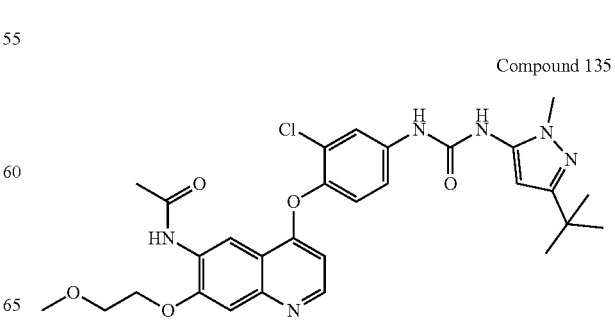

Compound 135

The preparation method was the same as Example 66, except that 4-amino-2-chlorophenol was used instead of 4-amino-3-chlorophenol hydrochloride in step 3, and 5-tert-butyl-2-methyl-2H-pyrazol-3-ylamine was used instead of 5-tert-butyl-2H-pyrazol-3-ylamine in step 6 to give N-[4-{4-[3-(5-tert-butyl-2-methyl-2H-pyrazol-3-yl)-ureido]-2-chloro-phenoxy}-7-(2-m ethoxy-ethoxy)-quinolin-6-yl]-acetamide.

$^1$HNMR (DMSO-$d_6$, 400 MHz) δ: 9.36 (s, 1H), 9.30 (s, 1H), 9.05 (s, 1H), 8.72 (s, 1H), 8.53-8.55 (d, 1H), 7.95 (d, 1H), 7.53 (s, 1H), 7.40-7.47 (m, 2H), 6.37-6.38 (d, 1H), 6.08 (s, 1H), 4.40 (m, 2H), 3.85 (m, 2H), 3.62 (s, 3H), 3.38 (s, 3H), 2.21 (s, 3H), 2.20 (s, 3H), 1.22 (s, 9H).

LC-MS: ESI 581.2 (M+H)$^+$.

Example 136

Preparation of N-[4-(4-{3-[5-tert-butyl-2-(2-morpholin-4-yl-ethyl)-2H-pyrazol-3-yl]-ureido}-2-fluoro-phenoxy)-7-(2-methoxy-ethoxy)-quinolin-6-yl]-acetamide (Compound 136)

Compound 136

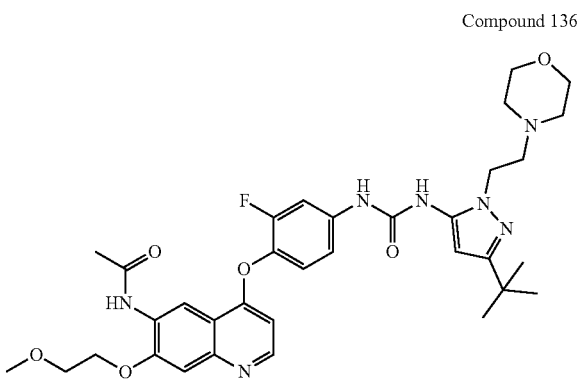 [SMILES: COCCOc1cc2nccc(Oc3ccc(NC(=O)Nc4cc(C(C)(C)C)nn4CCN4CCOCC4)cc3Cl)c2cc1NC(C)=O]

The preparation method was the same as Example 66, except that 4-amino-2-fluorophenol was used instead of 4-amino-3-chlorophenol hydrochloride in step 3, and 5-tert-butyl-2-(2-morpholin-4-yl-ethyl)-2H-pyrazol-3-ylamine was used instead of 5-tert-butyl-2H-pyrazol-3-ylamine in step 6 to give N-[4-(4-{3-[5-tert-butyl-2-(2-morpholin-4-yl-ethyl)-2H-pyrazol-3-yl]-ureido}-2-fluoro-phenoxy)-7-(2-methoxy-ethoxy)-quinolin-6-yl]-acetamide.

$^1$HNMR (DMSO-$d_6$, 400 MHz) δ: 9.53 (br, 1H), 9.30 (s, 1H), 9.02 (s, 1H), 8.89 (br, H), 8.53-8.54 (d, 1H), 7.74-7.78 (m, 1H), 7.52 (s, 1H), 7.39-7.44 (t, 1H), 7.26-7.28 (d, 1H), 6.44-6.46 (d, 1H), 6.11 (s, 1H), 4.38-4.41 (t, 2H), 4.13 (m, 2H), 3.83-3.86 (t, 2H), 3.63 (m, 4H), 3.38 (s, 3H), 3.07 (m, 2H), 2.50 (m, 4H), 2.20 (s, 3H), 1.23s, 9H).

LC-MS: ESI 664.3 (M+H)$^+$.

Example 137

Preparation of N-[4-(4-{3-[5-tert-butyl-2-(2-morpholin-4-yl-ethyl)-2H-pyrazol-3-yl]-ureido}-2-chloro-phenoxy)-7-(2-methoxy-ethoxy)-quinolin-6-yl]-acetamide (Compound 137)

Compound 137

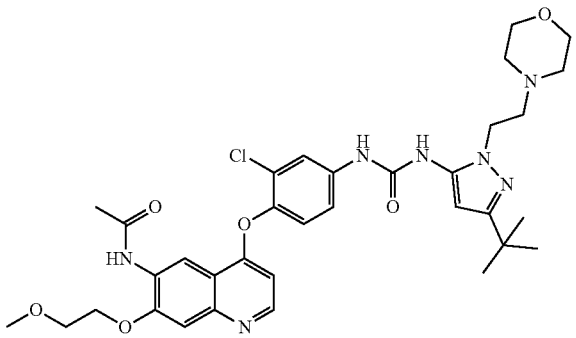

The preparation method was the same as Example 66, except that 4-amino-2-chlorophenol was used instead of 4-amino-3-chlorophenol hydrochloride in step 3, and 5-tert-butyl-2-(2-morpholin-4-yl-ethyl)-2H-pyrazol-3-ylamine was used instead of 5-tert-butyl-2H-pyrazol-3-ylamine in step 6 to give N-[4-(4-{3-[5-tert-butyl-2-(2-morpholin-4-yl-ethyl)-2H-pyrazol-3-yl]-ureido}-2-chloro-phenoxy)-7-(2-methoxy-ethoxy)-quinolin-6-yl]-acetamide.

$^1$HNMR (DMSO-$d_6$, 400 MHz) δ: 9.60 (br, 1H), 9.28 (s, 1H), 9.03 (s, 1H), 8.95 (br, 1H), 8.51-8.52 (d, 1H), 7.94-7.95 (d, 1H), 7.52 (s, 1H), 7.39-7.46 (m, 2H), 6.33-6.35 (d, 1H), 6.11 (s, 1H), 4.41 (m, 2H), 4.12 (m, 2H), 3.86 (m, 2H), 3.59 (m, 4H), 3.38 (s, 3H), 3.08 (m, 2H), 2.50 (m, 4H), 2.21 (s, 3H), 1.22 (s, 9H).

LC-MS: ESI 680.3 (M+H)$^+$.

Example 138

Preparation of 4-{4-[3-(5-tert-butyl-2H-pyrazol-3-yl)-ureido]-3-chloro-phenoxy}-7-(3-morpholin-4-yl-propoxy)-quinolin-6-carboxamide (Compound 138)

Compound 138

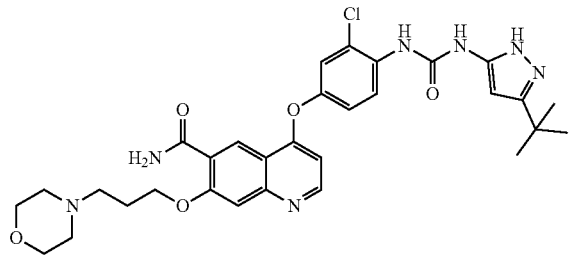

The preparation method was the same as Example 81, except that N-(3-chloropropyl)-morpholine hydrochloride was used instead of N-(2-chloroethyl)-morpholine hydrochloride to give 4-{4-[3-(5-tert-butyl-2H-pyrazol-3-yl)-ureido]-3-chloro-phenoxy}-7-(3-morpholin-4-yl-propoxy)-quinolin-6-carboxamide.

1HNMR (DMSO-d6, 400 MHz) δ: 12.11 (s, 1H), 9.60 (s, 1H), 8.67-8.69 (m, 2H), 8.40-8.42 (d, 1H), 7.80 (s, 1H), 7.55-7.56 (d, 1H), 7.53 (s, 1H), 7.28-7.31 (dd, 1H), 6.56-6.58 (d, 1H), 5.85 (br, 1H), 4.31-4.34 (t, 2H), 3.61 (m, 4H), 2.42-2.51 (m, 6H), 2.04 (m, 2H), 1.27 (s, 9H).
LC-MS: ESI 622.2 (M+H)+.

Example 139

Preparation of 4-{4-[3-(5-tert-butyl-2-cyclopentyl-2H-pyrazol-3-yl)-ureido]-3-chloro-phenoxy}-7-[3-(4-methyl-piperazinyl piperidin-1-yl)-propoxy]-quinolin-6-carboxamide (Compound 139)

Step 1: Preparation of 4-{4-[3-(5-tert-butyl-2-cyclopentyl-2H-pyrazol-3-yl)-ureido]-3-chloro-phenoxy}-7-hydroxy-quinolin-6-carboxamide (M-139)

The preparation method was the same as Example 80, except that 5-tert-butyl-2-cyclopentyl-2H-pyrazol-3-ylamine was used instead of 5-tert-butyl-2H-pyrazol-3-ylamine in step 9 to give 4-{4-[3-(5-tert-butyl-2-cyclopentyl-2H-pyrazol-3-yl)-ureido]-3-chloro-phenoxy}-7-hydroxy-quinolin-6-carboxamide (M-139).

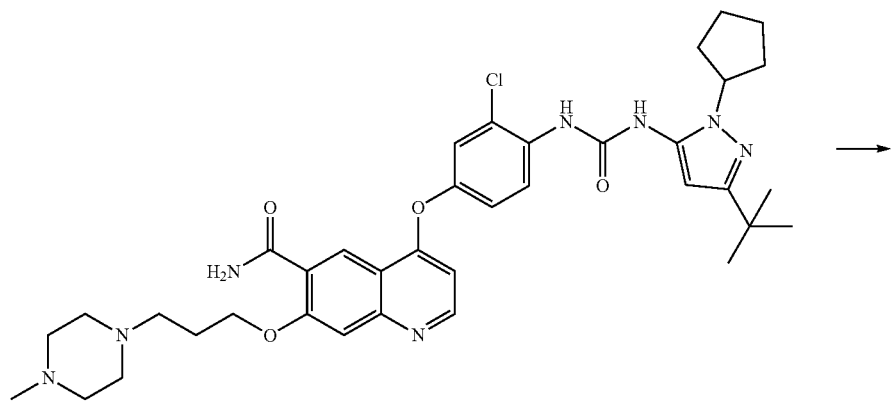

Compound 139

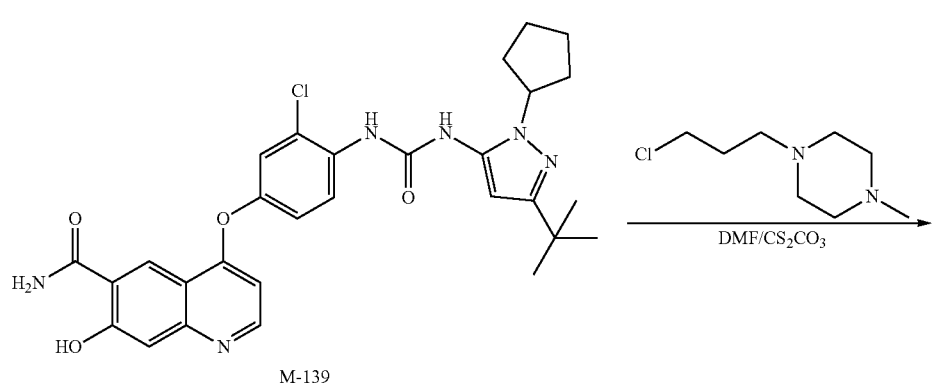

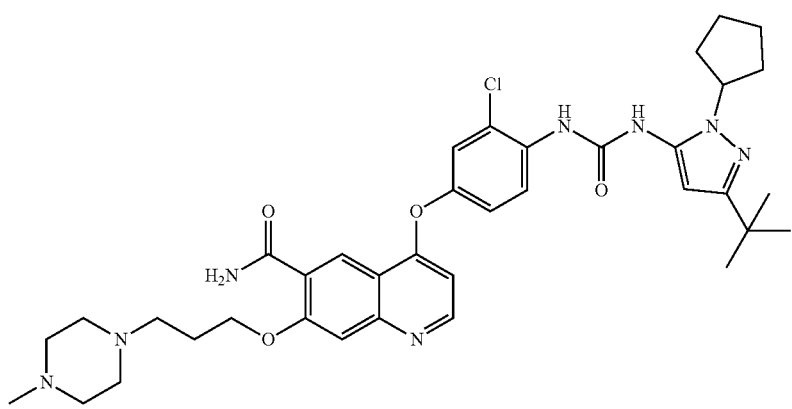

Step 2: Preparation of 4-{4-[3-(5-tert-butyl-2-cyclopentyl-2H-pyrazol-3-yl)-ureido]-3-chloro-phenoxy}-7-[3-(4-methyl-piperazinyl piperidin-1-yl)-propoxy]-quinolin-6-carboxamide 4-{4-[3-(5-Tert-butyl-2-cyclopentyl-2H-pyrazol-3-yl)-ureido]-3-chloro-phenoxy}-7-hydroxy-quinolin-6-carboxamide (150 mg, 0.27 mmol) obtained in step 1, 1-(3-chloropropyl)-4-methylpiperazine dihydrochloride (100 mg, 0.41 mmol) and cesium carbonate (352 mg, 1.08 mmol) were stirred in 10 ml of DMF at room temperature for 0.5 h. The mixture was heated to 80° C. for 3 hours. The reaction solution was poured into water, and extracted with ethyl acetate (50 ml×3). The organic phase was washed twice with saturated NaCl solution, dried over anhydrous sodium sulfate, and filtered. The filtrate was concentrated under reduced pressure and the residues were purified via column chromatography (eluent: dichloromethane/methanol) to give 20 mg of 4-{4-[3-(5-tert-butyl-2-cyclopentyl-2H-pyrazol-3-yl)-ureido]-3-chloro-phenoxy}-7-[3-(4-methyl-piperazine piperidin-1-yl)-propoxy]-quinolin-6-carboxamide as a solid.

$^1$HNMR (DMSO-d$_6$, 400 MHz) δ: 9.11 (s, 1H), 8.68-8.69 (d, 1H), 8.67 (s, 1H), 8.60 (s, 1H), 8.25-8.27 (d, 1H), 7.78 (br, 2H), 7.57-7.58 (d, 1H), 7.52 (s, 1H), 7.29-7.32 (dd, 1H), 6.56-6.58 (d, 1H), 6.09 (s, 1H), 4.54-4.58 (m, 1H), 4.29-4.32 (t, 2H), 2.26-2.50 (m, 10H), 2.17 (s, 3H), 1.61-2.05 (m, 10H), 1.22 (s, 9H).

LC-MS: ESI 703.3 (M+H)$^+$.

Example 140

Preparation of 4-{4-[3-(5-tert-butyl-2-cyclopentyl-2H-pyrazol-3-yl)-ureido]-3-chloro-phenoxy}-7-(3-morpholin-4-yl-propoxy)-quinolin-6-carboxamide (Compound 140)

Compound 140

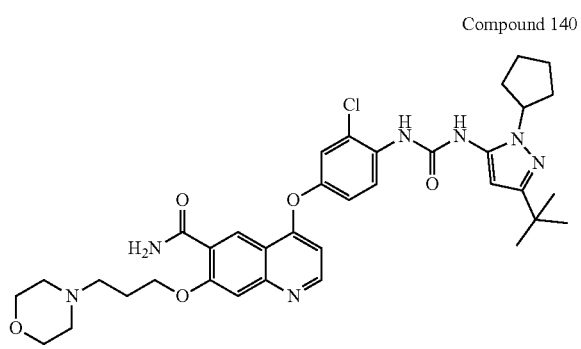 [SMILES: CC(C)(C)c1cc(NC(=O)Nc2ccc(Oc3ccnc4cc(OCCCN5CCOCC5)c(C(N)=O)cc34)cc2Cl)n(C2CCCC2)n1]

The preparation method was the same as Example 139, except that N-(3-chloropropyl)-morpholine hydrochloride was used instead of 1-(3-chloropropyl)-4-methylpiperazine dihydrochloride in step 2 to give 4-{4-[3-(5-tert-butyl-2-cyclopentyl-2H-pyrazol-3-yl)-ureido]-3-chloro-phenoxy}-7-(3-morpholin-4-yl-propoxy)-quinolin-6-carboxamide $^1$HNMR (DMSO-d$_6$, 400 MHz) δ: 9.11 (s, 1H), 8.68-8.69 (d, 1H), 8.67 (s, 1H), 8.60 (s, 1H), 8.25-8.27 (d, 1H), 7.79 (br, 2H), 7.57-7.58 (d, 1H), 7.53 (s, 1H), 7.28-7.31 (dd, 1H), 6.56-6.58 (d, 1H), 6.09 (s, 1H), 4.54-4.58 (m, 1H), 4.30-4.34 (t, 2H), 3.60 (m, 4H), 2.50 (m, 2H), 2.41 (m, 4H), 1.61-2.05 (m, 10H), 1.22 (s, 9H).

LC-MS: ESI 690.3 (M+H)$^+$.

Biological Test

Test Example 1 Determination of 50% Inhibition (IC$_{50}$) Concentration of the Present Compounds on the Growth of FGFR1-4, FLT3-ITD, KIT, PDGFRa and BCR-ABL Gene Amplification/High Expression or Mutant Tumor Cell Lines In Vitro Experimental Materials and Methods 1. Tumor Cell Lines and Cell Cultures Tumor cell lines are an effective model for studying in vitro tumor growth inhibition. In the present invention, a representative tumor cell line was selected to determine the cell growth inhibition activity of the present compound. All cell lines used were from ATCC, DSMZ, and cell banks of the Chinese Academy of Sciences. Cell culture conditions and methods were in accordance with the requirements of each cell line. Cells were subcultured in vitro for no more than 3 generations each time, and as required, single-clone purification and identification of cell lines could be carried out.

The cell culture media used were RPMI1640 (Gibco), DMEM (Gibco), MEM (Gibco), L15 (Gibco), IMDM (Gibco), McCOY'S5A, and William's (Gibco). 5-20% fetal bovine serum (Gibco), 1% double antibiotic, 2 mM glutamine, or 1 mM sodium pyruvate were added. The names, species, major gene characteristics, culture media and cell sources of the cell lines used are shown in table 1, wherein "amp" refers to gene amplification. "+++" refers to gene overexpression. The main genetic characteristics of cells were obtained from the COSMIC Cell Lines Project and related research papers, respectively.

TABLE 1

Cell lines used in the present invention

| Cell line | Type | Genetic characteristic | Culture media | Source |
|---|---|---|---|---|
| NCI-H1581 | Human non-small cell lung cancer | FGFR1 amp | RPMI 1640 | ATCC |
| Cal-120 | Human breast cancer | FGFR1 amp, CDK4+++ | DMEM | ATCC |
| DMS 114 | Human small cell lung cancer | FGFR1 amp, ROS1 T870N, AKT1 S266L/R249W | Waymouth's MB | ATCC |
| JIMT-1 | Human breast cancer | FGFR1 amp, HER2 amp, PI3KCA C420R, PI3KCB amp | DMEM | DSMZ |
| SNU-16 | Human gastric cancer | FGFR2 amp | RPMI 1640 | ATCC |
| KATO III | Human gastric cancer | FGFR2 amp | IMDM | ATCC |
| AN3 CA | Human endometrial adenocarcinoma | FGFR2 K310R/N549K/N547K/K221R/N460K/N550K | MEM | ATCC |

TABLE 1-continued

Cell lines used in the present invention

| Cell line | Type | Genetic characteristic | Culture media | Source |
|---|---|---|---|---|
| RT112/84 | Human bladder epithelial carcinoma | FGFR3-TACC3 | MEM | ATCC |
| Huh-7 | Human liver cancer | FGFR3+++, FGFR4 +++, | DMEM | JCRB |
| JHH-7 | Human liver cancer | FGFR3+++, FGFR4 +++, FGFR1-OP2+++ | William'sE | JCRB |
| Hep3B2.1-7 | Human liver cancer | FGFR3+++, FGFR4 +++ | MEM | ATCC |
| Hep G2 | Human liver cancer | FGFR3+++, FGFR4 +++ | MEM | ZK |
| PLC/PRF/5 | Human liver cancer | FGFR3+++, FGFR4 +++ | MEM | ZK |
| MOLM-13 | Human acute myeloid leukemia | FLT3-ITD | RPMI1640 | ATCC |
| RS4; 11 | Human acute lymphoid leukemia | FLT3 WT+++ | RPMI1640 | ATCC |
| KCL-22 | Human chronic myeloid leukemia | BCR-ABL, PI3KCA E545G | RPMI 1640 | ATCC |
| Kasumi-1 | Human acute myeloid leukemia | KIT N822K | RPMI 1640 | ATCC |
| NCI-H1703 | Human lung cancer | PDGFRa +++/amp | RPMI 1640 | ATCC |
| Jurkat | Human acute T cell leukemia | — | RPMI 1640 | ATCC |
| KYSE70 | Human esophageal squamous cell carcinoma | PI3KCA amp, FGFR3 N7205, KIT G779C | RPMI 1640 | JCRB |
| A2780 | Human ovarian cancer | PIK3CA E365K | RPMI 1640 | ATCC |
| AGS | Human gastric cancer | PI3KCA E453K/E545A, KRAS G12D, FGFR4 D425N/D465N | Ham's F12K | ZK |
| NCI-H460 | Human lung cancer | PI3KCA E545K, KRAS Q61H | RPMI 1640 | ATCC |
| SW48 | Human colon cancer | PI3KCA G914R, EGFR G7195, FGFR1 K502N, ALK p1453S | L15 | ATCC |
| HCT116 | Human intestinal cancer | PI3KCA H1047R, KRAS G13D | McCOY'S 5A | ATCC |
| HGC-27 | Human gastric cancer | PI3KCA H1047R, FGFR1OP2+++, HER4 M775I/M765I | MEM | ATCC |
| HCC1954 | Human breast cancer | PI3KCA H1047R, HER2 amp, FGFR4 amp | RPMI 1640 | ATCC |
| SK-OV-3 | Human ovarian cancer | PI3KCA H1047R, HER2 amp | McCOY'S 5A | ZK |
| MDA-MB-453 | Human breast cancer | PI3KCA H1047R, FGFR4+++/Y367C, HER2+++ | L15 | ATCC |
| MFM-223 | Human breast cancer | PI3KCA H1047R, FGFR1 amp, FGFR2 amp | MEM | DSMZ |
| A375 | Human malignant melanoma | BRAF V600E, FGFR2 E636K/E634K/E547K/E637K | DMEM | ZK |
| Karpas 299 | Human T lymphoma | NPM-ALK, CSF1R+++ | RPMI 1640 | DSMZ |
| H1299 | Human non-small cell lung cancer | MERTK+++, AXL+++, NRAS Q61K, FGFR1OP+++ | RPMI 1640 | ATCC |

2. Drug Treatment

Adherent cells were digested with 0.25% trypsin-EDTA (Gibco). Suspension culture cells were collected by centrifugation (1700 rpm, 3 minutes). The supernatant was discarded and the cells were counted. According to each cell growth cycle, different concentrations of cells were prepared ($5\sim10\times10^4$ cells per ml), and inoculated to 96-well plates (Corning), with 100 µl per well, and incubated overnight at 37° C., 5% $CO_2$. The next day, the test compound was added to the cultured cells (2 wells in parallel). The final concentration of the solvent was less than 1/1,000. The cells were further cultured for 3 to 5 days and assayed by MTT.

The compound of the present invention and the control compound (table 2 below) were dissolved in DMSO (Sigma) respectively, with the purity of more than 98%. The compound was stored at a concentration of 10 mM at −20° C. and diluted to 2- or 10-fold series prior to use. BGJ398 and AC220 were synthesized according to the methods of WO2006420A1 and US2007232604A1, respectively. Ponatinib, Trametinib and BAY 80-6946 were purchased from Selleck.

TABLE 2

| Compound | Structure | Inhibition targets | Source |
|---|---|---|---|
| BGJ398 | 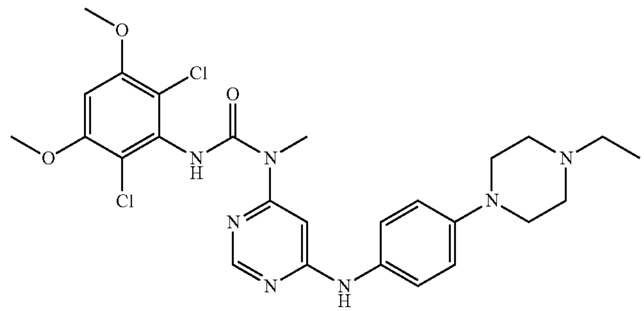 [SMILES: CCN1CCN(c2ccc(Nc3cc(N(C)C(=O)Nc4c(Cl)c(OC)cc(OC)c4Cl)ncn3)cc2)CC1] | FGFR1-4 | WO2006420A1 |
| Ponatinib | 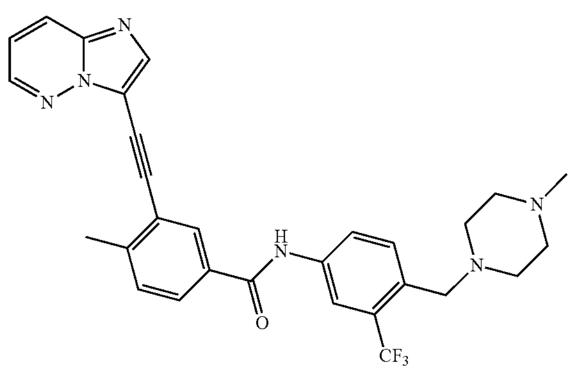 [SMILES: Cc1ccc(C(=O)Nc2ccc(CN3CCN(C)CC3)c(C(F)(F)F)c2)cc1C#Cc1cnc2cccnn12] | Abl PDGFRα, VEGFR2, FGFR1, KIT and SRC | Selleck |
| AC220 | 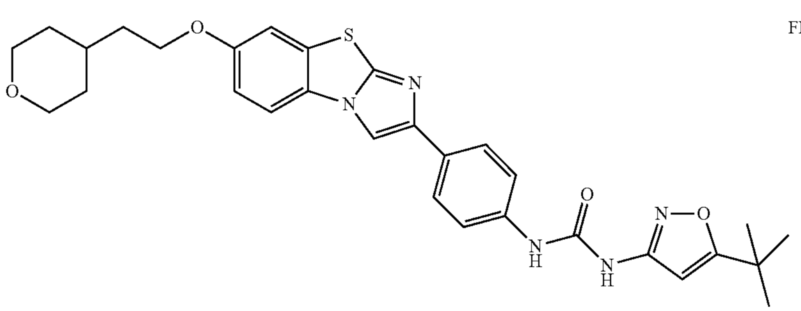 | FLT3 | US2007232604A1 |
| BAY 80-6946 | 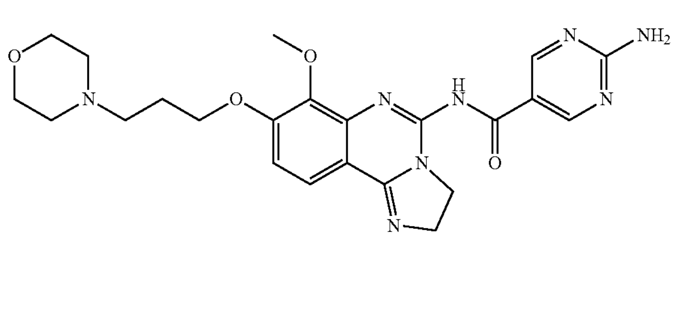 [SMILES: COc1c(OCCCN2CCOCC2)ccc2c1N=C(NC(=O)c1cnc(N)nc1)N1CCN=C21] | PI3Kα/β/γ/δ | Selleck |

TABLE 2-continued

| Compound | Structure | Inhibition targets | Source |
|---|---|---|---|
| Trametinib | (structure) | MEK1/2 | Selleck |

3. MTT Detection and IC$_{50}$ Calculation

The MTT test reagent was a Dojindo CCK8 kit and the Microplate Reader was a THERMO MULTISKAN FC instrument.

The adherent cells were taken out from the cell culture medium, and immediately added to a freshly prepared complete medium containing 10% CCK8 (5% FBS), 100 ul per hole. The suspended cells were directly added to a CCK8 reagent until reaching a final concentration of 10% and cultured for 1 to 4 hours. When a dark yellow color could be observed in the solvent control wells, the absorbance value at OD450 nm was measured and the cell growth rate was calculated according to the following formula:

Cell Growth Rate (%)=100×(T-T0)/(C-T0)

T=optical density of drug-treated cell wells−optical density of blank control wells; T0=optical density of cell wells before drug treatment−optical density of blank control wells; C=optical density of solvent control wells−optical density of blank control wells. The drug concentration for a 50% inhibition of cell growth, i.e. IC$_{50}$ was calculated by Graph-Pad Prism 7 software. The experiments were repeated 1 to 3 times and a statistical analysis of data was conducted.

Experimental Results

Table 3 summarizes the determination results of IC$_{50}$ concentration of in vitro growth inhibition (or inducing apoptosis) of the compound of the present invention on FGFRs, FLT3-ITD, PDGFRα, KIT gene amplification/overexpression or mutation, and BCR-ABL and NPM-ALK fusion gene expression positive tumor cells. The smaller the IC50 value is, the more active the compound is.

TABLE 3

IC$_{50}$ values of in vitro growth inhibition (or induction of apoptosis) of the present compounds on various gene amplification/overexpression or mutation tumor cells

| | IC$_{50}$ (nM) | | | | | | | |
|---|---|---|---|---|---|---|---|---|
| Compound | H1581 (FGFR1 amp) | KATO III (FGFR2 amp) | Hep3B2 (FGFR3/4+++) | MOLM-13 (FLT3-ITD) | KCL-22 (BCR-ABL) | Kasumi-1 (KIT N822K) | H1703 (PDGFRa amp) | Karpas 299 (NPM-ALK) |
| 1 | 16.14 | 1.28 | 281.9 | <0.05 | 64.66 | 90.11 | 9.45 | 393.7 |
| 2 | 3.35 | 0.51 | 25.62 | 6.49 | 7.58 | 26.14 | 7.9 | 587.2 |
| 3 | 6.87 | 1.46 | 27.4. | 35.36 | 13.97 | 27.75 | 16.6 | 724.6 |
| 4 | 13.20 | 2.93 | 27.8 | 122.0 | 10.45 | 14.49 | 21.8 | 755.5 |
| 5 | 65.34 | 9.76 | 156.4 | 4.26 | 2.15 | 12.90 | 18.8 | >1000 |
| 6 | 10.57 | 2.86 | 45.3 | 20.92 | 17.79 | 26.08 | 15.6 | 689.4 |
| 7 | 55.44 | 6.33 | 83.9 | <0.05 | 19.81 | 46.01 | 19.4 | 187.4 |
| 8 | 19.53 | 2.93 | 45.63 | <0.05 | 18.69 | 35.10 | 17.5 | 141.6 |
| 9 | 9.59 | 1.39 | 47.6 | <0.05 | 35.79 | 143.5 | 18.5 | 352.5 |
| 10 | >1000 | >1000 | >1000 | >1000 | >1000 | 71.94 | >1000 | >1000 |
| 11 | 270.2 | 12.12 | 677.12 | 2.41 | 28.14 | 89.77 | 20.4 | >1000 |
| 12 | 584.3 | 102.6 | 791.2 | 122.2 | 113.9 | 389.2 | 139.1 | >1000 |
| 13 | 0.86 | 0.84 | 6.61 | 5.41 | 3.19 | 5.46 | 9.74 | 251.8 |
| 14 | 10.52 | 2.16 | 24.15 | 5.56 | 8.97 | 33.32 | 10.24 | 725.4 |
| 15 | 1.06 | 1.34 | 24.06 | 5.25 | 4.09 | 5.43 | 12.90 | 516.1 |
| 16 | 126.9 | 12.22 | 253.0 | 51.27 | 315.0 | 724.7 | 47.3 | >1000 |
| 17 | 31.45 | 3.90 | 84.9 | 7.72 | 23.10 | 71.43 | 167.5 | 769.8 |
| 18 | 224.5 | 6.73 | 637.6 | 409.9 | 83.59 | 59.56 | 68.0 | >1000 |
| 19 | 787.9 | 46.80 | >1000 | 632.1 | 149.5 | 131.4 | 171.5 | >1000 |
| 20 | 1.75 | 1.14 | 13.88 | 2.21 | 5.55 | 22.09 | 8.71 | 194.6 |
| 21 | 17.36 | 2.80 | 37.5 | 7.07 | 26.64 | 88.88 | 156.8 | 397.6 |
| 22 | 40.67 | 8.54 | 18.7 | 16.92 | 61.69 | 91.67 | 27.8 | 609.9 |
| 23 | 227.1 | 10.51 | 214.1 | 94.90 | 436.2 | 547.0 | 420.5 | >1000 |
| 24 | 492.6 | 30.98 | 346.1 | 0.99 | >1000 | >1000 | 83.5 | 763.8 |

TABLE 3-continued

IC$_{50}$ values of in vitro growth inhibition (or induction of apoptosis) of the present compounds on various gene amplification/overexpression or mutation tumor cells

| | IC$_{50}$ (nM) | | | | | | | |
|---|---|---|---|---|---|---|---|---|
| Compound | H1581 (FGFR1 amp) | KATO III (FGFR2 amp) | Hep3B2 (FGFR3/4+++) | MOLM-13 (FLT3-ITD) | KCL-22 (BCR-ABL) | Kasumi-1 (KIT N822K) | H1703 (PDGFRa amp) | Karpas 299 (NPM-ALK) |
| 25 | 9.70 | 0.24 | 14.21 | 19.06 | 16.37 | 44.04 | 13.5 | 599.6 |
| 26 | 9.78 | 0.07 | 10.92 | 1.35 | 5.16 | 16.88 | 8.20 | 524.2 |
| 27 | 9.03 | 0.12 | 11.63 | 3.92 | 9.23 | 8.44 | 9.20 | 350.9 |
| 28 | 17.37 | 0.73 | 24.18 | 6.53 | 25.14 | 32.46 | 17.1 | 698.3 |
| 29 | 26.29 | 1.48 | 29.4 | 11.54 | 29.45 | 66.83 | 18.0 | 625.8 |
| 30 | 15.47 | 1.62 | 26.1 | 17.80 | 22.02 | 23.68 | 16.7 | 275.5 |
| 31 | 23.39 | 0.12 | 32.9 | 9.45 | 51.20 | 40.40 | 25.02 | 465.4 |
| 32 | 35.81 | 0.18 | 56.6 | 17.06 | 163.4 | 132.5 | 73.25 | 735.9 |
| 33 | 49.77 | 0.71 | 130.4 | 28.07 | 25.70 | 46.43 | 72.97 | 632.4 |
| 34 | 57.55 | 1.62 | 96.4 | 14.60 | 98.2 | 135.1 | 88.1 | 641.4 |
| 35 | 104.9 | 4.45 | 166.5 | <0.05 | 16.79 | 7.32 | 106.4 | 392.9 |
| 36 | 65.69 | 2.62 | 78.9 | <0.05 | 31.46 | 70.79 | 227.2 | 178.6 |
| 37 | 4.73 | 0.19 | 9.60 | 0.97 | 0.498 | 2.05 | 6.44 | 52.33 |
| 38 | 0.29 | 0.18 | 4.24 | 0.85 | 0.481 | 1.32 | 1.81 | 11.72 |
| 39 | >1000 | >1000 | >1000 | >1000 | >2500 | >1000 | >1000 | >1000 |
| 40 | 127.3 | 2.53 | 446.3 | 19.64 | 111.9 | 106.0 | 92.96 | 720.7 |
| 41 | 450.2 | 40.07 | 514.0 | 134.4 | 353.1 | 736.4 | 123.7 | >1000 |
| 42 | 9.19 | 0.98 | — | — | 46.45 | 191.4 | 11.9 | 93.0 |
| 43 | 38.47 | 5.69 | 64.28 | 51.54 | 102.0 | 149.2 | 37.2 | 557.6 |
| 44 | 1.61 | 1.08 | 11.32 | 3.81 | 2.21 | 7.94 | 6.49 | 297.5 |
| 45 | 16.50 | 1.46 | 39.59 | 6.32 | 21.77 | 34.23 | 25.7 | 413.3 |
| 46 | 3.06 | 0.98 | 39.11 | 6.98 | 8.17 | 14.38 | 8.80 | 384.1 |
| 47 | 4.93 | 0.73 | 39.31 | 7.42 | 9.38 | 15.88 | 14.7 | 466.5 |
| 48 | 11.69 | 1.36 | 44.08 | 11.56 | 22.34 | 35.68 | 25.9 | 502.5 |
| 49 | 63.14 | 2.93 | 93.14 | 18.14 | 31.16 | 100.5 | 15.4 | >1000 |
| 50 | 59.49 | 0.31 | 96.61 | 16.18 | 89.96 | 65.56 | 14.53 | 795.4 |
| 51 | 51.38 | 1.14 | 88.0 | 141.7 | 13.02 | 12.67 | 48.4 | 492.8 |
| 52 | 106.8 | 3.28 | 175.0 | 0.06 | 7.11 | 3.83 | 62.4 | 203.3 |
| 53 | 218.5 | 6.81 | 343.6 | 1.12 | 28.56 | 17.67 | 63.97 | 302.4 |
| 54 | 53.41 | 5.50 | 153.3 | 0.27 | 23.94 | 26.13 | 71.5 | 113.5 |
| 55 | 79.87 | 2.96 | 157.4 | 1.16 | 56.96 | 91.80 | 83.26 | 160.2 |
| 56 | 3.66 | 0.28 | 17.6 | 2.87 | 1.40 | 1.07 | 18.85 | 39.21 |
| 57 | 2.85 | 0.41 | 21.87 | 1.29 | 2.58 | 3.00 | 11.65 | 69.35 |
| 58 | 5.50 | 0.58 | 18.16 | 2.33 | 3.11 | 10.31 | 14.8 | 417.1 |
| 59 | 5.05 | 0.11 | 19.42 | 2.95 | 9.62 | 1.95 | 8.17 | 195.3 |
| 60 | 1.31 | 0.36 | 5.20 | 0.89 | 1.05 | 0.493 | 6.71 | 12.42 |
| 61 | 132.8 | 18.44 | 368.0 | 61.40 | 598.8 | 570.6 | 75.8 | 605.9 |
| 62 | 13.70 | 1.89 | 73.2 | 7.83 | 25.80 | 47.45 | 93.10 | 311.5 |
| 63 | 4.26 | 0.31 | 15.91 | 3.12 | 4.68 | 8.81 | 12.0 | 112.9 |
| 64 | 8.64 | 0.63 | 18.97 | 8.78 | 17.36 | 34.25 | 13.14 | 186.0 |
| 65 | 217.6 | 11.0 | 159.5 | 72.01 | 163.0 | 568.0 | 246.8 | >1000 |
| 66 | 2.03 | 0.08 | 6.06 | 0.87 | 3.12 | 1.13 | 7.54 | 44.08 |
| 67 | 163.5 | 6.83 | 270. | 72.20 | 19.16 | 24.80 | 436.2 | 863.1 |
| 68 | >1000 | >1000 | >1000 | >1000 | >1000 | >1000 | >1000 | >1000 |
| 69 | >1000 | >1000 | >1000 | >1000 | >1000 | >1000 | >1000 | >1000 |
| 70 | >1000 | >1000 | >1000 | >1000 | >1000 | >1000 | >1000 | >1000 |
| 71 | >1000 | >1000 | >1000 | >1000 | >1000 | 1000 | >1000 | >1000 |
| 72 | 164.8 | 6.18 | 158.9 | 50.82 | 116.7 | 137.0 | 250.3 | 735.8 |
| 73 | 137.5 | 264.9 | 287.9 | 197.0 | 80.60 | 129.2 | 222.5 | 88.45 |
| 74 | >1000 | >1000 | >1000 | >1000 | >1000 | >1000 | >1000 | >1000 |
| 75 | >1000 | >1000 | >1000 | >1000 | >1000 | >1000 | >1000 | >1000 |
| 76 | >1000 | 363.1 | >1000 | >1000 | >1000 | 1000 | 369.9 | >1000 |
| 77 | 242.6 | 17.0 | 493.8 | 42.45 | 293.9 | 517.7 | 211.8 | >1000 |
| 78 | 684.4 | 36.57 | 502.1 | 1.37 | >1000 | >1000 | 446.8 | >1000 |
| 79 | 254.0 | 19.90 | 383.6 | 106.8 | >1000 | >1000 | 278.1 | >1000 |
| 80 | 515.7 | 468.0 | 554.8 | 34.30 | >1000 | >1000 | 78.1 | >1000 |
| 81 | 4.94 | 0.31 | 44.69 | 11.89 | 34.89 | 26.67 | 11.32 | 465.9 |
| 82 | 3.61 | 2.94 | 23.85 | 1.70 | 20.64 | 5.21 | 9.43 | 174.1 |
| 83 | 92.92 | 5.94 | 150.5 | 15.30 | 190.0 | 259.6 | 59.49 | 850.7 |
| 84 | 113.7 | 6.09 | 148.44 | 35.17 | 287.2 | 240.3 | 127.3 | >1000 |
| 85 | 14.16 | 1.92 | 16.75 | 2.83 | 33.11 | 6.49 | 14.00 | 262.9 |
| 86 | 326.1 | 68.3 | 85.1 | — | — | 76.32 | 369.9 | 600.3 |
| 87 | — | 1.02 | 57.2 | 3.65 | 55.12 | 4.19 | 12.54 | 143.8 |
| 88 | — | 5.67 | 175.2 | 5.49 | 282.1 | 15.55 | 55.62 | 153.1 |
| 89 | — | 1.12 | 19.4 | 6.43 | 44.96 | 4.48 | 13.11 | 145.9 |
| 90 | — | 2.78 | 100.9 | 7.54 | 175.1 | 9.47 | — | 255.5 |
| 91 | — | 1.26 | 43.1 | 6.41 | 183.8 | 16.37 | — | 215.9 |
| 92 | 146.0 | 17.51 | 232.1 | 28.90 | 67.50 | 181.6 | 452.8 | 749.0 |
| 93 | 210.0 | 3.53 | 9.84 | 10.30 | 6.12 | 8.29 | 79.26 | 178.2 |
| 94 | 4.17 | 0.89 | 10.61 | 1.61 | 3.66 | 4.22 | 5.03 | 65.04 |
| 95 | 7.88 | 0.91 | 8.52 | 1.75 | 7.03 | 1.34 | 3.81 | 7.50 |
| 96 | 37.97 | 1.72 | 36.6 | 7.23 | 10.23 | 31.35 | 44.99 | >1000 |

TABLE 3-continued

IC$_{50}$ values of in vitro growth inhibition (or induction of apoptosis) of the
present compounds on various gene amplification/overexpression or mutation tumor cells

| | IC$_{50}$ (nM) | | | | | | | |
|---|---|---|---|---|---|---|---|---|
| Compound | H1581 (FGFR1 amp) | KATO III (FGFR2 amp) | Hep3B2 (FGFR3/4+++) | MOLM-13 (FLT3-ITD) | KCL-22 (BCR-ABL) | Kasumi-1 (KIT N822K) | H1703 (PDGFRa amp) | Karpas 299 (NPM-ALK) |
| 97 | 253.9 | 117.4 | 455.9 | 0.80 | 122.4 | >1000 | 341.7 | 802.9 |
| 98 | 432.8 | 269.5 | 842.9 | 6.00 | >1000 | >1000 | 605.1 | >1000 |
| 99 | 293.9 | 37.8 | 862.2 | 3.41 | 264.2 | 355.0 | 127.6 | >1000 |
| 100 | 270.7 | 49.7 | >1000 | 1.01 | 694.2 | >1000 | 202.0 | 838.5 |
| 101 | 9.56 | 2.34 | 110.1 | 0.08 | 11.04 | 24.14 | 61.32 | 64.32 |
| 102 | 8.39 | 1.32 | 75.8 | <0.05 | 10.21 | 97.45 | 71.2 | >1000 |
| 103 | 24.23 | 4.17 | 190.9 | 0.15 | 12.10 | 14.61 | 86.74 | 349.6 |
| 104 | 159.9 | 40.1 | 525.9 | 1.17 | >1000 | >1000 | 163.3 | 768.4 |
| 105 | 39.63 | 4.07 | 83.4 | 0.59 | 45.32 | 57.32 | 71.93 | 187.2 |
| 106 | 167.7 | 46.7 | >1000 | 9.37 | 115.0 | 176.4 | 120.5 | 380.2 |
| 107 | 341.3 | 345.2 | >1000 | 50.40 | 588.6 | >1000 | 263.4 | 759.2 |
| 108 | 146.5 | 31.3 | — | 3.81 | >1000 | >1000 | 666.5 | >1000 |
| 109 | 17.74 | 1.55 | 98.7 | 18.70 | 2.48 | 0.471 | 107.5 | 559.4 |
| 110 | 8.36 | 2.98 | 83.8 | 19.70 | 3.21 | 0.41 | 46.08 | 507.6 |
| 111 | 2.98 | 0.10 | 8.41 | — | 1.07 | 0.375 | 4.75 | 55.68 |
| 112 | 3.02 | 0.23 | 15.8 | — | 2.69 | 0.406 | 17.3 | 100.2 |
| 113 | >1000 | 498.1 | >1000 | >500 | >1000 | >1000 | 567.6 | >1000 |
| 114 | >1000 | >1000 | >1000 | >1000 | >5000 | >1000 | >1000 | >1000 |
| 115 | >1000 | 746.0 | >1000 | >1000 | >5000 | >1000 | >1000 | >1000 |
| 116 | 9.01 | 1.97 | — | 0.095 | — | — | — | — |
| 117 | 9.72 | 0.17 | — | 0.25 | — | — | — | — |
| 118 | 19.3 | 0.38 | — | 0.11 | — | — | — | — |
| 119 | 78.9 | 6.87 | — | <0.05 | — | — | — | — |
| 120 | 78.6 | 13.5 | — | 0.55 | — | — | — | — |
| 121 | 19.5 | 0.50 | — | 0.61 | — | — | — | — |
| 122 | 69.4 | 0.27 | — | 0.60 | — | — | — | — |
| 123 | 9.10 | <0.05 | — | 1.22 | — | — | — | — |
| 124 | 4.60 | 0.31 | — | 1.01 | — | — | — | — |
| 125 | 1.06 | 0.23 | — | 1.20 | — | — | — | — |
| 126 | 1.41 | 0.41 | — | 7.62 | — | — | — | — |
| 127 | 1.26 | 0.27 | — | 2.56 | — | — | — | — |
| 128 | 2.01 | 0.10 | — | 3.91 | — | — | — | — |
| 129 | 4.78 | 0.34 | — | 4.88 | — | — | — | — |
| 130 | 1.12 | 0.54 | — | 4.96 | — | — | — | — |
| 131 | 19.5 | 11.6 | — | 14.65 | — | — | — | — |
| 132 | 3.91 | 1.34 | — | 0.98 | — | — | — | — |
| 133 | 8.04 | 1.56 | — | 1.13 | — | — | — | — |
| 134 | 12.41 | 0.30 | — | <0.05 | — | — | — | — |
| 135 | 19.5 | 0.22 | — | 0.11 | — | — | — | — |
| 136 | 39.0 | 0.40 | — | 0.05 | — | — | — | — |
| 137 | 41.2 | 1.21 | — | 0.34 | — | — | — | — |
| 138 | 97.3 | 18.2– | — | 21.3 | — | — | — | — |
| 139 | 3.44 | 1.14 | — | 9.87 | — | — | — | — |
| 140 | 115.2 | 23.7 | — | 17.9 | — | — | — | — |
| BGJ-398 | 6.97 | 0.461 | 38.9 | — | >1000 | >1000 | >1000 | >1000 |
| Ponatinib | — | — | — | <1 | <0.5 | <1 | 31.5 | 798 |
| AC220 | >1000 | >1000 | — | 0.69 | >1000 | >1000 | >1000 | >1000 |

The results in table 3 show that the compounds of the present invention can inhibit the growth or inducing apoptosis of tumor cell lines positive expressing FGFR1, FGFR2, FGFR3, FGFR4, FLT3-ITD, BCR-ABL, KIT N822K and PDGFRa, respectively, and the IC$_{50}$ value may be lower to subnanomolar level. At the same time, the compounds have significant selective growth inhibition on different cancer cells.

Test Example 2 Determination of 50% Inhibition (IC$_{50}$) Concentration of the Present Compounds on the Growth of FGFR1, FGFR2, FGFR3, FGFR4 Gene Amplification/High Expression or Mutant Tumor Cell Lines In Vitro Mutations in the FGFR1-4 gene often occur in different types of cancer patients. In order to test the growth inhibition activity of the present compound against tumor cells expressing different FGFR variants, tumor cell lines expressing representative FGFR1-4 were selected for further determining the activity of compounds 25, 66, 38 and 95 of the present invention. BGJ398, a selective inhibitor of FGFR1-4, was used as the control compound. The specific test method is the same as test example 1. The experimental results are shown in Table 4 below.

TABLE 4

IC$_{50}$ values of the inhibition of the present compounds on the growth of FGFR1, FGFR2, FGFR3, FGFR4 gene amplification/high expression or mutant tumor cell lines in vitro

| Cell line | IC$_{50}$ (nM) | | | | |
|---|---|---|---|---|---|
| | Compound 25 | Compound 66 | Compound 38 | Compound 95 | BGJ398 |
| DMS114 | 15.6 | 3.92 | 4.1 | 2.94 | 6.97 |
| Cal-120 | 64.7 | 9.77 | 9.77 | 9.77 | >1000 |
| JIMT-1 | 467.2 | 19.6 | 19.12 | 20.6 | >1000 |
| SNU-16 | 1.95 | 1.01 | 2.03 | 3.34 | 2.18 |
| AN3-CA | 4.95 | 3.95 | 3.67 | 3.89 | 62.1 |
| MFM-223 | 21.6 | 17.9 | 14.9 | 32.6 | >1000 |
| MDA-MB-453 | 309.1 | 19.3 | 19.75 | 49.2 | >1000 |
| A375 | 129.3 | 31.5 | 16.7 | 62.1 | >1000 |
| RT112/84 | 31.5 | 25.6 | 10.1 | 9.76 | 8.12 |
| Huh-7 | 7.12 | 1.98 | 3.99 | 7.89 | 30.9 |
| JHH-7 | 4.88 | 12.9 | 9.89 | 17.6 | 31.8 |
| PLC/PRF/5 | 2.95 | 2.67 | 2.08 | 2.37 | — |
| Hep G2 | 127.1 | 79.1 | 119.2 | 128.1 | — |

The results in table 4 show that the compound has a high growth inhibition activity on different tumor cells with FGFR1, FGFR2, FGFR3 and FGFR4 gene amplification/high expression or mutation, and can inhibit the growth of non-sensitive cells of BGJ398 (pan-FGFR1-4 inhibitor) such as CAL-120, JIMT-1, MFM-223 and MDA-MB-453.

Test Example 3 Determination of 50% Inhibition (IC$_{50}$) Concentration of the Present Compounds on the Growth of Cells Positive Expressing FLT3 Wild Type In Vitro The present compounds which has a high growth inhibition activity on tumor cells positive expressing FLT3-ITD were selected for the determination of IC$_{50}$ concentration on FLT3 wild tyoverexpressing cells RS4:11 and FLT3 wild-type normal expressing cells Jurkat. The specific test method is the same as that of test example 1. The experimental results are shown in Table 5 below.

TABLE 5

IC$_{50}$ values of the inhibition of the inventive compounds on the growth of the cells positive expressing FLT3 wild type in vitro

| Compound | IC$_{50}$ (nM) | |
|---|---|---|
| | RS4:11 | Jurkat |
| 1 | 187.5 | 520.9 |
| 7 | 375 | 301.6 |
| 8 | 370 | 287.7 |
| 9 | 750 | 409.1 |
| 24 | >1000 | 571.7 |
| 35 | >1000 | 429.0 |
| 36 | 750 | 535.1 |
| 37 | 139.2 | 408.4 |
| 38 | 65.8 | 201.9 |
| 52 | >1000 | >1000 |
| 54 | 531 | — |
| 66 | 523 | 462.4 |
| 102 | 500 | — |

The results in table 5 show that the present compounds require a higher IC$_{50}$ value to inhibits the growth of cells over expressing FLT3 wild-type (RS4:11) or cells normally expressing FLT3 wild-type (Jurkat), indicating that these compounds are highly selective for the growth of FLT3-ITD-activated leukemia cells.

Test Example 4 Determination of 50% Inhibition (IC$_{50}$) Concentration of the Present Compounds on the Growth of PI3KCA Gene Amplification/High Expression or Mutant Tumor Cell Lines In Vitro In test examples 1 and 2, it was found unexpectedly that the present compounds have significant inhibitory effect on the growth of MFM-223, MDA-MB-453, JIMT-1 and Kcl22 cells, and the IC$_{50}$ is in the range of nanomolar concentration. In these cell lines, besides expressing FGFR1, 2, 4 and BCR-ABL genes, they also expressed the different PI3KCA mutations, respectively, i.e. MFM-223 and MDA-MB-453 expressing PI3KCA H1047R, JIMT-1 expressing PI3KCA C420R and Kcl22 expressing PI3KCA E545G. Thus, the growth inhibition of the present compounds on the other different tumor cells with PI3KCA gene amplification/high expression or mutation was further determined. The specific experimental methods are the same as test example 1. The experimental results are shown in table 6 below.

TABLE 6

IC$_{50}$ values of the inhibition of the present compounds on the growth of different tumor cells with PI3KCA gene amplification/high expression or mutation

| Cell line | PI3KCA genotype | Other genotype | Compound IC$_{50}$ (nM) | | | BAY 80-6946 |
|---|---|---|---|---|---|---|
| | | | 66 | 38 | 95 | |
| KYSE70 | PI3KCA amp | KIT G779C | 29.6 | 9.7 | 18.9 | 19.7 |
| A2780 | PIK3CA E365K | | 7.68 | 9.1 | 9.2 | 9.67 |
| HCT-116 | PI3KCA H1047R | KRAS G13D | 26.7 | 11.9 | 33.2 | 65.1 |
| HGC-27 | PI3KCA H1047R | FGFR1OP2+++ | 39.9 | 19.2 | 30.9 | 17.3 |
| AGS | PI3KCA E453K/E545A | KRAS G12D | 43.5 | 41.1 | 39.9 | 39.5 |
| NCI-H460 | PI3KCA E545K | KRAS Q61H | 26.2 | 25.7 | 34.5 | 30.4 |
| HCC1954 | PI3KCA H1047R | HER2 amp | 37.5 | 11.8 | 9.94 | 6.8 |
| SK-OV-3 | PI3KCA H1047R | HER2 amp | 42.3 | 32.3 | 26.4 | 10.18 |
| SW48 | PI3KCA G914R | EGFR G719S | 28.2 | 13.6 | 41.9 | 27.5 |

The results in table 6 show that the present compounds can inhibit the growth of tumor cells with PI3KCA gene amplification/high expression or mutation in vitro, and its inhibitory concentration (IC$_{50}$) is in the same range as the control compound BAY 80-6946 (PI3Kα/β/γ/δ inhibitor).

Test Example 5 Synergistic Inhibition Effect of the Present Compounds in Combination with MEK1/2 Inhibitor on the Growth of RAS Mutant Tumor Cells In Vitro The cell culture, drug treatment and MTT assay of human intestinal cancer cell line HCT116 (KRAS G13D mutation) and human non-small cell lung cancer cell line NCI-H1299 (NRAS Q61K mutation) were performed according to the method of test example 1. Cells were treated with the MEK1/2 inhibitor Trametinib at 25 nM, 2.5 nM and 0.25 nM alone or in combination with compound 66 or 125 of the present invention (5 days). The results of cell growth inhibition (percentage) are shown in table 7 below.

TABLE 7

The synergistic inhibition effect of the present compounds in combination with MEK1/2 inhibitor on the growth of RAS mutant cells in vitro

| Cell line | Compound | | Trametinib | | |
|---|---|---|---|---|---|
| | | Solvent | 25 nM | 2.5 nM | 0.25 nM |
| HCT116 | — | Solvent | 0 | 75.12 | 27.74 | 12.11 |
| | 66 | 15.6 nM | 21.98 | 81.03 | 77.07 | 66.72 |
| | | 7.8 nM | 7.67 | 80.52 | 73.79 | 62.24 |
| | 125 | 15.6 nM | 19.89 | 82.82 | 79.72 | 71.98 |
| | | 7.8 nM | 14.47 | 82.04 | 76.01 | 62.54 |
| H1299 | — | Solvent | 0 | 15.5 | 6.31 | 2.20 |
| | 66 | 15.6 nM | 4.59 | 42.52 | 26.10 | 16.82 |
| | | 7.8 nM | 1.39 | 37.88 | 20.73 | 11.67 |
| | 125 | 15.6 nM | 6.50 | 58.26 | 34.72 | 19.92 |
| | | 7.8 nM | 1.63 | 46.25 | 24.38 | 9.27 |

The results in table 7 show that the present compounds and MEK1/2 inhibitor can synergistically inhibit the growth of RAS mutant tumor cells in vitro.

Test Example 6 Determination of Binding Affinity of the Present Compounds on Protein Kinases In Vitro KINOMEscan screening platform of Discovery X company (USA) was used to identify the binding targets of the present compounds to protein kinases. Compound 66 of the present invention was dissolved in DMSO (Sigma Aldrich) at concentrations of 1000 nM, 10 nM and 1 nM, and then was subjected to in vitro binding reaction with 468 labeled protein kinases. Two samples were taken in parallel for each assay sample.

Table 8 shows the protein kinases screened by KINOMEscan which has high binding affinity to compound 66 of the present invention. The lower the percentage of the test compound to the solvent control, the stronger the binding affinity of the test compound to the protein kinase in vitro.

TABLE 8

The protein kinases capable of showing high binding affinity to compound 66 of the present invention

| | Test compound/solvent control (%) The concentration of compound 66 of the present invention | | |
|---|---|---|---|
| Protein kinase | 1 nM | 10 nM | 1000 nM |
| ABL1(E255K)-phosphorylated | 50 | 7.6 | 0.1 |
| ABL1(F317I)-unphosphorylated | 83 | 17 | 0.25 |
| ABL1(F317I)-phosphorylated | 100 | 31 | 15 |
| ABL1(F317L)-unphosphorylated | 49 | 6.8 | 0.25 |
| ABL1(F317L)-phosphorylated | 55 | 3.7 | 1.1 |
| ABL1(H396P)-unphosphorylated | 27 | 1.8 | 0.05 |
| ABL1(H396P)-phosphorylated | 55 | 9.7 | 0 |
| ABL1(M351T)-phosphorylated | 100 | 22 | 0.65 |
| ABL1(Q252H)-unphosphorylated | 48 | 7.8 | 0 |
| ABL1(Q252H)-phosphorylated | 71 | 12 | 0.15 |
| ABL1(T315I)-unphosphorylated | 96 | 32 | 0.15 |
| ABL1(T315I)-phosphorylated | 100 | 34 | 0.45 |
| ABL1(Y253F)-phosphorylated | 80 | 11 | 0.1 |
| ABL1-unphosphorylated | 41 | 8.3 | 0 |
| ABL1-phosphorylated | 49 | 9.9 | 0.1 |
| AXL | 53 | 7.2 | 4.1 |
| EGFR | 100 | 26 | 0 |
| EGFR(E746-A750del) | 60 | 18 | 2.8 |
| EGFR(G719C) | 83 | 30 | 0.2 |
| EGFR(G719S) | 77 | 18 | 0 |
| EGFR(L747-E749del, A750P) | 92 | 11 | 0 |
| EGFR(L747-S752del, P753S) | 67 | 16 | 1.6 |
| EGFR(L747-T751del, Sins) | 68 | 11 | 2.7 |
| EGFR(L858R) | 87 | 28 | 0 |
| EGFR(L858R,T790M) | 64 | 21 | 0.7 |

TABLE 8-continued

The protein kinases capable of showing high binding affinity
to compound 66 of the present invention

| Protein kinase | Test compound/solvent control (%) The concentration of compound 66 of the present invention | | |
|---|---|---|---|
|  | 1 nM | 10 nM | 1000 nM |
| EGFR(L861Q) | 73 | 9.5 | 0 |
| EGFR(S752-1759del) | 90 | 29 | 0 |
| EGFR(T790M) | 83 | 19 | 0.2 |
| FGFR1 | 56 | 4.5 | 0.3 |
| FGFR2 | 93 | 71 | 0.25 |
| FGFR3 | 100 | 82 | 0.2 |
| FGFR3(G697C) | 81 | 54 | 0.05 |
| FGFR4 | 93 | 74 | 0 |
| FLT3 | 92 | 20 | 1.9 |
| FLT3(D835H) | 79 | 15 | 1.1 |
| FLT3(K663Q) | 89 | 22 | 3.2 |
| FLT3(N841I) | 88 | 17 | 0.25 |
| FLT3(R834Q) | 83 | 45 | 0.6 |
| FYN | 94 | 41 | 0 |
| HCK | 60 | 1.7 | 0 |
| KIT | 90 | 27 | 0 |
| KIT(A829P) | 84 | 22 | 0 |
| KIT(L576P) | 95 | 32 | 0 |
| KIT(V559D) | 82 | 18 | 0 |
| LCK | 33 | 0.65 | 0.2 |
| LOK | 57 | 1.3 | 0 |
| MERTK | 57 | 4.1 | 0.65 |
| PDGFRA | 88 | 34 | 0.15 |
| PDGFRB | 81 | 6.2 | 0 |
| RET | 85 | 17 | 0 |
| RET(M918T) | 78 | 8.5 | 0 |
| RET(V804L) | 88 | 17 | 0 |
| RET(V804M) | 100 | 34 | 0 |
| ROS1 | 85 | 17 | 4.6 |
| SRC | 36 | 1.4 | 0.1 |
| TIE1 | 41 | 21 | 2 |
| TIE2 | 59 | 3.8 | 0.95 |
| TNIK | 44 | 6.4 | 7 |
| TRKA (NTRK1) | 48 | 5.5 | 0.2 |
| TRKB (NTRK2) | 65 | 12 | 0.35 |
| TRKC (NTRK3) ) | 84 | 28 | 0.2 |

The results in table 8 show that the present compounds exhibit strong in vitro binding affinity to a variety of protein kinases, and their concentration can be less than 1 nM.

Test Example 7 Inhibition of Tumour Cell Growth In Vivo

In order to establish subcutaneous transplantation tumor models of human non-small cell lung cancer and endometrial adenocarcinoma, Bab/c immunodeficient mice were subcutaneously inoculated with NCI-H1581 (ATCC) and AN3-CA (ATCC) cells, respectively.

Experimental animals: 6-week female Bab/c immunodeficient mice (about 20 g in weight). The mice were purchased from Shanghai Sippr-BK Experimental Animal Co., Ltd., raised in Animal Center of Shanghai University of Traditional Chinese Medicine, approved by Ethical Committee of Shanghai University of Traditional Chinese Medicine. The breeding environment was SPF grade.

Test samples: the present compounds 66 (purity: 99%), solid powder, stored at 4~8° C.

Cells and animal models: NCI-H1581 cells were cultured in RPMI 1640 medium containing 10% fetal bovine serum. Log-phase NCI-H1581 cells were collected and re-suspended with PBS to $2.5 \times 10^7$ cells per ml for subcutaneous single-point inoculation of Bab/c immunodeficient mice at the right side of the back of mouse ($5 \times 10^6$ cells, 0.2 ml).

AN3-CA cells were cultured in MEM medium containing 10% fetal bovine serum. Log-phase AN3-CA cells were collected and re-suspended with PBS to $5 \times 10^7$ cells per ml for subcutaneous single-point inoculation of Bab/c immunodeficient mice at the right side of the back of mouse ($1 \times 10^7$ cells, 0.2 ml).

When the tumor volume reached 100~200 mm$^3$, the mice were randomly divided according to tumor size. The experiment was divided into solvent control group and drug administration group (compound 66 group). 6 mice in each group were administered 0.1 ml per 10 g body weight by intraperitoneal injection (i.p) once a day. The tumor was measured three times a week, and the tumor volume was calculated as: long diameter×short diameter$^2$/2. When the average tumor volume of the control group reached 2000 mm$^3$, the experiment was over and then the tumor was weighed and subjected to molecular pathology assay. Efficacy was assessed based on relative tumor growth inhibition value (TGI), and safety was assessed based on animal weight change.

Preparation of test samples: appropriate amount of compound 66 was weighed and mixed with ultrapure water; and methanesulfonic acid was added for clarification; and then 4M NaOH was added to adjust the PH to 3.8; and a final volume was made up with ultrapure water. The final concentrations were 0.5 mg/ml and 0.25 mg/ml, respectively.

Result judgment standard: relative tumor growth inhibition value TGI (%), i.e. TGI=1−T/C (%).

T/C % refers to the relative tumor growth rate, that is, the percentage of relative tumor volume or tumor weight of the administration group and the control group at a certain time point. T and C were the relative tumor volumes (RTV) of the administration group and the control group at a specific time point, respectively. The calculation formula is as follows:

$$T/C\% = T_{RTV}/C_{RTV} \times 100\%$$

$T_{RTV}$: mean RTV of the administration group; $C_{RTV}$: mean RTV of solvent control group; RTV=$V_t/V_0$, $V_0$ is the tumor volume of the animal when grouping, $V_t$ is the tumor volume of the animal after treatment.

Statistical analysis: all test results were showed as mean tumor volume±SEM (mean standard error). Tumor volume data of 17 days after the start of administration were selected for statistical analysis among different groups, and independent sample T test was used to compare whether there were significant differences in relative tumor volume between the administration group and the control group. All data were analyzed using SPSS 18.0. P<0.05 was considered as significant difference.

TABLE 9

TGI and T/C values of each group on the 17th day after the administration

| Tumor model | Compound dose (mg/kg) | Administration method | TGI (%) | T/C (%) | P value (Compared to the control group) |
|---|---|---|---|---|---|
| NCI-H1581 | 5 | i.p | 98.93 | 1.07 | 0.0039 |
|  | 2.5 | i.p | 92.09 | 7.91 | 0.0049 |
| AN3-CA | 5 | i.p | 98.63 | 1.37 | 0.0051 |

Conclusion: The results in table 9 show that the present compound can inhibit the growth of human non-small cell lung cancer cell NCI-H1581 effectively in Bab/c immuno-deficient mouse subcutaneous transplantation tumor model at the doses of 5 mg/kg and 2.5 mg/kg, respectively. At a test dose of 5 mg/kg, the present compound can also effectively inhibit the growth of human endometrial adenocarcinoma AN3-CA effectively in Bab/c immunodeficient mouse subcutaneous transplantation tumor model.

At doses of 5 mg/kg and 2.5 mg/kg, the present compound maintains a stable weight during the administration of mice, and the drug is well tolerated.

What is claimed is:

1. A compound of general formula (I) or a pharmaceutically acceptable salt, solvate, or metabolite thereof,

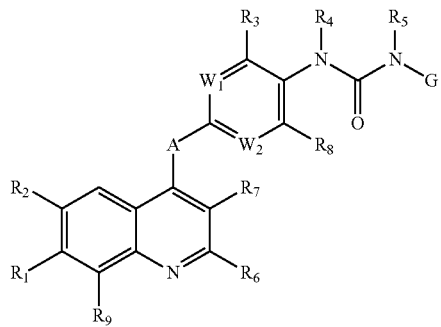

wherein:

A is O;

$W_1$ and $W_2$ are each independently $CR_3$;

$R_1$ is selected from the group consisting of H and $OR_{10}$;

$R_{10}$ is selected from the group consisting of hydrogen, alkyl, alkenyl, alkynyl, cycloalkyl, —R"OR$^x$, —R"N(R$^y$)(R$^z$), —R"S(O)$_n$N(R$^y$)(R$^z$) and —R"S(O)$_n$R$^x$; wherein the alkyl, alkenyl, alkynyl and cycloalkyl are each independently and optionally further substituted with one or more groups selected from the group consisting of halogen, cyano, hydroxyl, amino and alkyl;

$R_2$ is selected from the group consisting of Q groups and the following structures:

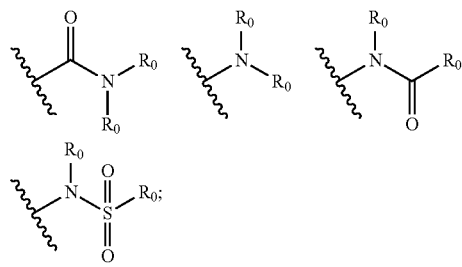

$R_0$ is identical or different and each independently selected from the group consisting of hydrogen, alkyl, cycloalkyl, alkenyl and alkynyl, wherein the alkyl is optionally substituted with one or more alkoxy groups;

$R_3$ and $R_8$ are each independently selected from the group consisting of halogens, —N(R$^y$)(R$^z$) and Q groups;

$R_4$ is selected from the group consisting of hydrogen, alkyl, alkoxy and cycloalkyl;

$R_6$ is selected from the group consisting of hydrogen, halogen, alkyl, haloalkyl, alkoxy, —OR"OR$^x$, —OR"(R$^y$)(R$^z$) and —N(R$^y$)(R$^z$);

$R_7$ is selected from the group consisting of hydrogen, halogen, alkyl and cyano;

$R_9$ is selected from the group consisting of hydrogen, halogen, alkyl and haloalkyl;

$R_5$ is selected from the group consisting of hydrogen, alkyl, alkoxy and cycloalkyl;

and G is

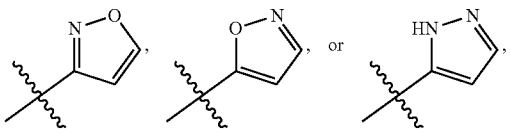 [SMILES: *c1ccon1 ; *c1ccno1 ; *c1ccn[nH]1]

which are each independently substituted with one or more groups selected from the group consisting of halogen, alkyl, alkenyl, alkynyl, alkoxy, hydroxyl, amino, acyl, cycloalkyl, heterocyclyl, aryl, heteroaryl and

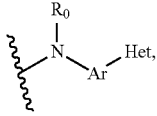

wherein the alkyl, alkenyl, alkynyl, alkoxy, acyl, cycloalkyl, heterocyclyl, aryl and heteroaryl are each independently and optionally substituted with one or more groups selected from the group consisting of halogen, alkyl haloalkyl, alkenyl, alkynyl, aryl, hydroxyl, alkoxy, haloalkoxy, —N(R$^y$) (R$^z$), cycloalkyl, heterocyclyl, ester and cyano groups; or $R_5$ and G are taken together with the nitrogen atom to which they are attached to form a heterocyclyl or heteroaryl group, wherein the heterocyclyl and heteroaryl are each independently and optionally substituted with one or more groups selected from the group consisting of halogen, alkyl, alkenyl, alkynyl, alkoxy, hydroxyl, amino, cycloalkyl, heterocyclyl, aryl and heteroaryl, wherein the alkyl, alkenyl, alkynyl, alkoxy, cycloalkyl, heterocyclyl, aryl and heteroaryl are each independently and optionally substituted with one or more groups selected from the group consisting of halogen, alkyl, haloalkyl, alkenyl, alkynyl, aryl, hydroxyl, alkoxy, haloalkoxy, cycloalkyl, ester, and cyano;

Ar is an aryl group optionally substituted with one or more $R_0$;

Het is a heterocyclyl group optionally substituted with one or more $R_0$;

R" is selected from the group consisting of a bond, alkylene, alkenylene and alkynylene;

R$^x$ is selected from the group consisting of hydrogen, alkyl, cycloalkyl, hydroxyalkyl, haloalkyl, alkenyl and alkynyl; or R"OR$^x$ together form an oxygen-containing 3-7 membered heterocyclic ring, which is optionally substituted with one or more groups selected from the group consisting of halogen, haloalkyl, alkyl, aryl, alkenyl, and alkynyl;

R$^y$ and R$^z$ are each independently selected from the group consisting of hydrogen, alkyl, alkoxy, aryl, alkenyl, alkynyl, cycloalkyl, haloalkoxy and haloalkyl; or R$^y$ and R$^z$ are taken together with the nitrogen atom to which they are attached to form heterocyclyl or heteroaryl, wherein the heterocyclyl and heteroaryl are each independently and optionally substituted with one or more groups selected from the group consisting of halogen, haloalkyl, alkyl, aryl, acyl, alkenyl and alkynyl, wherein the alkyl is optionally substituted with one or more groups selected from the group consisting of alkoxy and cycloalkyl group;

Q is selected from the group consisting of hydrogen, hydroxyl, alkyl, alkoxy, cycloalkyl, alkenyl, alkynyl, cyano, nitro, aryl, heterocyclyl and heteroaryl; wherein the alkyl, alkoxy, cycloalkyl, alkenyl, alkynyl, aryl, heterocyclyl and heteroaryl are each independently and optionally substituted with one or more groups selected from the group consisting of hydroxyl, halogen and alkyl;

n is 0, 1, or 2.

2. The compound of general formula (I) or a pharmaceutically acceptable salt, solvate, or metabolite thereof according to claim 1, wherein $W_1$ and $W_2$ are each independently $CR_3$, and $R_3$ is selected from the group consisting of hydrogen, alkyl and halogen.

3. The compound of general formula (I) or a pharmaceutically acceptable salt, solvate, or metabolite thereof according to claim 1, wherein $R_2$ is selected from the group consisting of Q group and the following structure:

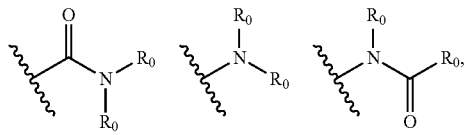

Q is selected from the group consisting of hydrogen, cyano, nitro, $C_1$-$C_6$ alkyl, $C_1$-$C_6$ haloalkyl, $C_1$-$C_6$ alkoxy, $C_1$-$C_6$ haloalkoxy, $C_3$-$C_7$ cycloalkyl, $C_5$-$C_7$ aryl, 5 to 7 membered heterocyclyl and 5 to 7 membered heteroaryl;

$R_0$ is as defined in claim 1.

4. The compound of general formula (I) or a pharmaceutically acceptable salt, solvate, or metabolite thereof according to claim 1, wherein $R_3$ and $R_8$ are each independently selected from the group consisting of hydrogen, halogen, alkyl, alkoxy, haloalkoxy and —N($R^y$)($R^z$) $R^y$ and $R^z$ are as defined in claim 1.

5. The compound of general formula (I) or a pharmaceutically acceptable salt, solvate, or metabolite thereof according to claim 1, wherein $R_4$ is selected from the group consisting of hydrogen, alkyl and alkoxy.

6. The compound of general formula (I) or a pharmaceutically acceptable salt, solvate, or metabolite thereof according to claim 1, wherein $R_6$ is selected from the group consisting of hydrogen, halogen, alkyl and alkoxy.

7. The compound of general formula (I) or a pharmaceutically acceptable salt, solvate, or metabolite thereof according to claim 1, wherein $R_7$ is selected from the group consisting of hydrogen and cyano.

8. The compound of general formula (I) or a pharmaceutically acceptable salt, solvate, or metabolite thereof according to claim 1, wherein:

$R_1$ is $OR_{10}$, $R_{10}$ is selected from the group consisting of hydrogen, $C_1$-$C_6$ alkyl, —$R^u OR^x$ and —$R^u N(R^y)(R^z)$, $R^u$ is $C_1$-$C_6$ alkylene, $R^x$ is selected from the group consisting of hydrogen, $C_1$-$C_6$ alkyl, $C_1$-$C_6$ hydroxyalkyl and $C_1$-$C_6$ haloalkyl, $R^y$ and $R^z$ are each independently selected from the group consisting of hydrogen, $C_1$-$C_6$ alkyl, $C_1$-$C_6$ alkoxy, $C_1$-$C_6$ haloalkyl, $C_1$-$C_6$ haloalkoxy and $C_3$-$C_7$ cycloalkyl; or $R^y$ and $R^z$ are taken together with the nitrogen atom to which they are attached to form 5 to 7 membered heterocyclyl or heteroaryl group; wherein the 5 to 7 membered heterocyclyl and heteroaryl are each optionally substituted with one or more groups selected from the group consisting of halogen, acyl, $C_1$-$C_6$ alkyl, $C_1$-$C_6$ haloalkyl and $C_6$-$C_{10}$ aryl, wherein the $C_1$-$C_6$ alkyl is optionally substituted with one or more groups selected from the group consisting of $C_1$-$C_6$ alkoxyl and $C_3$-$C_7$ cycloalkyl.

9. The compound of general formula (I) or a pharmaceutically acceptable salt, solvate, or metabolite thereof according to claim 1, wherein:

$R_5$ is selected from the group consisting of hydrogen and alkyl; and G is

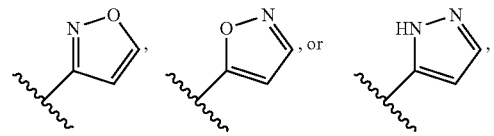 [SMILES: *c1ccon1 ; *c1ccno1 ; *c1ccn[nH]1]

which are each independently substituted with one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxyl, amino, acyl, $C_3$-$C_7$ cycloalkyl, 5 to 7 membered heterocyclyl, $C_5$-$C_7$ aryl and 5 to 7 membered heteroaryl groups, wherein the acyl, $C_1$-$C_6$ alkyl, $C_1$-$C_6$ alkoxy, $C_3$-$C_7$ cycloalkyl, 5 to 7 membered heterocyclyl, $C_5$-$C_7$ aryl and 5 to 7 membered heteroaryl are each independently and optionally substituted with one or more groups selected from the group consisting of halogen, $C_2$-$C_6$ alkenyl, hydroxyl, $C_1$-$C_6$ alkyl, $C_1$-$C_6$ alkoxy, $C_1$-$C_6$ haloalkyl, —N($R^y$)($R^z$), $C_1$-$C_6$ haloalkoxy, 5 to 7 membered heterocyclyl, esters and cyano; or, $R_5$ and G are taken together with the nitrogen atom to which they are attached to form 5 to 7 membered heterocyclyl or 5 to 7 membered heteroaryl groups, wherein the 5 to 7 membered heterocyclyl or 5 to 7 membered heteroaryl are each independently or optionally substituted with one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxyl, amino, $C_3$-$C_7$ cycloalkyl, 5 to 7 membered heterocyclyl, $C_5$-$C_7$ aryl and 5 to 7 membered heteroaryl;

$R^y$ and $R^z$ are each independently selected from the group consisting of hydrogen, $C_1$-$C_6$ alkyl, and $C_1$-$C_6$ haloalkyl group; or $R^y$ and $R^z$ are taken together with the nitrogen atom to which they are attached to form 5 to 7 membered heterocyclyl or 5 to 7 membered heteroaryl groups, wherein the 5 to 7 membered heterocyclyl or 5 to 7 membered heteroaryl are each independently and optionally substituted with one or more groups selected from the group consisting of halogen, $C_1$-$C_6$ haloalkyl and $C_1$-$C_6$ alkyl.

10. A compound is selected from the group consisting of:
1
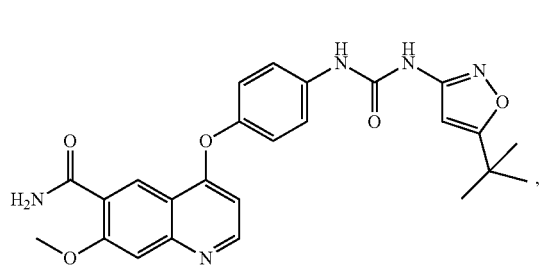
2
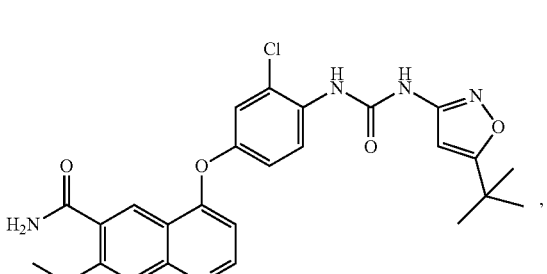
3
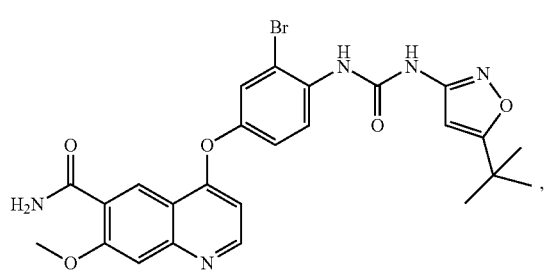
4
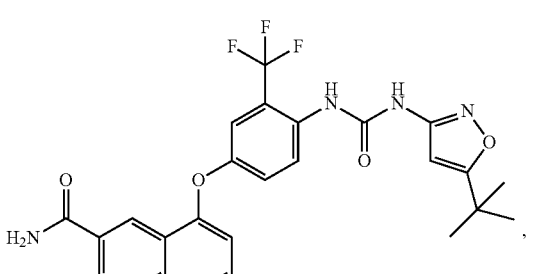
5
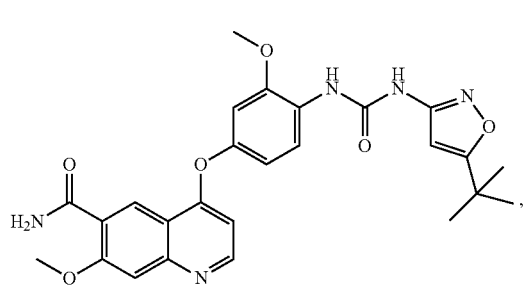
6
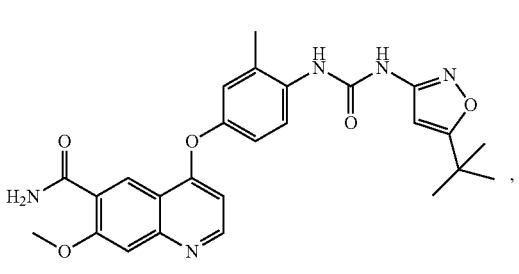
7
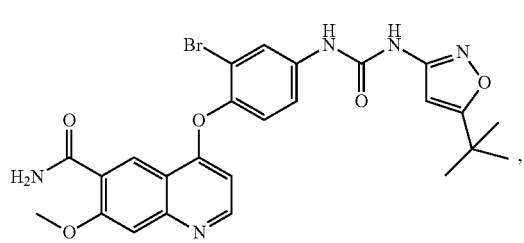
8
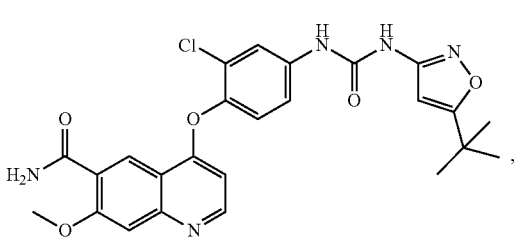
9
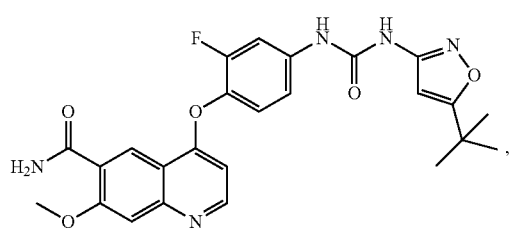
10
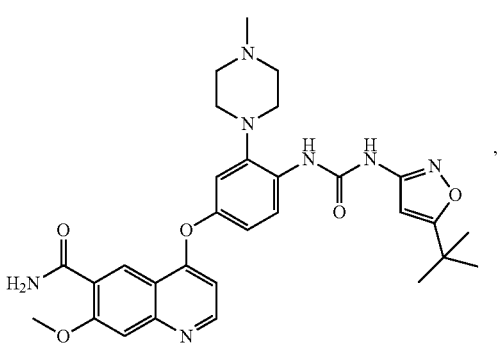

-continued
11
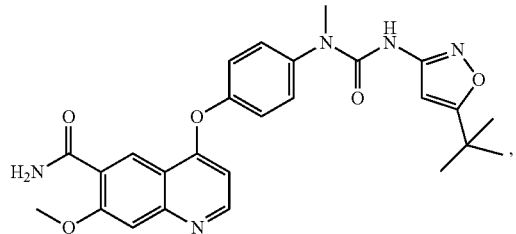
12
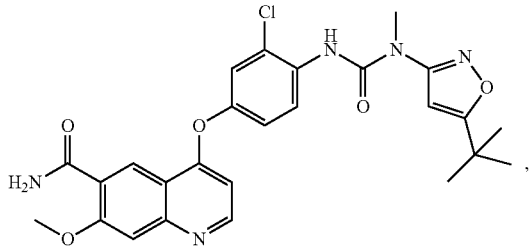
13
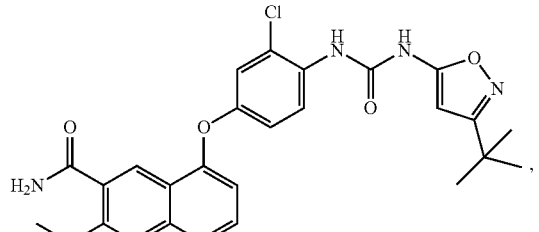
14
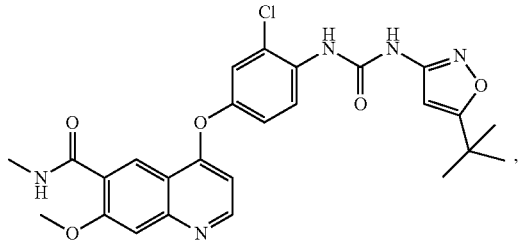
15
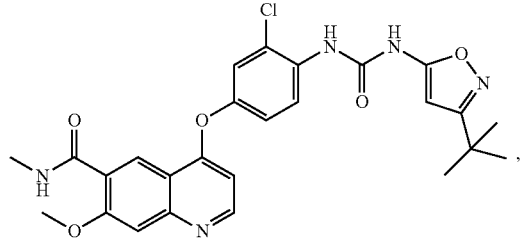
16
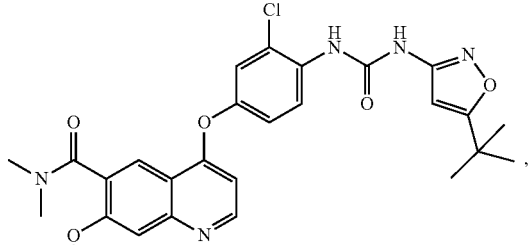
17
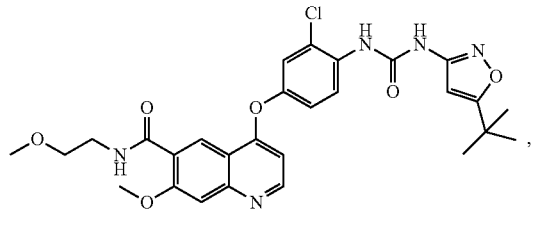
18
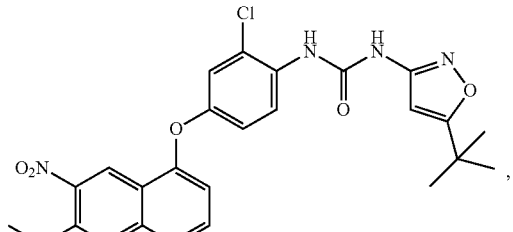
19
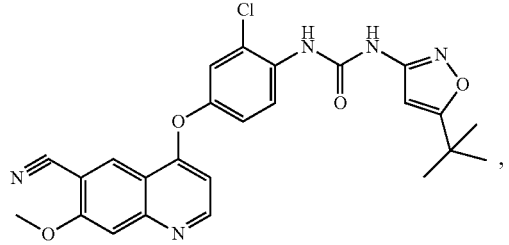
20
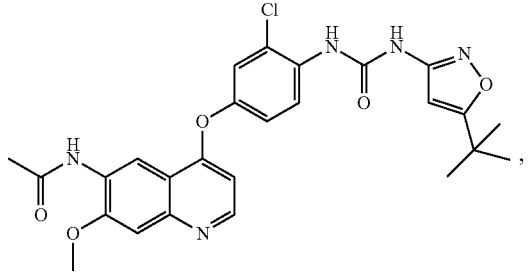
21
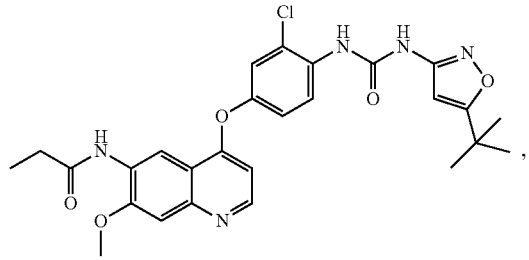
22
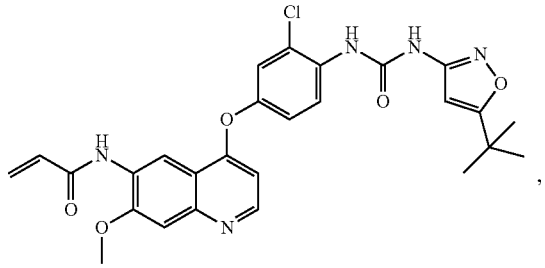

23 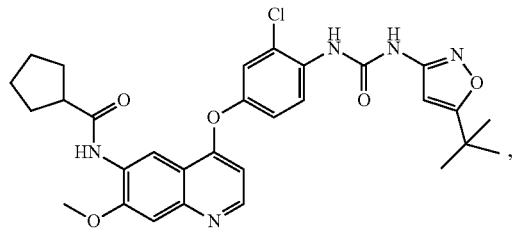
24 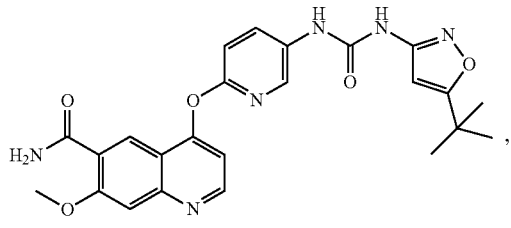
25 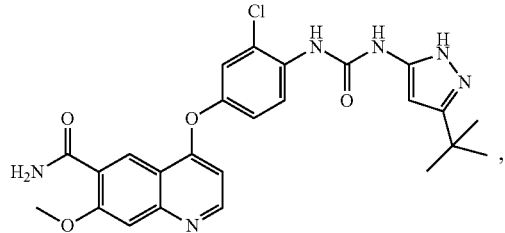
26 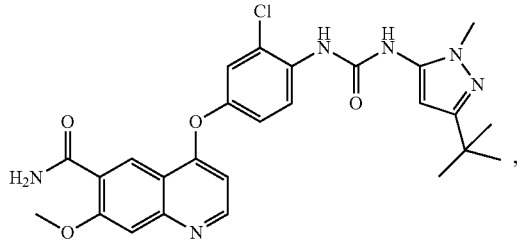
27 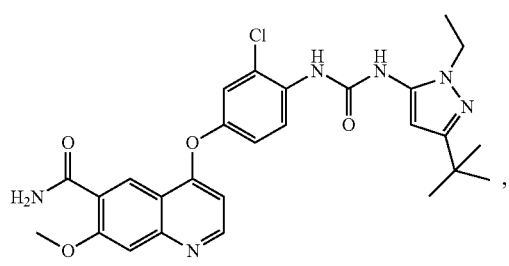
28 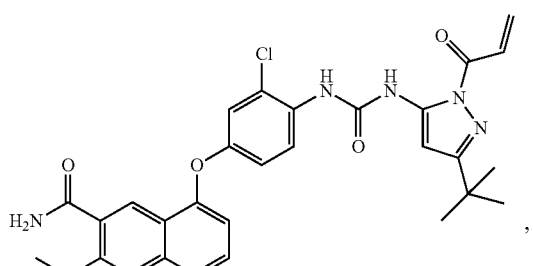
29 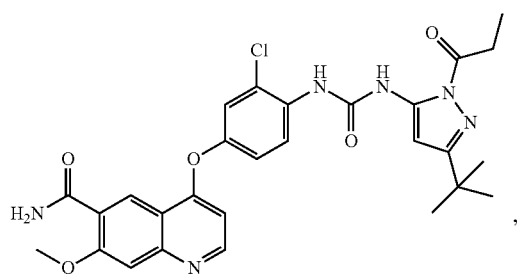
30 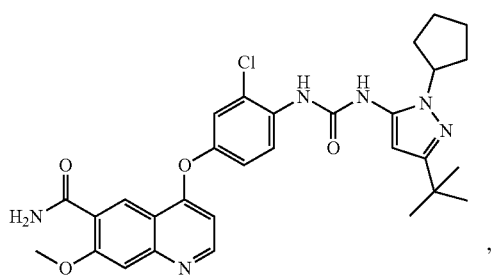
31 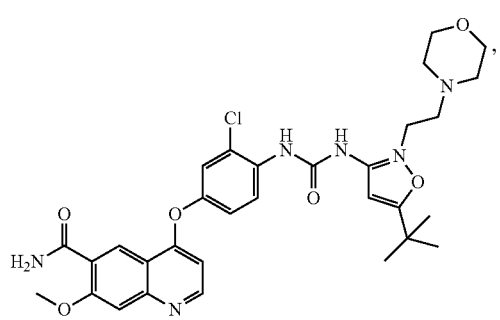
32 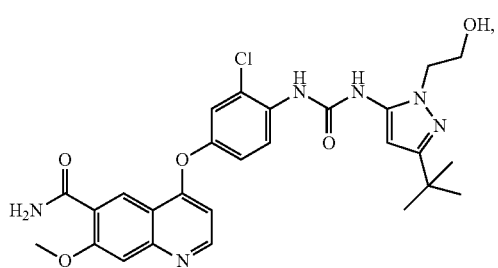

33
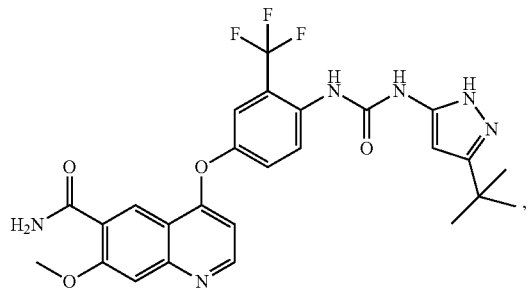
34
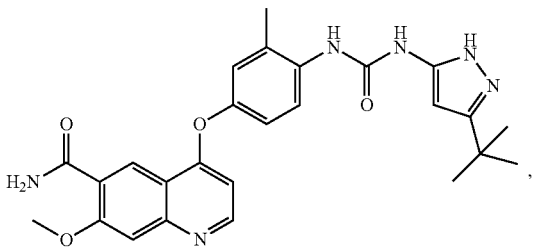
35
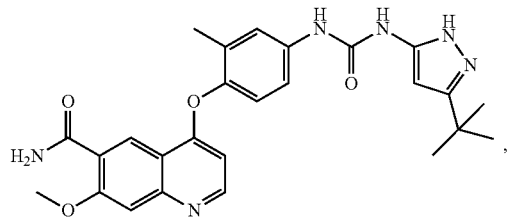
36
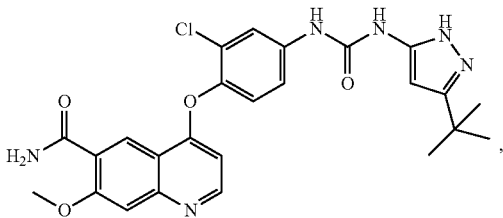
37
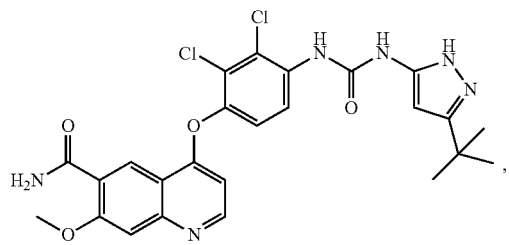
38
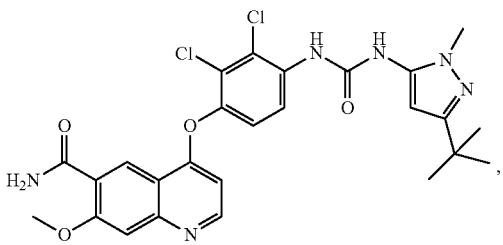
39
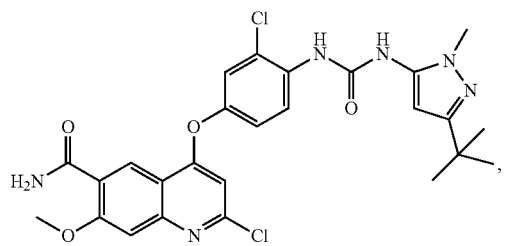
40
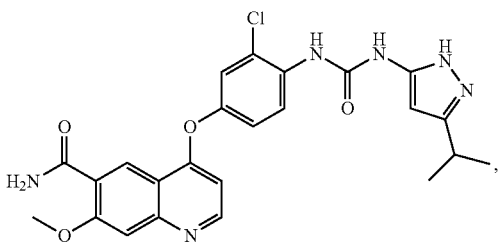
41
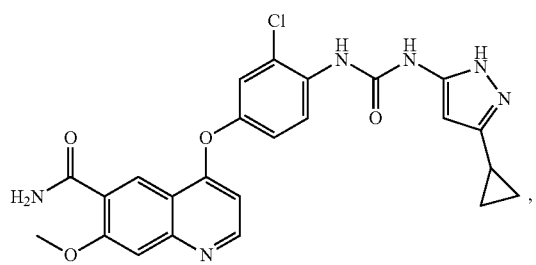
42
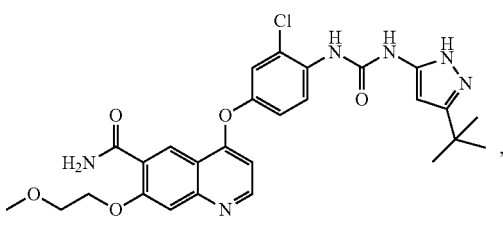
43
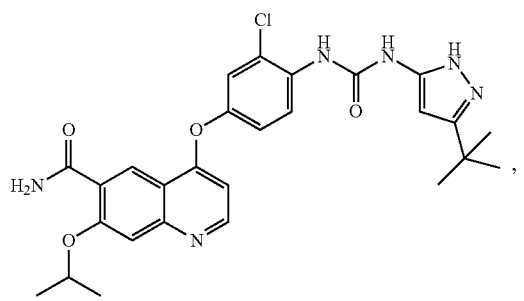
44
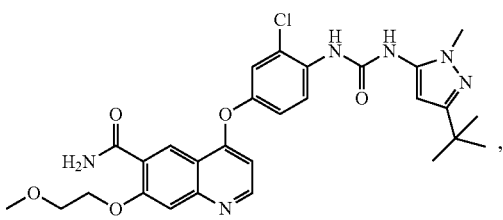

-continued
| | |
|---|---|
| 45 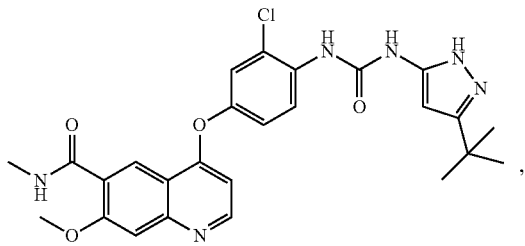 | 46 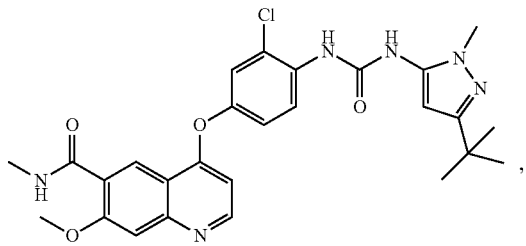 |
| 47 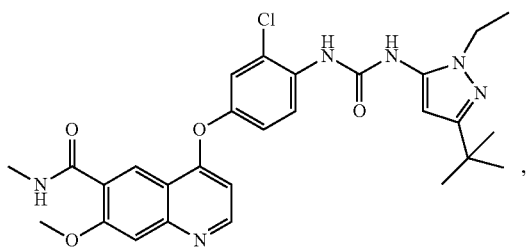 | 48 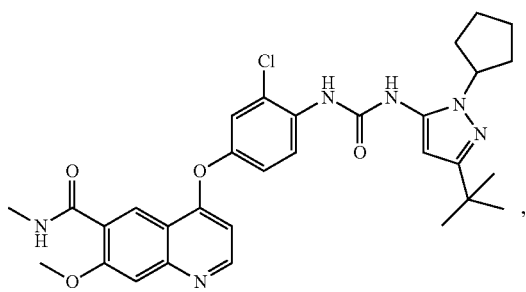 |
| 49 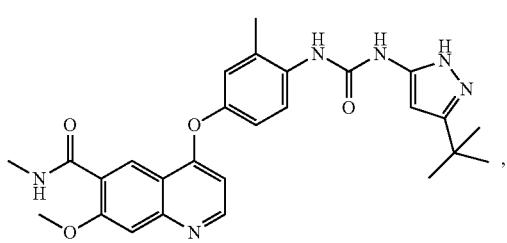 | 50 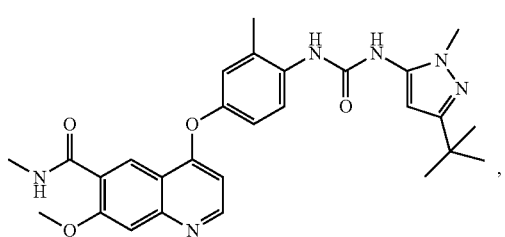 |
| 51 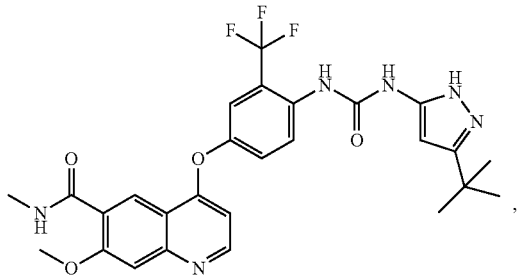 | 52 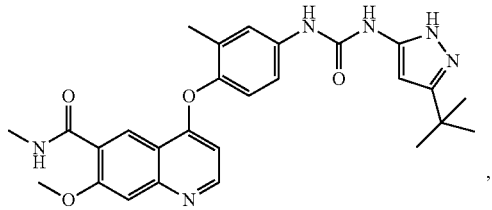 |
| 53 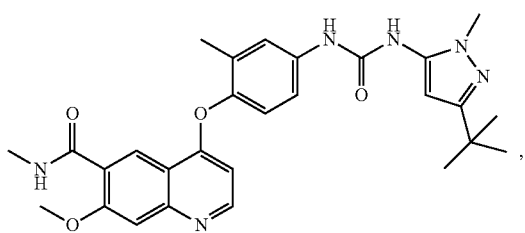 | 54 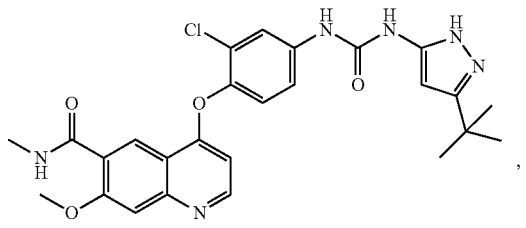 |
| 55 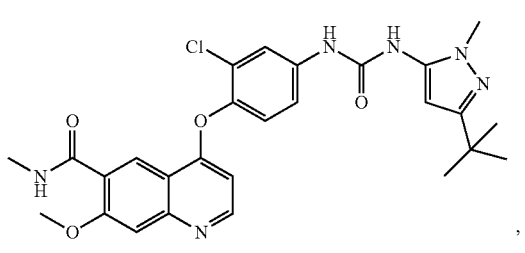 | 56 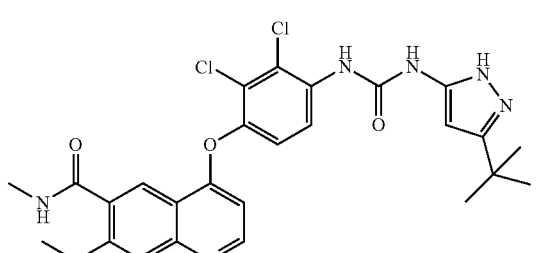 |

57
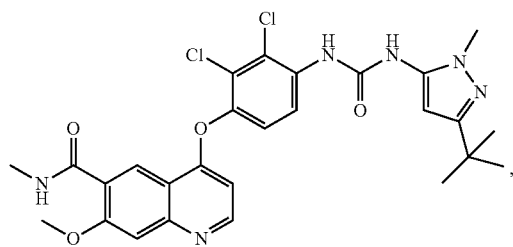
58
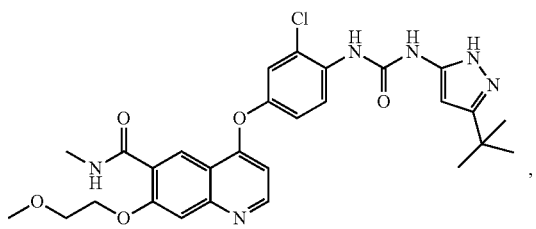
59
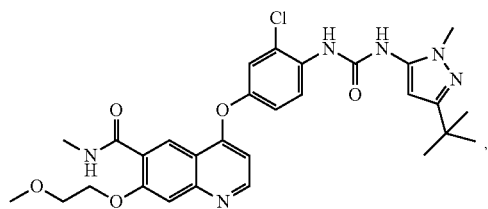
60
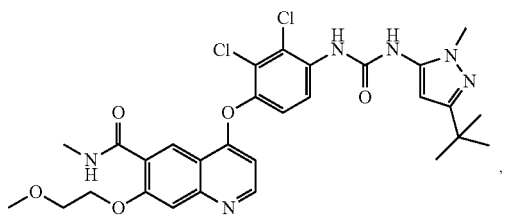
61
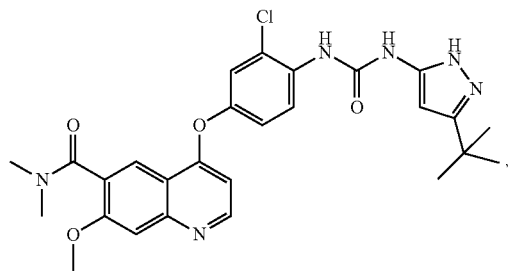
62
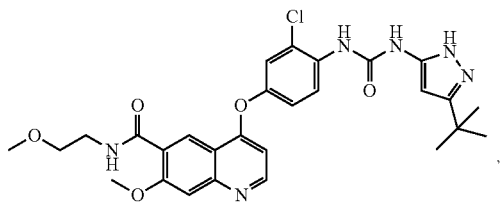
63
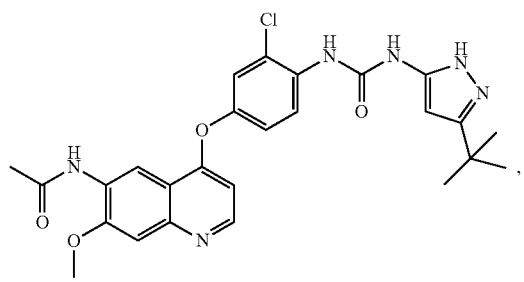
64
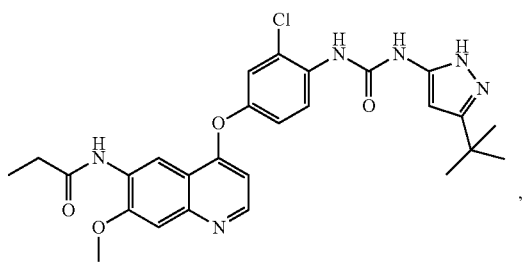
65
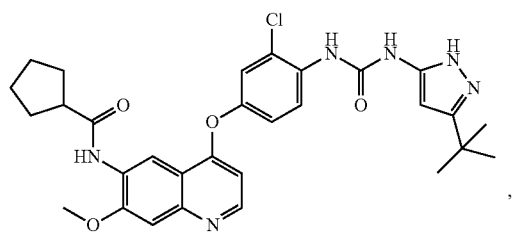
66
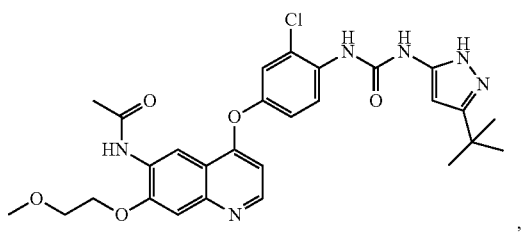

-continued
67
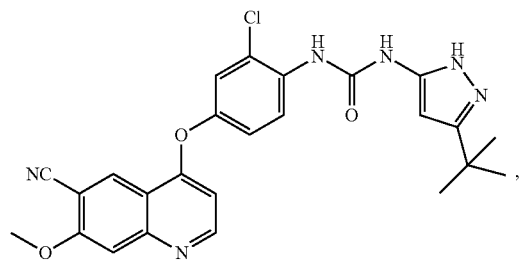
68
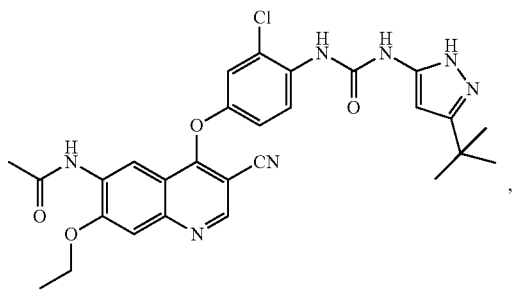
69
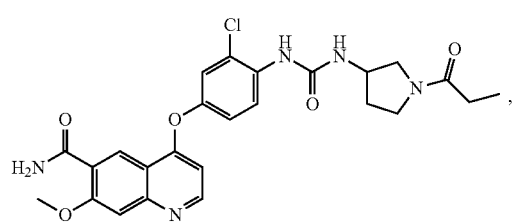
70
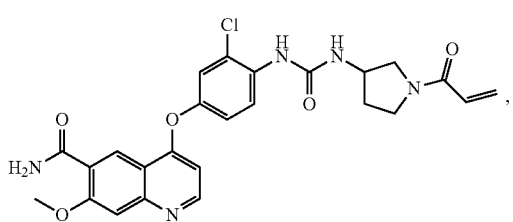
71
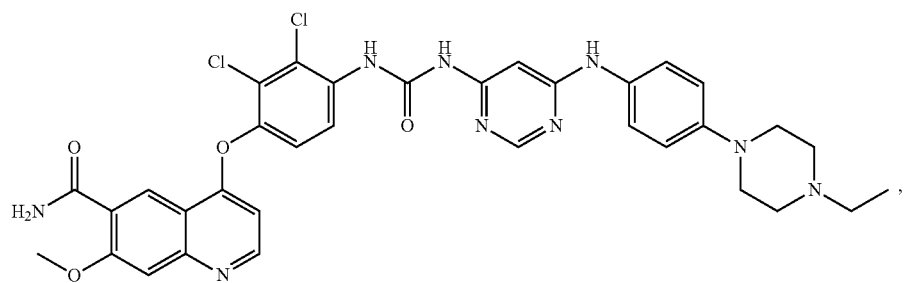
72
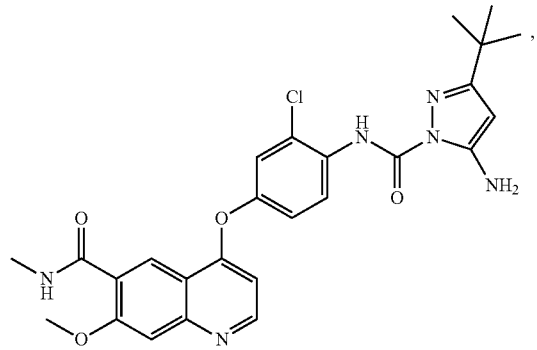
73
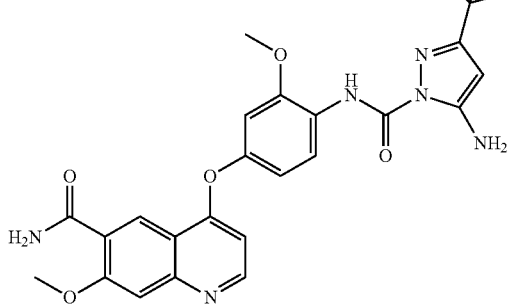
74
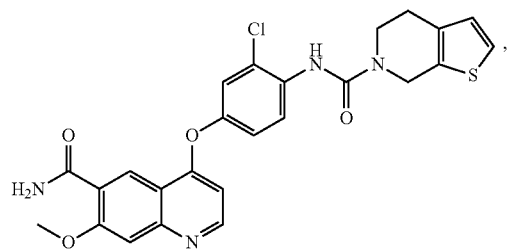
75
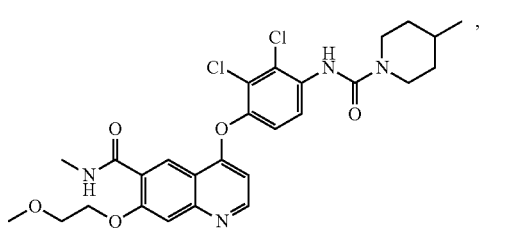

76
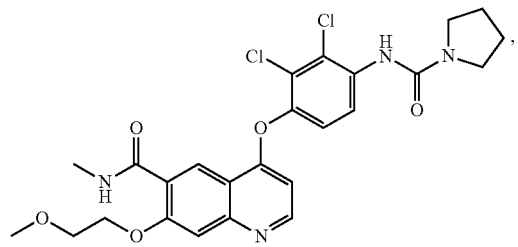
77
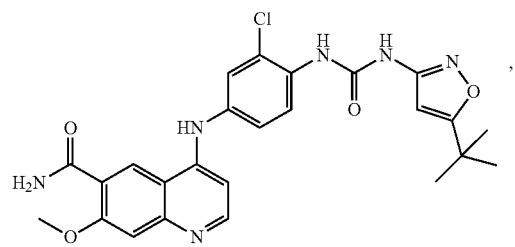
78
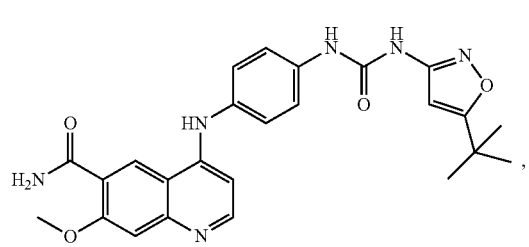
79
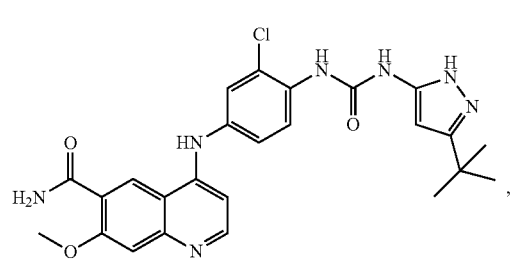
80
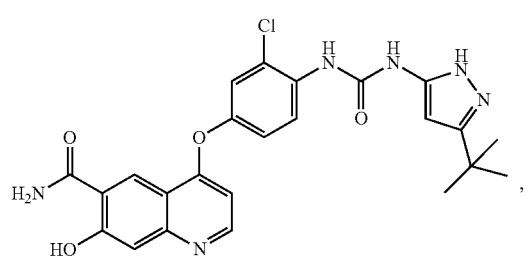
81
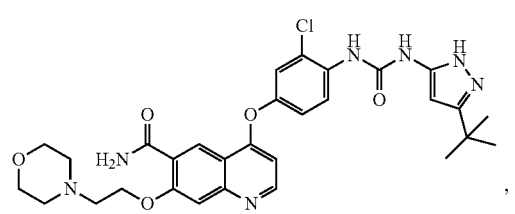
82
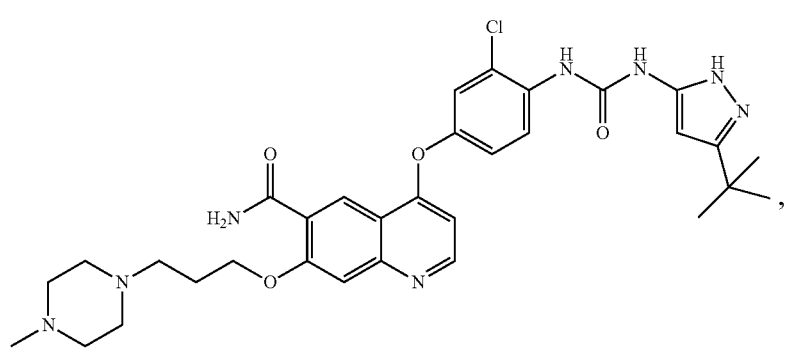
83
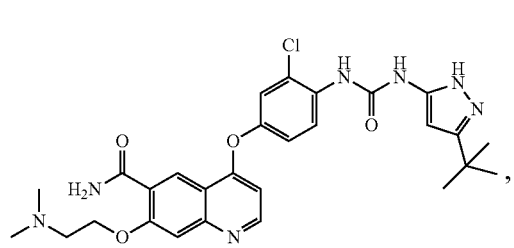
84
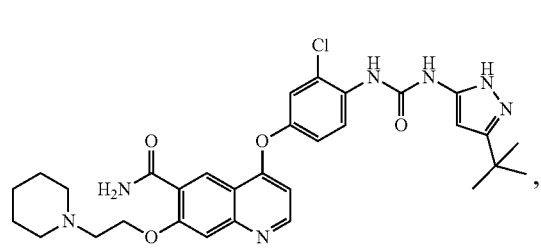

85
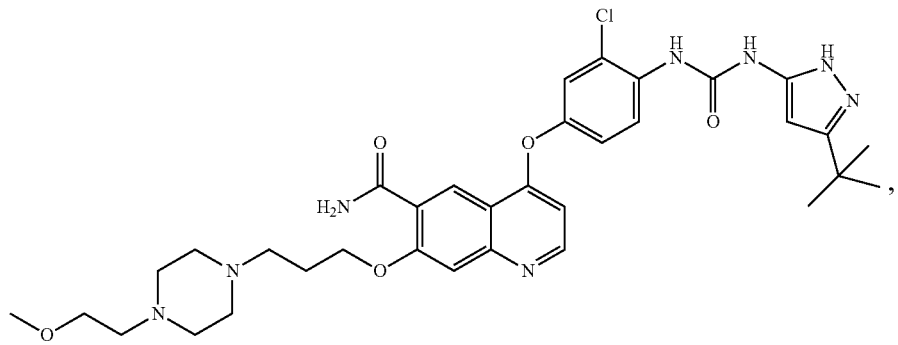
86
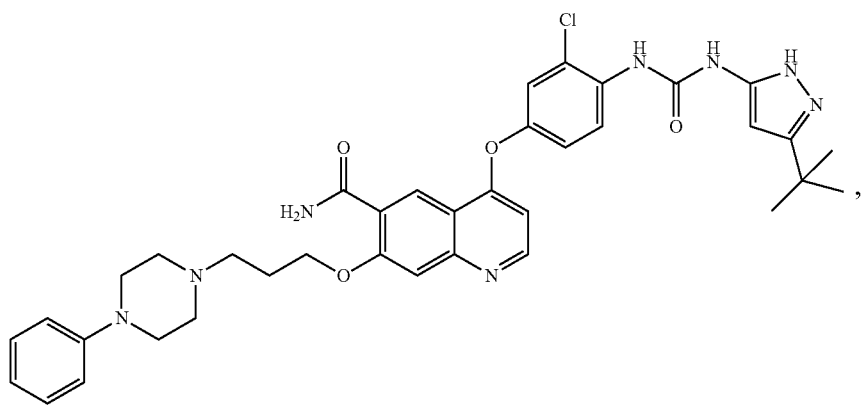
87
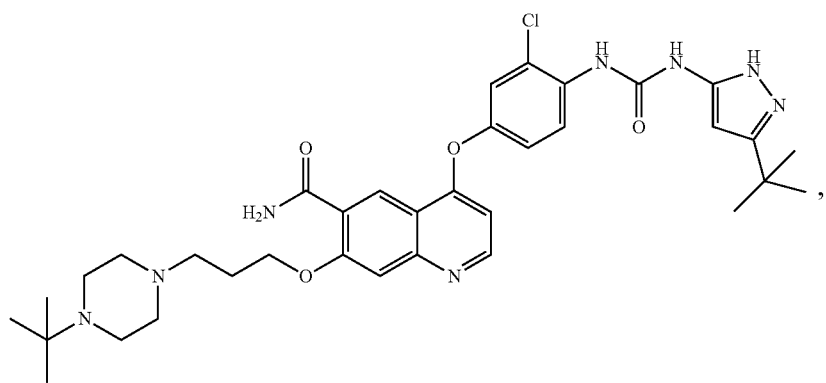
88
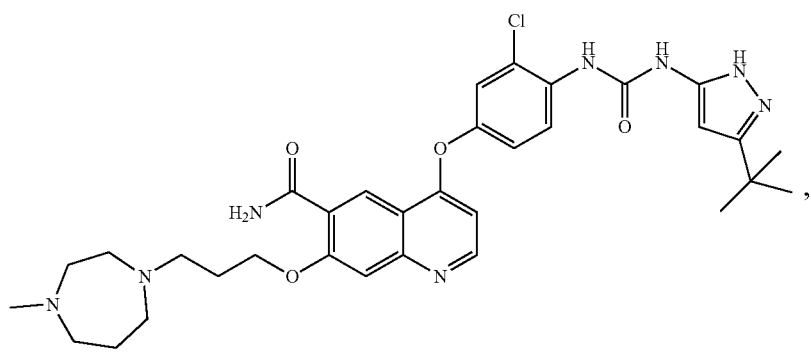

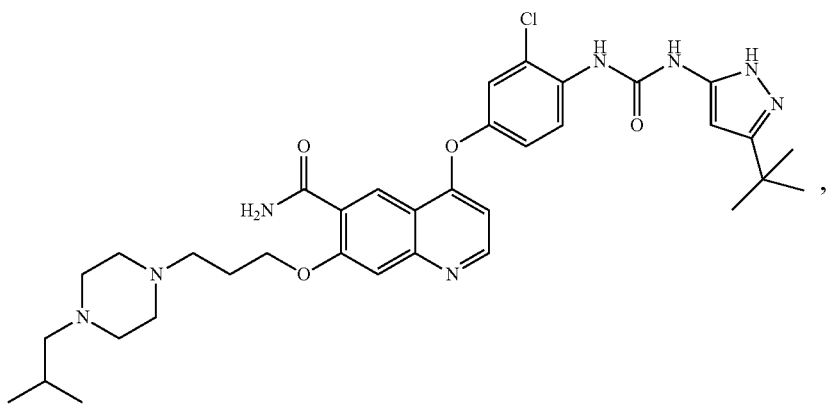
89
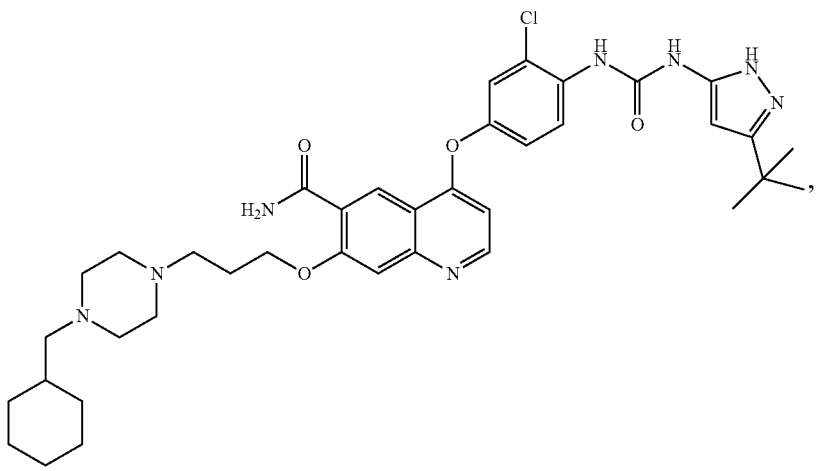
90
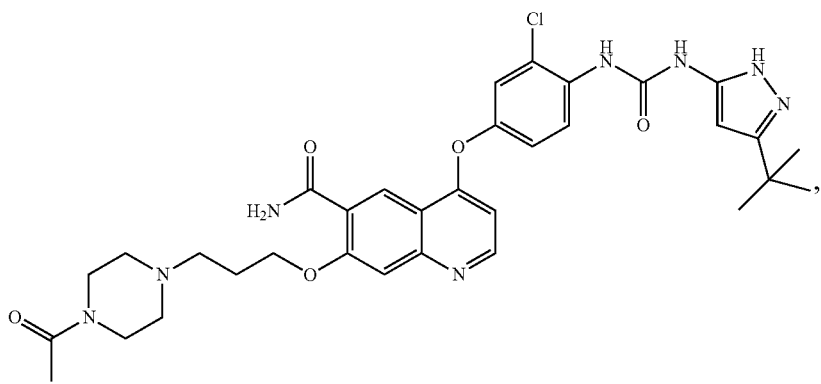
91
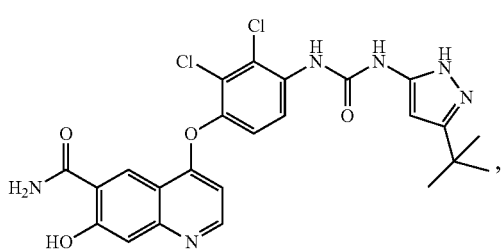
92
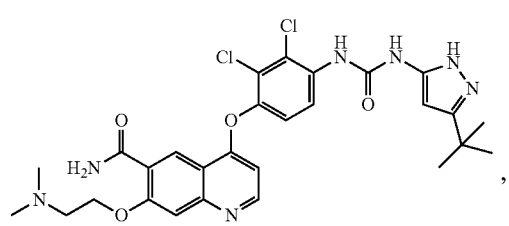
93

-continued
94
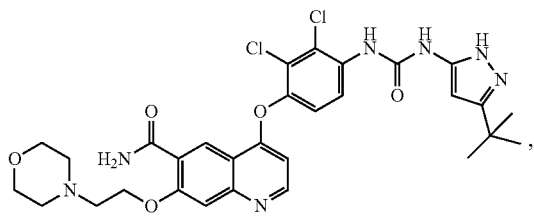
95
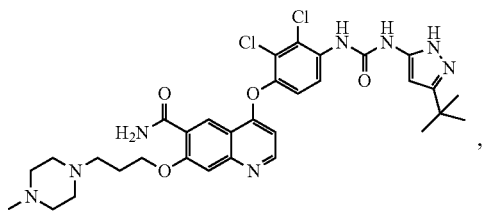
96
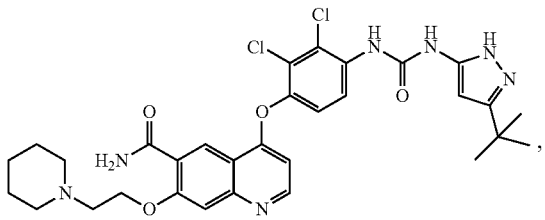
97
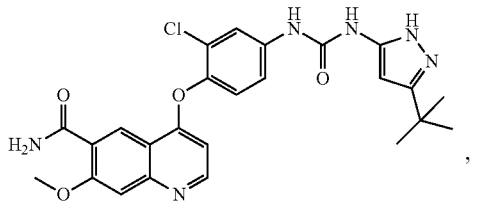
98
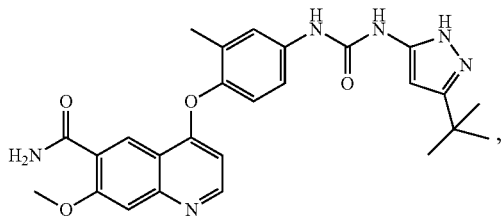
99
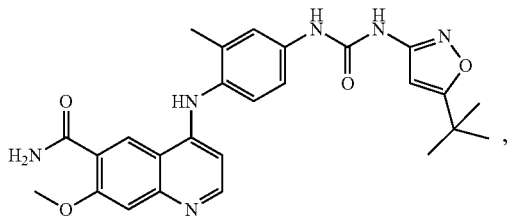
100
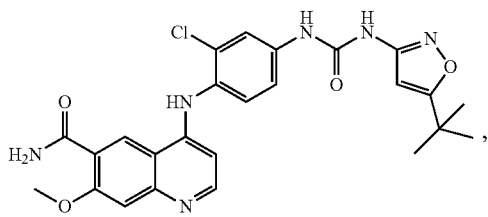
101
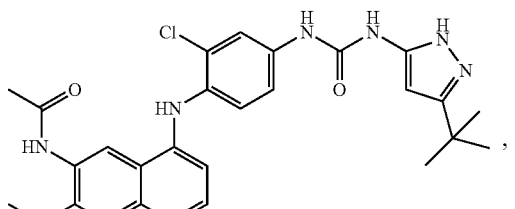
102
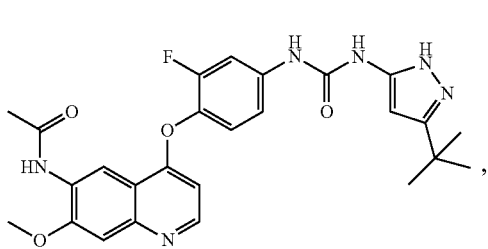
103
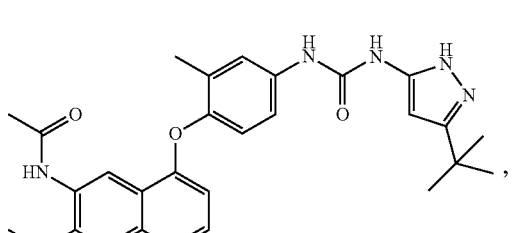
104
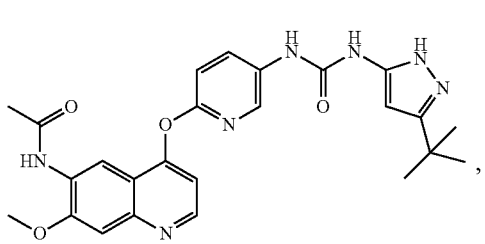
105
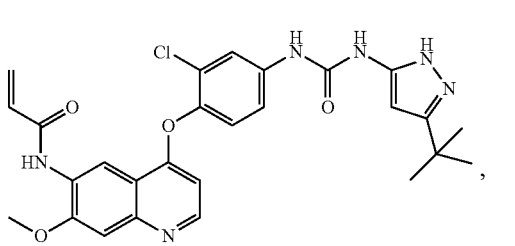

-continued
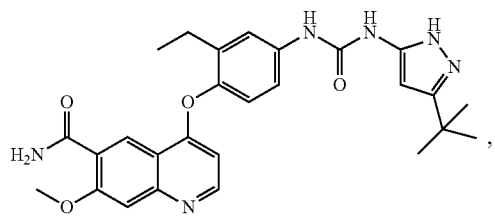 106
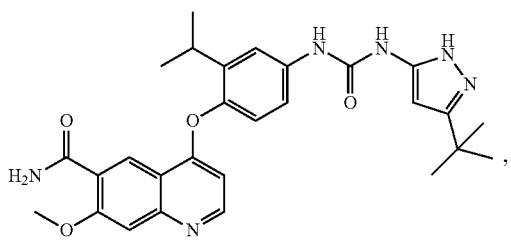 107
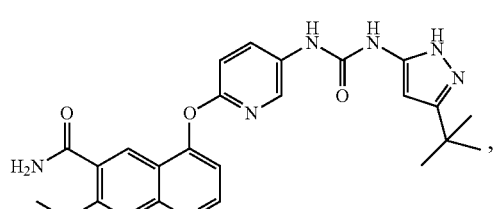 108
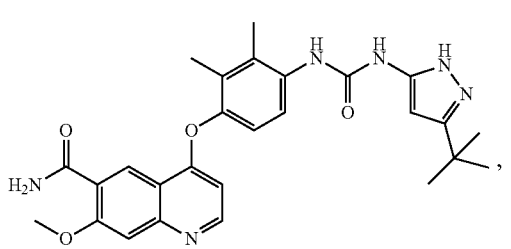 109
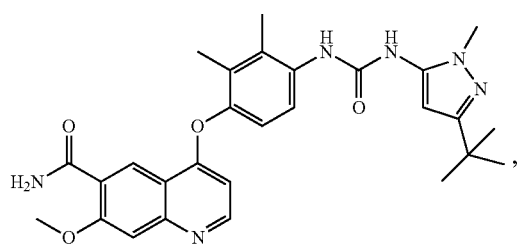 110
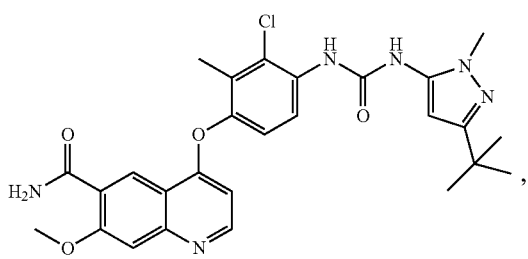 111
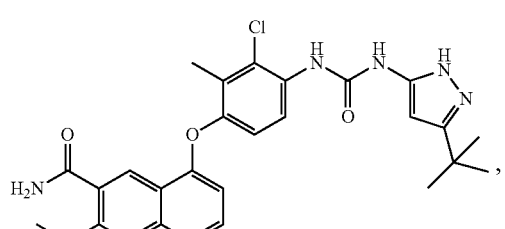 112
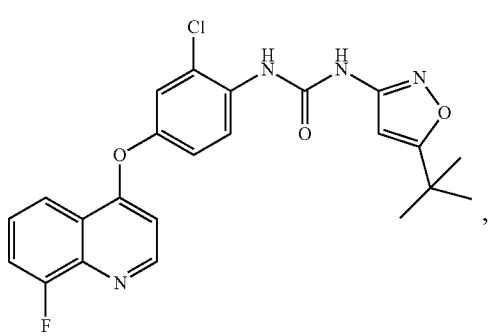 113
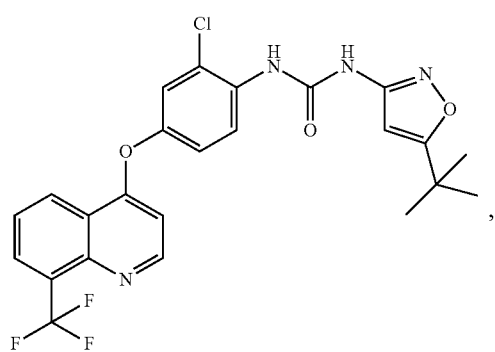 114
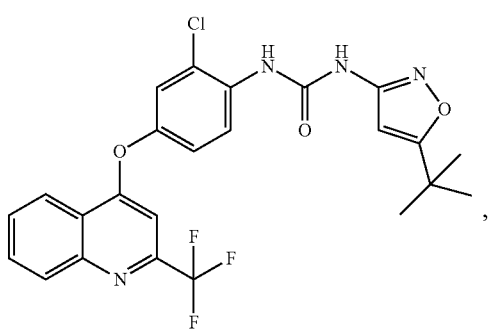 115

-continued
116
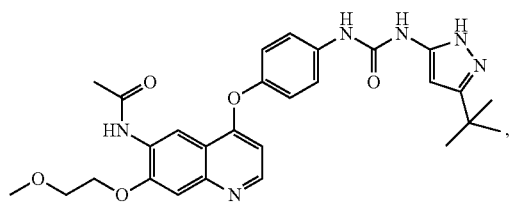
117
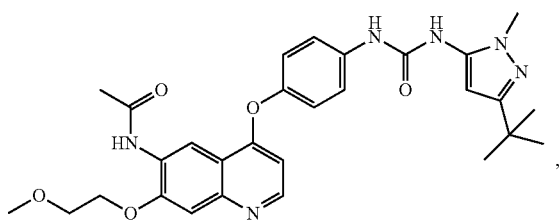
118
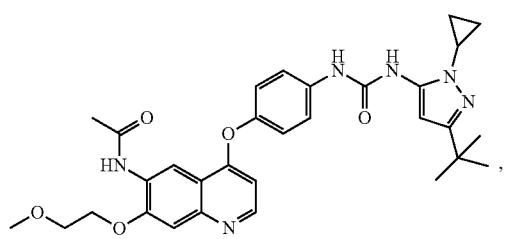
119
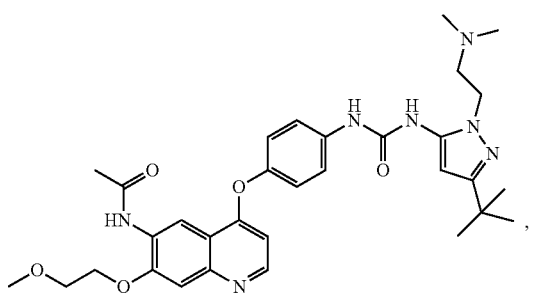
120
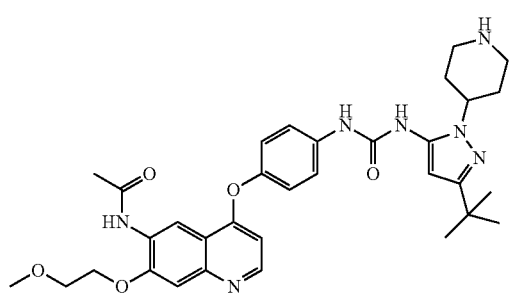
121
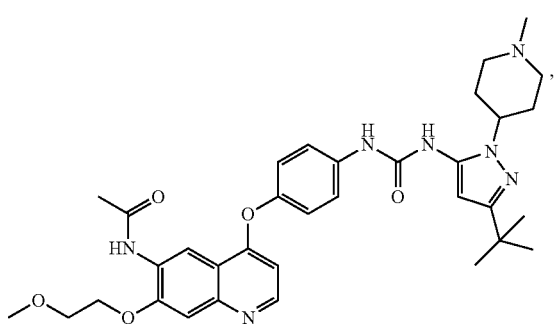
122
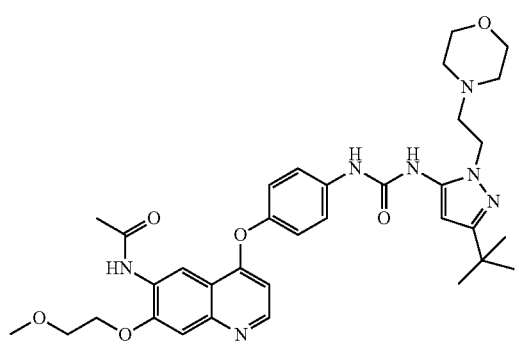
123
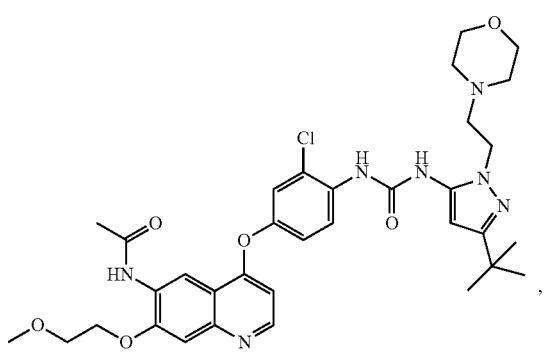
124
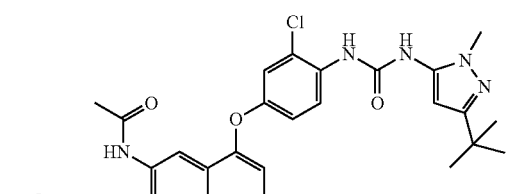
125
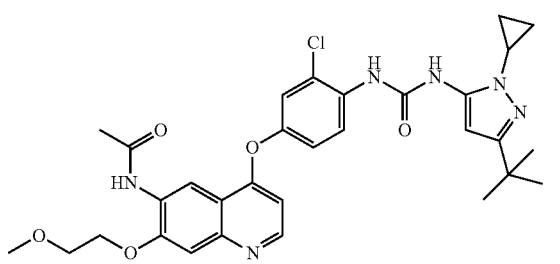

126
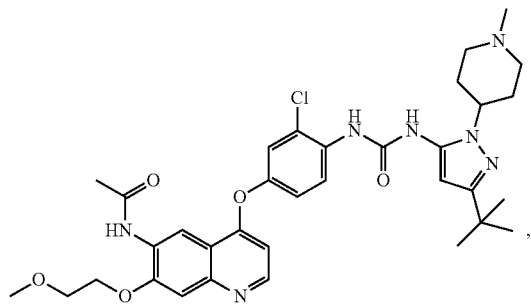
127
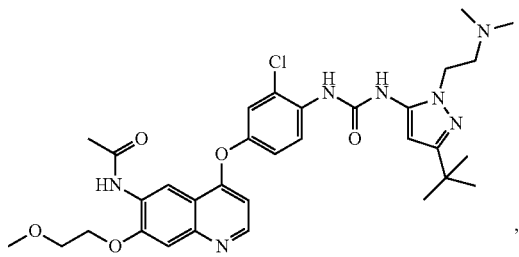
128
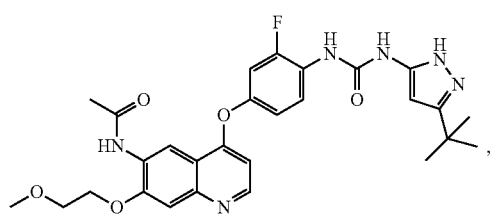
129
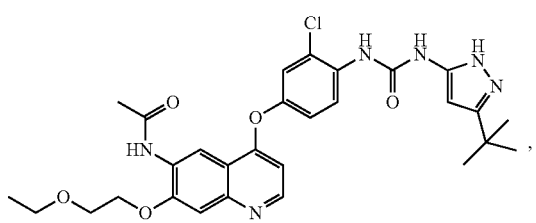
130
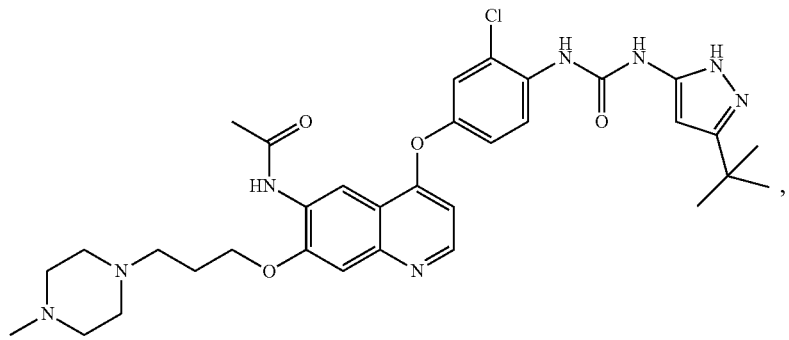
131
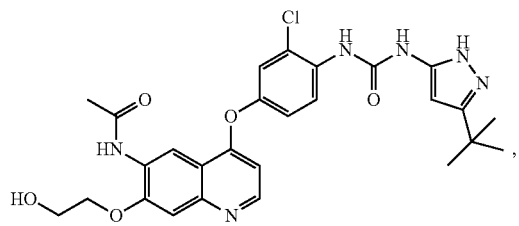
132
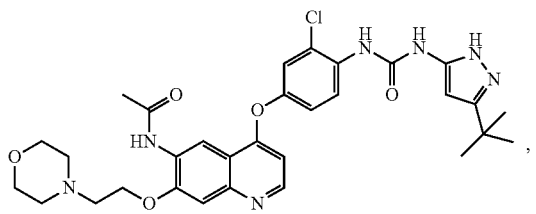
133
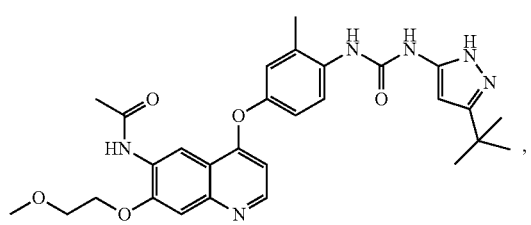
134
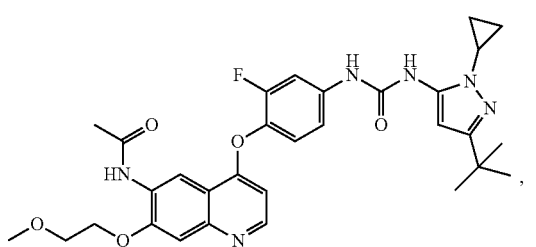

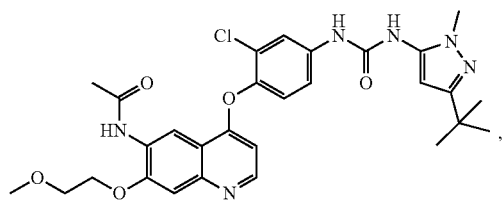
135
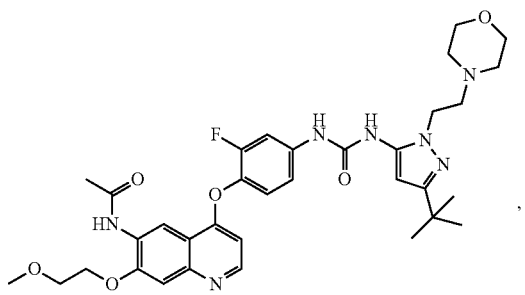
136
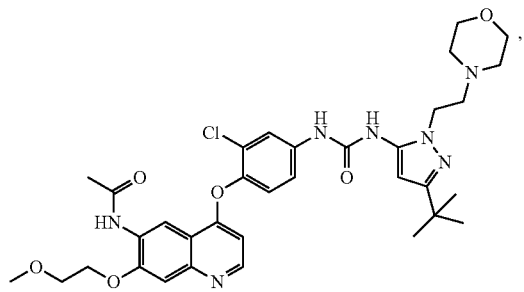
137
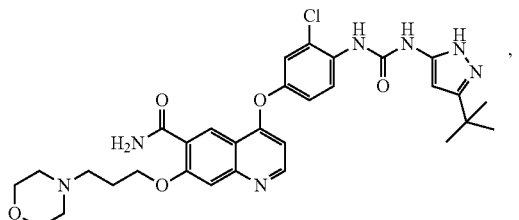
138
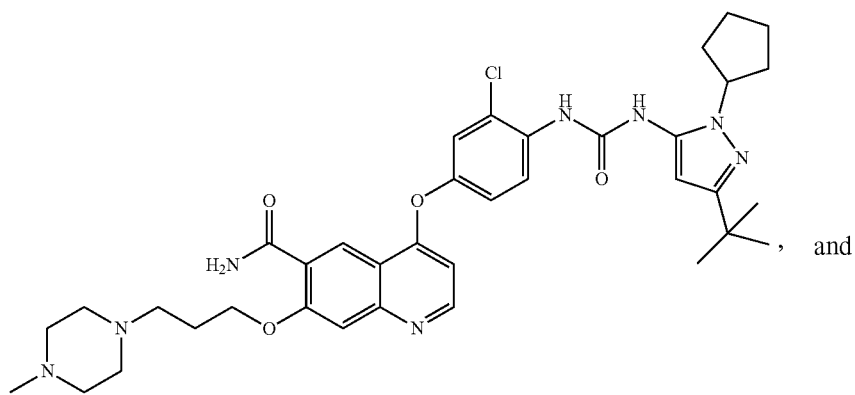
139
, and
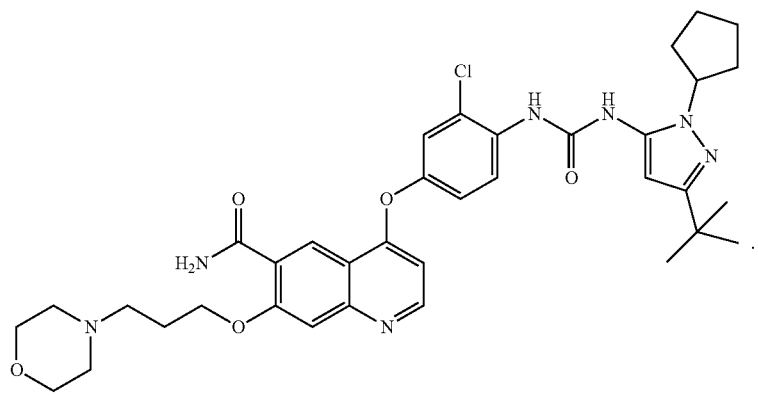
140
.
11. A deuterated compound of general formula (I) or a pharmaceutically acceptable salt, solvate, or metabolite thereof according to claim 1, wherein one or more H atoms in the compound of general formula (I) is independently replaced by D atom.
12. A deuterated compound is selected from the group consisting of:

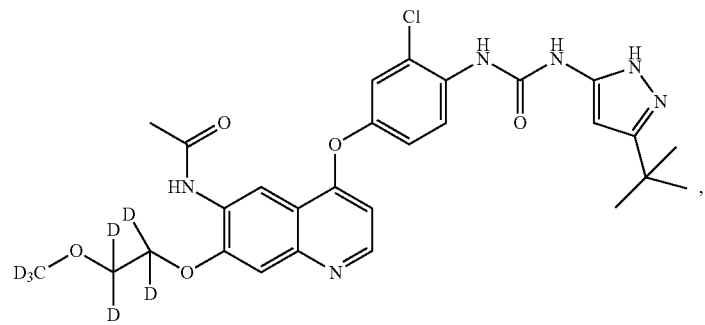
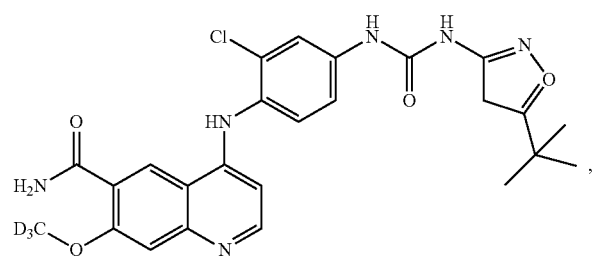
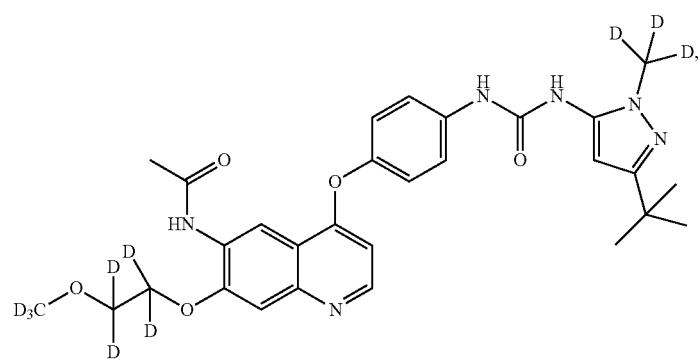
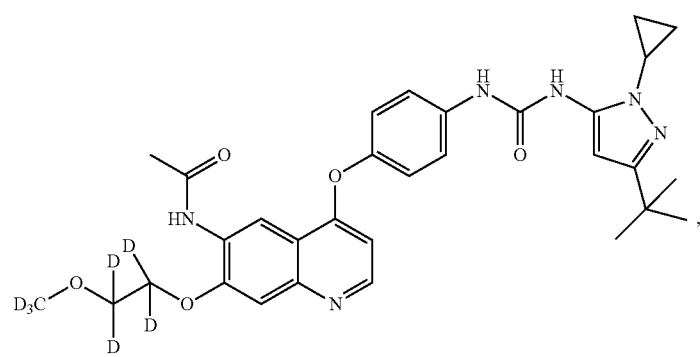
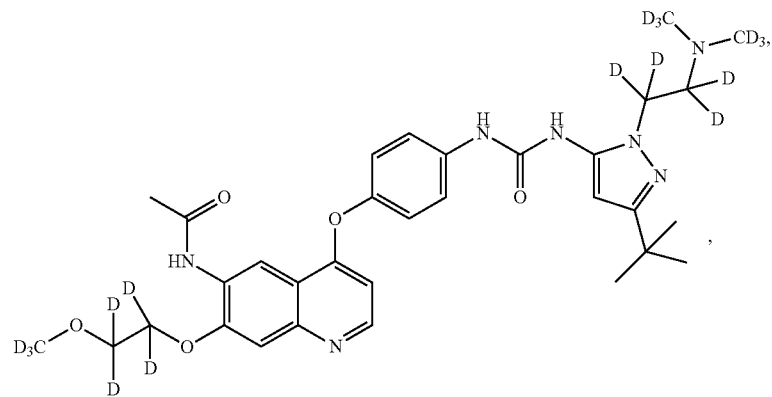

-continued
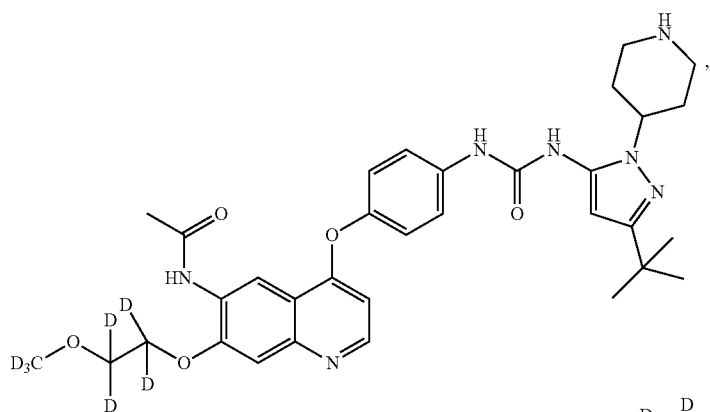
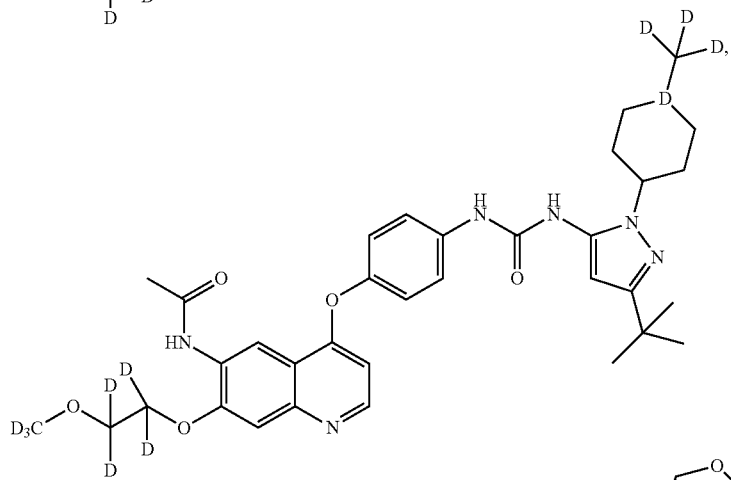
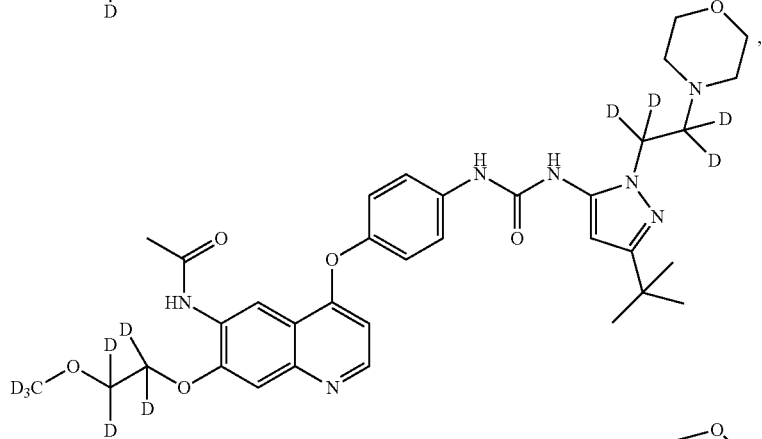
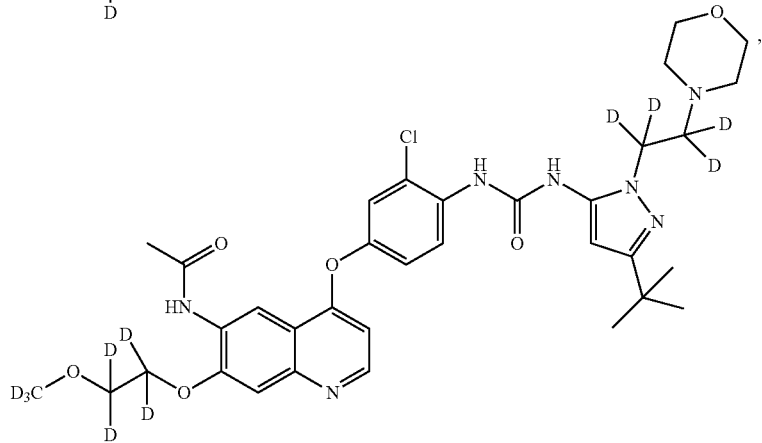

-continued
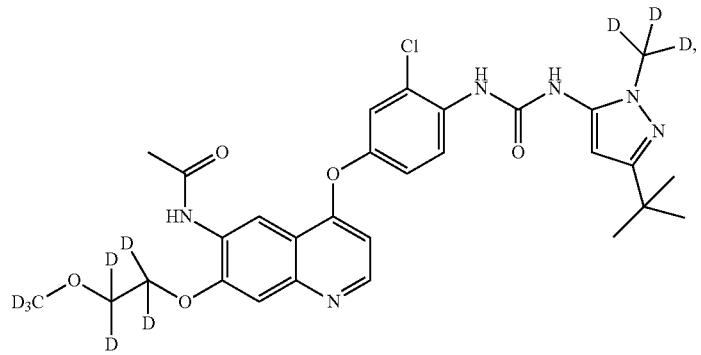
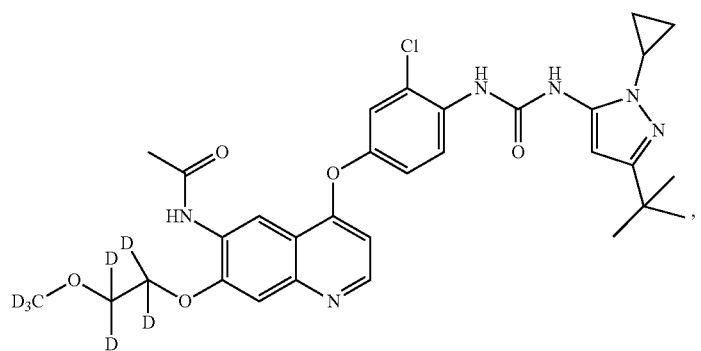
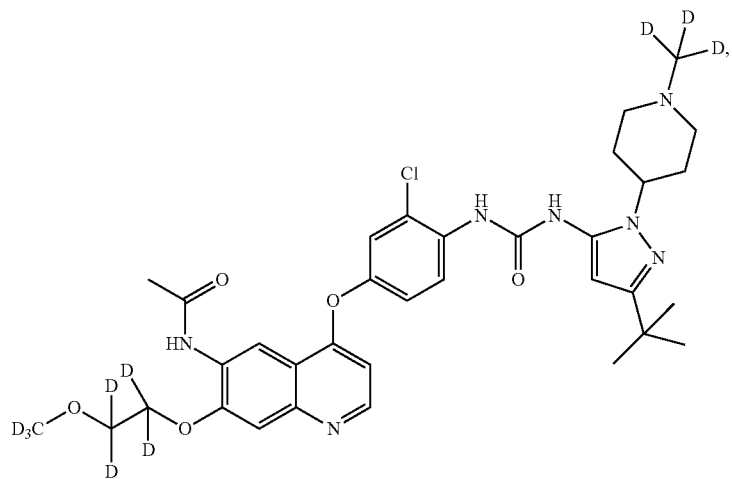
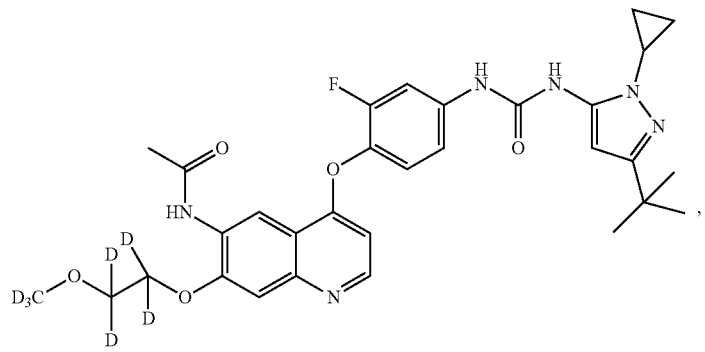

-continued
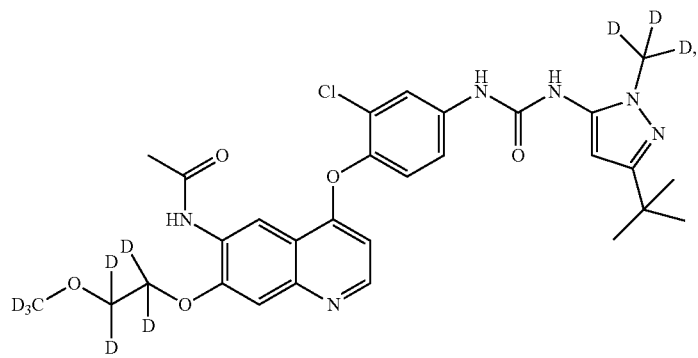
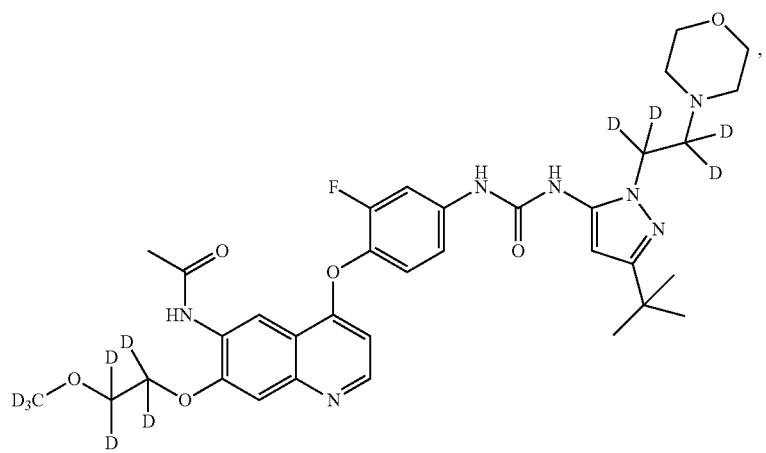
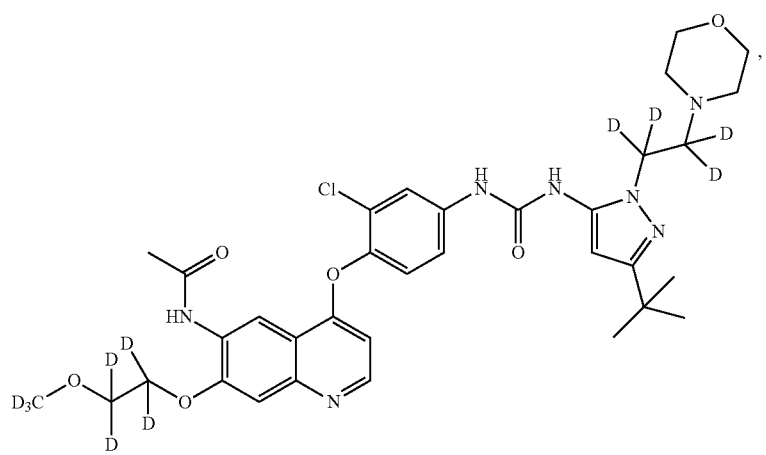
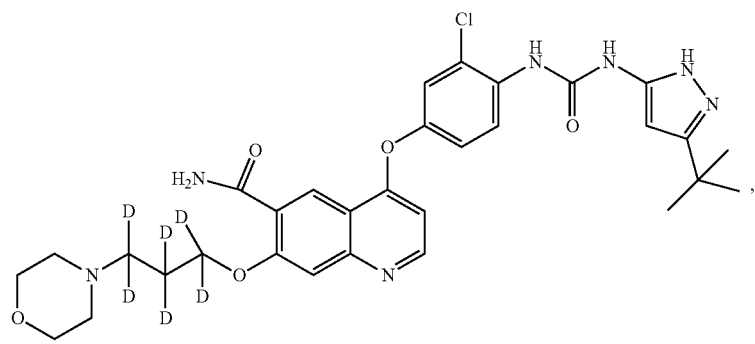

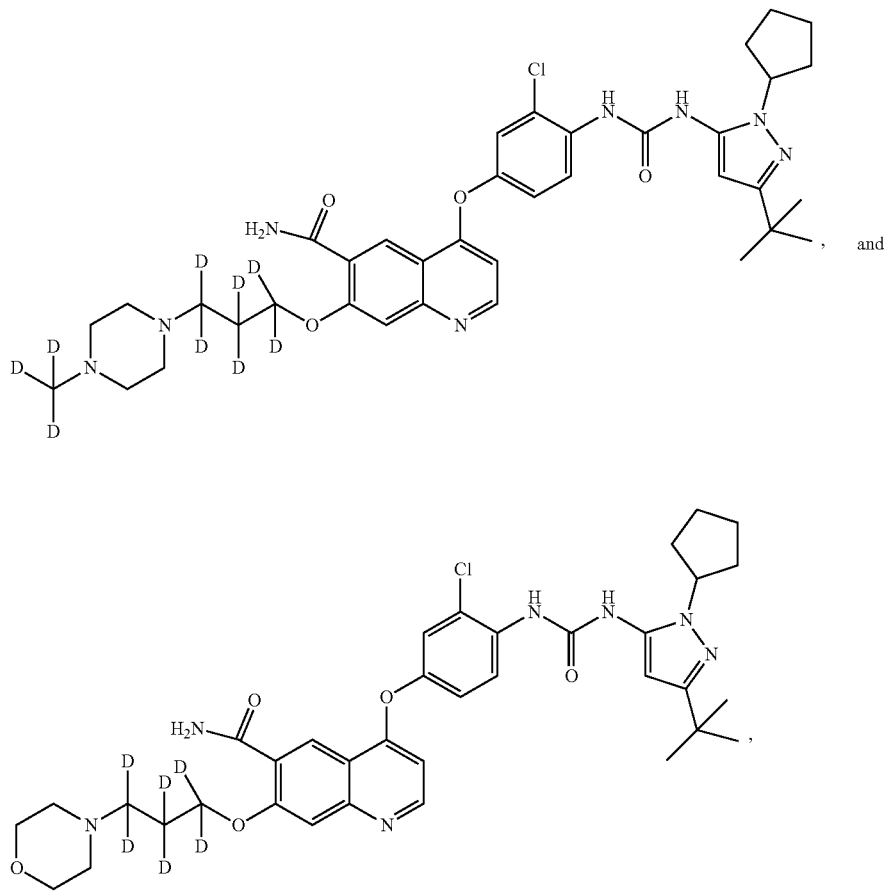

, and

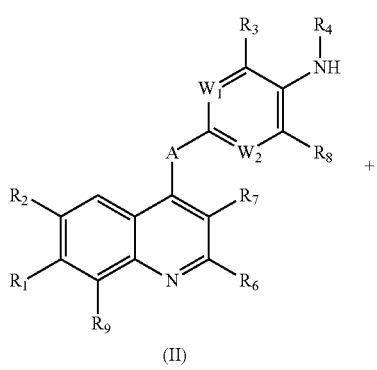

,

13. A method for preparing the compound of general formula (I) or a pharmaceutically acceptable salt, solvate, or metabolite thereof according to claim 1, comprising the following steps:

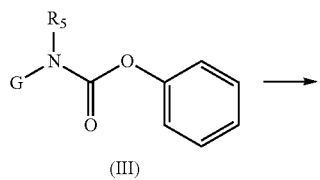

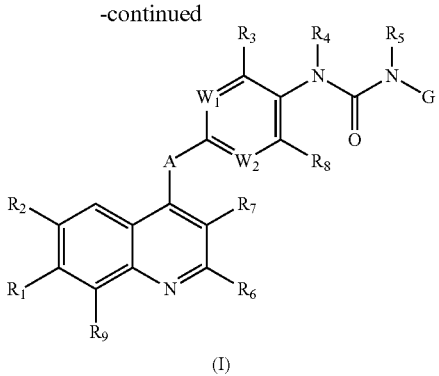

the compound of formula (II) is reacted with the compound of formula (III) in the presence of a base in a suitable solvent to give the compound of general formula (I);

the solvent is selected from the group consisting of THF, acetonitrile, dichloromethane and toluene, the base is selected from the group consisting of triethylamine, N,N-diisopropylethylamine, DMAP and pyridine;

$R_1$, $R_2$, $R_3$, $R_4$, $R_5$, $R_6$, $R_7$, $R_8$, $R_9$, A, $W_1$, $W_2$ and G are as defined in claim 1.

14. A method for preparing the compound of general formula (I) or a pharmaceutically acceptable salt, solvate, or metabolite thereof according to claim 1, comprising the following steps:

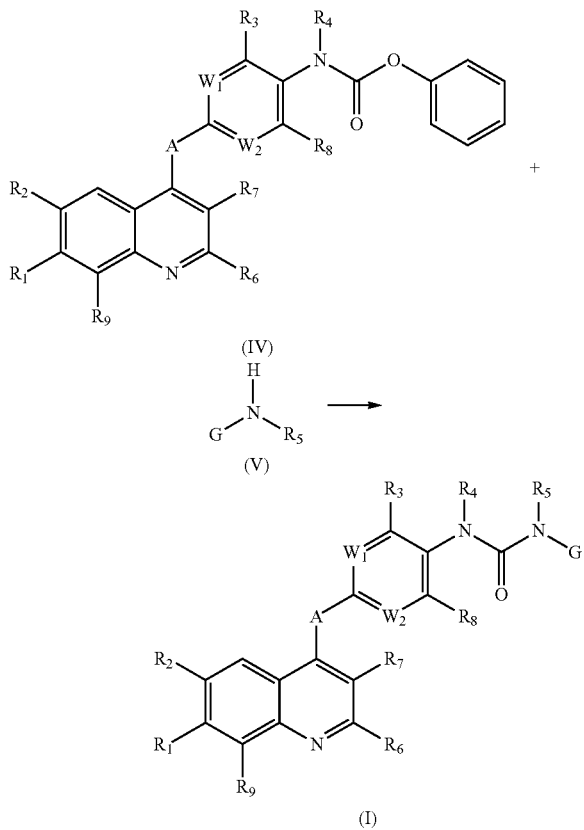

the compound of formula (IV) is reacted with the compound of formula (V) in the presence of a base in a suitable solvent to give the compound of general formula (I);
the solvent is selected from the group consisting of THF, acetonitrile, dichloromethane, and toluene;
the base is selected from the group consisting of triethylamine, N,N-diisopropylethylamine, DMAP, and pyridine;

$R_1$, $R_2$, $R_3$, $R_4$, $R_5$, $R_6$, $R_7$, $R_8$, $R_9$, A, $W_1$, $W_2$ and G are as defined in claim 1.

15. A pharmaceutical composition comprising a therapeutically effective amount of the compound of general formula (I) or a pharmaceutically acceptable salt, solvate, or metabolite thereof according to claim 1, or a deuterated compound of general formula (I) or a pharmaceutically acceptable salt, solvate, or metabolite thereof as well as one or more pharmaceutically acceptable carriers.

16. A method of inhibiting a protein kinase selected from the group consisting of ABL1, AXL, EGFR, FGFR1-4, FLT3, KIT, MERTK, PDGFRα/β, RET, ROS1, NTRK1-3, SRC protein kinase family and PIK3CA, the method comprising administering to a patient in need of it an inhibitory effective amount of a compound of general formula (I) or a pharmaceutically acceptable salt, solvate, or metabolite thereof according to claim 1 or a deuterated compound of the compound of general formula (I) or a pharmaceutically acceptable salt, solvate, or metabolite thereof or a pharmaceutical composition comprising the compound of general formula (I).

17. A method of treating cancer, the method comprising administering to a patient in need of it a therapeutically effective amount of a compound of general formula (I) or a pharmaceutically acceptable salt, solvate, or metabolite thereof according to claim 1, or a deuterated compound of general formula (I) or a pharmaceutically acceptable salt, solvate, or metabolite thereof, or a pharmaceutical composition comprising the compound of general formula (I) or a pharmaceutically acceptable salt, solvate, metabolite thereof, wherein said cancer is lung cancer, gastric cancer, liver cancer, bile duct cancer, breast cancer, nasopharyngeal cancer, pancreatic cancer, ovarian cancer, cervical cancer, endometrial cancer, colorectal cancer, glioma, melanoma, prostate cancer, kidney cancer, esophageal cancer, mesothelioma, head and neck cancer, bladder cancer, salivary gland cancer, anaplastic large cell lymphoma, leukemia, lymphoma, non-Hodgkin's lymphoma or multiple myeloma.

18. The method according to claim 17, wherein the compound of general formula (I) or pharmaceutically acceptable salt, solvate, or metabolite thereof or the deuterated compound of general formula (I) or pharmaceutically acceptable salt, solvate, or metabolite thereof or the pharmaceutical composition is administered in combination with other drugs or cancer therapies for the treatment of cancer.

* * * * *